United States Patent [19]

Minamida et al.

[11] Patent Number: 4,914,206

[45] Date of Patent: Apr. 3, 1990

[54] LANKACIDIN DERIVATIVES AND PRODUCTION THEREOF

[75] Inventors: Isao Minamida, Kawabegun; Naoto Hashimoto, Suita, both of Japan

[73] Assignee: Takeda Chemical Industries, LTD., Osaka, Japan

[21] Appl. No.: 285,302

[22] Filed: Dec. 15, 1988

Related U.S. Application Data

[63] Continuation of Ser. No. 937,625, Dec. 1, 1986, abandoned.

[30] Foreign Application Priority Data

Oct. 6, 1985 [JP] Japan .................. 61-238788
Dec. 5, 1985 [JP] Japan .................. 60-274256

[51] Int. Cl.$^4$ .................................... C07D 405/04
[52] U.S. Cl. ........................ 544/376; 544/69; 544/151; 544/229; 546/14; 546/196; 546/269; 548/110; 548/127; 548/135; 548/136; 548/138; 548/141; 548/157; 548/159; 548/187; 548/213; 548/220; 548/225; 548/243; 548/251; 548/253; 548/256; 548/328; 548/264.4; 549/4; 549/60; 549/214; 549/216; 549/270; 549/287
[58] Field of Search ...................... 544/376, 229

[56] References Cited

U.S. PATENT DOCUMENTS

| | | | |
|---|---|---|---|
| 3,262,055 | 12/1971 | Higashide | 424/120 |
| 3,676,300 | 7/1972 | Yamamoto et al. | 195/29 |
| 3,691,181 | 9/1972 | Kishi et al. | 260/295.5 P |
| 4,670,569 | 6/1987 | Nysted et al. | 544/376 |

FOREIGN PATENT DOCUMENTS

| | | |
|---|---|---|
| 0091781 | 10/1983 | European Pat. Off. . |
| 0091782 | 10/1983 | European Pat. Off. . |
| 2014277 | 12/1970 | Fed. Rep. of Germany . |
| 8052285 | 3/1983 | Japan . |
| 2088715 | 6/1982 | United Kingdom . |

OTHER PUBLICATIONS

McFarland et al., Antimicrobial Agents and Chemotherapy, vol. 25, No. 2, Feb. 1984, pp. 226–233.
Harada et al., The Journal of Antibiotics, vol. 26, No. 11, Nov. 1973, pp. 647–657.
Uramoto et al., Acta Cryst. (1971) B27, pp. 236–241.
Nakahama et al., The Journal of Antibiotics, 28(5) May, 1975, pp. 390–394.
Harada et al., The Journal of Antibiotics 26(11) Nov. 1973, pp. 647–657.
Uramoto et al., Acta. Cryst. (1971) B27, pp. 236–241, Jan. 1971.

*Primary Examiner*—Glennon H. Hollrah
*Assistant Examiner*—James H. Turnipseed
*Attorney, Agent, or Firm*—Wenderoth, Lind & Ponack

[57] ABSTRACT

The present invention provides lankacidin derivatives of the formula t,0010 and procedures for the production thereof.

The lankacidin derivatives [1] show excellent antimicrobial activities and thus can be used for prophylaxis and treatment of infectious disease in animals.

21 Claims, No Drawings

LANKACIDIN DERIVATIVES AND PRODUCTION THEREOF

This application is a continuation, of now abandoned application Ser. No. 937,625, filed Dec. 1, 1986.

The present invention relates to novel lankacidin derivatives having antimicrobial activities and a method of preparing them.

Lankacidins are produced by cultivation of strains belonging to the genus Streptomyces and have the structural formula (i) or (ii).

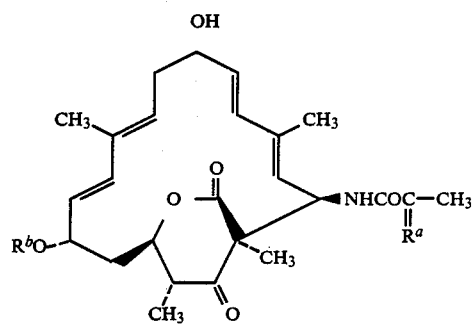

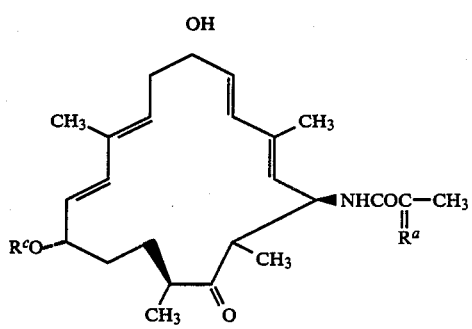

Lankacidin A is a compound of the general formula (i) wherein $R^a$:O, $R^b$:COCH$_3$, lankacidin C is a compound of the general formula (i) wherein $R^a$:O, $R^b$:H, lankacidinol A is a compound of the general formula (i) wherein $R^a$:

$R^b$:COCH$_3$ and lankacidinol is a compound of the general formula (i) wherein $R^a$:

$R^b$:H; and lankacyclinol is a compound of the general formula (ii) wherein $R^c$:H and lankacyclinol A is a compound of the general formula (ii) wherein $R^c$:COCH$_3$.

Among derivatives of the above-mentioned lankacidins, for example, esters at the 8- or/and 14 positins of lankacidin C [Acta Cryst., B27, P.236 (1971); J. Antibiotics, 26, P.647 (1973)], 3-amido modified derivatives [Antimicrobial Agents and Chemotherapy, 25 pp.226~233 (1984)] and acyloxy derivatives at 8- or/and 14-positions [The Journal of Antibiotics, 26, p.647 (1973)] have been known.

While, as stated above, lankacidins have been produced, the present invention is directed to production of novel derivatives of these lankacidins.

The present inventors synthesized from the above-mentioned lankacidins a variety of derivatives, and studied the pharmacological activities thereof, and found that these derivatives have excellent antimicrobial activities.

Based on these findings, the present inventors conducted further extensive studies and have completed the present invention.

The present invention relates to compounds representable by the general formula;

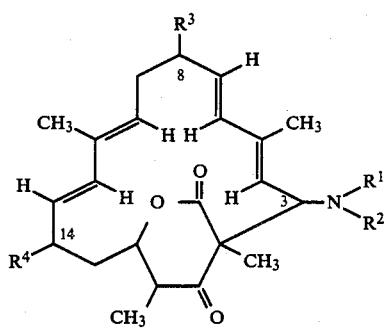

[1]

[wherein (i) one of $R^1$ and $R^2$ stands for hydrogen atom, and the other stands for a group representable by the formula;

(wherein Z stands for oxygen atom or sulphur atom, and $R^5$ stands for an organic radical which is bonded to the group to which it is attached through a carbon atom) or (ii) $R^1$ and $R^2$, taken together, stand for a group representable by the formula;

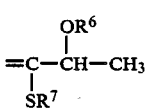

(wherein $R^6$ stands for acyl, sulfonyl or alkoxy carbonyl, and $R^7$ stands for a lower alkyl); $R^3$ and $R^4$ independently stand for hydroxyl, halogen, azido or an organic radical bonded to the group to which it is attached through an oxygen atom, a sulfur atom or a nitrogen atom; provided that, when $R^1$ stands for hydrogen atom and $R^2$ stands for

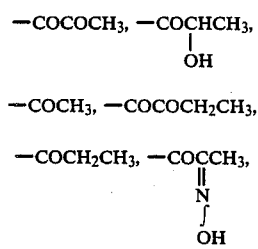

-continued

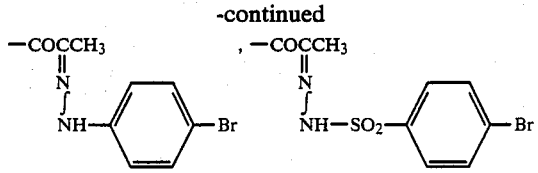

or a group representable by the formula;

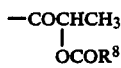

(wherein $R^8$ stands for a straight-chain alkyl having 1~13 carbon atoms), $R^3$ stands for groups other than hydroxyl or groups representable by the formula; —OCOR$^9$ (wherein $R^9$ stands for alkyl, alkenyl, aralkyl, aryl, 3-pyridyl, —CF$_3$, m-bromophenyl or —CH$_2$CH$_2$COOH) and $R^4$ stands for groups other than hydroxyl or groups representable by the formula; —OCOR$^9$ (wherein $R^9$ is as defined above) or both $R^3$ and $R^4$ stand for groups other than formyloxy, and provided that, when $R^1$ stands for a hydrogen atom, $R^2$ stands for —COCOCH$_3$ and $R^4$ stands for —OCOCH$_3$, $R^3$ stands for groups other than chlorine, —OSO$_2$CH$_3$ or

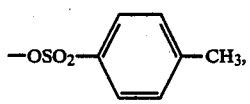

and provided that, when $R^1$ stands for hydrogen atom, $R^2$ stands for —COCOCH$_3$ and $R^3$ stands for —OCH$_3$, $R^4$ is not —OCH$_3$] or salts thereof, and the production thereof.

In the above formulae, organic residual groups bound through a carbon atom representable by $R^5$ are preferably those whose molecular weight is up to 400, as exemplified by alkyl, cycloalkyl, alkanoyl, alkenyl, alkynyl, aryl or heterocyclic group, which may have 1~3 substituents.

In the above formulae, the acyl group representable by $R^6$ is exemplified by groups representable by the formula; —CO—R$^{10}$ (wherein $R^{10}$ stands for alkyl, aralkyl or aryl).

In the above formulae, the sulfonyl group representable by $R^6$ is exemplified by groups representable by the formula; —SO$_2$—R$^{11}$ (wherein $R^{11}$ stands for alkyl, aralkyl or aryl).

In the above formulae, the alkoxy carbonyl group representable by $R^6$ is exemplified by groups representable by the formula; —COO—R$^{12}$ (wherein $R^{12}$ stands for alkyl, aralkyl or aryl).

In the above formulae, organic residual groups bound through an oxygen atom representable by $R^3$ and $R^4$ are exemplified by those representable by the formula; —OCOOR$^{13}$ or —OCOSR$^{13'}$ (wherein $R^{13}$ and $R^{13'}$ stand for an organic residual group bound through a carbon atom), those representable by the formula; —O—COR$^{14}$ (wherein $R^{14}$ stands for hydrogen or an organic residual group bound through a carbon atom), those representable by the formula;

(wherein $R^{15}$ and $R^{16}$ independently stand for hydrogen or an organic residual group bound through a carbon atom), those representable by the formula;

(wherein $R^{17}$ and $R^{18}$ independently stand for hydrogen or an organic residual group bound through a carbon atom), those representable by the formula;

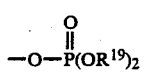

(wherein $R^{19}$ stands for hydrogen or an organic residual group bound through a carbon atom), those representable by the formula; —OSO$_2$R$^{20}$ (wherein $R^{20}$ stands for alkyl or aryl), those representable by the formula; —OR$^{21}$ (wherein $R^{21}$ stands for an organic residual group bound through carbon atom) and those representable by the formula;

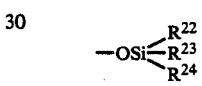

(wherein $R^{22}$, $R^{23}$, and $R^{24}$ independently stand for alkyl or phenyl), among others.

In the above formulae, organic residual groups bound through a carbon atom shown by $R^{13-19}$ and $R^{21}$ are preferably those whose molecular weight is up to 400, as exemplified by alkyl, cycloalkyl, alkenyl, alkynyl, aryl or heterocyclic group, which may have 1~3 substituents.

In the above formulae, organic residual groups bound through a sulfur atom shown by $R^3$ and $R^4$ are exemplified by those representable by the formula; —SR$^{25}$ (wherein $R^{25}$ stands for alkyl, cycloalkyl, alkenyl, alkynyl, aryl or heterocyclic group of a molecular weight of up to 400 optionally having substituents).

In the above formulae, organic residual groups bound through a nitrogen atom shown by $R^3$ and $R^4$ are exemplified by those representable by the formula;

(wherein $R^{26}$ and $R^{27}$ independently stand for hydrogen atom, alkyl, aryl, heterocyclic group, acyl, sulfonyl or phosphoryl of a molecular weight of up to 400 optionally having substituents). Acyl groups shown by $R^{26}$ and $R^{27}$ are exemplified by those similar to the acyl moiety (—COR$^{14}$) of a group representable by the above-mentioned formula; —OCOR$^{14}$.

As for $R^{13}$ to $R^{27}$ mentioned above, that $R^{13}$ is C$_{1-3}$ alkyl which may be substituted with halogen, tetrazolylthio, thiadiazolylthio, phenylthio, C$_{1-3}$alkylthio, pyrenylcarbonyloxy or C$_{1-3}$alkanoylaminomethylcarbonyloxy, or phenyl, that $R^{13'}$ is di-C$_{1-3}$alkylaminoethyl or thiadiazolylthiomethyl, that $R^{14}$ is hydrogen, C$_{1-3}$alkyl which may be substituted with halogen, azido, tetrazolylthiomethyl, thiadiazolylthiomethyl, di-$C_{1-3}$alkylamino-$C_{1-3}$alkylthio, mono-or di-$C_{1-3}$alkylamino, piperazino, halogeno or $C_{1-3}$alkylamino, morpholino, mono-or di-$C_{1-3}$-alkylamino, or phenyl, that $R^{15}$ and $R^{16}$ are independently hydrogen, $C_{1-3}$alkyl which may be substituted with $C_{1-3}$alkoxycarbonyl, halogen, pyridylamino, di-$C_{1-3}$alkylamino piperidino, pyridyl, tetrazolylthio or carboxyl, phenyl, or cyclohexyl, or $R^{15}$ and $R^{16}$ form morpholino, piperazino or piperidino together with the adjacent nitrogen atom, that $R^{17}$ and $R^{18}$ form morpholino, piperidino or piperazino together with the adjacent nitrogen atom, that $R^{19}$ is hydrogen, $C_{1-3}$alkyl or benzyl, that $R^{20}$ is $C_{1-3}$alkyl, that $R^{21}$ is $C_{1-3}$alkyl substituted with $C_{1-3}$alkoxy, $C_{1-3}$alkoxy-$C_{1-3}$alkyloxy, or $C_{1-3}$alkylthio, that $R^{22}$, $R^{23}$ and $R^{24}$ are independently $C_{1-4}$alkyl, that $R^{25}$ is phenyl, tetrazolyl, thiadiazolyl, thiazolyl, oxazolyl or triazolyl, and that $R^{26}$ and $R^{27}$ are independently hydrogen, $C_{2-5}$alkanoyl or tosyl are preferable.

Alkyl groups in the explanation of the respective groups in the foregoing are preferably those whose carbon number is 1~20, more preferably those of 1~8 carbon atoms. These alkyl groups may be straight-chain or branched ones, which are exemplified by methyl, ethyl, propyl, isopropyl, butyl, isobutyl, sec-butyl, tert-butyl, pentyl, hexyl, heptyl, octyl, nonyl, 2-ethylhexyl, decyl, undecyl, dodecyl, tridecyl, tetradecyl, pentadecyl, hexadecyl, octadecyl, nonadecyl and eicosyl.

Cycloalkyl groups in the foregoing explanation of the respective groups are preferably those of 3~6 carbon atoms, as exemplified by cyclopropyl, cyclobutyl, cyclopentyl or cyclohexyl.

Alkenyl groups in the foregoing explanation of the respective groups are preferably those of 2~6 carbon atoms, as exemplified by vinyl, allyl, isopropenyl, methallyl, 1,1-dimethyl allyl, 2-butenyl, 3-butenyl, 2-pentenyl and 5-hexenyl.

Alkynyl groups in the foregoing explanation of the respective groups are preferably those of 2~6 carbon atoms, as exemplified by ethynyl, propargyl, 2-butyn-1-yl, 3-butyn-1-yl, 3-butyn-2-yl, 1-pentyn-3-yl, 3-pentyn-1-yl, 4-pentyn-2-yl and 3-hexyn-1-yl.

Aryl groups in the foregoing explanation of the respective groups are exemplified by phenyl and naphthyl.

As heterocyclic groups in the foregoing explanation of the respective groups are mentioned 5~8-membered rings containing 1~4 hetero atoms such as oxygen atom, sulfur atom or nitrogen atom, as exemplified by thienyl, furyl, pyrrolyl, pyridyl, oxazolyl, thiazolyl, pyrazolyl, imidazolyl, isooxazolyl, isothiazolyl, 1,2,4-oxadiazolyl, 1,3,4-oxadiazolyl, 1,2,4-thiadiazolyl, 1,3,4-thiadiazolyl, 1,2,3-thiadiazolyl, 1,2,3-triazolyl, 1,2,4-triazolyl, 1,3,4-triazolyl, tetrazolyl, N-oxido-pyridyl, pyrimidinyl, N-oxido-pyrimidinyl, pyridazinyl, pyrazinyl, N-oxido-pyridazinyl, benzofuryl, benzothiazolyl, benzoxazolyl, triazinyl, tetrazolo[1,5-b]pyridazinyl, triazolo[4,5-b]pyridazinyl, oxoimidazolinyl, dioxotriazinyl, pyrrolidinyl, piperidinyl, pyranyl, thiopyranyl, 1,4-oxadinyl, morpholinyl, 1,4-thiazinyl, 1,3-thiazinyl, piperazinyl, benzoimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl, phenoxyazinyl, etc.

Aralkyl groups in the foregoing explanation of groups are preferably those having 7~12 carbon atoms, as exemplified by benzyl, 2-phenethyl, 1-phenethyl, benzhydryl and trityl. These aralkyls may have 1~3 substituents as exemplified by halogen, nitro, $C_{1-4}$alkyl, etc. Examples of substituted aralkyl groups are 4-chlorobenzyl, 4-nitrobenzyl, 2,4-dimethoxybenzyl, 3,4-dimethylbenzyl, 4-methylbenzyl, etc.

Lower alkyl groups shown by the above-mentioned $R^7$ are preferably those having 1~4 carbon atoms, as exemplified by methyl, ethyl, n-propyl, isopropyl, n-butyl, isobutyl, or tert-butyl.

Substituents of the afore-mentioned optionally substituted alkyl, cycloalkyl, alkenyl and alkynyl are exemplified by hydroxyl, $C_{3-6}$cycloalkyl, $C_{6-10}$aryl, $C_{1-4}$alkoxy, $C_{3-6}$cycloalkyloxy, $C_{6-10}$aryloxy, $C_{7-12}$aralkyloxy, $C_{1-4}$alkylthio, $C_{3-6}$cycloalkylthio, $C_{6-10}$arylthio, $C_{7-12}$aralkylthio, amino, mono-$C_{1-4}$alkylamino, di-$C_{1-4}$alkylamino, $C_{3-6}$cycloalkylamino, $C_{6-10}$arylamino, $C_{7-12}$aralkylamino, azido, nitro, halogen, cyano, carboxy, $C_{1-4}$alkoxycarbonyl, $C_{6-10}$aryloxycarbonyl, $C_{3-6}$cycloalkyloxycarbonyl, $C_{7-12}$aralkyloxycarbonyl, $C_{1-5}$alkanoyl, formyloxy, $C_{1-4}$alkylsulfinyl, $C_{6-10}$arylsulfinyl, $C_{1-4}$alkylsulfonyl, $C_{6-10}$arylsulfonyl, $C_{1-15}$alkanoyloxy, sulfo, carbamoyl, optionally substituted carbamoyl, carbamoyloxy, optionally substituted carbamoyloxy, formylamido, $C_{1-4}$alkanoylamido, $C_{6-10}$arylcarbonylamido, $C_{1-4}$alkoxycarbonylamino, $C_{7-12}$aralkyloxycarbonylamino, oxo, epoxy, thioxo, sulfonamido, heterocyclic group, heterocyclic thio, heterocyclic carbonylamino, heterocyclic oxy, heterocyclic amino, $C_{1-4}$alkoxycarbonyloxy, di-$C_{1-4}$alkyl-phosphinothioylamino, di-$C_{6-10}$aryl-phosphinothioylamino, hydroxyimino, $C_{1-4}$alkoxyimino, $C_{1-4}$alkylsulfonyloxy, $C_{6-10}$arylsulfonyloxy, thiocarbanoylthio, optionally substituted thiocarbamoylthio and silyloxy.

The cycloalkyl, aryl, alkyl of the groups containing $C_{1-4}$alkyl or heterocyclic group of the groups containing heterocyclic groups, which are optionally substituted on the above-mentioned alkyl, alkenyl, alkynyl or cycloalkyl, may optionally have further substituents. These substituents are exemplified by hydroxy, $C_{1-4}$alkyl (optionally substituted, the substituents being similar to those mentioned in the afore-mentioned alkyl; groups containing $C_{1-4}$alkyl to be mentioned hereafter may optionally have similar substituents); $C_{1-4}$alkoxy, $C_{1-4}$alkylthio, amino, $C_{1-4}$alkylamino, di-$C_{1-4}$alkylamino, $C_{6-10}$arylamino, azido, nitro, halogen, oxo, cyano, carboxy, $C_{1-4}$alkoxycarbonyl, $C_{6-10}$aryloxycarbonyl, $C_{1-5}$alkanoyl, $C_{1-5}$alkanoyloxy, sulfo, carbamoyl, substituted carbamoyl, carbamoyloxy, $C_{1-4}$alkanoylamido, $C_{1-4}$alkoxycarbonylamino and sulfonamido.

Substituents of the afore-mentioned optionally substituted aryl and heterocyclic groups are exemplified by hydroxyl, $C_{1-4}$alkyl, $C_{6-10}$aryl, $C_{3-6}$cycloalkyl, halogen, carboxyl, sulfo, $C_{1-4}$alkoxy, $C_{1-4}$alkylthio, nitro, $C_{1-4}$alkoxycarbonyl, amino, mono-$C_{1-4}$alkylamino, di-$C_{1-4}$alkylamino, $C_{1-4}$alkanoylamido, $C_{6-10}$aryloxy, $C_{7-12}$aralkyl, $C_{7-12}$aralkyloxy, $C_{6-10}$arylamino, $C_{7-12}$aralkylamino, cyano, $C_{6-12}$aryloxycarbonyl, $C_{7-12}$aralkyloxycarbonyl, $C_{1-5}$alkanoyl, $C_{2-5}$alkanoyloxy, carbamoyl, optionally substituted carbamoyl, optionally substituted carbamoyloxy, $C_{1-4}$alkoxycarbonylamino and oxo.

The alkyls, which are substituents at the afore-mentioned optionally substituted aryl and heterocyclic groups, groups containing $C_{1-4}$alkyl or aryl groups may have further substituents similar to those exemplified in the foregoing as substituents of alkyl and aryl groups.

The number of substituents in the respective groups described above is preferably 1~3.

These substituents will be described in more detail as follows.

$C_{1-4}$alkyls as the substituents are exemplified by methyl, ethyl, propyl, isopropyl, butyl, isobutyl, sec-butyl and tert-butyl.

$C_{3-6}$cycloalkyls are exemplified by cyclopropyl, cyclobutyl, cyclopentyl and cyclohexyl.

$C_{6-10}$aryls are exemplified by phenyl and naphthyl.

$C_{1-4}$alkoxy groups are exemplified by methoxy, ethoxy, propoxy, isopropoxy, butoxy and tert-butoxy.

$C_{3-6}$cycloalkyloxy groups are exemplified by cyclopropyloxy, cyclopentyloxy and cyclohexyloxy.

$C_{6-10}$aryloxy groups are exemplified by phenoxy and naphthyloxy.

$C_{7-12}$aralkyloxy groups are exemplified by benzyloxy, 2-phenethyloxy and 1-phenethyloxy.

$C_{1-4}$alkylthio groups are exemplified by methylthio, ethylthio, propylthio and butylthio.

$C_{3-6}$cycloalkylthio groups are exemplified by cyclopropylthio, cyclopentylthio and cyclohexylthio.

$C_{6-10}$arylthio groups are exemplified by phenylthio and naphthylthio.

$C_{7-12}$aralkylthio groups are exemplified by benzylthio, 2-phenethylthio and 1-phenethylthio.

Mono-$C_{1-4}$alkylamino groups are exemplified by methylamino, ethylamino, propylamino, isopropylamino, butylamino, isobutylamino and tert-butylamino.

Di-$C_{1-4}$alkylamino groups are exemplified by dimethylamino, diethylamino, dipropylamino, dibutylamino, N-methyl-N-ethylamino, N-methyl-N-propylamino and N-methyl-N-butylamino.

$C_{3-6}$cycloalkylamino groups are exemplified by cyclopropylamino, cyclopentylamino and cyclohexylamino.

$C_{6-10}$arylamino groups are exemplified by anilino.

$C_{7-12}$aralkylamino groups are exemplified by benzylamino, 2-phenethylamino and 1-phenethylamino.

Halogen is exemplified by fluorine, chlorine, bromine, and iodine.

$C_{1-4}$alkoxycarbonyl groups are exemplified by methoxycarbonyl, ethoxycarbonyl, propoxycarbonyl, isopropoxycarbonyl, butoxycarbonyl, tert-butoxycarbonyl and isobutoxycarbonyl.

$C_{6-10}$aryloxycarbonyl groups are exemplified by phenoxycarbonyl.

$C_{3-6}$cycloalkyloxycarbonyl groups are exemplified by cyclopropyloxycarbonyl, cyclopentyloxycarbonyl and cyclohexyloxycarbonyl.

$C_{7-12}$aralkyloxycarbonyl groups are exemplified by benzyloxycarbonyl, 1-phenethyloxycarbonyl and 2-phenethyloxycarbonyl.

$C_{1-5}$alkanoyl groups are exemplified by formyl, acetyl, propionyl, butyryl and pivaloyl.

$C_{1-15}$alkanoyloxy groups are exemplified by formyloxy, acetoxy, butyryloxy, pivaloyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy and pentadecanoyloxy.

Substituted carbamoyl groups are exemplified by N-methylcarbamoyl, N,N-dimethylcarbamoyl, N-ethylcarbamoyl, N,N-diethylcarbamoyl, N-phenylcarbamoyl, pyrrolidinocarbamoyl, piperidinocarbamoyl, piperazinocarbamoyl, morpholinocarbamoyl and N-benzylcarbamoyl.

Substituted carbamoyloxy groups are exemplified by N-methylcarbamoyloxy, N,N-dimethylcarbamoyloxy, N-ethylcarbamoyloxy, N-benzylcarbamoyloxy, N,N-dibenzylcarbamoyloxy and N-phenylcarbamoyloxy.

$C_{1-4}$alkanoylamido groups are exemplified by formylamino, acetamido, propionamido and butyrylamido.

$C_{6-10}$aryl carbonylamido groups are exemplified by benzamido.

$C_{1-4}$alkoxycarbonylamino groups are exemplified by methoxycarbonylamino, ethoxycarbonylamino, butoxycarbonylamino and tert-butoxycarbonylamino.

$C_{7-12}$aralkyloxycarbonylamino groups are exemplified by benzyloxycarbonylamino, 4-methoxybenzyloxycarbonylamino, 4-nitrobenzyloxycarbonylamino and 4-chlorobenzyloxycarbonylamino.

Sulfonamido groups are exemplified by methanesulfonylamino, ethanesulfonylamino, butanesulfonylamino, benzenesulfonylamino, toluenesulfonylamino, naphthalenesulfonylamino, trifluoromethanesulfonylamino, 2-chloroethanesulfonylamino and 2,2,2-trifluoromethanesulfonylamino.

As heterocyclic groups are mentioned cyclic groups containing 1~5 nitrogen atom, oxygen atom and sulfur atom, which are exemplified by pyrrolidinyl, pyrrolyl, pyrazolyl, imidazolyl, furyl, thienyl, oxazolyl, isoxazolyl, isothiazolyl, thiazolyl, piperidinyl, pyridyl, piperazinyl, pyrimidinyl, pyranyl, tetrahydropyranyl, tetrahydrofuryl, indolyl, quinolyl, 1,3,4-oxadiazolyl, thieno[2,3-d]pyridyl, 1,2,3-thiadiazolyl, 1,3,4-thiadiazolyl, 1,2,3-triazolyl, 1,2,4-triazolyl, 1,3,4-triazolyl, tetrazolyl, 4,5-dihydro-1,3-dioxolyl, tetrazolo[1,5-b]pyridazinyl, benzothiazolyl, benzoxazolyl, benzimidazolyl and benzothienyl.

As heterocyclic thio, heterocyclic oxy, heterocyclic amino and heterocyclic carbonylamino are mentioned groups formed by bonding by the above-mentioned heterocyclic ring to sulfur atom, oxygen atom, nitrogen atom or carbonylamino group, respectively.

Di-$C_{1-4}$alkylphosphinothioylamino groups are exemplified by dimethylphosphinothioylamino and diethylphosphinothioylamino.

Alkoxyimino groups are exemplified by methoxyimino, ethoxyimino, 2-fluoroethoxyimino, carboxymethoxyimino, 1-carboxy-1-methylethoxyimino, 2,2,2-trichloroethyloxycarbonylmethoxy, 1-(2,2,2-trichloroethyloxycarbonyl)-1-methylethoxyimino, (2-aminothiazol-4-yl)methoxyimino and (1H-imidazol-4-yl)methoxyimino.

$C_{1-4}$alkylsulfonyloxy groups are exemplified by methanesulfonyloxy, ethanesulfonyloxy and butanesulfonyloxy.

$C_{6-10}$arylsulfonyloxy groups are exemplified by benzenesulfonyloxy and toluenesulfonyloxy.

Di-$C_{6-10}$arylphosphinothioylamino groups are exemplified by diphenylphosphinothioylamino.

Substituted thiocarbamoylthio groups are exemplified by N-methylthiocarbamoylthio, N,N-dimethylthiocarbamoylthio, N-ethylthiocarbamoylthio, N-benzylthiocarbamoylthio, N,N-dibenzylthiocarbamoylthio and N-phenylthiocarbamoylthio.

Silyloxy groups are exemplified by trimethylsilyloxy, t-butyldimethylsilyloxy and t-butyldiphenylsilyloxy.

$C_{1-4}$alkylsulfinyl groups are exemplified by methylsulfinyl, ethylsulfinyl, propylsulfinyl and butylsulfinyl.

$C_{6-10}$arylsulfinyl groups are exemplified by phenylsulfinyl and naphthylsulfinyl.

$C_{1-4}$alkylsolfonyl groups are exemplified by methanesulfonyl, ethanesulfonyl and butanesulfonyl.

$C_{6-10}$arylsulfonyl groups are exemplified by benzenesulfonyl and toluenesulfonyl.

$C_{1-4}$alkoxycarbonyloxy groups are exemplified by methoxycarbonyloxy, ethoxycarbonyloxy and tert-butoxycarbonyloxy.

Description of each of the afore-mentioned groups will be given hereafter more concretely.

In the case where either one of $R^1$ and $R^2$ is hydrogen and the other is a group representable by the formula;

(wherein Z and $R^5$ are of the same meaning as defined above), in which $R^5$ is, for example, group representable by the formula; —C(=O)$R^{5A}$ (wherein $R^{5A}$ is $C_{1-3}$alkyl which may be substituted with halogen, or aryl or a heterocyclic group bound through a sulfur atom), —CH$_2$—$R^{5B}$ (wherein $R^{5B}$ is alkyl which may be substituted with optionally halogen substituted $C_{1-5}$alkyl, halogen, or aryl or a heterocyclic group bound through an oxygen or sulfur atom), —CH($Y^A$)$R^{5C}$ (wherein $Y^A$ is hydroxyl, $C_{2-8}$alkanoyloxy, optionally halogen-substituted $C_{1-3}$alkoxycarbonyl, a heterocyclic aminocarbonyl, halogen, amino which may be substituted with $C_{1-3}$alkoxycarbonyl, $C_{2-5}$alkanoyl or arylsulfinyl, hydroxycarbonyl, alkyl or arylsulfonyloxy, tri-$C_{1-3}$-alkylsilyloxy, arylthio, $C_{1-3}$alkylthio, alkylsulfonyl, azido or a heterocyclic group bound through a sulfur atom, and $R^{5C}$ is $C_{1-3}$alkyl which may be substituted with a heterocyclic group bound through a sulfur atom, aryloxy, aryl or halogen), —$R^{5D}$ (wherein $R^{5D}$ is aryl, $C_{5-7}$cycloalkyl or a heterocyclic group), —C(=NO$R^{5E}$)$R^{5F}$ (wherein $R^{RE}$ is hydroxyl or $C_{1-3}$alkoxy and $R^{5F}$ is a heterocyclic group bound through a sulfur atom, $C_{1-3}$alkyl optionally substituted with halogen) or —C$Y^B$=CH$_2$ (wherein $Y^B$ is hydrogen, $C_{2-5}$alkanoyloxy, $C_{1-5}$alkoxycarbonyloxy or tri-$C_{1-3}$alkylsilyl). The group representable by the formula;

is exemplified by acetyl, 1-thioxoethyl, chloroacetyl, 2-chloro-1-thioxoethyl, bromoacetyl, 2-bromo-1-thioxoethyl, iodoacetyl, 2-iodo-1-thioxoethyl, methoxyacetyl, 2-methoxy-1-thioxoethyl, ethoxyacetyl, 2-ethoxy-1-thioxoethyl, phenoxyacetyl, 2-phenoxy-1-thioxoethyl, benzyloxyacetyl, 2-benzyloxy-1-thioxoethyl, 4-chlorophenoxyacetyl, 2-(4-chlorophenoxy)-1-thioxoethyl, 4-hydroxyphenoxyacetyl, 2-(4-hydroxyphenoxy)-1-thioxoethyl, 4-acetoxyphenoxyacetyl, 2-(4-acetoxyphenoxy)-1-thioxoethyl, phenylacetyl, 2-phenyl-1-thioxoethyl, 4-hydroxyphenylacetyl, 2-(4-hydroxyphenyl)-1-thioxoethyl, 3,4-dihydroxyphenylacetyl, 2-(3,4-dihydroxyphenyl)-1-thioxoethyl, 4-acetoxyphenylacetyl, 2-(4-acetoxyphenyl)-1-thioxoethyl, 3,4-diacetoxyphenylacetyl, 2-(3,4-diacetoxyphenyl)-1-thioxoethyl, 3,4,5-triacetoxyphenylacetyl, 2-(3,4,5-triacetoxyphenyl)-1-thioxoethyl, 2-aminomethylphenylacetyl, 2-(2-aminomethylphenyl)-1-thioxoethy, 3-dimethylaminosulfonylphenylacetyl, 2-(3-dimethylaminosulfonylphenyl)-1-thioxoethyl, 3-aminosulfonylmethylphenylacetyl, 2-(3-aminosulfonylmethylphenyl)-1-thioxoethyl, 3-methanesulfonylaminophenylacetyl, 2-(3-methanesulfonylaminophenyl)-1-thioxoethyl, (1,2-oxazol-3-yl)acetyl, 2-(1,2-oxazol-3-yl)thi- oxoethyl, (1,2-oxazol-5-yl)acetyl, 2-(1,2-oxazol-5-yl)-1-thioxoethyl, (1H-imidazol-4-yl)acetyl, 2-(1H-imidazol-4-yl)-thioxoethyl, (1H-pyrazol-4-yl)acetyl, 2-(1H-pyrazol-4-yl)-1-thioxoethyl, (5-amino-1,2,4-thiadiazol-3-yl)acetyl, 2-(5-amino-1,2,4-thidiazol-3-yl)-1-thioxoethyl, 2-thienylacetyl, 2-(2-thienyl)-1-thioxoethyl, 2-furylacetyl, 2-(2-furyl)-1-thioxoethyl, (1H-tetrazol-1-yl)acetyl, 2-(1H-tetrazol-1-yl)-1-thioxoethyl, (thiazol-4-yl)acetyl, 2-(thiazol-4-yl)-1-thioxoethyl, (2-aminothiazol-4-yl)acetyl, 2-(2-aminothiazol-4-yl)-1-thioxoethyl, (2-chloroacetylaminothiazol-4-yl)acetyl, 2-(2-chloroacetylaminothiazol-4-yl)-1-thioxoethyl, cyanoacetyl, 2-cyano-1-thioxoethyl, methylthioacetyl, 2-methylthio-1-thioxoethyl, ethylthioacetyl, 2-ethylthio-1-thioxoethyl, phenylthioacetyl, 2-phenylthio-1-thioxoethyl, trifluoromethylthioacetyl, 2-trifluoromethylthio-1-thioxoethyl, difluoromethylthioacetyl, 2-difluoromethylthio-1-thioxoethyl, cyanomethylthioacetyl, 2-cyanomethylthio-1-thioxoethyl, 4-pyridylthioacetyl, 2-(4-pyridylthio)-1-thioxoethyl, (1-methyl-1H-triazol-2-yl)thioacetyl, 2-(1-methyl-1H-triazol-2-yl)thio-1-thioxoethyl, (1,5-dimethyl-1H-1,3,4-triazol-2-yl)thioacetyl, 2-(1,5-dimethyl-1H-1,3,4-triazol-2-yl)thio-1-thioxoethyl, (1-methyl-1H-tetrazol-5-yl)thioacetyl, 2-(1-methyl-1H-tetrazol-5-yl)thio-1-thioxoethyl, [1-(2-dimethylaminoethyl)-1H-tetrazol-5-yl]thioacetyl, 2-[1-(2-dimethylaminoethyl)-1H-tetrazol-5-yl]thio-1-thioxoethyl, [1-(3-dimethylaminopropyl)-1H-tetrazol-5-yl]thioacetyl, 2-[1-(3-dimethylaminopropyl)-1H-tetrazol-5-yl]thio-1-thioxoethyl, [1-(2-hydroxyethyl)-1H-tetrazol-5-yl]thioacetyl, 2-[1-(2-hydroxyethyl)-1H-tetrazol-5-yl]thio-1-thioxoethyl, (1-carboxymethyl-1H-tetrazol-5-yl)thioacetyl, 2-(1-carboxymethyl-1H-tetrazol-5-yl)thio-1-thioxoethyl, (1-sulfomethyl-1H-tetrazol-5-yl)thioacetyl, 2-(1-sulfomethyl-1H-tetrazol-5-yl)thio-1-thioxoethyl, (5-methyl-1,3,4-thiadiazol-2-yl)thioacetyl, 2-(5-methyl-1,3,4-thiadiazol-2-yl)thio-1-thioxoethyl, [5-(2-dimethylaminoethyl)-1,3,4-thiadiazol-2-yl]thioacetyl, 2-[5-(2-dimethylaminoethyl)-1,3,4-thiadiazol-2-yl]thio-1-thioxoethyl, (5-methoxymethyl-1,3,4-thiadiazol-2-yl)thioacetyl, 2-(5-methoxymethyl-1,3,4-thiadiazol-2-yl)thio-1-thioxoethyl, (5-methanesulfonylmethyl-1,3,4-thiadiazol-2-yl)thioacetyl, 2-(5-methanesulfonylmethyl-1,3,4-thiadiazol-2-yl)thio-1-thioxoethyl, (3-methyl-1,2,4-thiadiazol-5-yl)thioacetyl, 2-(3-methyl-1,2,4-thiadiazol-5-yl)thio-1-thioxoethyl, (1,2,3-thiadiazol-5-yl)thioacetyl, 2-(1,2,3-thiadiazol-5-yl)thio-1-thioxoethyl, 2-aminoethylthioacetyl, 2-(2-aminoethylthio)-1-thioxoethyl, 2-(2,2,2-trichloroethyloxycarbonylamino)ethylthioacetyl, 2-[2-(2,2,2-trichloroethyloxycarbonylamino)ethyl]thio-1-thioxoethyl, 2-aminovinylthioacetyl, 2-(2-aminovinyl)thio-1-thioxoethyl, 2-(2,2,2-trichloroethyloxycarbonylamino)vinylthioacetyl, 2-[2-(2,2,2-trichloroethyloxycarbonylamino)vinyl]thio-1-thioxoethyl, (2-amino-2-carboxy)ethylthioacetyl, 2-[(2-amino-2-carboxy)ethyl]thio-1-thioxoethyl, [3-(2-amino-2-carboxy)ethyl-1H-imidazol-2-yl]thioacetyl, 2-[3-(2-amino-2-carboxy)ethyl-1H-imidazol-2-yl]thio-1-thioxoethyl, (4-carboxy-3-hydroxy-1,2-thiazol-5-yl)thioacetyl, 2-(4-carboxy-3-hydroxy-1,2-thiazol-5-yl)thio-1-thioxoethyl, (1-amino-1H-tetrazol-5-yl)thioacetyl, 2-(1-amino-1H-tetrazol-5-yl)thio-1-thioxoethyl, (1-dimethylamino-1H-tetrazol-5-yl)thioacetyl, 2-(1-dimethylamino-1H-tetrazol-5-yl)thio-1-thioxoethyl, [1-(1H-tetrazol-5-yl)methyl-1H-tetrazol-5-yl]thioacetyl, 2-[1-(1H-tetrazol-5-yl)methyl-1H-tetrazol-5-yl]thio-1-thioxoethyl, (6-hydroxy-4- methyl-5,6-dihydro-1,2,4-triazin-5-on-3-yl)thioacetyl, 2-(6-hydroxy-4-methyl-5,6-dihydro-1,2,4-triazin-5-on-3-yl)thio-1-thioxoethyl, [5-(2-amino-2-carboxyethyl)-1H-imidazol-2-yl]thioacetyl, 2-[5-(2-amino-2-carboxyethyl-1H-imidazol-2-yl]thio-1-thioxoethyl, 5-(2-amino-2-carboxylethyl)-1,3,4-thiadiazol-2-yl)thioacetyl, 2-[5-(2-amino-2-carboxyethyl)-1,2,4-thiadiazol-2-yl]thio-1-thioxoethyl, (2-amino-1,3,4-thiadiazol-5-yl)thioacetyl, 2-(2-amino-1,3,4-thiadiazol-5-yl)thio-1-thioxoethyl, (4,5-dicarboxy-1H-imidazol-2-yl)thioacetyl, 2-(4,5-dicarboxy-1H-imidazol-2-yl)thio-1-thioxoethyl, (5-amino-4-carboxy-1-methyl-1H-imidazol-2-yl)thioacetyl, 2-(5-amino-4-carboxy-1-methyl-1H-imidazol-2-yl)thio-1-thioxoethyl, (tetrazolo[1,5-b]pyridazin-6-yl)thioacetyl, (2-carbamoyl-2-fluorovinylthio)acetyl, (2-carbamoyl-2-fluorovinylthio)-1-thioxoethyl, 2-(tetrazolo[1,5-b]pyridazin-6-yl)thio-1-thioxoethyl, 1,2-dioxopropyl, 2-oxo-1-thioxopropyl, 1,2-dioxobutyl, 2-oxo-1-1-thioxobutyl, 1,2-dioxopentyl, 2-oxo-1-thioxopentyl, (1,2-dioxo-3-phenyl)propyl, 3-phenyl-2-oxo-1-thioxopropyl, (1,2-dioxo-2-phenyl)ethyl, (2-oxo-2-phenyl-1-thioxo)ethyl, 1,2-dioxo-2-(thiazol-4-yl)ethyl, 2-oxo-2-(thiazol-4-yl)-1-thioxoethyl, 2-(2-aminothiazol-4-yl)-1,2-dioxoethyl, 2-(2-aminothiazol-4-yl)-2-oxo-1-thioxoethyl, 2-(2-chloroacetylaminothiazol-4-yl)-1,2-dioxoethyl, 2-(2-chloroacetylaminothiazol-4-yl)-2-oxo-1-thioxoethyl, 2-(5-amino-1,2,4-thiadiazol-3-yl)-1,2-dioxoethyl, 2-(5-amino-1,2,4-thiadiazol-3-yl)-2-oxo-1-thioxoethyl, 3-bromo-1,2-dioxopropyl, 3-bromo-2-oxo-1-thioxopropyl, 3-(benzothiazol-2-yl)thio-1,2-dioxopropyl, 3-(benzothiazol-2-yl)thio-2-oxo-1-thioxopropyl, 3-(benzoxazol-2-yl)thio-1,2-dioxopropyl, 3-(benzoxazol-2-yl)thio-2-oxo-1-thioxopropyl, 3-methylthio-1,2-dioxopropyl, 3-methylthio-2-oxo-1-thioxopropyl, 3-ethylthio-1,2-dioxopropyl, 3-ethylthio-2-oxo-1-thioxopropyl, 3-(2-pyridyl)dioxopropyl, 3-phenylthio-2-oxo-1-thioxopropyl, 3-(pyridyl)thio-1,2-dioxopropyl, 3-(2-pyridyl)thio-2-oxo-1-thioxopropyl, 3-(4-pyridyl)thio-1,2-dioxopropyl, 3-(4-pyridyl)thio-2-oxo-1-thioxopropyl, 3-(1-methyl-1H-1,3,4-triazol-2-yl)thio-1,2-dioxopropyl, 3-(1-methyl-1H-1,3,4-triazol-2-yl)thio-2-oxo-1-thioxopropyl, 3-[1-(2-dimethylaminoethyl)-1H-tetrazol-5-yl]thio-1,2-dioxopropyl, 3-[1-(2-dimethylaminoethyl)-1H-tetrazol-5-yl]thio-2-oxo-1-thioxopropyl, 2-hydroxy-3-(2-pyridyl)thiopropionyl, 2-hydroxy-3-(2-pyridyl)thio-1-thioxopropyl, 2-hydroxy-3-(4-pyridyl)thiopropionyl, 2-hydroxy-3-(4-pyridyl)thio-1-thioxopropyl, 3-[1-(2-dimethylaminoethyl)-1H-tetrazol-5-yl]thio-2-hydroxypropionyl, 3-[1-(2-dimethylaminoethyl)-1H-tetrazol-5-yl]thio-2-hydroxy-1-thioxopropyl, 2-hydroxy-3-phenylthiopropionyl, 2-hydroxy-3-phenylthio-1-thioxopropyl, 3-ethylthio-2-hydroxypropionyl, 3-ethylthio-2-hydroxy-1-thioxopropyl, 3-(2-aminoethyl)thio-2-hydroxypropionyl, 3-(2-aminoethyl)thio-2-hydroxy-1-thioxopropyl, 3-(2-benzothiazolyl)thio-2-hydroxypropionyl, 3-(2-benzothiazolyl)thio-2-hydroxy-1-thioxopropyl, 2-hydroxy-1-thioxopropyl, 2-hydroxy-3-(4-methyl-4H-1,2,4-triazol-3-yl)thiopropionyl, 2-hydroxy-3-(4-methyl-4H-1,2,4-triazol-3-yl)thio-1-thioxopropyl, 2-acetoxy-3-(2-pyridyl)thiopropionyl, 2-acetoxy-3-(2-pyridyl)thio-1-thioxopropyl, 2-acetoxy-3-(4-pyridyl)thiopropionyl, 2-acetoxy-3-(4-pyridyl)thio-1-thioxopropyl, 2-propionyloxy-3-(2-pyridyl)thiopropionyl, 2-propionyloxy-3-(2-pyridyl)thio-1-thioxopropyl, 2-benzoyloxy-3-(2-pyridyl)thiopropionyl, 2-benzoyloxy-3-(2-pyridyl)thio-1-thioxopropyl, 2-benzoyloxy-3-(4-pyridyl)thiopropionyl, 2-benzoyloxy-3-(4-pyridyl)thio-1-thioxopropyl, 2-acetoxy-3-[1-(2-dimethylaminoethyl)-1H-tetrazol-5-yl]thiopropionyl, 2-acetoxy-3-[1-(2-dimethylaminoethyl)-1H-tetrazol-5-yl]thio-1-thioxopropyl, 2-acetoxy-3-ethylthiopropionyl, 2-acetoxy-3-ethylthio-1-thioxopropyl, 2-acetoxy-3-(4-methyl-4H-1,2,4-triazol-3-yl)thiopropionyl, 2-acetoxy-3-(4-methyl-4H-1,2,4-triazol-3-yl)thio-1-thioxopropyl, 2-methanesulfonyloxy-3-(2-pyridyl)thiopropionyl, 2-methanesulfonyloxy-3-(2-pyridyl)thio-1-thioxopropyl, 2-methanesulfonyloxy-3-(4-pyridyl)thiopropionyl, 2-methanesulfonyloxy-3-(4-pyridyl)thio-1-thioxopropyl, 3-(2-pyridyl)thio-p-toluenesulfonyloxypropionyl, 3-(2-pyridyl)thio-2-p-toluenesulfonyloxy-1-thioxopropyl, 3-(4-pyridyl)thio-2-p-toluenesulfonyloxypropionyl, 3-(4-pyridyl)thio-2-p-toluenesulfonyloxy-1-thioxopropyl, 3-[1-(2-dimethylaminoethyl)-1H-tetrazol-5-yl]thio-2-methanesulfonyloxypropionyl, 3-[1-(2-dimethylaminoethyl)-1H-tetrazol-5-yl]thio-2-methanesulfonyloxy-1-thioxopropyl, 3-[1-(2-dimethylaminoethyl)-1H-tetrazol-5-yl]thio-2-p-toluenesulfonyloxypropionyl, 3-[1-(2-dimethylaminoethyl)-1H-tetrazol-5-yl]thio-2-p-toluenesulfonyloxy-1-thioxopropyl, 3-ethylthio-2-methanesulfonyloxypropionyl, 3-ethylthio-2-methanesulfonyloxy-1-thioxopropyl, 2-methanesulfonyloxy-3-phenylthiopropionyl, 2-methanesulfonyloxy-3-phenylthio-1-thioxopropyl, 2-iodo-3-methylthiopropionyl, 2-iodo-3-methylthio-1-thioxopropyl, 3-ethylthio-2-iodopropionyl, 3-ethylthio-2-iodo-1-thioxopropyl, 2-iodo-3-phenylthiopropionyl, 2-iodo-3-phenylthio-1-thioxopropyl, 2-iodo-3-(2-pyridylthio)propionyl, 2-iodo-3-(2-pyridylthio)-1-thioxopropyl, 2-iodo-3-(4-pyridyl)thio-1-thioxopropyl, 3-[1-(2-dimethylaminoethyl-1H-tetrazol-5-yl]thio-2-iodopropionyl, 3-[1-(2-dimethylaminoethyl-1H-tetrazol-5-yl]thio-2-iodo-1-thioxopropyl, 2-iodo-3-(4-methyl-4H-1,2,4-triazol-3-yl)thiopropionyl, 2-iodo-3-(4-methyl-4H-1,2,4-triazol-3-yl)thio-1-thioxopropyl, 3-(2-benzothiazolyl)thio-2-iodopropionyl, 3-(2-benzothiazolyl)thio-2-iodo-1-thioxopropyl, 2-iodo-3-(2-benzoxazolyl)thiopropionyl, 2-iodo-3-(2-benzoxazolyl)thio-1-thioxopropyl, 2,3-bis(ethylthio)propionyl, 2,3-bis(ethylthio)-1-thioxopropyl, 3-ethylthio-2-(2-pyridyl)thiopropionyl, 3-ethylthio-2-(2-pyridyl)thio-1-thioxopropyl, 3-ethylthio-2-(4-pyridyl)thiopropionyl, 3-ethylthio-2-(4-pyridyl)thio-1-thioxopropyl, 2-methylthio-3-(2-pyridyl)thiopropionyl, 2-methylthio-3-(2-pyridyl)thio-1-thioxopropyl, 2,3-bis(2-pyridyl)thiopropionyl, 2,3-bis(2-pyridyl)thio-1-thioxopropyl, 2,3-bis(4-pyridyl)thiopropionyl, 2,3-bis(4-pyridyl)thio-1-thioxopropyl, 2-(2-pyridyl)thio-3-(4-pyridyl)thiopropionyl, 2-(2-pyridyl)thio-3-(4-pyridyl)thio-1-thioxopropyl, 2-[1-(2-dimethylaminoethyl)-1H-tetrazol-5-yl]thio-3-(2-pyridyl)thiopropionyl, 2-[1-(2-dimethylaminoethyl)-1H-tetrazol-5-yl]thio-3-(2-pyridyl)thio-1-thioxopropyl, 2-(4-methyl-4H-1,2,4-triazol-3-yl)thio-3-(2-pyridyl)thiopropionyl, 2-(4-methyl-4H-1,2,4-triazol-3-yl)thio-1-thioxopropyl, 2-(2-aminoethyl)thio-3-phenylthiopropionyl, 2-(2-aminoethyl)thio-3-phenylthio-1-thioxopropyl, 3-[1-(2-dimethylaminoethyl)-1H-tetrazol-5-yl]thio-2-(2-pyridyl)thiopropionyl, 3-[1-(2-dimethylaminoethyl)-1H-tetrazol-5-yl]thio-2-(2-pyridyl)thio-1-thioxopropyl, 2-azido-3-methylthiopropionyl, 2-azido-3-methylthio-1-thioxopropyl, 2-azido-3-ethylthiopropionyl, 2-azido-3-ethylthio-1-thioxopropyl, 2-azido-3-phenylthiopropionyl, 2-azido-3-phenylthio-1-thioxopropyl, 2-azido-3-(2-pyridyl)thiopropionyl, 2-azido-3-(2-pyridyl)thio-1-thioxopropyl, 2-azido-3-(4-pyridyl)thiopropionyl, 2-azido-3-(4-pyridyl)thio-1-thioxopropyl, 2-azido-3-[1-(2-dimethylaminoethyl)-1H-tetrazol-5-yl]thiopropionyl, 2-azido-3-[1-(2-dimethylaminoethyl)-1H-tetrazol-5- yl]thio-1-thioxopropyl, 2-azido-3-[4-methyl-4H-1,2,4-triazol-3-yl]thiopropionyl, 2-azido-3-[4-methyl-4H-1,2,4-triazol-3-yl]thio-1-thioxopropyl, 2-azido-3-(2-benzothiazolyl)thiopropionyl, 2-azido-3-(2-benzothiazolyl)thio-1-thioxopropyl, 2-azido-3-(2-benzoxazolyl)thiopropionyl, 2-azido-3-(2-benzoxazolyl)thio-1-thioxopropyl, 2-azido-3-ethoxycarbonylmethylthiopropionyl, 2-azido-3-ethoxycarbonylmethylthio-1-thioxopropyl, 2-amino-3-ethylthiopropionyl, 2-amino-3-ethylthio-1-thioxopropyl, 2-amino-3-(2-methoxyethyl)thiopropionyl, 2-amino-3-(2-methoxyethyl)thio-1-thioxopropyl, 2-amino-3-phenylthiopropionyl, 2-amino-3-phenylthio-1-thioxopropyl, 2-amino-3-(2-pyridyl)thiopropionyl, 2-amino-3-(2-pyridyl)thio-1-thioxopropyl, 2-amino-3-(4-pyridyl)thiopropionyl, 2-amino-3-(4-pyridyl)thio-1-thioxopropyl, 2-amino-3-[1-(2-dimethylaminoethyl)-1H-tetrazol-5-yl]thiopropionyl, 2-amino-3-[1-(2-dimethylaminoethyl)-1H-tetrazol-5-yl]thio-1-thioxopropyl, 2-amino-3-[5-methoxymethyl-1,3,4-thiadiazol-2-yl]thiopropionyl, 2-amino-3-(5-methoxymethyl-1,3,4-thiazol-2-yl]thio-1-thioxopropyl, 2-amino-3-[1-(2-hydroxyethyl)-1H-tetrazol-5-yl]thiopropionyl, 2-amino-3-[1-(2-hydroxyethyl)-1H-tetrazol-5-yl]thio-1-thioxopropyl, 2-acetylamino-3-ethylthiopropionyl, 2-acetylamino-3-ethylthio-1-thioxopropyl, 2-acetylamino-3-phenylthiopropionyl, 2-acetylamino-3-phenylthio-1-thioxopropyl, 2-acetylamino-3-(2-pyridyl)thiopropionyl, 2-acetylamino-3-(2-pyridyl)thio-1-thioxopropyl, 2-methanesulfonylamino-3-(2-pyridyl)thiopropionyl, 2-methanesulfonylamino-3-(2-pyridyl)thio-1-thioxopropyl, 2-methylamino-3-(4-pyridyl)thiopropionyl, 2-methylamino-3-(4-pyridyl)thio-1-thioxopropyl, 2-benzylamino-3-(4-pyridyl)thiopropionyl, 2-benzylamino-3-(4-pyridyl)thio-1-thioxopropyl, 2-dimethylamino-3-[1-(2-dimethylaminoethyl)-1H-tetrazol-5-yl]thiopropionyl, 2-dimethylamino-3-[1-(2-dimethylaminoethyl)-1H-tetrazol-5-yl]thio-1-thioxopropyl, 2-(N-acetyl-N-methyl)amino-3-(5-methanesulfonylmethyl-1,3,4-thiadiazol-2-yl)thiopropionyl, 2-(N-acetyl-N-methyl)amino-3-(5-methanesulfonylmethyl-1,3,4-thiadiazol-2-yl)thio-1-thioxopropyl, 2-diphenylphosphinothioylamino-3-(2-pyridyl)thiopropionyl, 2-diphenylphosphinothioylamino-3-(2-pyridyl)thio-1-thioxopropyl, 3-(2-pyridyl)thio-2-p-toluenesulfonylaminopropionyl, 3-(2-pyridyl)thio-2-p-toluenesulfonylamino-1-thioxopropyl, 2-(4-ethyl-2,3-dioxo-1-piperazinecarbonylamino)-3-methylthiopropionyl, 2-(4-ethyl-2,3-dioxo-1-piperazinecarbonylamino)-3-methylthio-1-thioxopropyl, 3-azido-1,2-dioxopropyl, 3-azido-2-oxo-1-thioxopropyl, 3-amino-1,2-dioxopropyl, 3-amino-2-oxo-1-thioxopropyl, 3-acetylamino-1,2-dioxopropyl, 3-acetylamino-2-oxo-1-thioxopropyl, 3-methylamino-1,2-dioxopropyl, 3-methylamino-2-oxo-1-thioxopropyl, 3-dimethylamino-1,2-dioxopropyl, 3-dimethylamino-2-oxo-1-thioxopropyl, 3-ethylamino-1,2-dioxopropyl, 3-ethylamino-2-oxo-1-thioxopropyl, 3-(N-acetyl-N-ethyl)amino-1,2-dioxopropyl, 3-(N-acetyl-N-ethyl)amino-2-oxo-1-thioxopropyl, 3-(N-ethyl-N-methanesulfonyl)amino-1,2-dioxopropyl, 3-(N-ethyl-2-methanesulfonyl)amino-2-oxo-1-thioxopropyl, 3-benzylamino-1,2-dioxopropyl, 3-benzylamino-2-oxo-1-thioxopropyl, 3-(4-ethyl-2,3-dioxo-1-piperazinecarbonylamino)-1,2-dioxopropyl, 3-(4-ethyl-2,3-dioxo-1-piperazinecarbonylamino)-2-oxo-1-thioxopropyl, 3-p-toluenesulfonylamino-1,2-dioxopropyl, 3-p-toluenesulfonylamino-2-oxo-1-thioxopropyl, 3-(N-benzyloxycarbonyl-N-methyl)amino-1,2-dioxopropyl, 3-(N-benzyloxycarbonyl-N-methyl)amino-2-oxo-1-thioxopropyl, 3-formylamino-1,2-dioxopropyl, 3-formylamino-2-oxo-1-thioxopropyl, 3-acetylamino-2-hydroxypropionyl, 3-acetylamino-2-hydroxy-1-thioxopropyl, 3-ethylamino-2-hydroxypropionyl, 3-ethylamino-2-hydroxy-1-thioxopropyl, 3-(N-ethyl-N-propionyl)amino-2-hydroxypropionyl, 3-(N-ethyl-N-propionyl)amino-2-hydroxy-1-thioxopropyl, 3-benzylamino-2-hydroxypropionyl, 3-benzylamino-2-hydroxy-1-thioxopropyl, 2-hydroxy-3-anilinopropionyl, 2-hydroxy-3-anilino-1-thioxopropyl, 3-benzyloxycarbonylamino-2-hydroxypropionyl, 3-benzyloxycarbonylamino-2-hydroxy-1-thioxopropyl, 2-hydroxy-3-(N-methyl-N-methanesulfonyl)aminopropionyl, 2-hydroxy-3-(N-methyl-N-methanesulfonyl)amino-1-thioxopropyl, 3-(N-benzyl-N-methanesulfonyl)amino-2-hydroxypropionyl, 3-(N-benzyl-N-methanesulfonyl)amino-2-hydroxy-1-thioxopropyl, 3-(5-carboxyimidazol-4-yl)carbonylamino-2-hydroxypropionyl, 3-(5-carboxyimidazol-4-yl)carbonylamino-2-hydroxy-1-thioxopropyl, 2-hydroxy-3-(4-hydroxy-6-methylpyridin-3-yl)carbonylaminopropionyl, 2-hydroxy-3-(4-hydroxy-6-methylpyridin-3-yl)carbonylamino-1-thioxopropyl, 2-acetoxy-3-acetylaminopropionyl, 2-acetoxy-3-acetylamino-1-thioxopropyl, 3-acetylamino-2-propionyloxypropionyl, 3-acetylamino-2-propionyloxy-1-thioxopropyl, 2-acetoxy-3-dimethylaminopropionyl, 2-acetoxy-3-dimethylamino-1-thioxopropyl, 2-benzoyloxy-3-methylaminopropionyl, 2-benzoyloxy-3-methylamino-1-thioxopropyl, 3-benzylamino-2-heptanoyloxypropionyl, 3-benzylamino-2-heptanoyloxy-1-thioxopropyl, 2-phenylacetoxy-3-anilinopropionyl, 2-phenylacetoxy-3-anilino-1-thioxopropyl, 2-benzoyloxy-3-methanesulfonylaminopropionyl, 2-benzoyloxy-3-methanesulfonylamino-1-thioxopropyl, 3-(N-methyl-N-p-toluenesulfonyl)amino-2-phenoxyacetoxypropionyl, 3-(N-methyl-N-p-toluenesulfonyl)amino-2-phenoxyacetoxy-1-thioxopropyl, 2-acetoxy-3-(N-ethyl-N-formyl)aminopropionyl, 2-acetoxy-3-(N-ethyl-N-formyl)amino-1-thioxopropyl, 3-[N-(4-ethyl-2,3-dioxopiperazine-1-carbonyl)-N-methyl]amino-2-isobutyryloxypropionyl, 3-[N-(4-ethyl-2,3-dioxopiperazine-1-carbonyl)-N-methyl]amino-2-isobutyryloxy-1-thioxopropyl, 3-acetylamino-2-methanesulfonyloxypropionyl, 3-acetylamino-2-methanesulfonyloxy-1-thioxopropyl, 3-acetylamino-2-p-toluenesulfonyloxypropionyl, 3-acetylamino-2-p-toluenesulfonyloxy-1-thioxopropyl, 2-methanesulfonyloxy-3-propionylaminopropionyl, 2-methanesulfonyloxy-3-propionylamino-1-thioxopropyl, 3-benzylamino-2-methanesulfonyloxypropionyl, 3-benzylamino-2-methanesulfonyloxy-1-thioxopropyl, 2-methanesulfonyloxy-3-methylaminopropionyl, 2-methanesulfonyloxy-3-methylamino-1-thioxopropyl, 3-ethylamino-2-methanesulfonyloxypropionyl, 3-ethylamino-2-methanesulfonyloxy-1-thioxopropyl, 3-dimethylamino-2-p-toluenesulfonyloxypropionyl, 3-dimethylamino-2-p-toluenesulfonyloxy-1-thioxopropyl, 2-methanesulfonyloxy-3-(4-morpholino)propionyl, 2-methanesulfonyloxy-3-(B 4-morpholino)-1-thioxopropyl, 3-(N-ethyl-N-methyl)amino-2-methanesulfonyloxypropionyl, 3-(N-ethyl-N-methyl)amino-2-methanesulfonyloxy-1-thioxopropyl, 3-methanesulfonylamino-2-methanesulfonyloxypropionyl, 3-methanesulfonylamino-2-methanesulfonyloxy-1-thioxopropyl, 3-benzyloxycarbonylamino-2-methanesulfonyloxypropionyl, 3-benzyloxycarbonylamino-2-methanesulfonyloxy-1-thioxopropyl, 2-methanesulfonyloxy-3-(2-thiophenylsulfonyl)aminopropionyl, 2-methanesulfonyloxy-3-(2-thiophensulfonyl)amino-1-thioxopropyl, 3-acetylamino-2-iodopropionyl, 3-acetylamino-2-iodo-1-thioxopropyl, 2-iodo-3-propionylaminopropionyl, 2-iodo-3-propionylamino-1-thioxopropyl, 3-benzoylamino-2-iodopropionyl, 3-benzoylamino-2-iodothioxopropyl, 3-benzylamino-2-iodopropionyl, 3-benzylamino-2-iodo-1-thioxopropyl, 2-iodo-3-methylaminopropionyl, 2-iodo-3-methylamino-1-thioxopropyl, 3-ethylamino-2-iodopropionyl, 3-ethylamino-2-iodo-1-thioxopropyl, 3-diethylamino-2-iodopropionyl, 3-diethylamino-2-iodo-1-thioxopropyl, 2-iodo-3-piperidinopropionyl, 2-iodo-3-piperidino-1-thioxopropyl, 2-iodo-3-pyrrolidinopropionyl, 2-iodo-3-pyrrolidino-1-thioxopropyl, 2-iodo-3-(4-methyl-1-piperazinyl)propionyl, 2-iodo-3-(4-methyl-1-piperazinyl)-1-thioxopropyl, 3-(4-acetyl-1-piperazinyl)-2-iodopropionyl, 3-(4-acetyl-1-piperazinyl)-2-iodo-1-thioxopropyl, 2-iodo-3-(N-methanesulfonyl-N-methyl)aminopropionyl, 2-iodo-3-(N-methanesulfonyl-N-methyl)amino-1-thioxopropyl, 3-acetylamino-2-azidopropionyl, 3-acetyl-2-azido-1-thioxopropyl, 2-azido-3-propionylaminopropionyl, 2-azido-3-propionylamino-1-thioxopropyl, 2-azido-3-(N-benzoyl-N-methyl)aminopropionyl, 2-azido-3-(N-benzoyl-N-methyl)amino-1-thioxopropyl, 2-azido-3-diethylaminopropionyl, 2-azido-3-diethylamino-1-thioxopropyl, 2-azido-3-methanesulfonylaminopropionyl, 2-azido-3-methanesulfonylamino-1-thioxopropyl, 2,3-diamino-1-oxopropyl,2,3-diaminopropionyl, 2-amino-3-dimethylaminopropionyl, 2-amino-3-dimethylamino-1-thioxopropyl, 3-acetylamino-2-aminopropionyl, 3-acetylacetyl-2-amino-1-thioxopropyl, 2-amino-3-benzyloxycarbonylaminopropionyl, 2-amino-3-benzyloxycarbonylamino-1-thioxopropyl, 2-amino-3-p-toluenesulfonylaminopropionyl, 2-amino-3-p-toluenesulfonylamino-1-thioxopropyl, 2-amino-3-(N-benzyl-N-ethyl)aminopropionyl, 2-amino-3-(N-benzyl-N-ethyl)amino-1-thioxopropyl, 2,3-bisacetylaminopropionyl, 2,3-bisacetylamino-1-thioxopropyl, 3-acetylamino-2-dimethylaminopropionyl, 3-acetylamino-2-dimethylamino-1-thioxopropyl, 3-acetylamino-2-benzyloxycarbonylaminopropionyl, 3-acetylamino-2-benzyloxycarbonylamino-1-thioxopropyl, 3-ethylaminopropionyl, 3-ethylamino-2-methylamino-1-thioxopropyl, 2-methanesulfonylamino-3-morpholinopropionyl, 2-methanesulfonylamino-3-morpholino-1-thioxopropyl, 2-diethylaminoamino-3-methanesulfonylaminopropionyl, 2-diethylamino-B 3-methanesulfonylamino-1-thioxopropyl, 3-benzylamino-2-propionylaminopropionyl, 3-benzylamino-2-propionylamino-1-thioxopropyl, 3-acetylamino-2-ethylthiopropionyl, 3-acetylamino-2-ethylthiothioxopropyl, 3-acetylamino-2-(pyridyl)thiopropionyl, 3-acetylamino-2-(2-pyridyl)thio-1-thioxopropyl, 3-dimethylamino-2-(2-pyridyl)thiopropionyl, 3-dimethylamino-2-(2-pyridyl)thio-1-thioxopropyl, 3-ethylamino-2-(4-pyridyl)thiopropionyl, 3-ethylamino-2-(4-pyridyl)thio-1-thioxopropyl, 2-[1-(2-dimethylaminoethyl)-1H-tetrazol-5-yl]thio-3-methanesulfonylaminopropionyl, 2-[1-(2-dimethylaminoethyl)-1H-tetrazol-5-yl]thio-3-methanesulfonylamino-1-thioxopropyl, 2-phenylthio-3-pyrrolidinopropionyl, 2-phenylthio-3-pyrrolidino-1-thioxopropyl, 3-benzoylamino-2-(4-methyl-4H-1,2,4-triazol-3-yl)thiopropionyl, 3-benzoylamino-2-(4-methyl-4H-1,2,4-triazol-3-yl)thio-1-thioxopropyl, 2-hydroxyimino-3-(2-pyridyl)thiopropionyl, 2-hydroxyimino-3-(2-pyridyl)thio-1-thioxopropyl, 2-methoxyimino-3-[(2-pyridyl)thio]propionyl, 2-methoxyimino-3-(2-pyridyl)thio-1-thioxopropyl, 2-hydroxyimino-3-[(4-pyridyl)thio]propionyl, 2-hydroxyimino-3-(4-pyridyl)thio-1-thioxopropyl, 2-methoxyimino-3-[(4-pyridyl)thio]propionyl, 2-methoxyimino-3-(4-pyridyl)thio-1-thioxopropyl, 2-(2-aminothiazol-4-yl)-2-hydroxyiminoacetyl, 2-(2-aminothiazol-4-yl)-2-hydroxyimino-1-thioxoethyl, 2-(2-aminothiazol-4-yl)-2-methoxyiminoacetyl, 2-(2-aminothiazol-4-yl)-2-methoxyimino-1-thioxoethyl, 2-(5-amino-1,2,4-thiadiazol-3-yl)-2-methoxyiminoacetyl, 2-(5-amino-1,2,4-thiadiazol-3-yl)-2-methoxyimino-1-thioxoethyl, 2-(2-amino-5-chlorothiazol-4-yl)-2-methoxyiminoacetyl, 2-(2-amino-5-chlorothiazol-4-yl)-2-methoxyimino-1-thioxoethyl, 2-(2-aminothiazol-4-yl)-2-carboxymethoxyiminoacetyl, 2-(2-aminothiazol-4-yl)-2-carboxymethoxyimino-1-thioxoethyl, 2-(2-aminothiazol-4yl)-2-(1-carboxy-1-methylethoxyimino)acetyl, 2-(2-aminothiazol-4-yl)-2-(1-carboxy-1-methylethoxyimino)-1-thioxoethyl, 2-(2-aminothiazol-4-yl)-2-(1H-imidazol-4-yl)methoxyiminoacetyl, 2-(2-aminothiazol-4-yl)-2-(1H-imidazol-4-yl)methoxyimino-1-thioxoethyl, 2-(2-aminothiazol-4-yl)-2-(2-fluoroethoxy)iminoacetyl, 2-(2-aminothiazol-4-yl)-2-(2-fluoroethoxy)imino-1-thioxoethyl, 2-hydroxypropionyl, 2-hydroxy-1-thioxopropyl, 2-hydroxy-2-phenylacetyl, 2-hydroxy-2-phenyl-1-thioxoethyl, 2-hydroxy-3-[(1-methyl-1H-1,3,4-2-phenyl-1-thioxoethyl, 2-hydroxyiminopropionyl, 2-hydroxyimino-1-thioxopropyl, 2-methoxyiminopropionyl, 2-methoxyimino-1-thioxopropyl, 2-hydroxy-3-[(1-methyl-1H-1,3,4-triazol-2-yl)thio]propionyl, 2-hydroxy-3-(1-methyl-1H-1,3,4-triazol-2-yl)thio-1-thioxopropyl, 2-hydroxy-3-[(1-methyl-1H-tetrazol-5-yl)thio]propionyl, 2-hydroxy-3-(1-methyl-1H-tetrazol-5-yl)thio-1-thioxopropyl, 2-hydroxy-3-[5-(2-dimethylaminoethyl)-1,3,4-thiadiazol-2-yl]thiopropionyl, 2-hydroxy-3-[[5-2-dimethylaminoethyl)-1,3,4-thiadiazol-2-yl]-thio]-1-thioxopropyl, 2-hydroxy-2-[4-(2-amino-2-carboxyethoxycarbonylamino)phenyl]acetyl, 2-hydroxy-2-[4-(2-amino-2-carboxyethoxycarbonylamino)phenyl]-1-thioxoethyl, 2-formyloxypropionyl, 2-formyloxy-1-thioxopropyl, 2-acetoxypropionyl, 2-acetoxy-1-thioxopropyl, 2-propionyloxypropionyl, propionyloxy-1-thioxopropyl, 3-octanoyloxypropionyl, 3-octanoyloxy-1-thioxopropyl, α-formyloxy-2-phenyl-1-thioxoethyl, 2-formyloxy-2-phenyl-1-thioxoethyl, 2-acetoxy-3-(2-pyridyl)thio-1-thioxopropyl, 2-acetoxy-3-(4-pyridylthio)propionyl, 2-acetoxy-3-(4-pyridyl)thio-1-thioxopropyl, 2-acetoxy-3-(phenylthio)propionyl, 2-acetoxy-3-phenyl-1-thioxopropyl, α-acetoxyphenylacetyl, 2-acetoxy-2-phenyl-1-thioxoethyl, 2-methanesulfonyloxypropionyloxypropionyl, 2-methanesulfonyloxy-1-thioxopropyl, 2-(4-toluenesulfonyloxy)propionyl, 2-(4-toluenesulfonyloxy)-1-thioxopropyl, 2-chloropropionyl, 2-chloro-1-thioxopropyl, 2-bromopropionyl, 2-bromo-1-thioxopropyl, 2-iodopropionyl, 2-iodo-1-thioxopropyl, 2-(methylthio)propionyl, 2-methylthio-1-thioxopropyl, 2-(ethylthio)propionyl, 2-ethylthio-1-thioxopropyl, 2-(phenylthio)propionyl, 2-phenylthio-1-thioxopropyl, 2-(2-pyridylthio)propionyl, 2-(2-pyridylthio)-1-thioxopropyl, 2-(4-pyridylthio)propionyl, 2-(4-pyridylthio)-1-thioxopropyl, 2-[(1-methyl-1H-1,3,4-triazol-2-yl)thio]propionyl, 2-[(1-methyl-1H-1,3,4-triazol-2-yl)thio]-1-thioxopropyl, 2-[[1-(2-dimethylaminoethyl)-1H-tetrazol-5-yl]thio]propionyl, 2-[[1-(2-dimethylaminoethyl)-1H-tetrazol-5-yl]]thio]-1-thioxopropyl, α-methylthiophenylacetyl, 2-methylthio-2-phenyl-1-thioxoethyl, 2-(2-aminothiazol-4-yl)-2-(methylthio)acetyl, 2-(2-aminothiazol-4-yl)-2-methylthio-1-thioxoethyl, 2-(N-methylthiocarbamoylthio)propionyl, 2-N-ethylthiocarbamoylthio)- propionyl, 2-azidopropionyl, 2-azido-1-thioxopropyl, α-azidophenylacetyl, 2-azido-2-phenyl-1-thioxoethyl, 2-azido-2-(4-hydroxyphenyl)acetyl, 2-azido-2-(2-(4-hydroxy-phenyl)-1-thioxoethyl, 2-aminopropionyl, 2-amino-1-thioxopropyl, α-aminophenylacetyl, 2-amino-2-phenyl-1-thioxoethyl, 2-amino-2-(4-hydroxyphenyl)acetyl, 2-amino-2-(4-hydroxy-phenyl)-1-thioxoethyl, 2-amino-2-(3,4-dihydroxyphenyl)acetyl, 2-amino-2-(3,4-dihydroxyphenyl)-1-thioxoethyl, 2-amino-2-(2-aminothiazol-4-yl)acetyl, 2-amino-2-(2-aminothiazol-4-yl)-1-thioxoethyl, 2-amino-2-(3-benzothienyl)acetyl, 2-amino-2-(3-benzothienyl)-1-thioxoethyl, 2-amino-2-(2-naphthyl)acetyl, 2-amino-2(2-naphthyl)-1-thioxoethyl, 2-amino-2-(3-ethanesulfonylaminophenyl)acetyl, 2-amino-2-(3-ethanesulfonylaminophenyl)-1-thioxoethyl, 2-(4-ethyl-2,3-dioxopiperazine-1-carbonylamino)-2-phenylacetyl, 2-(4-ethyl-2,3-dioxopiperazine-1-carbonylamino)-2-phenyl-1-thioxoethyl, 2-(4-ethyl-2,3-dioxopiperazine-1-carbonylamino)-2-(4-hydroxyphenyl)acetyl, 2-(4-ethyl-2,3-dioxopiperazine-1-carbonylamino)-2-(4-hydroxyphenyl)-1-thioxoethyl, 2-formylamino-2-phenylacetyl, 2-formylamino-2-phenyl-1-thioxoethyl, 2-(2-aminothiazol-4-yl)-2-formylaminoacetyl, 2-(2-aminothiazol-4-yl)-2-formylamino-1-thioxoethyl, 2-acetylaminopropionyl, 2-acetylamino-1-thioxopropyl, 2-propionylaminopropionyl, 2-propionylamino-1-thioxopropyl, 2-butyrylaminopropionyl, 2-butyrylamino-1-thioxopropyl, 2-benzyloxycarbonylaminopropionyl, 2-benzyloxycarbonylamino-1-thioxopropyl, 2-(p-toluenesulfonylamino)propionyl, 2-(p-toluenesulfonylamino)-1-thioxopropyl, 2-(diphenylphosphinothioylamino)propionyl, 2-(diphenylphosphinothioylamino)-1-thioxopropyl, 2-(4-ethyl-2,3-dioxopiperazine-1-carbonylamino)-2-(3,4-dihydroxyphenyl)acetyl, 2-(4-ethyl-2,3-dioxopiperazine-1-carbonylamino)-2-(3,4-dihydroxyphenyl)-1-thioxoethyl, 2-(4-ethyl-2,3-dioxopiperazine-1-carbonylamino)-3-hydroxybutyryl, 2-(4-ethyl-2,3-dioxopiperazine-1-carbonylamino)-3-hydroxy-1-thioxobutyl, 2-(5-carboxy-1H-imidazol-4-yl)carbonylamino-2-phenylacetyl, 2-(5-carboxy-1H-imidazol-4-yl)carbonylamino-2-phenyl-1-thioxoethyl, 2-(4-hydroxy-6-methylpyridin-3-yl)carbonylamino-2-(4-hydroxyphenyl)acetyl, 2-(4-hydroxy-6-methylpyridin-3-yl)carbonylamino-2-(4-hydroxyphenyl)-1-thioxoethyl, 2-carboxy-2-phenylacetyl, 2-carboxy-2-phenyl-1-thioxoethyl, 2-sulfo-2-phenylacetyl, 2-sulfo-2-phenyl-1-thioxoethyl, 2-carboxy-2-(4-hydroxyphenyl)acetyl, 2-carboxy-2-(4-hydroxyphenyl)-1-thioxoethyl, 2-carboxy-2-(3,4-diacetoxyphenyl)acetyl, 2-carboxy-2-(3,4-diacetoxyphenyl)-1-thioxoethyl, 2-(4-hydroxyphenyl)-2-sulfoacetyl, 2-(4-hydroxyphenyl)-2-sulfo-1-thioxoethyl, 2-(3,4-dihydroxyphenyl)-2-sulfoacetyl, 2-(3,4-dihydroxyphenyl)-2-sulfo-1-thioxoethyl, 2-(4-chlorophenyl)-2-sulfoacetyl, 2-(4-chlorophenyl)-2-sulfo-1-thioxoethyl, 2-(4-methoxyphenyl)-2-sulfoacetyl, 2-(4-methoxyphenyl)-2-sulfo-1-thioxoethyl, 2-(4-acetylaminophenyl)-2-carboxyacetyl, 2-(4-acetylaminophenyl)-2-carboxy-1-thioxoethyl, benzoyl, phenyl-1-thiocarbonyl, (2-aminothiazol-4-yl)carbonyl, (2-aminothiazol-4-yl)-1-thioxomethyl, acryloyl, vinyl(thiocarbonyl), (3-ethoxycarbonyl)acryloyl, 3-ethoxycarbonyl-1-thioxoallyl, caproyl, 1-thioxohexyl, cyclohexanecarbonyl, cyclohexane-thiocarbonyl, (5-amino-1,2,4-thiadiazol-3-yl)carbonyl, (5-amino-1,2,4-thiadiazol-3-yl)-1-thioxomethyl, cyclopropanecarbonyl, cyclopropane-thiocarbonyl, cyclobutanecarbonyl, cyclobutane-thiocarbonyl, cyclopentanecarbonyl, cyclopentane-thiocarbonyl, cyclo-3-hexenecarbonyl, cyclo-3-hexene-thiocarbonyl, cyclo-1,4-hexadienecarbonyl, cyclo-1,4-cyclohexadiene-thiocarbonyl, 3,3-dichloroacryloyl, 2,2-dichlorovinyl-thiocarbonyl, 2-(2-aminothiazol-4-yl)-3-chloroacryloyl, 2-(2-aminothiazol-4-yl)-3-chlorovinyl-thiocarbonyl, 2-(2-aminothiazol-4-yl)-3-bromoacryloyl, 2-(2-aminothiazol-4-yl)-3-bromovinyl-thiocarbonyl, 2-hydrazono-2-(2-aminothiazol-4-yl)acetyl, 2-hydrazono-2-(2-aminothiazol-4-yl)-1-thioxoethyl, 2-trimethylsilyloxypropionyl, 2-trimethylsilyloxy-1-thioxopropyl, 2-tert-butyldimethylsilyloxypropionyl, 2-tert-butyl-dimethylsilyloxy-2-thioxopropyl, 2-phenylsulfinylpropionyl, 2-phenylsulfinyl-1-thioxopropl, 2-benzenesulfonylpropionyl, 2-benzenesulfonyl-1-thioxopropyl, etc. For $R^{5A}$ to $R^{5F}$, $Y^A$ and $Y^B$ mentioned above, that $R^{5A}$ is $C_{1-3}$alkyl, that $R^{5B}$ is a heterocyclic group bound through sulfur consisting of triazolylthio, tetrezolylthio, pyridylthio and thiazolylthio which may be substituted with dimethylaminoethyl, methyl or amino, that $Y^A$ is hydroxyl or benzothiazol-2-ylthio and $R^{5C}$ is pyridin-2-ylthiomethyl or methyl, that $R^{5D}$ is cyclohexyl, phenyl or 2-aminothiazol-4-yl, that $R^{5E}$ is hydroxyl or methoxyl and $R^{5F}$ is pyridin-2-ylthiomethyl, and that $Y^B$ is acetyloxy or t-bentoxycarbonyloxy and preferable. When $R^1$ and $R^2$, taken together, stand for the formula;

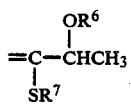

(wherein $R^6$ and $R^7$ are of the same meaning as defined in the foregoing), practical examples of $R^6$ are, among others, acetyl, propyl, butyryl, pivaloyl, pentanoyl, hexanoyl, methanesulfonyl, toluenesulfonyl, benzenesulfonyl, methoxycarbonyl, ethoxycarbonyl, isobutoxycarbonyl and benzyloxycarbonyl. As $R^7$ are practically mentioned, among others, methyl, ethyl, propyl and butyl.

Practical examples of $R^3$ or $R^4$ are, among others, hydroxyl, chlorine, bromine, iodine, azido, methoxycarbonyloxy, ethoxycarbonyloxy, propoxycarbonylloxy, butoxycarbonyloxy, tert-butoxycarbonyloxy, phenoxycarbonyloxy, benzyloxycarbonyloxy, 4-nitrobenzyloxycarbonyloxy, 2,4-dinitrobenzyloxycarbonyloxy, 4-methoxybenzyloxycarbonyloxy, 3,4-dimethoxybenzyloxycarbonyloxy, 2,2,2-trichloroethoxycarbonyloxy, methoxymethoxycarbonyloxy, 2-methoxyethoxycarbonyloxy, 1-methoxyethoxycarbonyloxy, methylthiomethoxycarbonyloxy, 2-methylthioethoxycarbonyloxy, acetoxymethoxycarbonyloxy, 1-acetoxyethoxycarbonyloxy, pivaloyloxymethoxycarbonyloxy, 2-pivaloyloxyethoxycarbonyloxy, allyloxycarbonyloxy, 4-methoxyphenoxycarbonyloxy, 2,4-dimethoxyphenoxycarbonyloxy, 2-aminoethoxycarbonyloxy, 2-dimethylaminoethoxycarbonyloxy, 2-methanesulfonylethoxycarbonyl, 2-trimethylsilylethoxycarbonyloxy, 2-cyanoethoxycarbonyloxy, 2-nitroethoxycarbonyloxy, ethoxycarbonylmethoxycarbonyloxy, chloromethoxycarbonyloxy, iodomethoxycarbonyloxy, [[1-(2-dimethylaminoethyl)-1H-tetrazol-5-yl]thio]methoxycarbonyloxy, [[1-(3-dimethylaminopropyl)-1H-tetrazol-5-yl[thio[methoxycarbonyloxy, [(1-methyl-1H-tetrazol-5-yl)thio]methoxycarbonyloxy, [(4-methyl-4H-1,2,4-triazol-3-yl)thio]methoxycarbonyloxy, [[5-(2-dimethylaminoethyl)-1,3,4-thiadiazol-2-yl]thio]methoxycarbonyloxy, [(5-methyl-1,3,4- thiadiazol-2-yl)thio]methoxycarbonyloxy, [(4,5-dimethylthiazol-2-yl)thio]methoxycarbonyloxy, [(4,5-dimethyloxazol-2-yl)thio]methoxycarbonyloxy, [(3-methyl-1,2,4-thiadiazol-5-yl)methoxycarbonyloxy, [(1,2,3-thiadiazol-5-yl)thio]methoxycarbonyloxy, [(1H-1,2,3-triazol-5-yl)thio]methoxycarbonyloxy, [(1-methyl-1H-imidazol-2-yl)thio]methoxycarbonyloxy, [(2-methyl-2H-1,2,4-triazol-3-yl)thio]methoxycarbonyloxy, (2-pyrimidinylthio)methoxycarbonyloxy, (2-benzothiazolythio)methoxycarbonyloxy, (2-benzimidazolylthio)methoxycarbonyloxy, (2-benzoxazolylthio)methoxycarbonyloxy, [(1,2,4-triazin-3-yl)thio]methoxycarbonyloxy, [(4-carboxy-3-hydroxy-1,2-thiazol-5yl)thio]-methoxycarboxyoxy, [(6-methylpyridazin-1-oxid-3-yl)thio]methoxycarbonyloxy, [(N-oxido-2-pyridyl)thio]methoxycarbonyloxy, (2-aminoethylthio)methoxycarbonyloxy, (2-acetylaminoethylthio)methoxycarbonyloxy, (2-dimethylaminoethylthio)methoxycarbonyloxy, (2-formimidoylaminoethylthio)methoxycarbonyloxy, (N-acetoimino-3-pyrrolidinothio)methoxycarbonyloxy, (phenylthio)methoxycarbonyloxy, (4-pyridylthio)methoxycarbonyloxy, formyloxy, acetoxy, propionyloxy, butyryloxy, isobutyryloxy, pentanoyloxy, hexanoyloxy, heptanoyloxy, pivaloyloxy, cyclopropanecarbonyloxy, cyclobutanecarbonyloxy, cyclopentanecarbonyloxy, cyclohexanecarbonyloxy, cycloheptanecarbonyloxy, acryloyloxy, crotonoyloxy, benzoyloxy, phenylacetyloxy, 2-methoxybenzoyloxy, 2-methylbenzoyloxy, 4-methylbenzoyloxy, 4-fluorobenzoyloxy, 3-phenylpropionyloxy, cinnamoyloxy, chloroacetoxy, bromoacetoxy, 3-chloropropanoyloxy, 4-chlorobutyryloxy, methoxyacetoxy, 3-ethoxypropanoyloxy, phenoxyacetoxy, 4-phenoxybutyryloxy, cyanoacetoxy, 4-nitrobenzoyloxy, pentachlorophenoxycarbonyloxy, 2,4,5-trichlorophenoxycarbonyloxy, [(5-methoxymethyl-1,3,4-thiadiazol-2-yl)thio]methoxycarbonyloxy, (ethylthio)methoxycarbonyloxy, (3,4-dihydro-2H-pyran-2-carbonyloxy)methoxycarbonyloxy, (acetylaminomethylcarbonyloxy)-methoxycarbonyloxy, (2-dimethylaminoethylthio)carbonyloxy, [(5-methoxymethyl-1,3,4-thiadiazol-2-yl)thio]carbonyloxy, (2-acethylaminoethylthio)carbonyloxy, 3-methoxycarbonylpropanoyloxy, 3-ethoxycarbonylacryloyloxy, azidoacetoxy, 2-thienylacetoxy, 2-pyridinecarbonyloxy, 3-pyridinecarbonyloxy, 4-pyridinecarbonyloxy, 4-cyclohexylbutyryloxy, 2-naphthylacetyloxy, 2-thiophenecarbonyloxy, 3-thiophenecarbonyloxy, 2-furancarbonyloxy, 3-furancarbonyloxy, (3-dimethylamino)propanoyloxy, (3-methylthio)propanoyloxy, (3-methanesulfonyl)propanoyloxy, 2-pyridinecarbonyloxy, 3-pyridinecarbonyloxy, 4-pyridinecarbonyloxy, 2-aminopropanoyloxy, 3-aminopropanoyloxy, α-aminophenylacetyloxy, 2-amino-4-carboxybutyryloxy, 2-amino-5-carboxypentanoyloxy, 2-amino-3-mercaptopropanoyloxy, aminoacetoxy, 2,5-diaminopentanoyloxy, 2-[(N-acetyl-N-methyl)amino]propanoyloxy, 2-[(N-butyryl-N-methyl)amino]acetoxy, iodoacetoxy, [(1-methyl-1H-tetrazol-5-yl)thio]acetoxy, [[1-(2-dimethylaminoethyl)-1H-tetrazol-5-yl]thio]acetoxy, [(5-methyl-1,3,4-thiadiazol-2-yl)thio]acetoxy, [(4-methyl-4H-1,2,4-triazol-3-yl)thio]acetoxy [(2-dimethylaminoethyl)thio]acetoxy, dihydroxyphosphinyloxy, dimethylphosphonoxy, diethylphosphonoxy, dipropylphosphonoxy, diisopropylphosphonoxy, diisobutylphosphonoxy, di-tert-butylphosphonoxy, dipentylphosphonoxy, dihexylphosphonoxy, dicyclopropylphosphonoxy, dicylobutylphosphonoxy, dicyclopentylphosphonoxy, [(2-dimethylaminoethyl)thio]acetoxy, [[1-(2-hydroxyethyl)-1H-tetrazol-5-yl thio]acetoxy, [(5-methoxymethyl-1,3,4-thiadiazol-2-yl)thio]acetoxy, [[5-(2-diethylphosphonoethyl)thio-1,3,4-thiadiazol-2-yl]thio]acetoxy, [(2-diethylaminoethyl)thio]acetoxy, dimethylaminoacetoxy, diethylaminoacetoxy, N'-methylpiperazinoacetoxy, N'-(2-pyridyl)piperazinoacetoxy, (2-chloroethylamino)acetoxy, (2-fluoroethylamino)acetoxy, n-propylaminoacetoxy, di-iso-propylaminoacetoxy, (2-hydroxyethylamino)acetoxy, iso-propylaminoacetoxy morpholinoacetoxy, 4-methylaminobutyryloxy, N'-(4-pyridyl)piperazinoacetoxy, (N-acetyl-N-methylamino)acetoxy, 3-dimethylaminopropanoyloxy, 4-dimethylaminobutyryloxy, dicyclohexylphosphonoxy, diphenylphosphonoxy, dibenzylphosphonoxy, divinylphosphonoxy, diallylphosphonoxy, di-2-butenylphosphonoxy, bis-4-chlorophenylphosphonoxy, bis-4-methoxyphenylphosphonoxy, bis-4-aminophenylphosphonoxy, bis-4-nitrophenylphosphonoxy, bis-4-methoxycarbonylphenylphosphonoxy, bis-4-acetoxyphenylphosphonoxy, bis-3,4-diacetoxyphosphonoxy, bis-3-chlorobenzylphosphonoxy, bis-4-acetamidobenzylphosphonoxy, bis(methoxymethyl)phosphonoxy, bis(2-methoxyethyl)phosphonoxy, bis(2-methylthioethyl)phosphonoxy, bis(2-dimethylaminoethyl)phosphonoxy, bis(3-dimethylaminopropyl)phosphonoxy, bis(ethoxycarbonylmethyl)phosphonoxy, bis(2-methanesulfonylaminoethyl)phosphonoxy, bis(2-chloroethyl)phosphonoxy, methanesulfonyloxy, ethanesulfonyloxy, propanesulfonyloxy, butanesulfonyloxy, benzenesulfonyloxy, toluenesulfonyloxy, naphthalenesulfonyloxy, methylthio, ethylthio, propylthio, butylthio, pentylthio, hexylthio, heptylthio, octylthio, phenylthio, 4-methylphenylthio, benzylthio, 2-phenylethylthio, trifluroromethylthio, difluoromethylthio, 2-aminoethylthio, 2-(2,2,2-trichloroethoxycarbonylamino)ethylthio, methoxycarbonylmethylthio, ethoxycarbonylmethylthio, carboxymethylthio, 3-dimethylaminopropylthio, 2-hydroxyethylthio, 2-chloroethylthio, 2-cyanoethylthio, 2-methoxycarbonylethylthio, 2-ethoxycarbonylethylthio, 2-carboxyethylthio, 3-aminopropylthio, 2-acetylaminovinylthio, 2-(2,2,2-trichloroethoxycarbonylamino)vinylthio, 2-amino-2-carboxyethylthio, 2-fluoro-2-carbamoylvinylthio, methoxymethylthio, 2-methoxyethylthio, 2-methylthioethylthio, 2-methanesulfonylethylthio, 3-pyrrolidinylthio, 2-carbamoyl-3-pyrrolidinylthio, 2-morpholinylcarbonyl-3-pyrrolidinylthio, N-acetoimino-3-pyrrolidinylthio, N-(N-methylacetoimino)-3-pyrrolidinylthio, 4-dimethylaminophenylthio, 3-aminophenylthio, 4-hydroxyphenylthio, 4-carboxymethylthiophenylthio, 4-carbamoylphenylthio, 4-methanesulfonylaminophenylthio, 2-sulfoethylthio, 2-pyridylthio, 4-pyridylthio, (2-aminothiazol-4-yl)methylthio, (1-methyl-1H-1,3,4-triazol-2-yl)thio, (5-amino-1-methyl-1H-1,3,4-triazol-2-yl)thio, (1-methyl-1H-1H-tetrazol-5-yl)thio, [1-(2-dimethylaminoethyl)-1H-tetrazol-5-yl]thio, [1-(3-dimethylaminopropyl)-1H-tetrazol-5-yl]thio, [1-(2-hydroxyethyl)-1H-tetrazol-5-yl]thio, [1-(3-hydroxypropyl)-1H-tetrazol-5-yl]thio, [1-(2-aminoethyl)-1H-tetrazol-5-yl]thio, [1-(2-acetamidoethyl)-1H-tetrazol-5-yl]thio, [1-(2-methylaminoethyl)-1H-tetrazol-5-yl]thio, [1-(2-ethylaminoethyl)-1-H-tetrazol-5-yl]thio, [1-(2-formylaminoethyl)-1H-tetrazol-5-yl]thio, (1-carboxymethyl-1H-tetrazol-5-yl]thio, [1-(2-carboxyethyl)-1H-tetrazol-5-yl]thio, (1-sulfomethyl-1H-tetrazol-5-yl)thio, [1-(2-sulfoethyl)-1H-tetrazol-5yl]thio, (1-amino-1H-tetrazol-5-yl)thio, (1-dimethylamino-1H-tetrazol-5-yl)thio, (1-methoxymethyl-1H-tetrazol-5-yl)thio, (1-methylthiomethyl-1H-tetrazol-5yl)thio, [1-ethyl(hydro)phosphonomethyl-1H-tetrazol-5-yl]thio, (1-diethylphosphonomethyl-1H-tetrazol-5-yl)thio, (1-carbamoylmethyl-1H-tetrazol-5-yl)thio, (1-dimethylcarbamoylmethyl-1H-tetrazol-5-yl)thio, (5-carboxy-1-methyl-1H-1,3,4-triazol-2-yl)thio, (5-carbamoyl-1-methyl-1H-1,3,4-triazol-2-yl)thio, (5-methoxymethyl-1,3,4-thiadiazol-2-yl)thio, (5-methylthiomethyl-1,3,4-thiadiazol-2-yl)thio, (5-methanesulfonylmethyl-1,3,4-thiadiazol-2-yl)thio, [5-(2-dimethylaminoethyl)-1,3,4-thiadiazol-2-yl]thio, [5-(3-dimethylminopropyl)-1,3,4-thiadiazol-2-yl]thio, (5-carboxymethyl-1,3,4-thiadiazol-2-yl)thio, 5-methoxycarbonylmethyl-1,3,4-thiadiazol-2-yl)thio, 5-carbamoylmethyl-1,3,4-thiadiazol-2-yl)thio, (5-dimethylcarbamoylmethyl-1,3,4-thiadiazol-2-yl)thio, (5-trifluoromethyl-1,3,4-thiadiazol-2-yl)thio, (5-amino-1,3,4-thiadiazol-2-yl)thio, (5-methoxycarbonylamino-1,3,4-thiadiazol-2-yl)thio, [5-(2-dihydrophosphonoethyl)thio-1,3,4-thiadiazol-2-yl[thio, [5-(2-diethylphosphonoethyl)thio-1,3,4-thiadiazol-2-yl]thio, (3-methyl-1,2,4-thiadiazol-2-yl)thio, (1,3,4-thiadiazol-2-yl)thio, (1,2,3-thiadiazol-5yl)thio, (1-methyl-1H-imidazol-2-yl)thio, (4,5-dimethyloxazol-2-yl)thio, (4-methylthiazol-2-yl)thio, (5-methylthiazol-2-yl)thio, (4,5-dimethylthiazol-2-yl)thio,, (1H-1,3,4-triazol-2-yl)thio, (1H-1,2,3-triazol-5-yl)thio, (1-methyl-1H-1,2,4-triazol-5-yl)thio, (1-ethyl-1H-1,2,4-triazol-3-yl)thio, (2-pyridyl)thio, (5,6-dimethyl-1,2,4-triazin-3-yl)thio, (2-benzothiazolyl)thio, [4-(2-amino-2-carboxyethyl)-1H-imidazol-2-yl]thio, (4-carboxy-3-hydroxyisothiazol-5-yl)thio, (6-hydroxy-4methyl-4,5-dihydro-triazin-5-on-3-yl)thio, [5-(2amino-2-carboxyethyl)-1,3,4-thiadiazol-2-yl]thio, (4,5-dicarboxy-1H-imidazol-2-yl)thio, (5-amino-4-carboxy-1-methyl-1H-imidazol-2-yl)thio, (tetrazolo[1,5-b]pyridazyl)thio, (6-methylpyridazin-1-oxido-3-yl)thio, (N-oxido-2-pyridyl)thio, (3-methoxypyridazin-1-oxido-6-yl)thio, (benzoxazol-2-yl)thio, (benzoimidazol-2-yl)thio, (5-carboxymethyl-4-methylthiazol-2-yl)thio, methoxy, ethoxy, propoxy, isopropoxy, butoxy, isobutoxy, sec-butoxy, tert-butoxy, hexyloxy, cyclopropoxy, cyclobutoxy, cyclopentyloxy, cyclohexyloxy, phenoxy, benzyloxy, 2-phenylethyloxy, 2-aminoethoxy, 2-dimethylaminoethoxy, ethoxycarbonylmethoxy, 2-hydroxyethoxy, 2-cyanoethoxy, methoxymethoxy, (2-methoxyethoxy)methoxy, 2-methoxyethoxy, 2-methylthioethoxy, carboxymethoxymethoxy, methoxycarbonylmethoxymethoxy, carbamoylmethoxymethoxy, N,N-dimethylcarbamoylmethoxymethoxy, (2-methylthioethoxy)methoxy, (2-methanesulfonylethoxy)methoxy, (2-dimethylaminoethoxy)methoxy, (3-dimethylaminopropoxy)methoxy, (2-phenoxyethoxy)methoxy, (2-allyoxyethoxy)methoxy, (2-cyclopropoxyethoxy)methoxy, [2-(2-pyridyloxy)ethoxy]methoxy, [2-(2-pyridylthio)ethoxy]methoxy, [2-[1-(2-dimethylaminoethyl)-1H-tetrazol-5-yl]thioethoxy]methoxy, amino, dimethylamino, diethylamino, methylamino, ethylamino, propylamino, dipropylamino, isopropylamino, diisopropylamino, butylamino, dibutylamino, isobutylamino, diisobutylamino, sec-butylamino, tert-butylamino, di-tert-butylamino, pyrrolidino, piperidino, piperazino, morpholino, benzylamino, anilino, N-benzyl-N-methylamino, N-methylanilino, N-benzyl-N-ethylamino, acetylamino, propionylamino, butyrylamino, isobutyrylamino, pentanoylamino, sec-pentanoylamino, pivaloylamino, cyclobutanecarbonylamino, cyclohexanecarbonylamino, cycloheptanecarbonylamino, cycloheptanecarbonylamino, N-acetyl-N-methylamino, N-methyl-N-propanoylamino, N-acetyl-N-ethylamino, N-ethyl-N-propanoylamino, 2-pyrimidylamino, bis(2-hydroxyethyl)amino, bis(2-ethoxyethyl)amino, bis(2-methoxyethyl)amino, bix(carboxymethyl)amino, N-ethyl-N-ethoxycarbonylamino, bis(2-ethylthioethyl)amino, bis(2-dimethylaminoethyl)amino, bis(3-oxobutyl)amino, bis(2-acetoxyethyl)amino, bis(2-carbamoylethyl)amino, 2-thiophenecarbonylamino, 2-furancarbonylamino, (2-aminothiadiazol-4-yl)carbonylamino, benzylcarbonylamino, 4-hydroxybenzylcarbonylamino, 2-thienylacetylamino, 3-thienylacetylamino, (2-aminothiazol-4yl)acetylamino, 2-(2-aminothiazol-4-yl)-2-oxoacetylamino, 2-(2-aminothiazol-4-yl)-2-methoxyiminoacetylamino, 2-(2-amino-5-chlorothiazol-4-yl)-2-methoxyiminoacetylamino, 2-(5-amino-1,2,4-thiadiazol-3-yl)-2-methoxyiminoacetylamino, 2-(2-aminothiazol-4-yl)-2-carboxymethoxyiminoacetylamino, 2-(2-aminothiazol-4-yl)-2-(1-carboxy-1-methyl)ethoxyiminoacetylamino, 2-(2-aminothiazol-4-yl)-2-(2-fluoroethoxyimino)acetylamino, [2-(2-aminothiazol-4-yl)-2-(1H-imidazol-4-yl)methoxyimino]acetylamino, 2-(4-ethyl-2,3-dioxo-1-piperazinecarbonylamino)-2-phenylacetylamino, 2-(4-ethyl-2,3-dioxo-1-piperazinecarbonylamino)-2-(4-hydroxyphenyl)acetylamino, 2-formylamino-2-phenylacetylamino, [2-(2-aminothiazol-4-yl)-2-formylamino]acetylamino, 2-(4-ethyl-2,3-dioxo-1-piperazinecarbonylamino)-2-(3,4-dihydroxyphenyl)acetylamino, 2-(4-ethyl-2,3-dioxo-1-piperazinecarbonylamino)-3-hydroxybutyrylamino, 2-(5-carboxy-1H-imidazol-4-yl)carbonylamino-2-phenylacetylamino, methoxycarbonylamino, ethoxycarbonylamino, isobutyloxycarbonylamino, benzyloxycarbonylamino, tert-butyloxycarbonylamino, (2,2,2-trichloroethoxy)carbonylamino, 4-methoxybenzyloxycarbonylamino, 4-methoxyphenoxycarbonylamino, methanesulfonylamino, benzenesulfonylamino, p-toluenesulfonylamino, 2-thiophenesulfonylamino, (5-methylthiophen-2-yl)sulfonylamino, 4-chlorobenzenesulfonylamino, 3,4-dichlorobenzenesulfonylamino, 4-acetamidobenzenesulfonylamino, dimethylphosphonoamino, diethylphosphonoamino, dipropylphosphonoamino, diphenylphosphonoamino, dibenzylphosphonoamino, trimethylsilyloxy, tert-butyldimethylsilyloxy, tert-butyldiphenylsilyloxy, N-methylcarbamoyloxy, N-propylcarbamoyloxy, N-phenylcarbamoyloxy, N-ethoxycarbonlymethylcarbamoyloxy, N-chloromethylcarbamoyloxy, N-(2-chloroethyl)carbamoyloxy, N-iodomethylcarbamoyloxy, N-(2-iodoethyl)carbamoyloxy, N-[1-(2-dimethylaminoethyl)-1H-tetrazol-5-yl]thiomethylcarbamoyloxy, N-[2-[1-(2-dimethylaminoethyl)-1H-tetrazol-5-yl]thioethyl]carbamoyloxy, N-[1-(3-dimethylaminopropyl)-1H-tetrazol-5-yl]thiomethylcarbamoyloxy, N-[2-[1-(3-dimethylaminopropyl)-1H-tetrazol-5-yl]thioethyl]carbamoyloxy, N-(1-methyl-1H-tetrazol-5-yl)thionmethylcarbamoyloxy, N-[2-(1-methyl-1H-tetrazol-5-yl)thioethyl]carbamoyloxy, N-(4-methyl-4H-1,2,4-triazol-3-yl)thiomethylcarbamoyloxy, N-[2-(4-methyl-4H-1,2,4-triazol-3-yl)thioethyl]carbamoyloxy, N-[5-(2-dimethylaminoethyl)1,3,4-thiadiazol-2-yl]thiomethylcarbamoyloxy, N-[2-[5-(2-dimethylaminoethyl)-1,3,4-thiadiazol-2-yl]thioethyl]carbamoyloxy, N-(5-methyl-1,3,4-thiadiazol-2-yl)thiomethylcarbamoyloxy, N-[2-(5-methyl-1,3,4-thiadiazol-2-yl)thioethyl]carbamoyloxy, N-(4,5-dimethylthiazol-2-yl)thiomethylcarbamoyloxy, N-[2-(4,5-dimethylthiazol-2-yl)thioethyl]carbamoyloxy, N-(4,5-dimethyloxazol-2-yl)thiomethylcarbamoyloxy, N-[2-(4,5-dimethyloxazol-2-yl)thioethyl]carbamoyloxy, N-(3-methyl-1,2,4-thiadiazol-5-yl)thiomethylcarbamoyloxy, N-[2-(3-methyl-1,2,4-thiadiazol-5-yl)thioethyl]carbamoyloxy, N-(1,2,3-thiadiazol-5-yl)thiomethylcarbamoyloxy, N-[2-(1,2,3-thiadiazol-5-yl)thioethyl]carbamoyloxy, N-(1H-1,2,3-triazol-5-yl)thiomethylcarbamoyloxy, N-[2-(1H-1,2,3-triazol-5-yl)thioethyl]carbamoyloxy, N-(-methyl-1H-imidazol-2-yl)thiomethylcarbamoyloxy, N-[2-(1-methyl-1H-imidazol-2-yl)thioethyl]carbamoyloxy, N-(2-methyl-2H-1,2,4-triazol-3-yl)thiomethylcarbamoyloxy, N-[2-(2-methyl-2H-1,2,4-triazol-3-yl)thioethyl]carbamoyloxy, N-(2-pyrimidinyl)thiomethylcarbamoyloxy, N-[2-(2-pyrimidinyl)thioethyl]carbamoyloxy, N-(2-benzthiazolyl)thiomethylcarbamoyloxy, N-[2-(2-benzthiazolyl)thioethyl]carbamoyloxy, N-(2-benzimidazolyl)thiomethylcarbamoyloxy, N[2-(2-benzimidazolyl)thioethyl]carbamoyloxy, N-(2-benzoxazolyl)thiomethylcarbamoyloxy, N-[2-(2-benzoxazolyl)thioethyl]carbamoyloxy, N[1,2,4-triazin-3-yl)thiomethyl]carbamoyloxy, N-[2-(1,2,4-triazin-3-yl)thioethyl ]carbamoyloxy, N-[(4-carboxy-3-hydroxy-isothiazol-5-yl)thiomethyl]carbamoyloxy, N-[2-(4-carboxy-3-hydroxy-1,2-thiazol-5-yl)thioethyl]carbamoyloxy, N-[(6-methylpyridazin-1-oxid-3-yl)thiomethyl]carbamoyloxy, N-[2-(6-methylpyridazin-1-oxid-3-yl)thioethyl]carbamoyloxy, N-[(N-oxido-2-pyridyl)thiomethyl]carbamoyloxy, N-[2-oxido-2-pyridyl)thioethyl]carbamoyloxy, N-[(2-aminoethylthio)methyl]carbamoyloxy, N-[2-(2-aminoethyl)thioethyl]carbamoyloxy, N-[(2-acetylaminoethyl)thiomethyl]carbamoyloxy, N-[2-(2-acetylaminoethyl)thioethyl]carbamoyloxy, N-[(2-dimethylaminoethyl)thiomethyl]carbamoyloxy, N-[2-(2-dimethylaminoethyl)thioethyl]carbamoyloxy, N-[(2-formimidoaminoethyl)thiomethyl]carbamoyloxy, N-[2-(2-formimidoylethyl)thioethyl]carbamoyloxy, N-[(N-acetoimino-3-pyrrolidinyl)thiomethyl]carbamoyloxy, N-[2-(N-acetoimino-3-pyrrolidinyl)thioethyl]carbamoyloxy, N-(phenylthiomethyl)carbamoyloxy, N-[2-(phenylthio)ethyl]carbamoyloxy, N-[(4-pyridyl)thiomethyl]carbamoyloxy, N[2-(4-pyridyl)thioethyl]carbamoyloxy, N-ethylcarbamoyloxy, N-iso-propylcarbamoyloxy, N-n-butylcarbamoyloxy, N-tert-butylcarbamoyloxy, N-cyclohexylcarbamoyloxy, N,N-dimethylcarbamoyloxy, N,N-diethylcarbamoyloxy, N,N-dipropylcarbamoyloxy, N,N-dibutylcarbamoyloxy, N-ethyl-N-methylcarbamoyloxy, N-benzyl-N-methylcarbamoyloxy, pyrrolidinocarbonyloxy, piperidinocarbonyloxy, morpholinocarbonyloxy, N'-methylpiperazinocarbonyloxy, N'-acetylpiperazinocarbonyloxy, N-methyl-thiocarbamoyloxy, N-ethyl-thiocarbamoyloxy, N-phenyl-thiocarbamoyloxy, piperazinocarbamoyloxy, N-(2-dimethylaminoethyl)carbamoyloxy, N'-(2-pyridyl)piperazinocarbamoyloxy, carbamoyloxy, N-[2-(N'-methyl)piperazinoethyl]carbamoyloxy, [N'-(2-dimethylaminoethyl)piperazino]carbamoyloxy, N-(3-pyridylmethyl)carbamoyloxy, [N'-(2-hydroxyethyl)-piperazino]carbamoyloxy, N-[2-(2-pyridiyl)ethyl]carbamoyloxy, N-(2-pyridylmethyl)carbamoyloxy, N-(4-pyridylmethyl)carbamoyloxy, (4-piperidinopiperidino)carbamoyloxy, (N'-benzylpiperazino)carbamoyloxy, N'-(4-pyridyl)piperazinocarbamoyloxy, [N'-(morpholinocarbonylmethyl)piperazino]carbamoyloxy, N'-(pyrrodinocarbonylmethyl)piperazino]carbamoyloxy, [N'-(isopropylaminocarbonylmethyl)piperazino]carbamoyloxy, N-[2-(2-pyridyl)aminoethyl]carbamoyloxy, [N'-(2-pyridylmethyl)piperazino]carbamoxyloxy, N-(1-carboxyethyl)carbamoyloxy, N-(3-carboxypropyl)carbamoyloxy etc.

Regarding $R^1$ and $R^2$ in compound (I), preferably alkanoyl, α-hydroxyalkyl which may be substituted etc., more preferably $C_{1-5}$alkanoyl are exemplified for $R^5$. $C_{1-5}$alkanoyl for $R^6$ and $C_{1-4}$loweralkyl for $R^7$ are preferably exemplified.

As to $R^3$, the groups representable by the formulae: —OCOOR$^{13}$ (wherein $R^{13}$ has the same meanings as defined above), —OCOSR$^{13'}$ (wherein $R^{13'}$ has the same meanings as defined above), —OCOR$^{14}$ (wherein $R^{14}$ has the same meanings as defined above) and —OCONR$^{15}$R$^{16}$ (wherein $R^{15}$ and $R^{16}$ have the same meanings as defined above, respectively) are preferable.

As to OR$^3$ and SR$^{13'}$ mentioned above, $C_{1-4}$lower alkyloxy for OR$^{13}$ and ω-$C_{2-4}$lower alkanoylamino alkylthio for SR$^{13'}$ are more preferable.

Hydrogen, $C_{1-4}$lower alkyl or alkyl substituted at the terminus with di($C_{1-4}$alkyl)amino or heterocyclic group (thiadiazole, tetrazole etc.) and having optionally an intermediate sulfur atom are preferable for $R^{14}$.

$R^{15}$ and $R^{16}$ preferably are respective $C_{1-5}$lower alkyl or form a heterocyclic group containing nitrogen atoms (piperidine, pyrrolidine, piperazine etc.) which may have substitutents (lower alkyl, pyridyl etc.)

$R^4$ is especially hydroxyl or $C_{1-4}$loweralkenoyloxy (acetyloxy etc.)

Compound [1] of the present invention can be produced, for example, by subjecting a compound representable by the general formula;

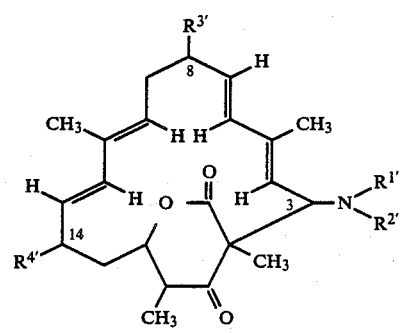

[1']

[wherein $R^{1'}$, $R^{2'}$, $R^{3'}$ and $R^{4'}$ are respectively the same as $R^1$, $R^2$, $R^3$ and $R^4$ defined above or the groups convertible thereto]to alkylation, acylation, hydrolysis, thioamidation, halogenation, azidation and/or a reaction for introducing an organic residual group through oxygen atom, sulfur atom or nitrogen atom.

More concretely, a compound representable by the general formula;

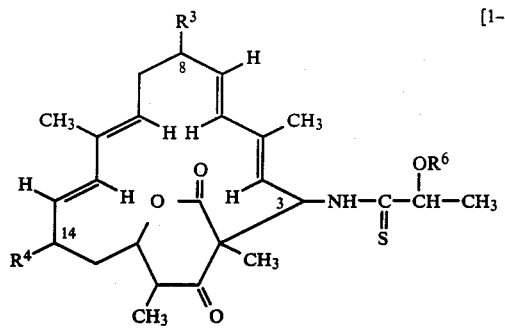

[wherein $R^3$, $R^4$ and $R^6$ are of the same meanings as defined above] is subjected to alkylation to produce a compound representable by the general formula;

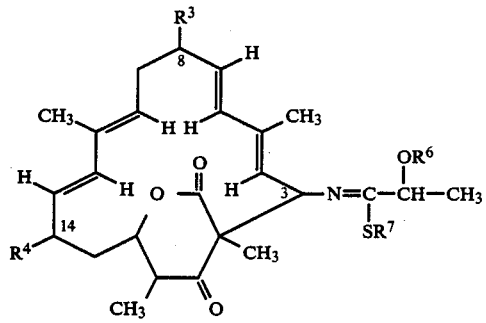

[$R^3$, $R^4$, $R^6$ and $R^7$ are of the same meaning as defined above]to alkylation, the compound [2] is subjected to 8i) acylation, followed by hydrolysis, or (ii) hydrolysis, followed by acylation, to produce a compound representable by the general formula;

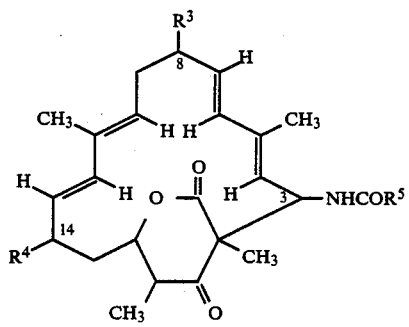

[wherein $R^3$, $R^4$ and $R^5$ and of the same meanings as defined above] a compound representable by the general formula;

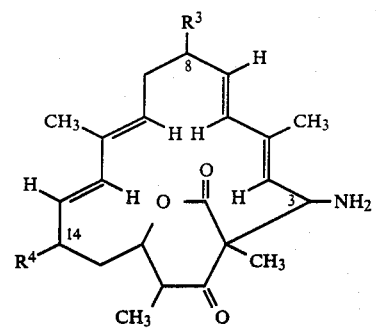

[wherein $R^3$ and $R^4$ are of the same meaning as defined above] is subjected to acylation, then, upon necessity, to thioamidation and to alkylation to produce a compound representable by the general formula;

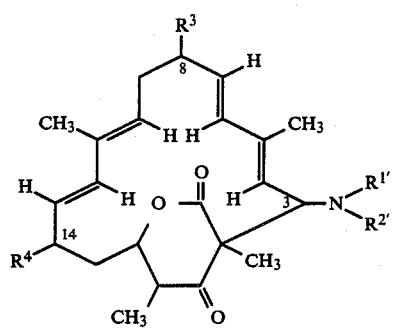

[wherein $R^{1'}$, $R^{2'}$, $R^3$ and $R^4$ are of the same meanings as defined above], or a compound representable by the general formula;

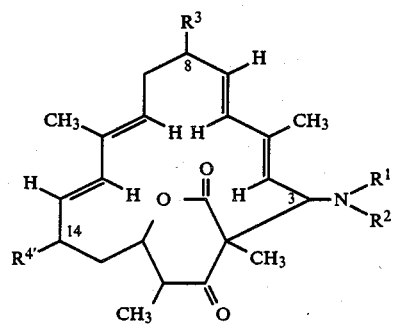

[wherein $R^1$, $R^2$, $R^{3'}$ and $R^{4'}$ are of the same meanings as defined above] is subjected to halogenation, azidation or a reaction for introducing an organic residual group bound through an oxygen atom, sulfur atom or nitrogen atom, to produce the compound [1].

The compound [1-2], which is a compound of the general formula [1] wherein $R^1$ and $R^2$ combinedly stand for a group representable by the formula;

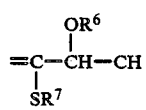

(wherein $R^6$ and $R^7$ are of the same meaning as defined above), can be prepared by, for example, the reaction process as shown below:

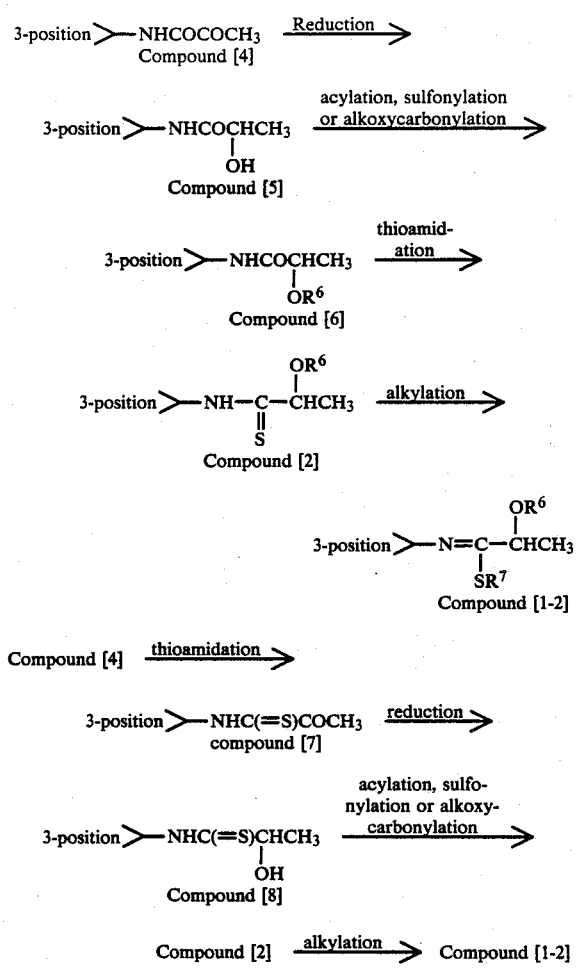

Namely, a compound [1] wherein the group

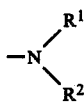

is pyruvoylamino, which is the compound [4], is subjected to reduction to give 2'-hydroxy compound [5], which is subjected to acylation, sulfonylation or alkoxycarbonylation to give the compound [6], which is subjected to thioamidation to give the compound [2], then the compound [2] is subjected, to alkylation or the compound [4] is subjected to thioamidation to give the compound [7], which is subjected to reduction to give the compound [8], which is subjected to acylation, sulfonylation or alkoxycarbonyllation to give the compound [2], followed by subjecting the same to alkylation to obtain the compound [I-2].

The reduction of the compound [4]→the compound [5] or the reduction of the compound [7]→the compound [8] is preferably conducted in general by bringing the starting material into contact with a borohydride compound. The borohydride compound is exemplified by sodium borohydride, lithium borohydridde or sodium cyanoborohydride. In general, the reaction is preferably conducted in a solvent such as alcohols e.g. methanol or ethanol, ethers e.g. tetrahydrofuran, 1,4-dioxane, 2-dimethoxyethane or 2-methoxyethylether or a mixture of these solvents with water. It is not advantageous to use a large excess of the reducing reagent, because there are other positions at which the reaction occurs with the reagent (e.g. 18-position), and it is preferable in general to employ about 1∼2 times as much of the theoretical amount, even when taking into the consideration amount to be consumed by the reaction with the solvent used. The reaction temperature is suitably selected within the range of from about −70° C. to room temperature, preferably within the range of from about −30° C. to about 0° C. The reaction time ranges from about one minute to three hours.

The reaction of the compound [5]→the compound [6] oracylation, sulfonylation or alkoxycarbonylation of the compound [8]→the compound [2] can be conducted by a per se conventional method or a method analogous thereto.

The acylating agent employed for the acylation is exemplified by acyl halide containing an acyl group shown by $R^6$, and acid anhydride, etc. The sulfonylating agent for the sulfonylation is exemplified by, amony others, sulfonyl halide containing a sulfonyl group shown by $R^6$ or sulfonic anhydride. The alkoxycarbonylating agent for the alkoxycarbonylation is exemplified by alkoxycarbonyl halide containing an alkoxycarbonyl group shown by $R^6$ or bicarbonate ester, etc. As the halogen in the above-mentioned halide, bromine and chlorine are especially preferable. The amount of the reagent is equimolar or more, preferably about 1∼5 molar equivalents. In the above acylation, when an acid anhydride is employed as the acylating agent it may be used in an excess amount. As the solvent for the reaction, any solvent which is capable of dissoving the compound [5] or the compound [8] and the reducing agent can be employed, and these are preferably exemplified by dichloromethane, chloroform, dichloroethane, tetrahydrofuran, dioxane, N,N-dimethylformamide, N,N-dimethylacetamide, dimethylsulfoxide, hexamethylphosphorotriamide, pyridine, etc. The reaction temperature ranges from about −50° C. to 30° C., and the reaction time ranges from about 0.1 to 24 hours. By allowing amines such as triethylamine, dimethylaminopyridine, pyridine, N,N-dimethylaniline, N,N-diethylaniline, etc. to coexist in the reaction system, the reaction time can be shortened and the yield can be improved while controlling possible side reactions.

The reaction of the compound [6]→the compound [2] or the thioamidation of the compound [4]→the compound [7] can be conducted by employing for example phosphorus pentasulfide or Lawesson's reagents. The Lawesson's reagents are exemplified by 2,4-bis(4-methoxyphenyl)-1,3-dithia-2,4-diphosphetane-2,4-disulfide, 2,4-bis(4-phenoxyphenyl)-1,3-dithia-2,4-diphosphethane-2,4-disulfide, 2,4-bis(4-methylthiophenyl)-1,3-dithia-2,4-diphosphethane-2,4-disulfide, 2,4-bis(4-phenylthiophenyl)-1,3-dithia-2,4-diphosphethane-2,4-disulfide, etc. The amount of the regents for the reaction is about 0.5∼30 molar equivalent in general, but, when the reaction is conducted at a high temperature, the amount is desirably within the range of about 0.5∼3 molar equivalent. The solvent to be employed for the reaction is exemplified by dichloromethane, tetrahydrofuran, 1,4-dioxane, hexamethylphosphorotriamide, pyridine, etc. The reaction temperature ranges from about 20° C. to 110° C., and the reaction time is about 0.1–24 hours.

The alkylation from the compound [2] to the compound [1-2] is conducted by bringing the compound [2] into contact with an alkylating agent. The reagent to be employed is exemplified by alkyl halides such as alkyl iodide, alkyl bromide and alkyl chloride, dialkylsulfuric acid, Meerwein reagent, etc. The amount of the reagent to be used for the reaction, when the reagent is alkyl halide or dialkyl sulfuric acid, is 1 molar equivalent to a large excess, desirably about 3 molar equivalent to a large excess. When a Meerwein reagent is employed, use of about 1–2 molar equivalent brings about a preferable result. The solvent to be employed for the reaction is exemplified by dichloromethane, chloroform, tetrahydrofuran, ethyl acetate etc., and, when an alkyl halide or dialkyl sulfuric acid is employed as the alkylating agent, it is desirable to have an inorganic base such as sodium hydrogencarbonate, sodium carbonate, potassium hydrogencarbonate or potassium carbonate coexist, and it is also desirable to have water to coexist with the above-mentioned solvent so as to dissolve these inorganic bases. The reaction temperature is within the range of about 0.5 hour~10 days. When a Meerwein reagent is used as the alkylating agent, the reaction proceeds quickly and completes generally in about 5 hours. Incidentally, when a Meerwein reagent is used as the alkylating agent, a salt of the compound [1-2] is obtained, and, in case of isolating the compound [1-2], it is necessary to neutralize this salt with a base (e.g. sodium hydrogencarbonate, potassium hydrogencarbonate, sodium carbonate, potassium carbonate, sodium dihydrogenphosphate, potassium dihydrogenphosphate, sodium acetate, etc.).

Acylation of the compound [1-2] can be conducted by bringing the compound [1-2] into contact with an acylating agent containing a group shown by $R^5$, The acylating agent is exemplified by acid halide, a mixed acid anhydride, activated ester, etc., and acid chloride and acid bromide are especially preferably employed. The amount of the acid halide is about 1–3 molar equivalent. The reaction is conducted preferably in a solvent, and the solvent is exemplified by acetic acid esters such as methyl acetate, ethyl acetate, propyl acetate, butyl acetate, etc., halogenated hydrocarbons such as dichloromethane, chloroform, etc., ethers such as ethylether, 1,4-dioxane, tetrahydrofuran, etc., N,N-dimethylformamide, N,N-dimethylacetamide, dimethyl sulfoxide, hexamethyl phosphorotriamide, etc. The reaction temperature is about 0° C.~ about 80° C., and it is convenient to conduct the reaction around room temperature. The reaction time is about 1 hour~24 hours. The subsequent hydrolysis proceeds by the addition of water after completion of the above-mentioned acylation, and, depending on cases, the hydrolysis completes by the presence of moisture contained in the solvent used when the acylation is conducted. In case of adding water, the amount is, for example, 1~10 molar equivalent. The reaction temperature is about 0° C.~50° C. and the reaction time is about 1 hour~24 hours to bring about preferable results.

By-products formed when the compound [1-3] is prepared from the above-mentioned compound [1-2] can be eliminated by conventional means such as chromatography, recrystallization, reprecipitation, etc.

For preparing the compound [1-4] by acylating the compound [3], and, upon necessity, by subjecting the acylated compound to thioamidation, firstly the compound [1-2] is subjected to acid hydrolysis, then the resultant compound [3] is subjected to acylation.

Acid hydrolysis of the compound [1-2] is conducted by bringing the compound [1-2] into contact with an inorganic acid e.g. hydrochloric acid, sulfuric acid, hydrobromic acid, hydriodic acid, hydrofluoric acid, nitric acid, perchloric acid, chromic acid, periodic acid or hydrofluoric acid, or an organic acid such as methanesulfonic acid, benzenesulfonic acid or toluenesulfonic acid in the presence of water. The reaction is conducted preferably in an organic solvent so as to dissolve the compound [1-2]. The solvent to be used is exemplified by acetone, tetrahydrofuran, 1,4-dioxane, dichloromethane, chloroform, dichloroethane, methanol, ethanol, etc. The reaction temperature ranges from about 0° C. to about 50° C., and it is convenient to conduct the reaction at room temperature. The reaction time varies with reaction temperatures, acid concentrations and kinds of organic solvent employed, and it ranges from 0.5 hour to 24 hours. The compound ;b [3] produced by acid hydrolysis of the compound [1-2], the former being unstable, is desirably subjected to acylation without isolation to lead to the compound [1-3]. More concretely, the desirable method comprises allowing an acylating agent to coexist when the compound [1-2] is subjected to acid hydrolysis then acylating the compound [3] immediately to lead to the compound [1-3].

The acylation of the compound [3] can be conducted in a manner similar to the afore-mentioned reaction for acylating the compound [1-2].

The reaction in case of subjecting the compound obtained by the said acylation to thioamidation upon necessity can be conducted in a manner similar to the reaction in case of subjecting the afore-mentioned compound [6] or the compound [4] to thioamidation.

Among the compounds [1-3], the following compounds [9]~[44] for example can be produced also by the conversion reaction at 3-position shown as below.

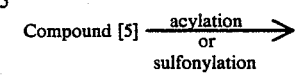

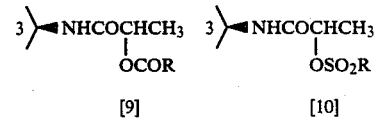

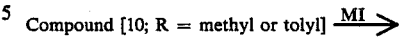

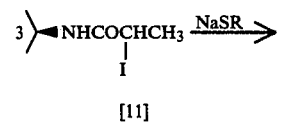

-continued
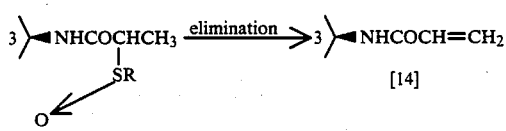
[13]
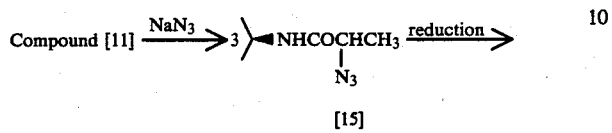
[15]
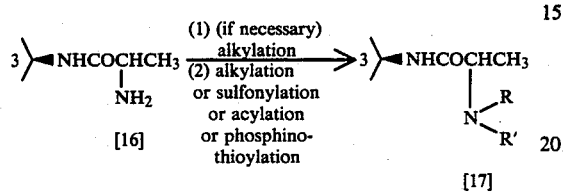
[16] → [17]
Compound [4] —enosilyl etherification→
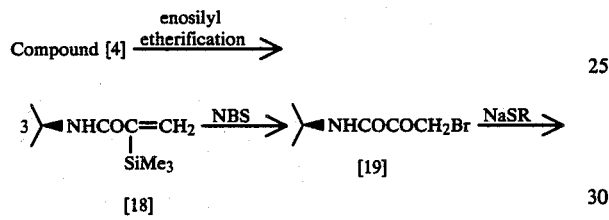
[18] —NBS→ [19] —NaSR→
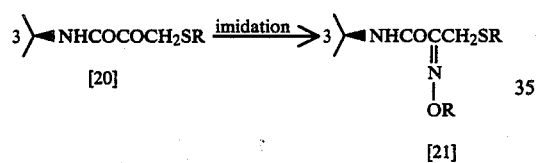
[20] —imidation→ [21]
Compound [20] —Reduction→
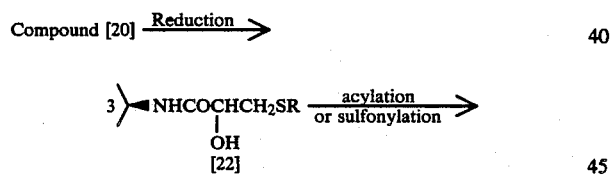
[22] —acylation or sulfonylation→
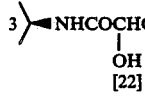
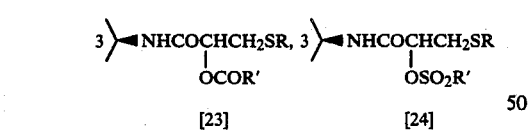
[23]  [24]
Compound [24; R' = methyl or tolyl] —MI→
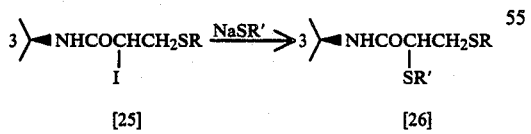
[25] —NaSR'→ [26]
Compound [25] —NaN3→
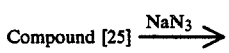
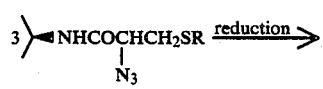
[27]
-continued
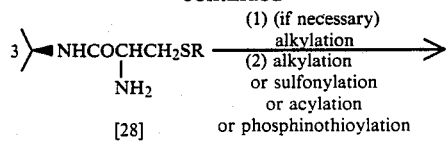
[28]
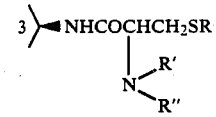
[29]
Compound [19] —NaN3→
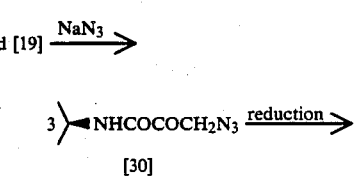
[30]
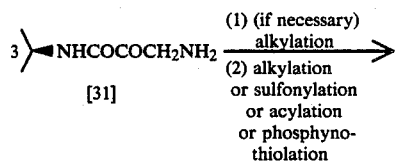
[31]
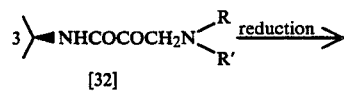
[32]
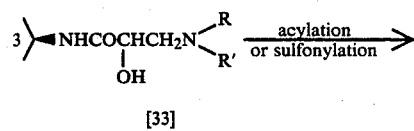
[33]
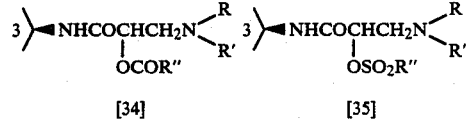
[34]  [35]
Compound[35: R"methyl or tolyl] —MI→
[36] —NaSR"→
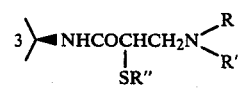
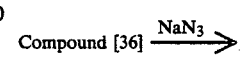
[37]
Compound [36] —NaN3→
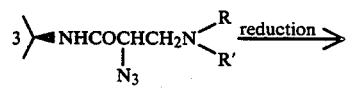
[38]

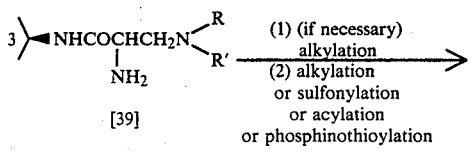

[39]

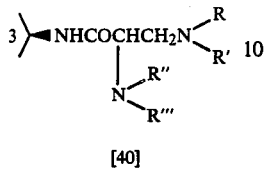

[40]

Compound [32] —imidation→ 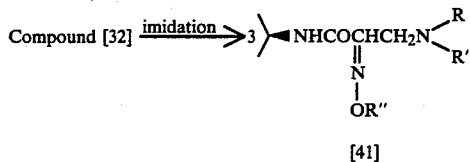

[41]

Compound [4] —enol carbonation or enol acylation→

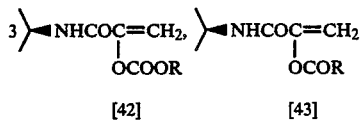

[42]   [43]

Compound [19] —H₂NSCNH₂→

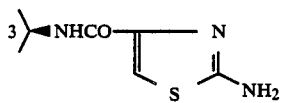

[44]

Acylation or sulfonylation of Compound [5]→Compound [9] or [10], Compound [22]→Compound [23] or [24], and Compound [33]→Compound [34] or [35] can be conducted under conditions similar to those for the conversion of Compound [5]→Compound [6] described in the foregoing. Reduction of Compound [20]→Compound [22] and Compound [32]→Compound [33] can be conducted similarly to the conversion of Compound [4]→Compound [5] described in the foregoing.

Iodination of Compound [10; R=methyl or tolyl]-→Compound [11], Compound [24; R'=methyl or tolyl]→Compound [25] and Compound [35; R''=methyl or tolyl]→Compound [36] can be conducted by per se conventional methods. The iodinating agent is exemplified by metal salts of potassium, such as sodium iodide, potassium iodide, which is used in general in an amount of about 1 molar equivalent or more, preferably about 1~5 molar equivalent. The reaction is conducted preferably by using a solvent, for example, acetone, methylethylketone, acetonitrile, N,N-dimethylformamide, N,N-dimethylacetamide, dimethylsulfoxide and hexamethylphosphorotriamide. The reaction is conducted in most cases under reflux when acetone is employed as the solvent. When N,N-dimethylformamide of N,N-dimethylacetamide is employed, the reaction often proceeds at relatively lower temperatures. The reaction time varies with the amount of an iodinating agent, kinds of solvents and reaction temperatures, and ranges in general about 1 hour~24 hours.

For conversion of Compound [11]→Compound [12], Compound [19]→Compound [20], Compound [25]→Compound [26], and Compound [36]→Compound [37], a thiol or a salt thereof is employed. When a thiol is employed, coexistence of a base, for example, an organic amine such as triethylamine, diisopropylamine and pyridine or an inorganic base, for example, sodium hydroxide, potassium hydroxide, sodium carbonate, sodium hydrogencarbonate and potassium hydrogencarbonate often serves to allow the reaction to proceed smoothly bring about favorable results. The amount of the reagent for the reaction usually ranges from about 1 molar equivalent to 5 molar equivalent, and, when a salt of thiol is employed, about 1~2 molar equivalent is in most cases sufficient. The reaction is conducted in a solvent. As the solvent, use is often made of, for example, tetrahydrofuran, 1,4-dioxane, ethanol, methanol, N,N-dimethylformamide, N,N-dimethylacetamide, dimethylsulfoxide, hexamethylphosphorotriamide, acetonitrile, nitromethane, etc. The reaction temperature ranges from about −30° C. to 50° C. Usually, it is desirable to start the reaction under cooling then to heat up to room temperature so that drastic reaction may be avoided. Reaction time is about 1 minute~24 hours. Azidation of Compound [11]→Compound [15], Compound [25]→Compound [27], Compound [19]→Compound [30] and Compound [36]→Compound [38] is generally conducted by using an alkali metal salt of hydrogen azide such as sodium azide, potassium azide, etc. under conditions similar to those for the above-mentioned conversion to thiol. Incidentally, when a solvent hardly dissolves an alkali metal salt of hydrogen azide is employed, it is preferable to allow water to coexist in the reaction system. The reaction temperature ranges from about 0° C. to 100° C., and the reaction time is within a range of from about 10 minutes to 24 hours. As the oxidizing agent for the oxidation of Compound [12]→Compound [13], use is made of, for example, metachloroperbenzoic acid, sodium meta-periodide, etc., preferably in an amount of about 1 molar equivalent. As the reaction solvents, those which are capable of dissolving Compound [12] and the oxidizing agent then used are desirably employed. When meta-chlorperbenzoic acid is employed as the oxidizing agent, dichloromethane, chloroform, ethyl acetate, methanol or ethanol for example is preferably used. When sodium meta-periodide is used as the oxidizing agent, a mixture solvent containing water is desirable employed. The reaction temperature ranges from relatively low temperature to room temperature, usually about −30° C.~25° C., and the reaction time is about 0.1~24 hours.

The conversion reaction of Compound [13]→Compound [14] can be conducted by heating to allow sulfinic acid to leave. The reaction is conducted in a solvent, and the solvent is exemplified by benzene, toluene, xylene, etc. As the sulfinic acid formed decomposes Compound [13] and [14], it often brings about favourable results to allow an agent for capturing sulfinic acid to coexist in the reaction system. The capturing agent of sulfinic acid is exemplified by trimethylphosphite, triethylphosphite, triisopropylphosphite, tributylphosphite, triphenylphosphine, tributylphosphine, etc., which is in general used in an amount of about 1~10 molar equivalent to give favorable results. The reaction temperature is about 80°~120° C., and the reaction time is about 0.5~24 hours.

The conversion of Compound [15]→Compound [16], Compound [27]→Compound [28], Compound [30]→Compound [31] and Compound [38]→Compound [39] can be conducted by reducing the azide group. The method of reducing azide group into amino group is per se known, which is exemplified by (a) catalytic reduction using Lindlar catalyst, (b) a method using 1,3-propanedithiol and triethylamine, (c) a method comprising allowing a trivalent phosphorus compound to react and subjecting the resultant to hydrolysis (Standinger reaction), (d) a method using chromous chloride [Cr(II)Cl$_2$] and (e) reduction with zinc-acetic acid. In the method (a), by using Lindlar catalyst, the azide compound is stirred at room temperatures under hydrogen streams. The solvent to be employed is exemplified by ethyl acetate, benzene, ethanol, methanol, etc. The reaction time varies with the amount and activity of the catalyst used, but it is usually about 1 hour~24 hours. In the method (b), about 1~3 molar equivalents of 1,3-propanedithiol or triethylamine is employed, and the reaction system is stirred for about 1~24 hours. As the solvent for the reaction, use is made of, for example, methanol, ethanol, dichloromethane, chloroform, tetrahydrofuran, ethyl acetate or a mixture solvent thereof. In the method (c), a tri-valent phosphorus compound [e.g. triphenylphosphine, trimethylphosphite, triethylphosphite, etc.] is allowed to react with an azide compound, and the resultant iminophosphorane is subjected to decomposition with hydrochloric acid [cf. Synthesis, 1985 p. 202], and, as the solvent, use is made of, for example, benzene. In the method (d), chromous chloride is dissolved in 0.6M hydrochloric acid, and the solution is added dropwise to a azide compound dissolved in acetone, then the mixture is stirred at 0° C. for 5 minutes [cf. The Journal of Antibiotic, 38, 477 (1985)] to thereby reduce the azide compound to amino compound. In the method (e), reduction is conducted by the use of an excess amount of zinc and acetic acid, and acetic acid can be used as the solvent as well, or any other solvent [e.g. dichloromethane, chloroform, ethyl acetate, etc.], and the reaction temperature ranges from about 0° C. to 50° C. the reaction time being about 1 minute~24 hours.

Conversion of Compound [16]→Compound [17], Compound [28]→Compound [29], Compound [31]→Compound [32] and Compound [39]→Compound [40] can be conducted by per se conventional means. Namely, alkylation is conducted by employing an alkylating agent such as alkyl chloride, alkyl bromide, alkyl iodide or alkylsulfuric acid to alkylate the amino compound. The amount of the alkylating agent is in most cases about 1~3 equivalent. Any solvent can be used for the reaction, but ethanol, methanol or the like is preferably employed. The reaction temperature is, in many cases, required to be relatively high, usually about 50° C.~100° C. The reaction time is about 1~24 hours. When these reaction conditions are employed, N-dialkyl compounds sometimes occur as by-products. When the formation of these N-dialkyl compounds is undesirable, N-monoalkyl compound can be obtained by reductive alkylation using aldehyde. In this case, an aldehyde compound is subjected to reaction under cooling to around room temperature, and the resulting imino compound is subjected to reduction with a reducing agent e.g. sodium cyanoborohydride to obtain a monoalkyl compound. The amount of the aldehyde is about 1~3 molar equivalent, and the amount of sodium cyanoborohydride is desirably about 1~3 times as much as the theoretical amount. As the reaction solvent, use is made of methanol, ethanol, tetrahydrofuran, etc., and the reaction time is about 0.1~24 hours. In the acylation, sulfonylation or phosphinothioylation, the reaction can be conducted under conditions similar to those for conversion of Compound [5]→Compound [6] as described above, by using a corresponding halide (a chloride is less expensive and convenient), but it can also be conducted by Schotten-Baumann reaction allowing water and an inorganic base to coexist with a solvent used.

Conversion of Compound [4]→Compound [18] can be conducted by adding chlorotrimethylsilane to the reaction mixture in the presence of a base. Use of about 1~1.5 molar equivalent of chlorotrimethylsilane is sufficient for the purpose, and, as the base, triethylamine or diisopropylethylamine for example is preferably used. Referring to the amount of the base, about 1~1.5 molar equivalent is sufficient for the purpose. The reaction is conducted in a solvent exemplified by preferably dichloromethane, chloroform or dichloroethane. The reaction is conducted preferably within the range of from about 0° C. to 50° C., especially conveniently around room temperatures. The reaction time is about 1~5 hours.

Conversion of Compound [18]→Compound [19] can be conducted by allowing N-bromosuccinimide to react with Compound [18]. Use of about 1~1.5 molar equivalent of N-bromosuccinimide is sufficient for the purpose, and the reaction proceeds smoothly even under ice-cooling. As the reaction solvent, use is preferably made of for example dichloromethane, chloroform or dichloroethane. The reaction temperature is about −50° C.~0° C., and the reaction time is about 1~60 minutes.

Conversion of Compound [20]→Compound [21] and Compound [32]→Compound [41] is conducted by subjecting hydroxylamine or O-substituted hydroxylamine to the reaction. The amount of these reagents is desirably about 1~3 molar equivalent in usual cases. When they are in a form of salt with an acid, e.g. hydrochloride, sulfate or the like, they are desirably subjected to the reaction in the free form by addition of the same molar equivalent of a base such as pyridine or triethylamine. The reaction solvent is preferably exemplified by methanol, ethanol, tetrahydrofuran, 1,4-dioxane or an aqueous mixture thereof. The reaction temperature is about 0° C.∞50° C., preferably around room temperatures, and the reaction time is about 1~24 hours.

Conversion of Compound [4]→Compound [42] or [43] can be conducted by subjecting a carbonate or a carbonic acid anhydride to the reaction in the presence of a base. The amount of the carbonate or the carbonic acid anhydride is usually about 1~5 molar equivalent. The base is exemplified by triethylamine or diisopropylethylamine, which is used in an amount of usually about 1~5 molar equivalent. The reaction solvent is exemplified by dichloromethane, chloroform or dichloroethane, and coexistence of about 1 molar equivalent of 4-N,N-dimethylaminopyridine as the acylation promoter in the reaction system often serves to allow the reaction to proceed promptly. The reaction temperature is about −50° C.~50° C., and the reaction time is about 1~24 hours.

Conversion of Compound [19]→Compound [44] can be conducted by the reaction with thiourea, and use of the latter in an amount of about 1~1.5 molar equivalent is sufficient for attaining the purpose. As the reaction solvent, use is made of preferably N,N-dimethylformamide, N,N-dimethylacetamide, tetrahydrofuran, 1,4-dioxane and an aqueous mixture thereof. When an equimolar amount of an inorganic base such as sodium hydrogencarbonate is allowed to coexist in the reaction system, the reaction proceed promptly without causing formation of by-product thus being preferable in most cases. The reaction temperature is about 0° C.~50° C., preferably around room temperatures, and the reaction time is about 0.1~5 hours.

Compound [45], which is a compound of the general formula [1] wherein one of $R^1$ and $R^2$ is hydrogen and the other is

can be prepared by subjecting corresponding 3-amido compound [1-3] to thioamidation. This conversion reaction of Compound [1-3]→Compound [45] can be conducted in a manner similar to the above-mentioned conversion of Compound [6]→Compound [2].

Further, the above-mentioned conversion conducted on corresponding 3-amido compound can also be applied to a 3-thioamido compound, and by these conversion reactions any other derivatives mentioned above can be prepared.

Compound [46], which is a compound of the general formula [1] wherein $R^3$ and/or $R^4$ are hydroxyl, can be prepared, for example, by liberating it from its carbonic acid ester, carboxylic acid ester, phosphoric acid ester, sulfonic acid ester or ether compound as described later.

In case of using a carbonic acid ester or carboxylic acid ester for the purpose of liberating the acid, in other words, in case of the use of the acyl group as the protective group of the hydroxyl group of $R^3$ and/or $R^4$, the liberation can be performed more easily. Such carbonic acid ester and carboxylic acid ester are exemplified by, besides benzyloxycarbonyloxy, 2,2,2-trichloroethoxycarbonyloxy, aryloxycarbonyloxy, chloroacetyloxy, etc., those described on literature references [for example, "Protective Groups in Organic Synthesis" written by Theodora W. Greene, published by John Wiley & Sons, New York, 1981].

Ether is usually difficult to be removed. Therefore, when an ether (compound) is used for the purpose of obtaining hydroxyl compound, the ether is limited to that usable as a protective group. As such ether compounds, use is made of, besides trimethylsilylether, tert-butyldimethylsilylether, tert-butyldiphenylether, methylether, methoxyethoxyether, etc., those described on the literature reference cited above.

Removal of the carbonic acid ester, carboxylic acid ester, phosphoric acid ester or sulfonic acid ester can be conducted by a per se known method or a method analogous thereto. More specifically, the reaction is hydrolysis and can be conducted under conditions similar to conventional ester hydrolysis.

Namely, the hydrolysis can be conducted generally in a solvent (singly or in admixture of one or more solvents), exemplified by water, alcohols (e.g. methanol, ethanol, propanol, butanol, diethylene glycol, 2-methoxyethanol, etc.), ketones (e.g. acetone, etc.), ethers (e.g. tetrahydrofuran, dioxane, dimethoxyethane, etc.), amides (e.g. dimethylformamide, dimethylacetamide, hexamethylphosphorotriamide, etc., sulfoxides (e.g. dimethylsulfoxide, etc.), sulfones (e.g. sulfolane), carboxylic acids (e.g. formic acid, acetic acid, etc.), etc. by using an acid (e.g. mineral acids such as hydrochloric acid, hydrobromic acid, sulfuric acid, etc., organic acids such as p-toluenesulfonic acid, etc., strongly acid ion-exchange resin, etc.) or a base (e.g. sodium hydroxide, potassium hydroxide, potassium carbonate, sodium hydrogencarbonate, barium hydroxide, calcium carbonate, sodium methoxide, ammonia, etc.), and the hydrolysis by using a base is preferable. The amount of a base is about 1~10 times as much moles, preferably about 1.2~4 times as much moles. The reaction temperature and time greatly depend on the kinds of acyl moiety in the ester group then employed, they are respectively about $-20°$ C.$\sim 70°$ C., preferably about $-5°$ C.$\sim 30°$ C. and about 0.1~24 hours, preferably about 0.1~3 hours.

When an ether compound is employed as the hydroxy-protected compound, the ether group can be cleaned by a per se conventional means. More specifically, when a silyl group such as trimethylsilyl, tert-butyldimethylsilyl, tert-butyldiphenylsilyl, etc. is used as the protective group, the removal of the group can be performed by bringing it into contact with a compound containing fluoride ion (e.g. potassium fluoride, sodium fluoride, tetra-n-butylammonium fluoride, etc.), The reaction is conducted in a solvent such as tetrahydrofuran, dioxane, methanol and ethanol, optionally in the coexistence of water. The amount of the compound containing fluoride ion is about 1~10 times as much moles, preferably about 1~2 times as much moles. The reaction temperature and time are respectively about $-20°$ C.$\sim 100°$ C., preferably about $-5°$ C.$\sim 30°$ C. and about 0.1~24 hours, preferably about 0.1~10 hours. The removal of these silyl groups can be performed bringing them into contact with a mineral acid such as hydrochloric acid, sulfuric acid, etc. or an organic acid such as methanesulfonic acid, toluenesulfonic acid, etc. The reaction is conducted, in most cases, in the coexistence of water, and, as the solvent, use is made of ethanol, methanol, tetrahydrofuran, dioxane or acetone which is miscible with water. In most cases, use of the acid in a catalytic amount is sufficient for the purpose, but optionally in excess amount. The reaction temperature is about $-5°$ C.$\sim 100°$ C., preferably about 0° C.$\sim 30°$ C., and the reaction time is about 0.1~24 hours, preferably about 0.1~2 hours. Also in case of using, as the protective group, an ether-containing compound such as methoxymethyl, methoxyethoxy, etc., it can be removed by bringing the compound into into contact with an acid as mentioned above. In case of employing methyl or benzyl as the protecting group, it can be eliminated by bringing into contact with iodotrimethylsilane. The amount of iodotrimethylsilane is about 1~10 times as much moles, preferably about 1~3 times as much moles. The reaction is conducted in a solvent, as exemplified by chloroform, dichloromethane, ethyl acetate, tetrahydrofuran, dioxane, acetone, etc. The reaction temperature is about $-50°$ C.$\sim 100°$ C., preferably about $-20°$ C.$\sim 30°$ C., and the reaction time is about 0.1~24 hours, prederably about 0.1~10 hours.

When $R^3$ of the general formula [1] is pentanoyloxy, isopentanoyloxy, butyryloxy, isobutyryloxy or propionyloxy, the acyloxy group of the group $R^3$ can be changed into hydroxyl group by bringing an enzyme having the activity of changing the acyloxy of the group $R^3$ into hydroxyl group into contact with the compound. As the enzyme is mentioned, for example, a deacylating esterase which is produced by a strain belonging to the genus Bacillus and being capable of producing the said enzyme. As examples of microorganisms belonging to the genus Bacillus are mentioned those of Bacillus megaterium. These methods are described, for example, in The Journal of Antibiotics, 28, 390(1975).

When $R^4$ of the general formula [1] is acetoxy, propionyloxy or butyryloxy, the acyloxy group of the group $R^4$ can be changed into hydroxyl group by bringing an enzyme having the activity of changing the acyloxy group of the group $R^4$ into hydroxy group into contact with the compound. These method are described in detail in U.S. Pat. No. 3,691,181 and U.S. Pat. No. 3,676,300.

The above-mentioned enzyme is preferably a refined one, but, a non-refined crude material containing the said enzyme, for example, culture broth of the above-mentioned microorganisms or a solution, mycelia or crushed mycelia obtained by subjecting the culture broth to suitable physico-chemical treatment such as filtration, centrifuge, ultrasonic treatment, French-press tretment, osmotic shock, freeze-thaw method, alumina-milling, bacteriolytic enzyme treatment, or treatment with a surfactant or an organic solvent are usable, or a fixed enzyme is also employable. The concentration the said starting compound in the reaction system where the said starting material is brought into contact with the above-mentioned enzyme or a material containing the said enzyme is about $10^{-4} \sim 1$ mol/l, more preferably about $10^{-3} \sim 10^{-1}$ mol/l. The amount of the said enzyme or a material containing the enzyme to be used is about $0.1 \sim 100$ mg/ml in terms of the amount of the enzyme, more preferably, about $0.5 \sim 50$ mg/ml.

The above-mentioned reaction is conducted at pH about $4 \sim 10$, more preferably about $5 \sim 8$, at a reaction temperature of about $0° \sim 60°$ C., more preferably about $20° \sim 40°$ C. for about $0.1 \sim 48$ hours, more preferably about $0.1 \sim 24$ hours.

Compound [47], which is a compound of the general formula [1] wherein $R^3$ and/or $R^4$ are/is chlorine, can be prepared by, for example, allowing chlorinating agent to react with Compound [46] wherein $R^3$ and/or $R^4$ are/is hydroxy to thereby substitute the said hydroxy group with chlorine. As the chlorinating agent, thionyl chloride can be employed conveniently, and it is preferable to allow a base to coexist for capturing hydrogen chloride generated. The amount of thionyl chloride to be used is about $1 \sim 1.5$ molar equivalent, which is sufficient for attaining the purpose. The base is exemplified by pyridine, picoline, lutidine, dimethylaniline, diethylaniline, triethylamine, diisopropylethylamine, etc., and the amount thereof is preferably about the amount as that of thionyl chloride. The reaction is conducted in a solvent, and the solvent is preferably exemplified by dichloromethane, chloroform, dichloroethane, etc. The reaction temperature is about $-50°$ C.$\sim 30°$ C., especially preferably $-30°$ C.$\sim 0°$ C. The reaction time is about $0.1 \sim 3$ hours.

Compound [48], which is a compound of the general formula [1] wherein $R^3$ and/or $R^4$ are/is bromine, be prepared by using for example thionyl bromide, instead of thionyl chloride used for the conversion of Compound [46]→Compound [47], or an alkali metal bromide, instead of the alkali metal iodide used for the conversion of Compound [49]→Compound [50] to be described later.

Compound [50], which is a compound of the general formula [1] wherein $R^3$ and/or $R^4$ are/is iodine, can be prepared by subjecting Compound [49] to be described later to a treatment similar to the afore-mentioned conversion reaction of Compound [10]→Compound [11].

Compound [51], which is a compound of the general formula [1] wherein $R^3$ and/or $R^4$ are/is azido, can be prepared by, for example, subjecting Compound [50] to a treatment similar to the afore-mentioned conversion reaction of Compound [11]→Compound [15].

The following is a method of preparing compound of the general formula [1] wherein $R^3$ and/or $R^4$ are/is organic residual group(s) through oxygen atom.

Compound [52], which is a compound of the general formula [1] wherein $R^3$ and/or $R^4$ are/is $OCOOR^{13}$, and Compound [53], which is a compound of the general formula [1] wherein $R^3$ and/or $R^4$ are/is $OCOR^{14}$, can be prepared by, for example, subjecting compound [46] to a treatment similar to the afore-mentioned conversion reaction of Compound [5]→Compound [6].

Compound [52'], which is a compound of the general formula [1] wherein $R^3$ and/or $R^4$ are/is $OCOSR^{13'}$ can be prepared, for example, reacting Compound [52] with a thiol or a salt threof representable by the general formula: $HSR^{13'}$. In the reaction Compound [52] is preferably in an activated form such as those in which $R^{13'}$ is, for example, $CHCl_3$, $C_6Cl_5$, $2,2,5$-$C_6H_2Cl_3$ etc. As to the salt thereof, a sodium salt is preferably exemplified. The reaction is preferably conducted in an organic solvent such as methanol, ethanol, tetrahydrofuran, N,N-dimethylformamide, N,N-dimethylacetamide, dimethyl sulfoxide, acetonitrile. The amount of the thiol or a salt thereof to be used is preferably about 1 to 5 molar equivalent, the reaction temperature is about $0°$ C. to $50°$ C. and the reaction time is about 1 minute to about 10 hours Compound [54], which is a compound of the general formula [1] wherein $R^3$ and/or $R^4$ are/is

and Compound [55], which is a compound of the general formula [1] wherein $R^3$ and/or $R^4$ are/is

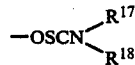

can be prepared by, for example, allowing isocyanate representable by the general formula $OCN-R^{15}$ or isothiocyanate representable by the general formula $SCN-R^{17}$ to react with Compound [46]. The reaction is conducted preferably in an organic solvent exemplified by dichloromethane, chloroform, 1,2-dichloroethane, tetrahydrofuran, 1,4-dioxane, acetonitrile, N,N-dimethylformamide, N,N-dimethylacetamide, etc. The amount of isocyanate or isothiocyanate to be employed is preferably about $1 \sim 10$ molar equivalent, the reaction temperature is about $0°$ C.$\sim 150°$ C. and the reaction time is about 10 minutes$\sim 48$ hours. When about $0.1 \sim 5$ molar equivalent of, for example, zinc chloride, zinc bromide, zinc iodide, cuprous chloride or di-n-butyltin dilaurate is allowed to coexist in the reaction system, the reaction temperature can be lowered by the aid of catalytic action thereof to shorten the reaction time.

Compound [54] can also be prepared by reacting Compound [52] with amines representable by the general formula: $HNR^{15}R^{16}$. Compound [52] to be used under such a reaction is preferably an activated form in which $R^{18}$ is for example, $C_6Cl_5$, $2,4,5\text{-}C_6H_2Cl_3$ etc. The reaction is preferably conducted in an organic solvent such as dichloromethane, chloroform, 1,2-dichloroethane, tetrahydrofuran, 1,4-dioxane, acetonitrile etc. Water may be allowed to coexist in the solvent. The amount of amine is preferably about 1 to 10 molar equivalent. The reaction temperature and the reaction time is variable according to the amine used and is about 0° C. to 100° C. and about 1 minute to about 168 hours, respectively.

Compound [56], which is a compound of the general formula [1] wherein $R^3$ and/or $R^4$ are/is

can be prepared by, for example, subjecting Compound [46] to phosphoesterification. As the phosphonating agent, use is made of, for example, di(alkyl, alkenyl, alkynyl, heterocyclic ring, cycloalkyl, aryl or aralkyl)-phosphochloridate, conveniently. The amount of the phosphonating agent is about 1~20 molar equivalent, and use of a base as solvent often bring about favourable results. A typical example of the base is pyridine. The reaction temperature at the initial stage of the reaction is about $-70°$ C.$\sim -50°$ C., then it is raised gradually and maintained within the range of about $-30°$ C.$\sim -10°$ C. for several hours to bring about favorable results. The phosphochloridate then used can be prepared by allowing N-chlorosuccinimide to react with phosphinic acid diester.

Compound [49], which is a compound of the general formula [1] wherein $R^3$ and/or $R^4$ are/is $OSO_2R^{20}$, can be prepared by, for example, subjecting Compound [46] to a treatment similar to the afore-mentioned conversion reaction of Compound [5]→Compound [10].

Compound [57], which is a compound of the general formula [1] wherein $R^3$ and/or $R^4$ are/is $OR^{21}$ can be prepared by for example subjecting Compound [46] to etherification or subjecting Compound [50] to substitution reaction. The etherification can be conducted as, in most cases, alkylation, alkenylation, alkynylation or cycloalkylation.

The alkylation, alkenylation, alkynylation or cycloalkylation can be conducted by per se known methods or in a manner analogous thereto. As the agents for alkylation, alkenylation, alkynylation and cycloalkylation are mentioned most preferably the corresponding alkyl, alkenyl, alkynyl and cycloalkyl halide (e.g. chloride, bromide, etc.) respectively, but dialkyl sulfuric acid, alkyl sulfate, etc. can also be conveniently employed.

The amount of these agents to be used for alkylation, alkenylation, alkynylation and cycloalkylation varies depending upon, for example, reactivity of them, but it is usually within the range of 1~100 times as much mol. relative to Compound [46], and, preferably, when a highly reactive halide (e.g. optionally substituted benzyl halide, phenacyl halide, halogenoketone, halogenoacetic acid, allylhalide, propargyl halide or, generally, alkyl, alkenyl or alkynyl iodide, etc.) is employed for example, the amount is about 1~10 times as much mol., when bromide is employed, the amount is generally about 1~20 times as much mol. and, when chloride is employed, the amount is about 1~50 times as much mol.

The solvent to be employed for alkylation, alkenylation or alkynylation, is not especially limited but anyone which dissolves relatively well the reagents can be used. Examples of such solvent are alcohols such as methanol, ethanol, etc., ethers diethyl ether, tetrahydrofuran, dimethoxyethane, etc., ketones such as acetone, methylethylketone, etc., amides such as dimethylformamide, dimethylacetamide, etc., sulfoxides and sulfones such as dimethyl sulfoxide, sulfolane, etc., hydrocarbon halogenides such as dichloromethane, chloroform, etc., and aromatic hydrocarbons such as benzene, toluene, xylene, etc.

The reaction temperature is about $-10°$ C.$\sim 50°$ C., and the reaction time is about 1~24 hours.

By allowing a silver salt such as silver oxide or a base (e.g. inorganic base such as potassium carbonate etc., alkali metal alcoholate such as sodium methylate, lithium methylate, etc., amines such as triethylamine, diisopropylethylamine, pyridine, dimethylaminopyridine, etc.) to coexist in the reaction system, the reaction velocity can be raised and/or the yield can be improved. Besides, addition of a crown ether (e.g. 18-crown-6) or a quaternary ammonium salt (e.g. tetraethylammonium chloride, benzyl trimethylammonium chloride, cetyl trimethylammonium chloride, etc.) to the reaction system often serves to improve the results of the reaction. In these cases, the reaction may be conducted in a two-phase system of such a solvent as above and water. Further, as is often used, especially when chloride is employed as the reagent, addition of an iodine ion source such as potassium iodide, sodium iodide, etc. to the reaction system may bring about a favorable result.

The alkylation can also be conducted by using as analkylating reagent diazoalkanes such as diazomethane, etc. The reaction is conducted preferably in a solvent such as alcohols (e.g. methanol, etc.), ethers (e.g. diethylether, tetrahydrofuran, etc.) and esters (e.g. ethyl acetate, etc.), etc., and, as a reaction accelarator, boron trifluoride or fluoro-boron, for example, may be added. The reaction is conducted at $-20°$ C.$\sim 30°$ C.

The alkylation can be conducted also by employing as the reagent O-alkyl-N,N'-disubstituted isourea (e.g. O-methyl, O-ethyl, O-benzyl-N,N'-dicyclohexyl isourea, etc.). The solvent is exemplified by ethers (e.g. tetrahydrofuran, dioxane, etc.), halogenated hydrocarbons (e.g. dichloromethane, chloroform and carbon tetrachloride), esters (e.g. ethyl acetate, etc.) or aromatic hydrocarbons (e.g. benzene, toluene, xylene, etc.). The reaction temperature is about 40° C.~150° C.

The said alkylation and alkenylation can be conducted also by allowing a reagent having a reactive unsaturated bond [e.g. alkenes (e.g. isobutylene, methyl acrylate, ethyl acrylate, acrylonitrile, methacrylonitrile, etc.) alkynes (e.g. methylpropiolate, cyanoacetylene, etc.)] to react with compound [46]. These reactions are preferably conducted in a solvent [e.g. ethers (e.g. diethylether, dioxane, tetrahydrofuran, etc.), haloganated hydrocarbon (e.g. dichloromethane, etc.), etc.] in the coexistence of an acid (e.g. sulfuric acid, etc.) or a base [e.g. alkali metal alkoxide (e.g. sodium methylate, etc.), tertiary amine (e.g. N-methyl morpholine, etc.), or quarternary ammonium salt (e.g. benzyltrimethyl ammonium hydroxide, etc.), etc.]. The reaction temperature is about $-20°$ C.$\sim 50°$ C.

The substitution reaction employing Compound [50] can be conducted by using alkanol, alkenol, alkynol, cycloalkanol, aryl hydroxy compounds, heterocyclic hydroxy compounds and alkyl metals or amine salts thereof. In order to enhance the nucleophilic properties of these alcohols and hydroxy compounds, use of the corresponding salts is desirable. The amount of these alcohols or hydroxy compounds to be used is usually $1 \sim 100$ molar equivalent, and when it is a simple alcohol such as methanol, ethanol, etc., it may be used also as solvent. As the solvent are employable any ones which are capable of dissolving Compound [50] and the reaction reagent relatively well, but alcohols e.g. methanol, ethanol, etc., solvents of high polarity e.g. acetone, acetonitrile, N,N-dimethylformamide, N,N-dimethylacetamide, dimethylsulfoxide, sulfolane, etc. are preferably used to bring about favorable results. The reaction temperature is about $-10°$ C.$\sim 100°$ C., and the reaction time is $1 \sim 24$ hours.

By allowing a silver salt such as silver oxide or alkali metal alcoholate or amines to co-exist in the reaction system, the reaction rate can often be raised or the yield can be improved. Addition of a crown ether or a phase-transfer catalyst serves to bring about similar results.

Compound [58], a compound of the general formula [1] wherein $R^3$ and/or $R^4$ are/is $OSiR^{22}R^{23}R^{24}$, can be prepared by subjecting Compound [46] to silyl-etherification. Reaction conditions of the silyl-etherification are essentially the same as those of etherification of Compound [46]-Compound [57], and, as the silyl-etherifying agent, silyl halide (especially chloride) is preferably employed. Use of about $1 \sim 3$ molar equivalent of a silyl-etherifying agent is sufficient for attaining the purpose, and allowing a suitable amount of a base to coexist in the reaction system brings about favorable results. As the base are exemplified by triethylamine, diisopropylethylamine, imidazole, etc. As the reaction solvent, use is preferably made of N,N-dimethylformamide, N,N-dimethylsulfoxide, dimethylfulfoxide, sulfolane, hexamethyl phosphorotriamide, etc. The reaction temperature is about $-30°$ C.$\sim 50°$ C., preferably about $0°$ C.$\sim 25°$ C., and the reaction time is about $1 \sim 10$ hours.

Compounds of the general formula [1] wherein $R^3$ and/or $R^4$ are/is organic residual group through sulfur atom are prepared by a method as described below. Compound [59], a compound of the general formula [1] wherein $R^3$ and/or $R^4$ are/is $SR^{25}$, can be prepared by subjecting e.g. Compound [50] to afore-mentioned conversion reaction of Compound [11]→Compound [12]. Compounds of the general formula [1] wherein $R^3$ and/or $R^4$ are/is organic residual group through nitrogen atom are prepared by a method as described below.

Compound [60], a compound of the general formula [1] wherein $R^3$ and/or $R^4$ are/is $NR^{26}R^{27}$, can be prepared by, for example, subjecting Compound [51] to reduction to obtain reduced compound [61] whose $R^3$ and/or $R^4$ are/is amino group, which is, upon necessity, subjected to alkylation, then to alkylation or acylation or sulfonylation or phosphorylation. This conversion reaction can be conducted in a manner similar to afore-mentioned conversion reaction of Compound [15]→Compound [16]→Compound [17], and phosphorylation of Compound [61] or an N-alkyl derivative thereof can be conducted by a manner similar to the afore-mentioned phosphorylation of Compound [46]→Compound [56].

Compound [60] can be prepared also by subjecting amine or an alkali metal salt of Compound [50] to a substitution reaction. Conditions required in such reactions are almost similar to those in the substitution reaction using alcohols or hydroxyl derivatives of Compound [50], but, in general with an, amine, the reaction is often conducted milder conditions due to its relatively high nucleophilic property.

The starting materials employable in the method of this invention are those described in, for example, U.S. Pat. No. 3,625,055 and they can be prepared by methods similar to those described in the literature references cited above.

Thus-obtained objective compounds [1] can be isolated and refined by per se conventional means such as concentration, sovent-extraction, chromatography, crystallization, recrystallization, etc.

Compound [1] of this invention, when having an acid group such as carboxylic acid, sulfonic acid, phosphoric acid, etc. at its $R^1 \sim R^4$ portion, may form a salt with a base. As the base are mentioned inorganic bases e.g. sodium, potassium, lithium, calcium, magnesium-hydroxide, ammonia, etc. and organic bases e.g. pyridine, collidine, triethylamine, triethanolamine, etc., or the like.

And, in case of having a basic group such as an amino group, a substituted amino group, etc. at the $R^1 \sim R^4$ portion, Compound [1] may be in the form of an acid addition salt. As such acid addition salts are mentioned hydrochloride, hydrobromide, hydroiodide, nitrate, sulfate, phosphate, benzoate, maleate, fumarate, succinate, tartrate, citrate, oxalate, glyoxylate, asparaginate, methanesulfonate, 1,2-ethanedisulfonate, benzenesulfonate, etc.

When Compound [1] is obtained in the free form, it may be led to a salt by conventional means, or, conversely, the one obtained in the form of a salt may be led to the free form by conventional means.

Compound [1], depending on cases, may form an internal salt, and these cases are also included in the present invention.

Steric isomers of Compound [1] can be independently or as a suitable admixture of them used as anti-microbial agents.

Thus-obtained Compound [1] shows strong antibacterial activity against Gram positive bacteria and also against some of Gram negative ones. Compound [1] shows strong antibacterial actions against macrolide-resistant *Staphylococcus aureus* and methicillin.cephem-resistant *Staphylococcus aureus* (MRSA), is well absorbed from digestive tracts and is stable in the body. Compound [1] shows antibacterial activity against Mycoplasma. Besides, toxicity of Compound [1] is low.

As described heretofore, Compound [1] of the present invention has excellent antimicrobial activities and its toxicity is low. Therefore, it can be used as an antibacterial agent for the treatment of microbial infections of animals (e.g. domestic fowl, sheep, dog, cat, rabbit, cow, horse, monkey, man) and for the treatment of animals infected with Micoplasma, and, besides, can be used as an additive to feedstuff for the purpose of preventing animals from being infected with microorganisms or of promoting their growth.

The daily dosage of Compound [1] or a salt thereof varies with administration methods, species of animals to which it is to be administered and purposes of administration, but it is usually about 0.01~1000 mg/kg, more preferably about 0.1~300 mg/kg in terms of Compound [1].

Compound [1] or a pharmceutically acceptable salt thereof can be administered orally as, for example, tablets, granules, capsules, drops, etc. prepared by mixing with a suitable pharmcologically acceptable carrier, excipient and diluent by a conventional means, or non-orally as injections prepared by incorporating into a sterile carrier.

In producing the above-described oral pharmaceutical preparations such as tablets, there can suitable be formulated binding agents (e.g., hydroxylpropyl cellulose, hydroxylpropylmethyl cellulose, macrogol, etc.), disintegrating agents (e.g., starch, carboxymethylcellulose calcium, etc.), excipients (e.g., lactose, starch, etc.), lubricants (e.g., magnesium stearate, talc, etc.) and the like.

In manufacturing non-oral or parenteral pharmaceutical preparations, such as injectable solutions, there can suitably be formulated isotonizing agents (e.g. glucose, D-sorbitol, D-mannitol, sodium chloride, etc.), preservatives (e.g., benzyl alcohol, chlorobutanol, methyl p-oxybenzoate, propyl p-oxybenzoate, etc.), buffering agent (e.g., phosphate buffers, sodium acetate buffer, etc.) and the like.

EXAMPLES

The following reference examples and working examples illustrate the present invention more specifically.

The abbreviations used in Tables 1 to 9 in Examples indicate by the following manner:

Cy: 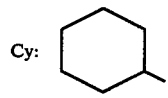

ThMe: 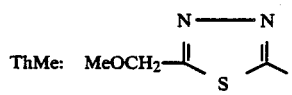

Pyn: 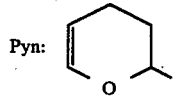

Pipe: 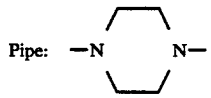

ThPe: 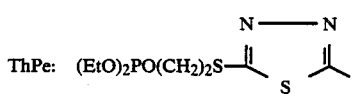

2-Py: 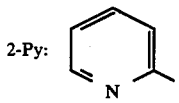

ThSm: 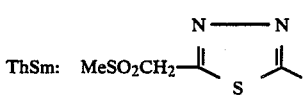

-continued

3-Py: 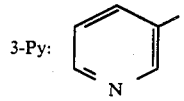

ThOh: 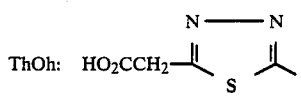

4-Py: 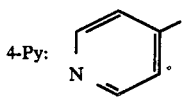

Ph: 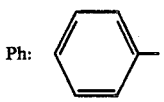

Piri: 

Me:  CH₃—

Mor: 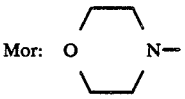

Et: CH₃CH₂—

Pr: CH₃(CH₂)₂— iPr: (CH₃)₂CH—

Bu: CH₃(CH₂)₃— tBu: (CH₃)₃C—

Pyr: 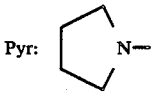

Ac: CH₃CO—

TeEn: 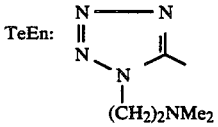

TeEO: 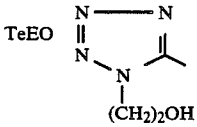

TeM: 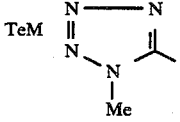

L-Ala: 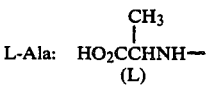

-continued

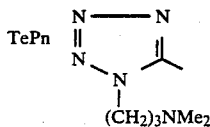
TePn
(CH₂)₃NMe₂

All NMR's shown in the Example, unless otherwise specified, were mesured by 90 MHz in CDCl₃.

The note of "DM" shows that NMR is mesured in DMSO-d⁶ in addition to CDCl₃.

"N.A." indicates uncertain proton among the signals. IR's were mesured by use of KBr and shown by cm⁻¹.

EXAMPLES

The following reference examples and working examples illustrate the present invention more specifically.

REFERENCE EXAMPLE 1

Preparation of lankacidin C 8,14-diacetate

In 50 ml of pyridine was dissolved 5.0 g of lankacidin A. To the solution was added 25 ml of acetic anhydride. The mixture was stirred at room temperature for two hours. The resultant was left standing overnight at room temperature, to which was added 600 ml of ice-water. Precipitates then formed were collected by filtration and dissolved in ether. The ether layer was separated and dried over MgSO₄, from which ether was distilled off. The residue was cooled to yield crystals. The crystals were collected by filtration, washed with ether, and then dried to give 3.418 g of the above-titled compound.

NMR (90 MHz, CDCl₃) δ: 1.30(d, 3H, J=8 Hz), 1.37(s, 3H), 1.54(s, 3H), 1.89(s, 3H), 2.01(s, 3H), 2.04(s, 3H), 2.16~2.60(m, 5H), 2.44(s, 3H), 4.40(dt, 1H, J=12 Hz & 3 Hz), 4.70(d, 1H, J=14 Hz), 5.05(q, 1H, J=8 Hz), 5.20~5.87(m, 6H), 6.26(d, 1H, J=14 Hz), 8.06(d, 1H, J=10 Hz).

IR (KBr): 3410, 1735, 1730, 1710, 1685, 1235 cm⁻¹.

REFERENCE EXAMPLE 2

Preparation of 3-(2-hydroxypropionamido)-lankone 8,14-diacetate (lankacidinol 8,14-diacetate)

In 250 ml of methanol was dissolved 5.5 g of lankacidin C-8,14-diacetate and the solution was cooled with ice-water, to which was added dropwise a solution of 120 mg of sodium borohydride in 15 ml of methanol, followed by stirring for 30 minutes at the same temperature. To the mixture was added 1 ml of acetic acid, then methanol was distilled off to leave crystals. The crystals were dissolved in ethyl acetate (ca. 150 ml), washed with water, then dried. The solvent was distilled off, and the residue was subjected to a column chromatography with 250 g of silica gel using ethyl acetate-benzene (2:1) as solvent to give 1.5827 g of the title compound (an isomer of a larger Rf value, assumed as 2'-L-compound), 1.7803 g of the title compound (an isomer showing a smaller Rf value, assumed as 2'-D-compound) and 1.7344 g of the above-titled compound (2'-DL-compound).

2'-(L)-compound:
NMR (90 MHz, CDCl₃) δ: 1.30(d, 3H, J=7 Hz), 1.37(s, 3H), 1.40(d, 3H, J=7 Hz), 1.54(s, 3H), 1.88(s, 3H), 2.02(s, 3H), 2.04(s, 3H), 2.17~2.60(m, 5H), 3.67(s, 1H), 4.21(q, 1H, J=7 Hz), 4.28~4.56(m, 1H), 4.72(d, 1H, J=10 Hz)5.05(q, 1H, J=7 Hz), 5.20~5.90(m, 6H), 6.29(d, 1H, J=14 Hz), 7.66(d, 1H, J=10 Hz).

IR (KBr): 3380, 1750, 1730, 1715, 1680, 1250 cm⁻¹

2'-(D)-compound:
NMR (90 MHz, CDCl₃) δ: 1.24~1.49(m, 9H), 1.55(s, 3H), 1.88(s, 3H), 2.03(s, 3H), 2.05(s, 3H), 2.16~2.60(m, 5H), 3.70(s, 1H), 4.10~4.55(m, 2H), 4.70(d, 1H, J=10 Hz), 5.03(q, 1H, J=7 Hz), 5.22~5.88(m, 6H), 6.30(d, 1H, J=14 Hz), 7.66(d, 1H, J=10 Hz).

IR (KBr): 3400, 1740, 1725, 1715, 1670, 1245 cm⁻¹.

REFERENCE EXAMPLE 3

Preparation of 3-(2-hydroxypropionamido)-lankone 14-acetate (lankacidinol 14-acetate)

In 500 ml of methanol was dissolved 20.0 g of lankacidin A. The solution was cooled with ice-water, to which was added dropwise with stirring 600 mg of sodium borohydride dissolved in 60 ml of methanol, followed by stirring for 40 minutes. To the mixture was added 2 ml of acetic acid, then methanol was distilled off to leave crystals, which were dissolved in ethyl acetate-tetrahydrofuran (2:1, ca. 600 ml), then washed with water, and then dried over MgSO₄. The solvent was evaporated to give crystals. To the crystals was added a mixture of ethyl acetate and ether (1:2), and the crystals were collected by filtration, washed with the same solvent mixture, and dried to give 19.4 g of the title compound, which was an about 1:1 mixture of the isomers at 2'-position.

NMR (90 MHz, CDCl₃-DMSO-d₆) δ: 1.25~1.50(m, 9H), 1.53(s, 3H), 1.87(s, 3H), 2.02 (s, 3H), 2.2~2.6(m, 5H), 3.8~4.3(m, 2H), 4.45(m, 1H), 4.69(m, 1H), 5.25~5.85(m, 6H), 6.30(d, 1H, J=14 Hz), 7.82 & 7.87(each d, 1H, J=10 Hz), IR (KBr): 1740, 1720(sh.), 1706, 1634, 1234, 1010, 956 cm⁻¹.

REFERENCE EXAMPLE 4

Preparation of 3-(2-acetoxypropionamido)-lankone 8,14-diacetate (lankacidinol 2',8,14-triacetate)

In 140 ml of pyridine was dissolved 19.3 g of 3-(2-hydroxypropionamido)-lankone 14-acetate. To the solution was added 70 ml of acetic anhydride. The mixture was stirred for 4 hours and then left standing overnight at room temperature. The reaction mixture was poured into ice-water (ca. 1.3 l) and precipitates were collected by filtration. The precipitates were dissolved in ethyl acetate-tetrahydrofuran (small volume). The aqueous layer was discarded, the organic layer was dried over MgSO₄ and concentrated. To the concentrate was added ether, and the vessel was scratched to cause crystallisation, to which was added a mixture of ether-hexane (1:1, ca. 200 ml). The crystals were collected by filtration, washed with the same solvent system and dried to obtain 18.3 g of the title compound, which was an about 1:1 mixture of the isomers at 2'-position. NMR, IR and TLC data of this product were in agreement with those of the mixtures obtained in the following Reference Example 5 and 6.

REFERENCE EXAMPLE 5

Preparation of 3-(2-(L)-acetoxypropionamido)-lankone 8,14-diacetate(lankacidinol 2',8,14-triacetate)

In 10 ml of pyridine was dissolved 1.019 g of 3-(2-(L)-hydroxy-propionamido)-lankone 8,14-diacetate (the isomer showing a larger Rf value). To the solution was added 5 ml of acetic anhydride, and the mixture was stirred for 2.5 hours. The mixture was left standing overnight at room temperature and then poured into ice-water (ca. 80 ml). The resulting precipitate was collected by filtration and re-dissolved in ethyl acetate-ether. The aqueous layer was discarded and the organic layer was dried over MgSO$_4$. The solvent was distilled off to leave crystals, to which was added ether, followed by collecting by filtration and drying to obtain 950.1 mg of the above-titled compound, m.p. 209°-211° C. (decomp.).

NMR (90 MHz, CDCl$_3$) δ: 1.30(d, J=7 Hz, 17-Me), 1.42(s, 2-Me), 1.46(d, J=7 Hz, 2'-Me), 1.54(s, 11-Me), 1.88(s, 5-Me), 2.02 and 2.04(each s, 8-OAc, 14-OAc), 2.1~2.7(m, 9-H$_2$, 15-H$_2$, 17-H), 2.19(s, 2'-OAc), 4.42(m, 16-H), 4.67(d, J=11 Hz, 4-H), 4.9~5.9(m, 2'-H, 8-H, 3-H, 6-H, 7-H, 10-H, 13-H, 14-H), 6.27(d, J=15 Hz, 12-H), 7.36(d, J=10 Hz, NH).

IR (KBr): 3430, 1730, 1705, 1675, 1500, 1368, 1240, 1022 cm$^{-1}$.

REFERENCE EXAMPLE 6

Preparation of 3-(2-(D)-acetoxypropionamido)-lankone 8,14-diacetate

Using 0.995 g of 3-(2-(D)-hydroxypropionamido)-lankone 8,14-diacetate (the isomer showing a smaller Rf value) obtained in Reference Example 2, similar process to that of Reference Example 5 was followed to give 745.1 mg of the above-titled compound, m.p. 163°-165° C.

NMR (90 MHz, CDCl$_3$) δ: 1.30(d, J=7 Hz, 17-Me), 1.33(s, 2-Me), 1.40(d, J=7 Hz, 2'-Me), 1.53(s, 11-Me), 1.86(s, 5-Me), 2.00 & 2.03(each s, 8-OAc, 14-OAc), 2.1~2.7(m, 9-H$_2$, 15-H$_2$, 17-H), 2.23(s, 2'-OAc), 4.37(m, 16-H), 4.67(d, J=11 Hz, 4-H), 4.9~5.9(m, 2'-H, 8-H, 3-H, 6-H, 7H, 10-H, 13-H, 14-H), 6.28(d, J=15 Hz, 12-H), 7.18(d, J=10 Hz, NH).

IR (KBr): 3430, 1730, 1706, 1684, 1506, 1366, 1240, 1020, 960 cm$^{-1}$.

REFERENCE EXAMPLE 7

Preparation of lankacidin C 8-benzyl carbonate

In 4.5 ml of pyridine was dissolved 459 mg of lankacidin C. The solution was cooled with ice-water, to which was added while stirring 0.343 ml of carbobenzoxychloride. The stirring was continued for 30 minutes at the same temperature, then for 1.5 hour at room temperature. The resultant was left standing overnight at room temperature, to which was added ice-water (ca. 50 ml), followed by extraction with ethyl acetate. The ethyl acetate layer was washed with 1N HCl and water in sequence, then dried over MgSO$_4$. The solvent was distilled off, and the residue was subjected to a silica-gel (50 g) column chromatography. Elution was conducted with ethyl acetate-chloroform (1:1), and the eluate was fractionated by 10 g each. The 12th~the 18th fractions were combined and concentrated to give 71.65 mg of the above-titled compound as an oily product, which was left standing in a freezer to become crystals, m.p. 185°-187° C. (decomp.)

NMR (90 MHz, CDCl$_3$) δ: 1.29(d, J=7 Hz, 17-Me), 1.35(s, 2-Me), 1.52(s, 11-Me), 1.88(s, 5-Me), 2.1~2.7(m, 9-H$_2$, 15-H$_2$, 17-H), 2.43(s, COCOCH$_3$), 4.07(m, 8-H), 4.41(m, 16-H), 4.66(d, J=11 Hz, 4-H), 5.11(s, C$_6$H$_5$CH$_2$), 5.1~5.8(m, 3H, 6-H, 7-H, 10-H, 13-H, 14-H), 6.30(d, J=15 Hz, 12-H), 7.32(s, C$_6$H$_5$), 8.05(d, J=10 Hz, NH).

IR (KBr): 1738, 1708, 1680, 1500, 1314, 1252, 1136, 962 cm$^{-1}$.

$[\alpha]_D^{26}$ −161.8° (c=0.555, CHCl$_3$).

REFERENCE EXAMPLE 8

Preparation of lankacidin C 8-benzyl carbonate

The 22nd~the 33rd fractions of the column chromatography conducted in Reference Example 7 were combined and concentrated to obtain 65.15 mg of the title compound as an oily product. which was left standing in a freezer to become crystals, m.p. 182°-184° C. (decomp.).

NMR (90 MHz, CDCl$_3$) δ: 1.24(d, J=7 Hz, 17-Me), 1.36(s, 2-Me), 1.54(s, 11-Me), 1.88(s, 5-Me), 2.0~2.7(m, 9-H$_2$, 15-H$_2$, 17-H), 2.44(s, COCOCH$_3$), 4.2~5.1(m, 16-H, 4-H, 13-H, 8-H, 14-H), 5.11(s, C$_6$H$_5$CH$_2$), 5.1~6.0(m, 3-H, 6-H, 7-H, 10-H), 6.14(d, J=15 Hz, 12-H), 7.33(s, C$_6$H$_5$), 8.06(d, J=10 Hz, NH).

IR (KBr): 1740, 1706, 1682, 1380, 1354, 1256, 1162, 1000, 960 cm$^{-1}$. $[\alpha]_D^{26}$ −140.9° (c=0.46, CHCl$_3$).

REFERENCE EXAMPLE 9

Preparation of lankacidin C 8,14-bischloroacetate

In 10 ml of dichloromethane was suspended 459 mg of lankacidin C. To the suspension were added 366 mg of 4-dimethylaminopyridine and 513 mg of monochloroacetic anhydride. The mixture was stirred for 8.5 hours at room temperature, followed by being left standing overnight. The resultant was washed with water, then dried over MgSO$_4$. The dichloromethane was evaporated to leave crystals. To the crystals was added ether, and the insoluble crystals were filtered off. The filtrate was concentrated. The concentrate was purified by means of preparative TLC using TLC-plates (manufactured by Merck, Art. No. 5715, 20×20 cm, 2 plates, developing solvent: ethyl acetate-hexane (2:1)) to give 3.9 mg of the above-titled compound as a colorless oily product.

NMR (90 MHz, CDCl$_3$) δ: 1.31(d, J=7 Hz, 17-Me), 1.38(s, 2-Me), 1.53(s, 11-Me), 1.90(s, 5-Me), 2.2~2.7(m, 9-H$_2$, 15-H$_2$, 17-H), 2.45(s, COCOCH$_3$), 4.01 and 4.03(each s, ClCH$_2$×2), 4,43(m, 16-H), 4.72(d, J=10 Hz, 4-H), 5.0~6.1(m, 8-H, 3-H, 6-H, 7-H, 10-H, 13-H, 14-H), 6.32(d, J=15 Hz, 12-H), 8.05(d, J=10 Hz, NH).

IR (KBr): 1740, 1704, 1680, 1252, 1160, 960 cm$^{-1}$.

REFERENCE EXAMPLE 10

Preparation of lankacidin A8-benzoate

In 5 ml of pyridine was dissolved 501 mg of lankacidin A. To the solution was added, while stirring under cooling with ice-water, dropwise 0.174 ml of benzoyl chloride. Five minutes later, the ice-water bath was removed, and the mixture was stirred at room temperature. Thirty-five minutes later, 0.087 ml of benzoyl chloride was further added, followed by stirring for further 30 minutes. The resultant was poured into ice-water and the resulting precipitate was extracted with ethyl acetate. The ethyl acetate layer was washed with 1N HCl and an aqueous NaCl solution in sequence, followed by dring over MgSO$_4$. The solvent was distilled off to leave crystals, to which was added a mixture of ether and petroleum ether (1:1). The crystals were collected by filtration and washed with the same solvent and then dried to give 476.8 mg of the above-titled compound, m.p. 221°-223° C. (decomp.).

NMR (90 MHz, CDCl₃) δ: 1.32(d, J=7 Hz, 17-Me), 1.38(s, 2-Me), 1.59(s, 11-Me), 1.92(s, 5-Me), 2.02(s, OAc), 2.2~2.7(m, 9-H₂, 15-H₂17-H), 2.43(s, COCOCH₃), 4.32(m, 16-H), 4.73(d, J=11 Hz), 4-H), 5.2~5.9(m, 8-H, 3-H, 6-H, 7-H, 10-H, 13), 14-H), 6.32(d, J=15 Hz, 12-H), ~7.5(m, 3H, C₆H₅), ~8.1(m, 3H, C₆H₅, NH).

IR (KBr): 1708, 1356, 1270, 1240, 1112, 952 cm⁻¹.

$[α]_D^{25}$ −124.2° (c=0.48, CHCl₃).

REFERENCE EXAMPLE 11

Preparation of the esterase for 14-O-deacylation

In a 40 l vessel was put 5 l of the culture filtrate of *Streptomyces rochei* var. volubilis No. T-2636 (IFO 12507, FERM P-6155) [the culture filtrate described in the working example disclosed on an official gazette of Toku Ko Sho 47-20959], to which was added to 20 l of 95% ethanol. The mixture was stirred sufficiently and then left standing for 12 hours at 10° C. or below. The supernatant was removed by means of a siphon to leave a slurry consisting of white precipitates and liberated products. This slurry was subjected to centrifuge (5°~10° C., 2000×g or more). The soil-like substance thus obtained was dried in vacuo at 10° C. or below for one full day (50 μHg or below) to give a greyish white enzyme preparation.

REFERENCE EXAMPLE 12

Preparation of lankacidin C

In 20 ml of methanol was dissolved 102 mg of lankacidin A. To the solution was added a 80 ml aqueous solution of 2.0 g of the enzyme prepared in Reference Example 11. The mixture was stirred at room temperature for 35 minutes, then methanol was distilled off. The residue was extracted with methyl isobutyl ketone-tetrahydrofuran (1:1). The extract was dried on MgSO₄, then the solvent was distilled off. To the residue was added ether to give a white powdery crystalline substance, which was collected by filtration and dried to obtain 24.85 mg of the title compound. This product was in agreement with lankacidin C obtained by a fermentative method in NMR, IR and TLC.

REFERENCE EXAMPLE 13

Preparation of lankacidin C-8-acetate

In a mixture of 20 ml of methanol and 10 ml of tetrahydrofuran was dissolved in 109 mg of lankacidin C 8,14-diacetate. To the solution was added 80 ml of an aqueous solution of 2.0 g of the enzyme prepared in Reference Example 11, and the mixture was stirred at room temperature for 50 minutes. Methanol and tetrahydrofuran were distilled off, and the residue was extracted with chloroform-acetone. The organic layer was dried over MgSO₄, then the solvent was distilled off. The residue was subjected to a silica gel (60 g) column chromatography, then elution was conducted with ethyl acetate-chloroform (2:1), and the eluate was fractionated by 8 g each. The 25th~the 36th fractions were combined and the solvent distilled off to yield 42.2 mg of the title compound as white crystals NMR (90 MHz, CDCl₃) δ: 1.28(d, J=7 Hz, 17-Me), 1.37(s, 2-Me), 1.55(s, 11-Me), 1.90(s, 5-Me), 2.03(s, OAc), 2.2~2.6(m, 9-H₂, 15-H₂,17-H), 2.43(s, COCOCH₃), 4.33(m, 14-H), 4.43(m, 16-H), 4.70(d, J=11 Hz, 4-H), 5.05(m, 8-H), 5.2~5.9(m, 3-H, 6-H, 7-H, 10-H, 13-H), 6.15(d, J=15 Hz, 12-H), 8.07(d, J=10 Hz, NH).

IR (KBr): 3475, 1728, 1706, 1672, 1256, 1234 (sh.), 1012, 960 cm⁻¹.

REFERENCE EXAMPLE 14

Preparation of lankacidin C

In a mixture of 10 ml of dichloromethane and 1 ml of acetic acid was dissolved 405 mg of lankacidin C 8,14-bis(2,2,2-trichloroethylcarbonate). To the solution was added 810 mg of zinc powder, and the mixture was stirred at room temperature for 5 hours. To the resultant was added ethyl acetate, then insolubles were filtered off by using filter aid, and the filtrate was concentrated. The concentrate was subjected to a silica gel (50 g) column chromatography, elution being conducted with a mixture of tetrahydrofuran and chloroform (1:2). The eluate was fractionated by 10 g each. The 20th~the 28th fractions were combined, from which was distilled off the solvent. To the residue was added ether, and the wall of the vessel was scratched to yield 45.5 mg of the above-titled compound. This product was in agreement with the lakacidin C obtained by a fermentative process in NMR, IR, and TLC.

REFERENCE EXAMPLE 15

Preparation of lankacidin C

In 1 ml of tetrahydrofuran was dissolved 60.4 mg of lankacidin C 8,14-bistrimethylsilylether. To the solution was added 0.3 ml of 1N HCl, and the mixture was stirred for 10 minutes at room temperature. To the resultant was added ethyl acetate, which was washed with water, an aqueous solution of sodium hydrogencarbonate and an aqueous saline solution in sequence, then dried over Na₂SO₄, followed by distilling off the solvent to leave 50.5 mg of the above-titled compound. This product was in agreement with the lankacidin C obtained by a fermentative process in NMR, IR and TLC.

REFERENCE EXAMPLE 16

Preparation of lankacidin C

In 0.5 ml of tetrahydrofuran was dissolved 20.6 mg of lankacidin C 8,14-bis(dimethyl-t-butylsilylether). To the solution was added 0.1 ml of 2N HCl, and the mixture was stirred at room temperature for 2.5 hours. To the resultant was added ethyl acetate, which was washed with water, an aqueous solution of sodium hydrogencarbonate and an aqueous saline solution in sequence, then dried over Na₂SO₄, followed by distilling off the solvent. The residue was purified by means of preparative TLC using TLC-plates (manufactured by Merck, Art. No. 5715, 20×20 cm, developing solvent: ethyl acetate) to obtain 17.4 mg of the above-titled compound. This product was in agreement with the lankacidin C obtained by a fermentative process in NMR, IR AND TLC.

REFERENCE EXAMPLE 17

Preparation of 8-dehydroxy-8-chloro-lankacidin A

In 5 ml of dichloromethane was dissolved 501 mg of lankacidin A. To the solution was added 89 μl of pyridine, and the mixture was cooled at 0° C. To the resultant mixture was added dropwise 80.2 μl of thionyl chloride. The mixture was stirred at the same temperature for 30 minutes, to which was added ice-water, followed by extraction with dichloromethane. The extract was dried over MgSO$_4$ and the solvent was distilled off. The residue was subjected to a silica gel (50 g) column chromatography with ethyl acetate-chloroform (1:4). The eluate was fractionated by 15 g each. The 11th to the 23rd fractions were combined and the solvent was distilled off. To the residue was added ether, whereupon crystals separated, to which was added ether-petroleum ether (1:2). The crystals were collected by filtration and then dried to obtain 339.9 mg of the title compound as crystals.

NMR (90 MHz, CDCl$_3$) δ: 1.30(d, J=7 Hz, 17-Me), 1.37(s, 2-Me), 1.56(s, 11-Me), 1.91(s, 5-Me), 2.02(s, OAc), 2.1∼2.8(m, 15-H$_2$, 17-H), 9-H$_2$), 2.45(s, COCOCH$_3$), 4.14(m, 8-H), 4.42(m, 16-H), 4.71(d, J=11 Hz, 4-H), 5.2∼5.9(m, 3-H, 6-H, 10-H, 13-H, 14-H), 6.26(d, J=15 Hz, 12-H), 8.06(d, J=10 Hz, NH).

IR (KBr): 3380, 1740, 1708, 1700(sh.), 1506, 1356, 1256, 1224, 1138, 946 cm$^{-1}$.

Mass m/e: 519(M$^+$), 483(M$^+$-36(HCl)), 459(M$^+$-60(AcOH), 423(M$^+$-36-60).

REFERENCE EXAMPLE 18

Preparation of bis[3-(2-(D)-hydroxy-propionamido)-lankone 8,14-diacetate-2'(O)-yl]sulfone In 0.5 ml of pyridine was dissolved 86.7 mg of 3-(2-(D)-hydroxypropionamido)-lankone 8,14-diacetate. To the solution was added 12.7 μl of thionyl chloride under cooling with ice-water, and the mixture was stirred for 20 minutes. To the resultant was added ice-water and the precipitates formed were collected by filtration, followed by recrystallization from ethyl acetate-ether to give 60.1 mg of the above-titled compound, m.p. 182°–183° C.

NMR (90 MHz, CDCl$_3$) δ: 1.20∼1.67(m, 12H), 1.87(s, 3H), 2.02(s, 3H), 2.04(s, 3H), 2.15∼2.60(m, 5H), 4.60∼5.90(m, 10H), 6.28(d, 1H, J=14 Hz), 7.40∼7.70(m, 1H).

IR (KBr): 3420, 1730, 1715, 1690, 1245 cm$^{-1}$.

REFERENCE EXAMPLE 19

Preparation of 2-(2,2,2-trichloroethoxycarbonyl)phenylacetyl chloride (1) In 80 ml of dichloromethane was suspended 5.0 g of phenylmalonic acid. To the suspension was added 4.25 g of 2,2,2-trichloroethanol. To the mixture was added little by little 5.8 g of dicyclohexylcarbodiimide under ice-cooling while stirring. The stirring was continued at the same temperature for 20 minutes, then at room temperature for further 3 hours. The precipitates formed were then filtered off, and the precipitates were washed with a small volume of dichloromethane. The filtrate was washed with water and extracted with an aqueous solution of sodium hydrogen-carbonate. The aqueous layer was acidified with 1N HCl, then extracted with ethyl acetate. The extract was washed with saline, dried over MgSO$_4$ and the solvent was distilled off. To the residue was added chloroform and some precipitated phenyl malonic acid was removed by filtration. The filtrate was concentrated to give 3.2 g of crude phenyl malonic acid mono(2,2,2-trichloroethyl)ester.

NMR (60 MHz, CDCl$_3$) δ: 4.78(s, 3H), 7.37 (s, 5H), 9.5(br., 1H).

(2) In 12 ml of thionyl chloride was dissolved 3.2 g of the above-mentioned phenyl malonic acid mono(2,2,2-trichloroethyl)ester. The solution was stirred at 50° C. for one hour, which was then refluxed for 30 minutes. The reaction solution was concentrated, followed by removing distillate by means of a vacuum pump (bath temperature: 140° C.) to obtain 2.4 g of the above-titled compound as an orange oily product.

NMR (60 MHz, CDCl$_3$) δ: 4.80 (s, 2H), 5.13 (s, H), 7.40(s, 5H).

REFERENCE EXAMPLE 20

Preparation of D-(−)-2-(2,2,2-trichloroethoxycarbonylamino)-phenylacetyl chloride In 12 ml of dichloromethane was suspended 0.88 g of D(−)-2-(2,2,2-trichloroethoxycarbonylamino)phenylacetic acid. To the suspension, while stirring under ice-cooling, were added one drop of N,N-dimethylformamide and 0.6 ml of oxalyl chloride. The mixture was stirred for 10 minutes at the same temperature and for 20 minutes at room temperature, followed by concentration to obtain 1.0 g of a crude product of the above-titled compound as yellowish orange oily substance.

NMR (60 MHz, CDCl$_3$) δ: 4.77(s, 2H), 5.62(br, d, 1H, J=7 Hz), 5.9(br., 1H), 7.42(s, 5H).

EXAMPLE 1

Preparation of lankacidin C 8,14-bis(2,2,2-trichloroethyl)carbonate

In 4.5 ml of pyridine was dissolved 459 mg of lankacidin C. To the solution was added dropwise while stirring 0.413 ml of chloroformic acid 2,2,2-trichloroethyl ester. The mixture was stirred for one hour and then poured into 50 ml of ice-water, followed by extraction with ethyl acetate. The extract was washed with 1N HCl and water in sequence, then dried over MgSO$_4$. The solvent was distilled off. To the residue was added ether, which was then cooled, whereupon crystals occurred. After addition of a mixture of ether and petroleum ether (1:1), the crystals were collected by filtration and dried to obtain 411.4 mg of the above-titled compound, m.p. 188°–190° C. (decomp.)

NMR (90 MHz, CDCl$_3$) δ: 1.30(d, J=7 Hz, 17-Me), 1.38(s, 2-Me), 1.56(s, 11-Me), 1.90(s, 5-Me), 2.2∼2.7(m, 9-H$_2$, 15-H$_2$, 17-H), 2.43(s, COCOCH$_3$), 4.45(m, 16-H), 4.65∼5.2(m, 4-H, 8-H), 4.73 (s, CCl$_3$CH$_2$×2), 5.2∼5.9(m, 3-H, 6-H), 7-H, 10-H. 13-H, 14-H), 6.35(d, J=15 Hz, 12-H), 8.05(d, J=10 Hz, NH).

IR (KBr): 1754, 1712, 1690, 1380, 1246 cm$^{-1}$.

EXAMPLE 2

Preparation of lankacidin A 8-(2,2,2-trichloroethylcarbonate)

In 5 ml of pyridine was dissolved 501 mg of lankacidin A. To the solution was added dropwise while stirring under cooling with ice-water 0.206 ml of 2,2,2-trichloroethyl chloroformate. The mixture was stirred at the same temperature for 5 minutes, then at room temperature for 70 minutes. To this was added 0.103 ml of 2,2,2-trichloroethyl chloroformate, followed by stirring for further 30 minutes. The resultant was poured into ice-water, which was extracted with ethyl acetate. The extract was washed with 1N HCl and saline solution in sequence, then dried over MgSO$_4$. The solvent was distilled off. To the residue was added ether, which was then cooled, whereupon crystals separated. After addition of a mixture of ether and petroleum ether (1:1), the crystals were collected by filtration and dried to obtain 429 mg of the above-titled compound, m.p. 214°–216° C. (decomp.)

NMR (90 MHz, CDCl$_3$)δ: 1.30(d, J=7 Hz, 17-Me), 1.37(s, 2-Me), 1.54(s, 11-Me), 1.89(s, 5-Me), 2.00(s, OAc), 2.2~2.7(m, 9-H$_2$, 15-H$_2$, 17-H), 2.43(s, COCOCH$_3$), 4.40(m, 16-H), ~4.7(m, 4-H), 4.73(s, CCl$_3$CH$_2$), ~4.95(m, 8-H), 5.2~5.9(m, 3-H, 6-H, 7-H, 10-H, 13-H, 14-H), 6.27(d, J=15 Hz, 12-H), 8.05(d, J=10 Hz, NH).

IR (KBr): 1746, 1706, 1684, 1376, 1358, 1242, 946 cm$^{-1}$.

$[\alpha]_D^{24}$ −185.6° (c=0.555, CHCl$_3$).

EXAMPLE 3

Preparation of lankacidin A 8-dibenzylphosphate

In 40 ml of benzene was dissolved 5.24 g of dibenzyl phosphite. To the solution was added 2.67 g of N-chlorosuccinimide, and the mixture was stirred for 2 hours under nitrogen atmosphere. Insolubles were removed by decantation, then the benzene was distilled off. The residue was added to a solution of 1.003 g of lankacidin A in 25 ml of pyridine at −60° C. The temperature of the mixture was raised to −20° C. over 30 minutes. The mixture was stirred at −20° C. for 2.5 hours, which was then poured into 100 ml of ice-water, followed by extraction with ethyl acetate. The extract was washed with 2N HCl, water, an aqueous solution of sodium hydrogencarbonate, water and saline in sequence, followed by dring over Na$_2$SO$_4$. The solvent was then distilled off, and the residue was subjected to a silica gel column chromatography, eluting with ethyl acetate-hexane (1:1) then with ethyl acetate-benzene (1:1). The eluate containing the desired product was concentrated and the residue crystallized from ehter to yiled 1.2747 g of the above-titled compound, m.p. 179° C. (decomp.).

NMR (90 MHz, CDCl$_3$)δ: 1.30(d, J=7 Hz, 3H), 1.37(s, 3H), 1.50(s, 3H), 1.83(s, 3H), 2.00(s, 3H), 2.15~2.60(m, 5H), 2.46(s, 3H), 4.27~4.76(m, 3H), 4.98(d, J=9 Hz, 2H), 5.01(d, J=9 Hz, 2H), 4.95~5.80(m, 6H), 6.22(d, J=15 Hz, 1H), 7.30(s, 5H), 7.31(s, 5H), 8.07(br, d, J=10 Hz, 1H).

IR (KBr): 1755, 1735, 1715, 1695, 1245, 1010 cm$^{-1}$.

$[\alpha]_D^{24}$ −159.6° (c=0.0535, CHCl$_3$).

EXAMPLE 4

Preparation of lankacidin A 8-diethylphosphate

In place of dibenzyl phosphite in Example 3, diethyl phosphite was employed, and the reaction was carried out in a manner similar to Example 3 to give the above-titled compound in a yield of 85.5%, m.p. 151°–152° C.

NMR (90 MHz, CDCl$_3$): 1.27(d, J=7 Hz, 3H), 1.28(t, J=7 Hz, 6H), 1.38(s, 3H), 1.54(s, 3H), 1.90(s, 3H), 2.01(s, 3H), 2.02~2.70(m, 5H), 2.45(s, 3H), 3.88~4.80(m, 7H), 5.15~5.85(m, 6H), 6.25(d, J=15 Hz, 1H), 8.09(br. d, J=10 Hz, 1H).

IR (KBr): 1735, 1715, 1690, 1265, 1245, 1015 cm$^{-1}$.

$[\alpha]_D^{24}$ −203.6° (c=0.47, CHCl$_3$).

EXAMPLE 5

Preparation of lankacidin A 8-dimethyl phosphate

In place of dibenzyl phosphite in Example 3, dimethyl phosphate was employed, and the reaction was carried out in a manner similar to Example 3 to give the above-titled compound in a yield of 92.1%, m.p. 138°–140° C.

NMR (90 MHz, CDCl$_3$)δ: 1.30(d, J=7 Hz, 3H), 1.37(s, 3H), 1.54(s, 3H), 1.91(s, 3H), 2.01(s, 3H), 2.20~2.70(m, 5H), 2.44(s, 3H), 3.68(d, J=12 Hz, 3H), 3.70(d, J=12 Hz, 3H), 4.30~4.83(m, 3H), 5.20~5.90(m, 6H), 6.26(d, J=15 Hz, 1H), 8.10(br, d, J=10 Hz, 1H).

IR (KBr): 1735, 1715, 1690, 1245, 1010 cm$^{-1}$.

$[\alpha]_D^{24}$ −216.8° (c=0.5, CHCl$_3$).

EXAMPLE 6

Preparation of lankacidin A 8-diphenylphosphate

Employing a commercially available diphenyl phosphorochloridate, the reaction was carried out in a manner similar to Example 3 to obtain the above-titled compound in a yield of 85.9%, m.p. 153°–154° C. (decomp.).

NMR (90 MHz, CDCl$_3$)δ: 1.29(d, J=7 Hz, 3H), 1.35(s, 3H), 1.51(s, 3H), 1.84(s, 3H), 2.00(s, 3H), 2.15~2.65(m, 5H), 2.47(s, 3H), 4.25~4.95(m, 3H), 5.15~5.85(m, 6H), 6.23(d, J=15 Hz, 1H), 7.00~7.50(m, 10H), 8.08(br, d, J=10 Hz, 1H).

$[\alpha]_D^{24}$ −161.6° (c=0.485, CHCl$_3$).

EXAMPLE 7

Preparation of lankacidin C 8-acetate-14-dibenzylphosphate

In place of lankacidin A in Example 3, lankacidin C-8-acetate was employed, and the reaction was carried out in a manner similar to Example 3 to obtain the title compound in a yield of 37.9%. As this product was unstable to silica gel, this was not subjected to column chromatography but purified by means of recrystallization (solvent: AcOEt-Et$_2$O), m.p. 137°–138° C.

NMR (90 MHz, CDCl$_3$)δ: 1.16(d, J=7 Hz, 3H), 1.35(s, 3H), 1.48(s, 3H), 1.87(s, 3H), 2.04(s, 3H), 2.20~2.60(m, 5H), 2.43(s, 3H), 4.20~5.85(m, 9H), 4.96(d, J=8 Hz, 2H), 5.01(d, J=8 Hz, 2H), 6.18(d, J=15 Hz, 1H), 7.31(s, 5H), 7.34(s, 5H), 8.05(br, d, J=10 Hz, 1H).

IR (KBr): 1730, 1710, 1690, 1240, 1010, 965 cm$^{-1}$.

$[\alpha]_D^{24}$ −119.4° (c=0.515, CHCl$_3$).

EXAMPLE 8

Preparation of lankacidin C 8-acetate-14-diethylphosphate

In place of dibenzyl phosphite and lankacidin A in Example, 3, diethyl phosphite and lankacidin C-8-acetate were employed respectively, and the reaction was carried out in a manner similar to Example 3 to obtain the above-titled compound in a yield of 51.8%. As this product was unstable to silica gel, this was not subjected to column chromatography but purified by means of recrystallization (solvent: AcOEt-Et$_2$O), m.p. 163°–164° C.

NMR (90 MHz, CDCl$_3$)δ: 1.20~1.40(m, 12H), 1.56(s, 3H), 1.90(s, 3H), 2.05(s, 3H), 2.25~2.60(m, 5H), 2.45(s, 3H), 3.87~5.90(m, 13H), 6.30(d, J=15 Hz, 1H), 8.06(br, d, J=10 Hz, 1H).

IR (KBr): 1735, 1715, 1695, 1265, 1245, 1035, 970 cm$^{-1}$.

$[\alpha]_D^{24}$ −173.7° (c=0.505, CHCl$_3$).

EXAMPLE 9

Preparation of lankacidin C 8,14-bis(dibenzylphosphate)

In place of lankacidin A in Example 3, lankacidin C was employed, and the reaction was carried out in a manner similar to Example 3 to obtain the above-titled compound in a yield of 72.8%. As this product was unstable to silica gel, this was not subjected to column chromatography but purified by means of recrystallization (solvent: Et$_2$O), m.p. 120°–122° C.

NMR (90 MHz, CDCl$_3$)δ: 1.15(d, J=7 Hz, 3H), 1.34(s, 3H), 1.43(s, 3H), 1.81(s, 3H), 2.05~2.60(m, 5H), 2.45(s, 3H), 4.20~5.85(m, 17H), 6.13(d, J=15 Hz, 1H), 7.30(s, 10H), 7.32(s, 10H), .8.06(br, d, J=10 Hz, 1H).

IR (KBr): 1750, 1715, 1690, 1265, 1010 cm$^{-1}$.

$[\alpha]_D^{24}$ −82.8° (c=0.495, CHCl$_3$).

EXAMPLE 10

Preparation of lankacidin C 8,14-bis(diethylphosphate)

Instead of dibenzyl phosphite and lankacidin A in Example 3, diethyl phosphite and lankacidin C were employed respectively, and the reaction was carried out in a manner similar to Example 3 to obtain the title compound in a yield of 51.1%. As this product was unstable to silica gel, this was not subjected to column chromatography but purified by means of recrystallization (solvent: Et$_2$O), m.p. 153°–154° C.

NMR (90 MHz, CDCl$_3$)δ: 1.10~1.45(m, 18H), 1.54(s, 3H), 1.90(s, 3H), 2.20~2.70(m, 5H), 2.44(s, 3H), 3.85~4.28(m, 8H), 4.28~5.90(m, 9H), 6.25(d, J=15 Hz, 1H), 8.08(br, d, J=10 Hz, 1H).

IR (KBr): 1755, 1715, 1690, 1260, 1035, 990 cm$^{-1}$.

$[\alpha]_D^{24}$ −140.8° (c=0.495, EtOH).

EXAMPLE 11

Preparation of lankacidin C 8,14-bis-(2-methoxyethoxymethylether)

To 459 mg of lankacidin C were added 10 ml of dichloromethane, 0.523 ml of N,N-diisopropylethylamine and 0.343 ml of 2-methoxyethoxymethyl chloride. The mixture was stirred at room temperature for 7.5 hours, which was then left standing overnight. To the mixture was added dichloromethane, followed by washing with an saline then by dring over MgSO$_4$. The solvent was distilled off, and the residue was subjected to a column chromatography of silica gel (50 g), eluting with ethyl acetate-hexane (2:1). The eluate was fractionated by 10 g each, and the 18th-the 28th fractions were combined and concentrated to give 419 mg of the above-titled compound as an oil product.

NMR (90 MHz, CDCl$_3$)δ: 1.25(d, J=7 Hz, 17-Me), 1.37(s, 2-Me), 1.53(s, 11-Me), 1.90(s, 5-Me), 2.2~2.7(m, 9-H$_2$, 15-H$_2$, 17-H), 2.43(s, COCOCH$_3$), 3.36(s, OMe×2), 3.62(A$_2$B$_2$, OCH$_2$CH$_2$O×2), 3.9~4.9(m, 8-H, 14-H, 16-H, 4-H), 4.70(s, OCH$_2$O×2), 5.2~5.8(m, 3-H, 6-H, 7-H, 10-H, 13-H), 6.12(d, J=16 Hz, 12-H), 8.06(d, J=10 Hz, NH).

IR (KBr): 1744, 1706, 1680, 1498, 1354, 1256, 1132, 1100, 1038 cm$^{-1}$.

EXAMPLE 12

Preparation of lankacidin A 8-(2-methoxyethoxymethylether)

In place of lankacidin C in Example 11, 230 mg of lankacidin A was employed, and the reaction was carried out proceed in a manner similar to Example 11 to obtain 159.7 mg of the above-titled compound. The product was further purified by recrystallization from chloroform-hexane. The yield was 105.5 mg. Melting point: 130°–131° C.

NMR (90 MHz, CDCl$_3$)δ: 1.30(d, J=6.5 Hz, 17-Me), 1.37(s, 2-Me), 1.52(s, 11-Me), 1.89(s, 5-Me), 2.01(s, OAc), 2.2~2.55(m, 9-H$_2$, 15-H$_2$, 17-H). 2.44(s, CO-COCH$_3$), 3.35(s, OMe), 3.45~3.8(m, OCH$_2$CH$_2$O), 4.02(m, 8-H), 4.37(m, 16-H), 4.65(d, J=11 Hz, 4-H), 4.70(s, OCH$_2$O), 5.2~5.85(m, 3-H, 6-H, 7-H, 10-H, 13-H, 14-H), 6.27(d, J=15 Hz, 12-H), 8.07(d, J=10 Hz, NH).

IR (KBr): 3420, 2940, 1755(sh.), 1735, 1715, 1685, 1510, 1355, 1235, 1145, 1110, 1080, 1045, 1030 (sh.), 1020, 975 cm$^{-1}$.

EXAMPLE 13

Preparation of lankacidin A 8-methoxymethylether

Employing 230 mg of lankacidin A and methoxymethylchloride respectively in place of lankacidin C and 2-methoxyethoxymethylchloride in Example 11, the reaction was carried out in a manner similar to Example 11 to yield 276.7 mg of the above-titled compound, which was recrystallized from chloroform-ether to give 147.2 mg of a pure product, m.p. 200°–202° C.

NMR (90 MHz, CDCl$_3$)δ: 1.30(d, J=6.5 Hz, 17-Me), 1.37(s, 2-Me), 1.48(s, 11-Me), 1.89(s, 5-Me), 2.01(s, OAc), 2.2~2.55(m, 9-H$_2$, 15-H$_2$, 17-H), 2.43(s, CO-COCH$_3$), 3.32(s, OMe), 3.97(m, 8-H), 4.44(m, 16-H), 4.57 & 4.64(ABq, J=10 Hz, OCH$_2$O), 4.67(d, J=11 Hz, 4-H), 5.25~5.85(m, 3-H, 6-H, 7-H, 10-H, 13-H, 14-H), 6.29(d, J=15 Hz, 12-H), 8.06(d, J=10 Hz, NH).

IR (KBr): 3400, 2950, 1750 (sh.), 1730, 1710, 1690, 1510, 1440, 1360, 1320, 1240, 1150, 1100, 1070, 1040, 1020, 960, 910, 745 cm$^{-1}$.

EXAMPLE 14

Preparation of lankacidin C 8,14-ditrimethylsilylether

In 120 ml of N,N-dimethylformamide was dissolved 13.79 g of lankacidin C, and the solution was cooled with ice water. To the solution were added dropwise, while stirring, 10.46 ml of triethylamine then 9.52 ml of chlorotrimethylsilane. The mixture was stirred for 3 hours at the same temperature, for which was further added 2.0 ml of triethylamine, followed by stirring at the same temperature for one hour. To the resultant was added ether, which was washed with water and saline in sequence and then dried over MgSO$_4$. The solvent was distilled off and the residue was subjected to a silica gel column chromatography, eluting with ethyl acetate-hexane (1:1). The desired fractions were combined and concentrated to obtain 17.0 g of the above-titled compound.

NMR (90 MHz, CDCl$_3$)δ: 0.01(s, 18H), 1.25(d, J=7 Hz, 3H), 1.36(s, 3H), 1.88(s, 3H), 2.10~2.60(m, 5-H), 2.43(s, 3H), 3.90~4.55(m, 3H), 4.70(d, J=10 Hz, 1H), 5.19~5.85(m, 5H), 6.05(d, J=15 Hz, 1H), 8.10(d, J=10 Hz, 1H).

IR (KBr): 1750, 1710, 1695 cm$^{-1}$.

EXAMPLE 15

Preparation of lankacidin C 8,14-bis(dimethyl-t-butylsilylether)

In 50 ml of N,N-dimethylformamide was dissolved 9.19 g of lankacidin C, and the solution was cooled with ice-water. To the solution were added while stirring 4.08 g of imidazole and 6.78 g of t-butyldimethylchlorosilane, followed by stirring at the same temperature for 10 minutes and at room temperature for one hour. To the resultant was added ether, and the mixture was washed with water, 1N HCl and saline in sequence, followed by drying over MgSO$_4$. The solvent was distilled off to leave 13.8 g of the above-titled compound, which was further refined by means of reprecipitation from chloroform-petroleum ether, m.p. 218°-220° C.

NMR (90 MHz, CDCl$_3$)δ: 0.00(s, 12H), 0.82(s, 18H), 1.20(d, J=6 Hz, 3H), 1.33(s, 3H), 1.48(s, 3H), 1.86(s, 3H), 2.00~2.60(m, 5H), 2.40(s, 3H), 3.80~4.70(m, 4H), 5.00~5.83(m, 5H), 6.00(d, J=15 Hz, 1H), 8.06(d, J=10 Hz, 1H).

IR (KBr): 1755, 1715, 1690, 1060 cm$^{-1}$.

EXAMPLE 16

Prepration of lankacidinol 8,14-bis(2,2,2-trichloroethyl)carbonate[2'-(L)isomer] and lankacidinol 8,14-bis(2,2,2-trichloroethyl)carbonate[2'-(D)isomer] (assignment of configuration at 2'-position is tentative—the same applies to the subsequent Examples)

In 10 ml of tetrahydrofuran was dissolved 810 mg of lankacidin C 8,14-bis(2,2,2-trichloroethyl)carbonate. To the solution was added 10 ml of methanol, to which was added while cooling with ice-water 12.0 mg of sodium borohydride under stirring, followed by stirring for further 20 minutes at the same temperature. To the resultant was added 0.1 ml of acetic acid and the solvent was distilled off. The residue was subjected to a column chromatography on 50 g of silica gel, followed by development with ethyl acetate-chloroform (1:1). The eluate was fractionated by 10 g each. The 15th to the 20th fractions were combined and concentrated to yield 188.4 mg of the above-titled compound[2'-(L)isomer], the 25th to the 40th fractions were combined and concentrated to yield 316.9 mg of the above-titled compound[2'-(D)isomer], and the 21st~the 24th fractions were combined and concentrated to yield 151.5 mg of a mixture of them.

2'-(L)-isomer: Melting point-172°-174° C. (decomp.)
NMR (90 MHz, CDCl$_3$)δ: 1.30(d, J=7 Hz, 17-Me), 1.40(s, 2-Me), 1.43(d, J=7 Hz, 2'-Me), 1.57(s, 11-Me), 1.89(s, 5-Me), 2.2~2.7(m, 9-H$_2$, 15-H$_2$, 17-H), 4.26(q, J=7 Hz, 2'-H), 4.45(m, 16-H), 4.6~5.2(m, 4-H, 8-H), 4.74(s, CCl$_2$X), 5.2~5.9(m, 3-H, 6-H, 7-H, 10-H, 13-H, 14-H), 6.35(d, J=15 Hz, 12-H), 7.55(d, J=10 Hz, NH).

IR (KBr): 1746, 1708, 1652, 1376, 1244, 812 cm$^{-1}$.
$[\alpha]_D^{24}$ −140.2° (c=0.565, CHCl$_3$).

2'-(D)-isomer: Melting point-152°-154° C. (decomp.)
NMR (90 MHz, CDCl$_3$)δ: 1.23(d, J=7 Hz, 17-Me), 1.40(s, 2-Me), 1.40(d, J=7 Hz, 2'-Me), 1.57(s, 11-Me), 1.89(s, 5-Me), 2.2~2.7(m, 9-H$_2$, 15-H$_2$, 17-H), 4.23(q, J=7 Hz, 2'-H), 4.45(m, 16-H), 4.6~5.2(m, 4-H, 8-H), 4.76(s, CCl$_3$CH$_2$×2), 5.2~5.9(m, 3-H, 6-H, 7-H, 10-H, 13-H, 14-H), 6.37(d, J=15 Hz, 12-H), 7.46(d, J=10 Hz, NH).

IR (KBr): 1752, 1705, 1654, 1376, 1242, 936, 814 cm$^{-1}$.
$[\alpha]_D^{24}$ −133.6° (c=0.59, CHCl$_3$).

EXAMPLE 17

Preparation of O(2')-acetyl lankacidinol 8,14-bis(2,2,2-trichloroethyl)carbonate (2'-(L)isomer]

In 7.45 ml of pyridine was dissolved 1.132 g of lankacidinol 8,14-bis(2,2,2-trichloroethyl)carbonate[2'-(L)-isomer]. To the solution was added 3.73 ml of acetic anhydride, and the mixture was stirred at room temperature for 2.5 hours and then left standing overnight. The resultant was poured into ice-water (ca. 100 ml), which was then extracted with ethyl acetate. The extract was washed with 1N-HCl then with water, followed by drying over MgSO$_4$. The solvent was distilled off, and, to the residue was added a small volume of ether to cause crystallization. To the resultant was added petroleum ether, and the crystals were collected by filtration, followed by drying to afford 1.0723 g of the above-titled compound, m.p. 194°-196° C. (decomp.).

NMR (90 MHz, CDCl$_3$)δ:1.30 (d, J=7 Hz, 17-Me), 1.42 (s, 2-Me), 1.45 (d, J=7 Hz, 2'-Me), 1.55 (s, 11-Me), 1.88 (s, 5-Me), 2.19 (s, OAc), 2.2~2.8 (m, 9-H$_2$15-H$_2$, 17-H), 4.45 (m, 16-H), 4.6~5.1 (m, 4-H, 8-H), 4.74 (s, CCl$_3$CH$_2$×2), 5.13 (q, J=7 Hz, 2'-H), 5.3~6.0 (m, 3-H, 6-H, 7-H, 10-H, 13-H, 14-H). 6.35 (d, J=15 Hz, 12-H), 7.36 (d, J=10 Hz, NH).

IR (KBr): 1740, 1706, 1668, 1370, 1276, 1244, 958, 932, 808 cm$^{-1}$.
$[\alpha]_D^{24}$ −125° (c=0.525, CHCl$_3$).

EXAMPLE 18

Preparation of O(2')-acetyl lankacidinol 8,14-bis(2,2,2-trichloroethyl)carbonate [2'-(D)-isomer]

Employing 2.029 g of lankacidinol-8,14-bis(2,2,2-trichloroethyl)carbonate[2'-(D)-isomer], the reaction was carried out in a manner similar to Example 17 to obtain 2.0223 g of the above-titled compound, m.p. 150°-152° C. (decomp.).

NMR (90 MHz, CDCl$_3$) δ: 1.28 (d, J=7 Hz, 17-Me), 1.35 (s, 2-Me), 1.41 (d, J=7 Hz, 2'-Me), 1.56 (s, 11-Me), 1.88 (s, 5-Me), 2.23 (s, OAc), 2.2~2.8 (m, 9-H$_2$, 15-H$_2$, 17-H), 4.41 (m, 16-H), 4.6~5.2 (m, 4-H, 8-H), 4.74 (s, CCl$_3$CH$_2$×2), 5.19 (q, J=7 Hz, 2'-H), 5.2~6.0 (m, 3-H, 6-H, 7-H, 10-H, 13-H, 14-H), 6.35 (d, J=15 Hz, 12-H), 7.24 (d, J=10 Hz, NH).

IR (KBr): 1746, 1700, 1676, 368, 1240, 1070, 936,808 cm$^{-1}$.
$[\alpha]_D^{24}$ −100.2° (c=0.505, CHCl$_3$).

EXAMPLE 19

Preparation of 3-(2-oxo-1-thioxo)propylamino-lankone 8,14-diacetate

In 2 ml of dichloromethane was dissolved 54.3 mg of lankacidin C 8,14-diacetate. To the solution were added 72.8 μl of pyridine and 450 mg of phosphorus pentasulfide. The mixture was stirred at room temperature, to which was added, 70 minutes later, 150 mg of phosphorus pentasulfide supplementally, followed by stirring for further 7 hours. To the resultant was added dichloromethane, then insolubles were filtered off. The filtrate was concentrated, and the concentrate was subjected to separation by means of preparative TLC. (Plates: manufactured by Merck, At. No. 5715, 20×20 cm, 2 plates, developing solvent: ethyl acetate-chloroform (1:4)) to give 27.3 mg of the title compound, m.p. 219°-221° C. (decomp.).

NMR (90 MHz, CDCl$_3$) δ: 133 (d, J =7 Hz, 17-Me), 1.39 (s, 2-Me), 1.56 (s, 11-Me), 1.96 (s, 5-Me), 2.01 and 2.03 (each s, 8 -OAc, 14-OAc), 2.2~2.6 (m, 9-H$_2$, 15-H$_2$, 17-H), 2.64 (s, CSCOCH$_3$), 4.43 (m, 16-H), 4.70 (d, J=10 Hz, 4-H), 5.06 (m, 8-H), 5.25~6.2 (m, 3-H, 6-H, 7-H, 10-H, 13-H, 14-H), 6.30 (d, J=15 Hz, 12-H), 10.00 (d, J=10 Hz, NH).

IR (KBr): 1728, 1706, 1368, 1240, 1208, 1014, 960 cm$^{-1}$.

EXAMPLE 20

Preparation of 3-(2-(L)-acetoxy-1-thioxo)propylamino-lankone 8,14-diacetate

In 4 ml of dichloromethane was dissolved 117.4 mg of 3-(2-(L)-acetoxypropionamido)-lankone 8,14-diacetate. To the solution were added 16.2 μl of pyridine and 100 mg of phosphorus pentasulfide, and the mixture was stirred at room temperature. To the resultant was added 100 mg each of phosphorus pentasulfide 15 minutes later and 3 hours later, respectively. To the mixture was added dichloromethane 4.5 hours later, then insolubles were filtered off. The filtrate was concentrated, and the concentrate was subjected to chromatogrpahy on the column of 30 g of silica-gel, developing with ethyl acetate-chloroform (1:4), and the eluate was fractionated in 5-g portions. The 18th to the 25th fractions were combined and concentrated to obtain 31.1 mg of the above titled compound, m.p. 241°–243° C. (decomp.).

NMR (90 MHz, CDCl$_3$) δ:1.33 (d, J=7 Hz, 17-Me), 1.43 (s, 2-Me), 1.56 (s, 11-Me), 1.59 (d, J=7 Hz, 2'-Me), 1.95 (s, 5-Me), 2.03 (s, 8-OAc, 14-OAc), 2.20 (s, 2'-OAc), 2.2~2.6 (m, 9-H$_2$, 15-H$_2$, 17-H), 4.43 (m, 16-H), 4.63 (d, J=11 Hz, 4-H), 4.9~6.3 (m, 2'-H, 8-H, 3-H, 6-H, 7-H, 10-H, 13-H, 14-H), 6.27 (d, J=15 Hz, 12-H), 9.23 (d, J=9 Hz, NH).

IR (KBr): 3360, 1758, 1734, 1708, 1370, 1240 cm$^{-1}$.

EXAMPLE 21

Preparation of 3-(2-(D)-acetoxy-1-thioxo)propylamino-lankone 8,14-diacetate

Employing 117.4 mg of 3-(2-(D)-acetoxypropionamide)lankon 8,14-diacetate, the reaction was carried out in a manner similar to Example 20 to obtain 17.6 mg of the above-title compound, m.p. 155°–157° C.

NMR (90 MHz, CDCl$_3$) δ:1.32 (d, J=7 Hz, 17-Me), 1.33 (s, 2-Me), 1.53 (d, J=7 Hz, 2'-Me). 1.55 (s, 11-Me), 1.95 (s, 5-Me), 2.01 and 2.03 (each s, 8-OAc, 14-OAc), 2.2~2.7 (m, 9-H$_2$, 15H$_2$, 17-H), 2.27 (s, 2'-OAc), 4.40 (m, 16-H), 4.68 (d, J=12 Hz, 4-H), 4.9~6.3 (m, 2'-H, 8-H, 3-H, 6-H, 7-H, 10-H, 13-H, 14-H), 6.27 (d, J=15 Hz, 12-H), 8.95 (d, J=9 Hz, NH).

IR (KBr): 1735, 1704, 1365, 1238 cm$^{-1}$.

EXAMPLE 22

Preparation of 3-(2-(DL)-acetoxy-1-thioxo)propylamino-lankone 8,14-diacetate In 328 ml of pyridine was dissolved 9.63 g of 3-(2-(DL)-acetoxypropionamido)-lankone 8,14-diacetate. To the solution was added 8.2 g of phosphorus pentasulfide, and the mixture was stirred at 110° C. for 9 hours. Pyridine was distilled off, and to the residue was added dichloromethane (ca. 500 g) to loosen the residue, then insolubles were filtered off through cotton. The filtrate was concentrated, and the concentrate was subjected to a column chromatography using 250 g of silica gel, developing with ethyl acetate-chloroform (1:4). The desired fractions were combined and subjected to concentration to leave crystals, to which was added ether. The crystals were collected by filtration and then dried to obtain 3.136 g of the above titled compound.

EXAMPLE 23

Preparation of 3-(2-(L)-hydroxy-1-thioxo)propylamino-lankone 8,14-diacetate and 3-(2-(D)-hydroxy-1-thioxo)propylaminolankone, 8,14-diacetate Employing 603 mg of 3-(2-oxo-1-thioxo)-propylaminolankone 8,14-diacetate, the reaction was carried out in a manner similar to Example 16 to give 158.5 mg of the above titled compound [2'-(L)isomer], 281.2 mg of the above titled compound [2'-(D)isomer] and 136.8 mg of a mixture of them.

2'-(L)isomer, m.p. 220°–222° C. (decomp.)

NMR (90 MHz, CDCl$_3$) δ:1.32 (d, J=7 Hz, 17-Me), 1.40 (s, 2-Me), 1.53 (d, J=7 Hz, 2'-Me), 1.55 (s, 11-Me), 1.96 (s, 5-Me), 2.01 and 2.03 (each s, 8-OAc, 14-OAc), 2.2~2.7 (m, 9-H$_2$, 15-H$_2$, 17-H), 3.40 (d, J=5 Hz, OH), 4.3~4.7 (m, 16-H, 2'-H), 4.73 (d, J=11 Hz, 4-H), 5.04 (m, 8-H), 5.2~6.4 (m, 3-H, 6-H, 7-H, 10-H, 13-H, 14-H), 6.28 (d, J=15 Hz, 12-H), 9.40 (d, J=10 Hz, NH).

IR (KBr): 3320, 1728, 1706, 1495, 1360, 1240, 1014, 960 cm$^{-1}$.

$[α]_D^{25}$ −352.9° (c=0.505, CHCl$_3$).

2'-(D)isomer, m.p. 157°–159° C.

NMR (90 MHz, CDCl$_3$) δ:1.32 (d, J=7 Hz, 17-Me), 1.40 (s, 2-Me), 1.49 (d, J=7 Hz, 2'-Me), 1.56 (s, 11-Me), 1.96 (s, 5-Me), 2.02 and 2.03 (each s, 8-OAc, 14-OAc), 2.2~2.7 (m, 9-H$_2$, 15-H$_2$, 17-H), 3.47 (d, J=5 Hz, OH), 4.32 (m, 16-H), ~4.6 (m, 2'-H), 4.73 (d, J=11 Hz, 4-H), 5.06 (m, 8-H), 5.25~6.4 (m, 3-H, 6-H, 7-H, 10-H, 13-H, 14-H), 6.31 (d, J=15 Hz, 12-H), 9.37 (d, J=10 Hz, NH).

IR (KBr): 1728, 1708, 1496, 1368, 1240, 1014, 958 cm$^{-1}$.

$[α]_D^{25}$ −314.5° (c=0.525, CHCl$_3$).

EXAMPLE 24

Preparation of 3-(2-oxo-1-thioxo)propylaminolankone 8,14-bis(2,2,2-trichloroethyl)carbonate In 20 ml of pyridine was dissolved 810 mg of lankacidin C 8,14-bis(2,2,2-trichloroethyl)carbonate. To the solution was added 500 mg of phosphorus pentasulfide, and the mixture was stirred at 80° C. for 75 minutes. Pyridine was distilled off. To the residue was added dichloromethane (ca. 50 ml), and the mixture was loosened well, then insolubles were filtered off through cotton. The filtrate was concentrated, and the concentrate was subjected to chromatography on the column of 50 g of silica gel. Elution was conducted using ethyl acetate-chloroform (1:10). The eluate was fractionated by 10 g each. The 9th-the 14th fractions were combined and concentrated, to which was added a small volume of ether to cause crystallization, followed by drying the crystals to obtain 203.2 mg of the above-titled compound, m.p. 190°–192° C. (decomp.).

NMR (90 MHz, CDCl$_3$) δ: 1.33 (d, J=7 Hz, 17-Me), 1.39 (s, 2-Me), 1.56 (s, 11-Me), 1.95 (s, 5-Me), 2.2~2.7 (m, 9-H$_2$, 15-H$_2$, 17-H), 2.64 (s, CSCOCH$_3$), 4.46 (m, 16-H), 4.5~5.2 (m, 4-H, 8-H), 4.72 (s, CCl$_3$CH$_2$×2), 5.2~6.2 (m, 3-H, 6-H, 7-H, 10-H, 13-H, 14-H), 6.36 (d, J=15 Hz, 12-H), 9.96 (d, J=9 Hz, NH).

IR (KBr): 1756, 1708, 1378, 1248, 1210 cm$^{-1}$.

EXAMPLE 25

Preparation of
3-(2-(L)-hydroxy-1-thioxo)propylamino-lankone
8,14-bis(2,2,2-trichloroethyl)-carbonate and
3-(2-(D)-hydroxyl-1-thioxo)-propylamino-lankone
8,14-bis(2,2,2-trichloroethyl)carbonate Employing 1.68 g of 2-(2-oxo-1-thioxo)propylamino-lankon-8,14-bis(2,2,2-trichloroethyl)carbonate, the reaction was carried out in a manner similar to Example 16 to give 480 mg of the above titled compound [2'-(L)isomer] and 839 mg of the above titled compound [2'-(D)isomer].

2'-(L)isomer, m.p. 155°–157° C. (decomp.):
NMR (90 MHz, CDCl$_3$) δ: 1.32 (d, J=7 Hz, 17-Me), 1.42 (s, 2-Me), 1.53 (d, J=7 Hz, 2'-Me), 1.57 (s, 11-me), 1.97 (s, 5-Me), 2.1~2.8 (m, 9-H$_2$, 15-H$_2$, 17-H), 2.94 (d, J=5 Hz, OH), 4.3~5.2 (m, 16-H, 4-H, 8-H, 2'-H), 4.74 (s, CCl$_3$CH$_2$×2), 5.2~6.35 (m, 3-H, 6-H, 7-H, 10-H, 13-H, 14-H), 6.36 (d, J=15 Hz, 12-H), 9.32 (d, J=10 Hz, NH).
IR (KBr): 1758, 1714, 1508, 1380, 1248, 940, 820 cm$^{-1}$.

2'-(D)isomer, m.p. 178°–180° C. (decomp.)
NMR (90 MHz, CDCl$_3$) δ:1.32 (d, J=7 Hz, 17-Me), 1.42 (s, 2-Me), 1.50 (d, J=7 Hz, 2'-Me), 1.57 (s 11-Me), 1.97 (s, 5-Me), 2.1~2.8 (m, 9-H$_2$, 15-H$_2$, 17-H), 3.06 (d, J=5 Hz, OH), 4.3~5.2 (m, 16-H, 4-H, 8-H, 2'-H), 4.74 (s, CCl$_3$CH$_2$×2), 5.2~6.35 (m, 3-H, 6-H, 7-H, 10-H, 13-H, 14-H), 6.37 (d, J=15 Hz, 12-H), 9.32 (d, J=10 Hz, NH).
IR (KBr): 1754, 1708, 1502, 1380, 1244, 940, 818 cm$^{-1}$.

EXAMPLE 26

Preparation of
3-(2-(L)-acetoxy-1-thioxo)propylamino-lankone
8,14-(2,2,2-trichloroethyl)carbonate Employing 397 mg of 3-(2-(L)-hydroxy-1-thioxo)-propylamino-lankone 8,14-bis(2,2,2-trichloroethyl)carbonate, the reaciton was carried out in a manner similar to Example 17 to obtain 387 mg of the above titled compound, m.p. 137°–139° C.
NMR (90 MHz, CDCl$_3$) δ: 1.35 (d, J=7 Hz, 17-Me), 1.46 (s, 2-Me), 1.59 (s, 11-Me), 1.62 (d, J=7 Hz, 2'-Me), 1.98 (s, 5-Me), 2.22 (s, OAc), 2.2~2.8 (m, 9-H$_2$, 15-H$_2$, 17-H), 4.3~5.2 (m, 16-H, 4-H, 8-H, 2'-H), 4.74 (s, CCl$_3$CH$_2$×2), 5.2~6.3 (m, 3-H, 6-H, 7-H, 10-H, 13-H, 14-H), 6.36 (d, J=15 Hz, 12-H), 9.22 (d, J=10 Hz, NH).
IR (KBr): 1756, 1710, 1506, 1376, 1244, 1046, 940 cm$^{-1}$.
$[\alpha]_D^{24} = -202°$ (c=0.5, CHCl$_3$).

EXAMPLE 27

Preparation of
3-(2-(D)-acetoxy-1-thioxo)propylamino-lankone
8,14-bis(2,2,2-trichloroethyl)carbonate Employing 754 mg of 3-(2-(D)-hydroxy-1-thioxo)-propylamino-lankone 8,14-bis(2,2,2-trichloroethyl)carbonate, the reaction was carried out in a manner similar to Example 17 to obtain 728 mg of the above titled compound, m.p. 194°–196° C. (decomp).
NMR (90 MHz, CDCl$_3$) δ: 1.31 (d, J=7 Hz, 17-Me), 1.35 (s, 2-Me), 1.54 (d, J=7 Hz, 2'-Me) 1.58 (s 11-Me), 1.96 (s, 5-Me), 2.26 (s, OAc), 2.0~2.7 (m, 9-H$_2$, 15-H$_2$, 17-H), 4.3~5.2 (m, 16-H, 4-H, 8-H, 2'-H), 4.74 (s, CCl$_3$CH$_2$×2), 5.2~6.4 (m, 3-H, 6-H, 7-H, 10-H, 13-H, 14-H), 6.36 (d, J=15 Hz, 12-H), 8.95 (d, J=10 Hz, NH).
IR (KBr): 1748, 1710, 1374, 1244, 1044, 934, 816 cm$^{-1}$.
$[\alpha]_D^{24} = -173.3°$ (c=0.505, CHCl$_3$).

EXAMPLE 28

Preparation of 3-(2-oxo-1-thioxo)propylaminolankone 14-acetate-8-(2,2,2-trichloroethyl)carbonate Employing 1.354 g of lankacidin A 8-(2,2,2-trichlroethyl(carbonate, the reaction was carried out in a manner similar to Example 24 to obtain 270.7 mg of the above title compound, m.p. 237°–238° C. (decomp.).
NMR (90 MHz, CDCl$_3$) δ: 1.33 (d, J=7 Hz, 17-Me), 1.40 (s, 2-Me), 1.57 (s, 11-Me), 1.96 (s, 5-Me), 2.02 (s, OAc), 2.2~2.7 (m, 9-H$_2$, 15H$_2$, 17-H), 2.64 (s, CSCOCH$_3$), 4.44 (m, 16-H), ~4.7 (m, 4-H), 4.73 (s, CCl$_3$CH$_2$×2), ~5.0 (m, 8-H), 5.2~6.2 (m, 3-H, 6-H, 7-H, 10-H, 13-H, 14-H), 6.28 (d, J=15 Hz, 12-H), 9.98(d, J=9 Hz, NH).
IR (KBr): 1742, 1706, 1494, 1378, 1244, 1208, 954 cm$^{-1}$.
$[\alpha]_D^{24} = -305.0°$ (c=0.48, CHCl$_3$).

EXAMPLE 29

Preparation of
3-(2-(L)-hydroxy-1-thioxo)propylamino-lankone
14-acetate-8-(2,2,2-trichloroethyl)carbonate and
3-(2-(D)-hydroxy-1-thioxo)propylamino-lankone
14-acetate-8-(2,2,2-trichloroethyl)carbonate Employing 3.511 g of 3-(2-oxo-1-thioxo)-propylaminolankone 14-acetate-8-(2,2,2-trichloroethyl)carbonate, the reaction was carried out in a manner similar to Example 16 to obtain 1.0942 g of the above titled compound [2'-(L)isomer], 1.0811 g of the above titled compound [2'-(D)isomer] and 725.7 mg of a mixture of them. 2'-(L)-isomer, m.p. 206°–208° C. (decomp.)
NMR (90 MHz, CDCl$_3$) δ: 1.32 (d, J=7 Hz, 17-Me), 1.41 (s, 2-Me), 1.53 (d, J=7 Hz, 2'-Me), 1.57 (s, 11-Me), 1.97 (s, 5-Me), 2.02 (s, OAc), 2.2~2.7 (m, 9-H$_2$, 15-H$_2$, 17-H), 3.05 (d, J=5 Hz, OH), 4.3~5.2 (m, 16-H, 4-H, 8-H, 2'-H), 4.74 (s, CCl$_3$CH$_2$), 5.2~6.35 (m, 3-H, 6-H, 7H, 10-H, 13-H, 14-H), 6.28 (d, J=15 Hz, 12-H), 9.35 (d, J=9 Hz, NH).
IR (KBr): 1748, 1706, 1500, 1372, 1244, 958 (sh.), 940 cm$^{-1}$.
$[\alpha]_D^{24} = 251.8°$ (c=0.51, CHCl$_3$).

2'-(D)isomer, m.p. 214°–216° C. (decomp.):
NMR (90 MHz, CDCl$_3$)δ: 1.31(d, J=7 Hz, 17-Me), 1.41(s, 2-Me), 1.50(d, J=7 Hz, 2'-Me), 1.56(s, 11-Me), 1.97(s, 5-Me), 2.02(s, OAc), 2.2~2.7(m, 9-H$_2$, 15-H$_2$, 17-H), 3.16(d, J=5 Hz, OH), 4.3~5.2(m, 16-H, 4-H, 8-H, 2'-H), 4.73(s, CCl$_3$CH$_2$), 5.2~6.35(m, 3-H, 6-H, 7-H, 10-H, 13-H, 14-H), 6.29 (d, J=14 Hz, 12-H), 9.33(d, J=9 Hz, NH).
IR (KBr): 1754, 1728, 1706, 1498, 1374, 1240, 960(sh), 944 cm$^{-1}$.
$[\alpha]_D^{23} = -259.7°$ (c=0.595, CHCl$_3$)

EXAMPLE 30

Preparation of
3-(2-(L)-acetoxy-1-thioxo)propylamino-lankone
14-acetate-8-(2,2,2-trichloroethyl)carbonate Employing 972.6 mg of 3-(2-(L)-hydroxy-1-thioxo)-propylamino-lankone 14-acetate-8-(2,2,2-trichloroethyl) carbonate, the reaction was carried out in a manner similar to Example 17 to obtain 839.9 mg of the above titled compound, m.p. 188°–190° C.

NMR (90 MHz, CDCl$_3$)δ: 1.33(d, J=7 Hz, 17-Me), 1.45(s, 2-Me), 1.58(s, 11-Me), 1.62(d, J=7 Hz, 2'-Me), 1.98(s, 5-Me), 2.03(s, 14-OAc), 2.2~2.7(m, 9-H$_2$, 15-H$_2$, 17-H), 2.23(s, 2'-OAc). 4.3~5.2(m, 16-H, 4-H, 8-H, 2'-H), 4.76(s, CCl$_3$CH$_2$), 5.2~6.3(m, 3-H, 6-H, 7-H, 10-H, 13-H, 14-H), 6.24(d, J=15 Hz, 12-H), 9.25(d, J=9 Hz, NH).

IR (KBr): 1752, 1730(sh.), 1704, 1380, 1366, 1270(sh.), 1240, 1218(sh.) cm$^{-1}$.

[α]$_D^{25}$ −252.0° (c=0.49, CHCl$_3$).

EXAMPLE 31

Preparation of
3-(2-(D)-acetoxy-1-thioxo)propylamino-lankone 14-acetate-8-(2,2,2-trichloroethyl)carbonate Employing 973.6 mg of 3-(2-(D)-hydroxy-1-thioxo)-propylamino-lankone 14-acetate-8-(2,2,2-trichloroethyl) carbonate, the reaction was carried out in a manner similar to Example 17 to obtain 915.2 mg of the above titled compound, m.p. 222°–224° C. (decomp.).

NMR (90 MHz, CDCl$_3$)δ: 1.32(d, J=7 Hz, 17-Me), 1.35(s, 2-Me), 1.54(d, J=7 Hz, 2'-Me), 1.58(s, 11-Me), 1.97(s, 5-Me), 2.02(s, 14-OAc), 2.2~2.7(m, 9-H$_2$, 15H$_2$, 17-H), 2.27(s, 2'-OAc), 4.3~5.2(m, 16-H, 4-H, 8-H, 2'-H), 4.74(s, CCl$_3$CH$_2$), 5.2~6.3(m, 3-H, 6-H, 7-H, 10-H, 13-H, 14-H), 6.28(d, J=15 Hz, 12-H), 8.98(d, J=10 Hz, NH).

IR (KBr): 1746, 1706, 1508, 1368, 1278, 1242, 1044, 940 cm$^{-1}$.

[α]$_D^{25}$ −217.1° (c=0.515, CHCl$_3$).

EXAMPLE 32

Preparation of 3-phenoxyacetamido-lankone 8,14-diacetate

In 1 ml of dichloromethane was dissolved 60.3 mg of 3-(2-(DL)-acetoxy-1-thioxo)propylamino-lankone 8,14-diacetate. To the solution was added 19.0 mg of triethyloxonium tetrafluoroborate. The mixture was stirred at room temperature for 70 minutes, to which were added 15.4 μl of phenoxyacetyl chloride and 0.1 ml of water. The resultant was stirred vigorously at room temperature, which was then extracted with dichloromethane, and the extract was washed with saline and dried over MgSO$_4$. The solvent was distilled off. The residue was subjected to separation by means of preparative TLC. Plate: manufactured by Merck, Art. No. 5715, 20×20 cm, 2 plates, developing solvent:ethyl acetate-chloroform (1:4)) to obtain 15.5 mg of the title compound, m.p. 217°–218° C. (decomp.).

NMR (90 MHz, CDCl$_3$)δ: 1.29(d, J=7 Hz, 17-Me), 1.30(s, 2-Me), 1.53(s, 11-Me), 1.90(s, 5-Me), 2.00 and 2.03(each s, 8-OAc, 14-OAc), 2.2–2.7(m, 9-H$_2$, 15-H$_2$, 17-H), 4.37(m, 16-H), 4.49(s, OCH$_2$ CO), 4.68(d, J=11 Hz, 4-H), 5.06(m, 8-H), 5.2~6.2(m, 3-H, 6-H, 7-H, 10-H, 13H, 14-H), 6.27(d, J=15 Hz, 12-H), ~7.0 and ~7.35(each m, C$_6$H$_5$), 7.82(d, J=10 Hz, NH).

IR (KBr): 1732, 1708, 1368, 1240 cm$^{-1}$.

Mass m/e: 607(M$^+$), 563(M$^+$−44(CO$_2$)), 447(M$^+$−60(AcOH)), 503(M$^+$−60-44), 487 (M$^+$−60-60), 443(M$^+$−60-60-44)

EXAMPLE 33

Preparation of
3-(2-(DL)-acetoxy-1-ethylthiopropylidene)amino-lankone 8,14-diacetate In 3 ml of dichloromethane was dissolved 180.9 mg of 3-(2-(DL)-acetoxy-1-thioxo)propylamino-lankone 8,14-diacetate. To the solution was added 68.4 mg of triethyloxonium tetrafluoroborate, and the mixture was stirred for 130 minutes. To the resultant was added 1.8 ml of an aqueous solution of 93.6 mg of NaH$_2$PO$_4$.2H$_2$O and 117.6 mg of Na$_2$HPO$_4$. The mixture was shaken, then extracted with dichloromethane. The dichloromethane layer was washed with an aqueous saline solution, dried over MgSO$_4$, followed by concentration to give 158.7 mg of the above titled compound as a solid foam.

IR (KBr): 1740, 1712, 1370, 1240, 1020, 962 cm$^{-1}$.

EXAMPLE 34

Preparation of 3-phenoxyacetamido-lankone 8,14-bis(2,2,2-trichloroethyl)carbonate Employing 87.0 mg of 3-(2-(D)-acetoxy-1-thioxo)-propylamino-lankone 8,14-bis(2,2,2-trichloro)carbonate, the reaction was allowed to proceed in a manner similar to Example 32 to give 13.2 mg of the above titled compound as an oil.

NMR (90 MHz, CDCl$_3$)δ: 1.23(d, J=7 Hz, 17-Me), 1.32(s, 2-Me), 1.59(s, 11-Me), 1.92(s, 5-Me), 2.2~2.8(m, 9-H$_2$, 15-H$_2$, 17-H), 4.42(m, 16-H), 4.50(s, OCH$_2$CO), 4.6~5.2(m, 4-H, 8-H), 4.74(s, CCl$_3$CH$_2$×2), 5.2~5.9(m, 3-H, 6-H, 7-H, 10-H, 13-H, 14-H), 6.15(d, J=15 Hz, 12-H), ~7.0 and ~7.3(m, C$_6$H$_5$), 7.84(d, J=10 Hz, NH).

IR (KBr): 1748, 1706, 1676, 1504, 1486, 1374, 1242, 1200, 958, 940 cm$^{-1}$.

EXAMPLE 35

Preparation of 3-phenoxyacetamido-lankone 8,14-bis(2,2,2-trichloroethyl)carbonate Employing 87.0 mg of 3-(2-(L)-acetoxy-1-thioxo)-propylamino-lankone 8,14-bis(2,2,2-trichloroethyl)carbonate, the reaction was carried out in a manner similar to Example 32 to obtain 14.9 mg of the above titled compound as an oil. This product was in good accord with the compound obtained in Example 34 in the data of TLC, IR and NMR.

EXAMPLE 36

Preparation of 3-phenoxyacetamido-lankone 8,14-bis(2,2,2-trichloroethyl)carbonate Employing 584.8 mg of 3-(2-(DL)-acetoxy-1-thioxo)-propylamino-lankone, 8,14-bis(2,2,2-trichloroethyl)carbonate, the reaction was carried out in a manner similar to Example 32 to obtain 131.4 mg of the above titled compound. (In place of TLC separation, silica gel chromatography was conducted.) This product was in good accord with the compound obtained in Example 34 in the data of TLC, IR and NMR.

EXAMPLE 37

Preparation of
3-[2-(2,2,2-trichloroethoxycarbonyl)phenylacetamido]-lankone 8,14-bis(2,2,2-trichloroethyl)carbonate Employing 2-(2,2,2-trichloroethoxycarbonyl)-phenylacetyl chloride, in place of phenoxyacetyl chloride, the reaction was carried out in a manner similar to Example 36 to obtain 26.0 mg of the above titled compound from 163 mg of 3-(2-(DL)-acetoxy-1-thioxo)-propylaminolankon 8,14-bis(2,2,2-trichloroethyl)carbonate.

NMR (90 MHz, CDCl$_3$)δ: 1.18 and 1.21(3H, each d, J=6.5 Hz, 17-Me), 1.27 and 1.34(3H, each s, 2-Me), 1.56(3H, s, 11-Me), 1.85 and 1.86(3H, each s, 5-Me), 2.25~2.7(5H, m, 9-H$_2$, 15-H$_2$, 17-H), 4.2~4.8 (2H, m, 4-H, 16-H), 4.66(1H, s, C$_6$H$_5$CH), 4.74 and 4.79 (6H, each s, CCl$_3$CH$_2$×3), 4.98(1H, m, 8-H), 5.25~5.7(6H, m, 3-H, 6-H, 7-H, 10-H, 13-H, 14-H), 6.12 and 6.13(1H, each d, J=15 Hz, 12-H), 7.40(5H, br, s, C$_6$H$_5$), ~7.4 and 7.73(1H, each d, J=10 Hz, NH), IR (KBr): 1755, 1710, 1680, 1500, 1450, 1380, 1250, 1140, 1070, 965, 945, 815, 720 cm$^{-1}$.

EXAMPLE 38

Preparation of 3-(2-(DL)-acetoxy-1-methylthiopropylidene)amino-lankone 8,14-diacetate In 200 ml of tetrahydrofuran was dissolved 6.03 g of 3-(2-(DL)-acetoxy-1-thioxo)propylamino-lankon 8,14-diacetate. To the solution were added 6.23 ml of methyl iodide, 100 ml of an aqueous solution of 2.12 g of Na$_2$CO$_3$ and 2.77 g of benzyltrimethylammonium iodide, and the mixture was stirred at room temperaure. After the lapse of 67 hours, 6.23 ml of methyl iodide was further added to the mixture. The resultant was subjected, after 91 hours, to extraction with ethyl acetate. The organic layer was washed with an saline, dried over MgSO$_4$, followed by distilling off the solvent to leave crystals, to which was added a small volume of ether to complete the crystallization, followed by addition of ether-petroleum ether (1:2), the crystals were collected by filtration. The crystals were washed with the same solvent to give 2.2588 g of the above titled compound. The filtrate was concentrated to obtain 3.6589 g of the above titled compound as a solid form. Crystalline substance, m.p. 190°-192° C. (decomp.)

IR (KBr): 1724, 1620, 1362, 1232, 1010, 958 cm$^{-1}$.

EXAMPLE 39

Preparation of 3-(2-(L)-acetoxy-1-methylthiopropylidene)amino-lankone 14-acetate-8-(2,2,2-trichloroethyl)carbonate Employing 73.7 mg of 3-(2-(L)-acetoxy-1-thioxo)-propylamino-lankone 14-acetate-8-(2,2,2-trichloroethyl)carbonate, the reaction was carried out in a manner similar to Example 38 to obtain 31.3 mg of the above titled compound as an oil.

IR (KBr): 1740, 1618, 1366, 1238, 1010, 956, 940 cm$^{-1}$.

EXAMPLE 40

Preparation of 3-phenoxyacetamido-lankone 14-acetate-8-(2,2,2-trichloroethyl)carbonate Employing 73.7 mg of 3-(D)-acetoxy-1-thioxo)-propylamino-lankone 14-acetate-8-(2,2,2-trichloroethyl)carbonate, the reaction was carried out in a manner similar to Example 32 to obtain 11.5 mg of the above titled compound.

NMR (90 MHz, CDCl$_3$) δ: 1.30(d, J=7 Hz, 17-Me), 1.32(s, 2-Me), 1.57(s, 11-Me), 1.93(s, 5-Me), 2.01(s, OAc), 2.1~2.7(m, 9-H$_2$, 15-H$_2$,17-H), 4.50(s, C$_6$H$_5$OCH$_2$), 4.2~5.15(m, 16-H, 4-H, 8-H), 4.74(s, CCl$_3$CH$_2$), 5.15~6.0(m, 3-H, 6-H, 7-H, 10-H, 13-H, 14-H), 6.28(d, J=15 Hz, 12-H), ~7.0 and ~7.3 (m, C$_6$H$_5$), 7.85(d, J=9 Hz, NH).

IR (KBr): 1750, 1708, 1678, 1488, 1376, 1244, 960, 944 cm$^{-1}$.

EXAMPLE 41

Preparation of 3-[D(−)-2-(4-ethyl-2,3-dioxo-1-piperazinecarboxamide)phenylacetamido]lankone 8,14-diacetate Employing D(−)-2-(4-ethyl-2,3-dioxo-1-piperazinecarboxamide)phenylacetyl chloride, the reaction was allowed carried out in a manner similar to Example 32 to obtained 2.9 mg of the above titled compound from 60.3 mg of 3-(2-(DL)-acetoxy-1-thioxo)-propylamino-lankone 8,14-diacetate.

NMR (90 MHz, CDCl$_3$) δ: 1.01(s, 2-Me), 1.20(t, J=7.5 Hz, NCH$_2$CH$_3$), 1.21(d, J=7 Hz, 17-Me), 1.52(s, 11-Me), 1.84(s, 5-Me), 2.00 and 2.04 (each s, 8-OAc, 14-OAc), 2.15~2.6(9-H$_2$, 15-H$_2$, 17-H), 3.51(q, J=7.5 Hz, NCH$_2$CH$_3$), 3.4~3.7 and 3.95~4.15(m, NCH$_2$CH$_2$N), 4.29(m, 16-H), 4.66(d, J=11 Hz, 4-H), 5.07(m, 8-H), 5.1~5.85(m, 3-H, 6-H, 7-H, 10-H, 13-H, 14-H, C$_6$H$_5$CH), 6.26(d, J=15 Hz, 12-H), 6.93(d, J=10 Hz, 3-NH), 7.39(br. s, C$_6$H$_5$), 9.95(d, J=6 Hz, C$_6$H$_5$CHNHCO).

IR (KBr): 1725(sh.), 1712, 1680(sh.), 1500, 1370, 1240, 1175, 1015, 960 cm$^{-1}$.

EXAMPLE 42

Preparation of 3-(2-oxo-1-thioxo)propylaminolankone 14-acetate-8benzoate

Employing 5.369 g of lankacidin C-14-acetate-8-benzoate, the reaction was carried out in a manner similar to Example 24 to obtain 1.0653 g of the above titled compound, m.p. 247°-249° C. (decomp.).

NMR (90 MHz, CDCl$_3$) δ: 1.35(d, J=7 Hz, 17-Me), 1.40 (s, 2-Me), 1.60(s, 11-Me), 1.98(s, 5-Me), 2.02(s, OAc), 2.2~2.7(m, 9-H$_2$, 15-H$_2$, 17-H), 2.64(s, CSCOCH$_3$), 4.45(m, 16-H), 4.73(d, J=11 Hz, 4-H), 5.2~6.2(m, 8-H, 3-H, 6-H, 7-H, 10-H, 13-H, 14-H), 6.33(d, J=15 Hz, 12-H), ~7.5 and ~8.05(each m, C$_6$H$_5$), 9.98(d, J=9 Hz, NH).

IR (KBr): 1730(sh.), 1712, 1495, 1355, 1274, 1244, 1212, 1112, 960 cm$^{-1}$.

[α]$_D^{26}$ −261.7° (c=0.525, CHCl$_3$).

EXAMPLE 43

Preparation of 3-phenoxyacetamido-lankone 8,14-diacetate

In 1 ml of ethyl acetate was dissolved 31.6 mg of 3-(2-(DL)-acetoxy-1-ethylthiopropylidene)amino-lankone 8,14-acetate. To the solution was added 7.7 μl of phenoxyacetyl chloride, and the mixture was stirred at room temperature for 250 minutes. To the result was added ethyl acetate, which was washed with saline, then dried over MgSO$_4$. Ethyl acetae was distilled off, and the residue was subjected to separation by means of preparative TLC. Plates: manufactured by Merck, Art, No. 5715, 20×20 cm, 2 plates, developing solvent: ethyl acetate - chloroform (1:4)) to obtain 5.4 mg of the above titled compound. This product was in good accord with the compound obtained in Example 32 in the data of TLC, IR, and NMR.

EXAMPLE 44

Preparation of 3-phenylacetamido-lankone 8,14-diacetate

Employing phenylacetyl chloride, the reaction was carried out in a manner similar to Example 43 to obtain the above titled compound in a yield of 10%.

NMR (90 MHz, CDCl$_3$) δ: 1.22(d, J=7 Hz, 17-Me), 1.25(s, 2-Me), 1.52(s, 11-Me), 1.86(s, 5-Me), 2.00 and 2.04(each s, 8-OAc, 14-OAc), 2.15~2.6 (m, 9-H$_2$, 15-H$_2$, 17-H), 3.57(s, C$_6$H$_5$CH$_2$), 4.32(m, 16-H), 4.57(d, J=12 Hz, 4-H), 5.05(m, 8-H), 5.2~5.85(m, 3-H, 6-H, 7-H, 10-H, 13-H, 14-H), 6.23(d, J=15Hz, 12-H), 6.63(d, J=10 Hz, NH), 7.30(s, C$_6$H$_5$).

IR (KBr): 1726, 1705, 1488, 1365, 1236, 1015, 956 cm$^{-1}$.

EXAMPLE 45

Preparation of 3-phenylthioacetamidolankone 8,14-diacetate

Employing phenylthioacetyl chloride, the reaction was carried out in a manner similar to Example 43 to give the above titled compound in a yield of 21%, m.p. 125°–128° C.

NMR (90 MHz, CDCl$_3$) δ: 1.09(s, 2-Me), 1.28(d, J=7 Hz, 17-Me), 1.53(s, 11-Me), 1.85(s, 5-Me), 2.01 and 2.05(each s, 8-OAc, 14-OAc), 2.2~2.7 (m, 9-H$_2$, 15-H$_2$, 17-H), 3.53 and 3.75(ABq, J=17 Hz, SCH$_2$), 4.33(m, 16-H), 4.56(d, J=11 Hz, 4-H), 5.07 (m, 8-H), 5.2~5.85(m, 3-H, 6-H, 7-H, 10-H, 13-H, 14-H), 6.26(d, J=15 Hz, 12-H), 7.25(m, C$_6$H$_5$), 7.95(d, J=10 Hz, NH).

IR (KBr): 1732, 1708, 1365, 1238, 1016 cm$^{-1}$.

EXAMPLE 46

Preparation of 3-(3-ethoxycarbonylacrylamido)-lankone 8,14-diacetate

Employing 3-ethoxycarbonylacrylyl chloride, the reaction was carried out in a manner similar to Example 43 to give the above titled compound in a yield of 20%.

NMR (90 MHz, CDCl$_3$) δ: 1.30 and 1.32 (each, t, J=7 Hz, CH$_3$CH$_2$), 1.31(d, J=7 Hz, 17-Me), 1.41(s, 2-Me), 1.54(s, 11-Me), 1.90(s, 5-Me), 2.03 and 2.04(each s, 8-OAc, 14-OAc), 2.2~2.7(m, 9-H$_2$, 15-H$_2$, 17-H), 4.23 and 4.26(each q, J=7 Hz, CH$_3$CH$_2$), ~4.4(m, 16-H), 4.67(d, J=11 Hz, 4-H), 5.07(m, 8-H), 5.2~6.0 (m, 3-H, 6-H, 7-H, 10-H, 13-H, 14-H), 6.28(d, J=15 Hz, 12-H), 6.74 and 6.93(ABq, J=15 Hz, CO      COO), 6.99(d, J=10 Hz, NH).

IR (KBr): 1724, 1710(sh.), 1672, 1362, 1296, 1238, 1020 cm$^{-1}$.

EXAMPLE 47

Preparation of 3-benzamido-lankone 8,14-diacetate

Employing benzoyl chloride, the reaction was carried out in a manner similar to Example 43 to give the above title compound in a yield of 9%.

NMR (90 MHz, CDCl$_3$)δ: 1.27 (d, J=7 Hz, 17-Me), 1.36 (s, 2-Me), 1.57 (s, 11-Me), 1.97 (s, 5-Me), 2.02 and 2.03 (each s, 8-OAc, 14-OAc), 2.2~2.6 (m, 9-H$_2$, 15-H$_2$, 17-H), 4.43 (m, 16-H), 4.76 (d, J= Hz, 4-H), 5.07 (m, 8-H), 5.2~6.1 (m, 3-H, 6-H, 7-H, 10-H, 13-H, 14-H), 6.28 (d, J=15 Hz, 12-H), ~7.5 and ~8.1 (each m, C$_6$H$_5$), 7.82 (d, J=9 Hz, NH)

IR (KBr): 1728, 1708, 1368, 1240, 1020 cm$^{-1}$.

EXAMPLE 48

Preparation of 3-chloroacetamido-lankone 8,14-diacetate

Employing chloroacetyl chloride, the reaction was carried out in a manner similar to Example 43 to give the above titled compound in a yield of 35%.

NMR (90 MHz, CDCl$_3$)δ: 1.31 (d, J=7 Hz, 17-Me), 1.41 (s, 2-Me), 1.54 (s, 11-Me), 1.88 (s, 5-Me), 2.01 and 2.03 (each s, 8-OAc, 14-OAc), 2.15~2.6 (m, 9-H$_2$, 15-H$_2$, 17-H), 4.01 (s, ClCH$_2$), 4.40 (m, 16-H), 4.70 (d, J=11 Hz, 4-H), 5.05 (m, 8-H), 5.2~6.1 (m, 3-H, 6-H, 7-H, 10-H, 13-H, 14-H), 6.28 (d, J=15 Hz, 12-H), 7.81 (d, J=10 Hz, NH).

IR (KBr): 1728, 1704, 1668, 1504, 1368, 1238, 1012, 958 cm$^{-1}$.

EXAMPLE 49

Preparation of 3-(difluoromethylthioacetamido)-lankone 8,14-diacetate

Employing difluoromethylthioacetyl chloride, the reaction was carried out in a manner similar to Example 43 to give the above titled compound in a yield of 15%.

NMR (90 MHz, CDCl$_3$)δ: 1.31 (d, J=7 Hz, 17-Me), 1.37 (s, 2-Me), 1.55 (s, 11-Me), 1.88 (s, 5-Me), 2.02 and 2.04 (each s, 8-OAc, 14-OAc), 2.1~2.6 (m, 9-H$_2$, 15-H$_2$, 17-H), 3.46 (s, COCH$_2$S), 4.43 (m, 16-H), 4.70 (d, J=11 Hz, 4-H), 5.08 (m, 8-H), 5.2~5.9 (m, 3-H, 6-H, 7-H, 10-H, 13-H, 14-H), 6.28 (d, J=15 Hz, 12-H), 6.90 (t, J=54 Hz, CHF$_2$), 7.61 (d, J=9 Hz, NH).

IR (KBr): 1730, 1712, 1670, 1368, 1240, 1060, 1020 cm$^{-1}$.

EXAMPLE 50

Preparation of 3-(2-chloroacetylaminothiazol-4-yl)acetamido-lankone 8,14-diacetate Employing (2-chloroacetylaminothiazol-4-yl)acetyl chloride hydrochloride and, as the reaction solvent, a mixture of tetrahydrofuran and ethyl acetate (1:2), the reaction was carried out in a manner similar to Example 43 to give the above titled compound in a yield of 17%.

NMR (90 MHz, CDCl$_3$)δ: 1.27 (d, J=7 Hz, 17-Me), 1.28 (s, 2-Me), 1.53 (s, 11-Me), 1.85 (s, 5-Me), 2.01 and 2.03 (each s, 8-OAc, 14-OAc), 2.1~2.7 (m, 9-H$_2$, 15-H$_2$ 17-H), 3.53 and 3.80 (ABq, thiazole-CH$_2$), 4.30 (s, ClCH$_2$), 4.35 (m, 16-H), 4.67 (d, J=11 Hz, 4-H), 5.05 (m, 8-H), 5.2~5.9 (m, 3-H, 6-H, 7-H, 10-H, 13-H, 14-H), 6.27 (d, J=15 Hz, 12-H), 6.97 (s, thiazole-5-H), 8.00 (d, J=9 Hz, NH).

IR (KBr): 1728, 1706, 1542, 1368, 1236 cm$^{-1}$.

EXAMPLE 51

Preparation of 3-n-hexanoylamino-lankone 8,14-diacetate

Employing n-hexanoyl chloride, the reaction was carried out to proceed in a manner similar to Example 43 to give the above titled compound in a yield of 4%.

NMR (90 MHz, CDCl$_3$)δ: 0.87 (t, J=6 Hz, CH$_3$(CH$_2$)$_4$CO), 1.1~1.8 (m, CH$_3$(CH$_2$)$_3$CH$_2$CO), 1.30 (d, J=7 Hz, 17-Me), 1.40 (s, 2-Me), 1.54 (s, 11-Me), 1.88 (s, 5-Me), 2.03 and 2.05 (each s, 8-OAc, 14-OAc), 2.05~2.55 (m, 9-H$_2$, 15-H$_2$ 17-H, CH$_2$CONH), 4.40 (m, 16-H), 4.65 (d, J=11 Hz, 4-H), 5.07 (m, 8-H), 5.2~5.9

(m, 3-H, 6-H, 7-H, 10-H, 13-H, 14-H), 6.25 (d, J=14 Hz, 12-H), 6.55 (d, J=10 Hz, NH).

IR (KBr): 3430, 2920, 1730, 1710 (sh.), 1660, 1365, 1230, 1100, 1010, 955 cm$^{-1}$.

EXAMPLE 52

Preparation of 3-cyclohexylcarboxanido-lankone 8,14-diacetate

Employing cyclohexylcarboxamide acid chloride, the reaction was carried out in a manner similar to Example 43 to give the above titled compound in a yield of 9%.

NMR (90 MHz, CDCl$_3$)δ: 1.28 (d, J=7 Hz, 17-Me), 1.37 (s, 2-Me), 1.54 (s, 11-Me), 1.86 (s, 5-Me), 1.1~2.0 (m, cychlohexyl-CH$_2$×5), 2.01 and 2.03 (each, s, 8-OAc, 14-OAc), 2.2~2.6 (m, 9-H$_2$, 15-H$_2$, 17-H, cychlohexyl-CH$_2$), 4.39 (m, 16-H), 4.63 (d, J=11 Hz, 4-H), 5.06 (m, 8-H), 5.25~6.10 (m, 3-H, 6-H, 7-H, 10-H, 13-H, 14-H), 6.28 (d, J=15 Hz, 12-H), 6.62 (d, J=10 Hz, NH).

IR (KBr): 3440, 2940, 1740, 1710(sh.), 1640, 1370, 1240, 1020, 965 cm$^{-1}$.

EXAMPLE 53

Preparation of 3-(2-thienyl)acetamido-lankone 8,14-diacetate

Employing (2-thienyl)acetyl chloride, the reaction was carried out in a manner similar to Example 43 to give the above titled compound in a yield of 19%.

NMR (90 MHz, CDCl$_3$)δ: 1.23 (d, J=7 Hz, 17-Me), 1.29 (s, 2-Me), 1.52 (s, 11-Me), 1.86 (s, 5-Me), 1.99 and 2.03 (each s, 8-OAc, 14-OAc, 2.15~2.6 (m, 9-H$_2$, 15-H$_2$, 17-H), 3.75 (s, CH$_2$CON), 4.33 (m, 16-H), 4.58 (d, J=11 Hz, 4-H), 5.05 (m, 8-H), 5.2~5.9 (m, 3-H, 6-H, 7-H, 10-H, 13-H, 14-H), 6.24 (d, J=15 Hz, 12-H), 6.79 (d, J=10 Hz, NH), 6.9~7.1 and 7.2~7.3 (each m, thienyl-H$_3$)

IR (KBr): 3440, 1730, 1710, 1670, 1500, 1370, 1240, 1020, 965 cm$^{-1}$.

EXAMPLE 54

Preparation of 3-[D(−)-2-(4-ethyl-2,3-dioxo-1-piperazinecarboxamido)phenylacetamido]-lankone 8,14-diacetate Employing D(−)-2-(4-ethyl-2,3-dioxo-1-piperazinecarboxamido)phenylacetyl chloride, the reaction was carried out to proceed in a manner similar to Example 43 to give the above titled compound in a yield of 8%. This product was in good accord with the compound obtained in Example 41 in the data of TLC, IR and NMR.

EXAMPLE 55

3-[D(−)-2-(2,2,2-trichloroethoxycarbonylamino)-phenylacetamido]-lankone 8,14-diacetate Employing D(−)-2-(2,2,2-trichloroethoxycarbonylamino)phenylacetyl chloride, the reaction was carried out in a manner similar to Example 43 to give the above titled compound in a yield of 10%.

NMR (90 MHz, CDCl$_3$)δ: 0.90 (s, 2-Me), 1.23 (d, J=6.5 Hz, 17-Me), 1.53 (s, 11-Me), 1.88 (s, 5-Me), 2.00 and 2.05 (each s, 8-OAc, 14-OAc), 2.15~2.55 (m, 9-H$_2$, 15-H$_2$, 17-H), 4.27 (m, 16-H), 4.65 (d, J=11 Hz, 4-H), 4.62 and 4.74 (each d, J=12 Hz, CCl$_3$CH$_2$), 4.95~5.2 (m, 8-H, C$_6$H$_5$CH), 5.25~5.85 (m, 3-H, 6-H, 7-H, 10-H, 13-H, 14-H), 6.26 (d, J=15 Hz, 12-H), 6.49 (br.d, J=7 Hz, NHCOOCH$_2$), 6.95 (br.d, J=10 Hz, C$_6$H$_5$CHCONH), 7.39 (br.s, C$_6$H$_5$).

IR (KBr): 3415, 1735, 1710, 1680, 1490, 1370, 1240, 1020, 960 cm$^{-1}$.

EXAMPLE 56

Preparation of 3-[2-(2,2,2-trichloroethoxycarbonyl)phenylacetamido]-lankone 8,14-diacetate Employing 2-(2,2,2-trichloroethoxycarbonyl)-phenylacetyl chloride, the reaction was carried out in a manner similar to Example 32 to give the above titled compound in a yield of 21%.

NMR (90 MHz, CDCl$_3$)δ: 1.28 (s, 2-Me), 1.28 (d, J=7.5 Hz, 17-Me), 1.52 (s, 11-Me), 1.84 (s, 5-Me), 2.00 and 2.03 (each s, 8-OAc, 14-OAc), 2.2~2.6 (m, 9-H$_2$, 15-H$_2$, 17-H), 4.38 (m, 16-H), 4.69 (s, C$_6$H$_5$CH), ~4.7 (m, 4-H), 4.81 (s, CCl$_3$CH$_2$), 5.05 (m, 8-H), 5.25~5.95 (m, 3-H, 6-H, 7-H, 10-H, 13-H, 14-H), 6.27 (d, J=15 Hz, 12-H), 7.43 (br.s, C$_6$H$_5$), 7.69 (d, J=10 Hz, NH).

IR (KBR): 3420, 2940, 1740, 1710, 1680, 1500, 1370, 1245, 1140, 1020, 965, 720 cm$^{-1}$.

EXAMPLE 57

Preparation of 3-chloroacetamido-lankone 8,14-diacetate

To 2.144 g of 3-(2-(DL)-acetoxy-1-methylthiopropylidene)amino-lankone 8,14-diacetate were added 34.7 ml of ethyl acetate, 17.4 ml of tetrahydrofuran and 0.277 ml of chloroacetyl chloride. The mixture was stirred for 6.5 hours at room temperature, to which was added ethyl acetate, followed by washing with saline and drying over MgSO$_4$. The solvent was distilled off, and the residue was subjected to a silica gel (120 g) column chromatography, eluting with ethyl acetate-chloroform (1:4). The desired fractions were combined and concentrated to obtain 523 mg of the above titled compound. This product was in good accord with the compound obtained in Example 48 in the data of TLC, IR and NMR.

EXAMPLE 58

Preparation of 3-phenoxyacetamido-lankone 8,14-diacetate

In 1 ml of dichloromethane was dissolved 60.3 mg of 3-(2-(DL)-acetoxy-1-thioxo)propylamino-lankone 8,14-diacetate. To the solution was added 17.8 mg of trimethyloxonium tetrafluoroborate, and the mixture was stirred for 30 minutes at room temperature. To the resultant were added 15.4 μl of phenoxyacetyl chloride and 0.1 ml of water, and the mixture was stirred vigorously at room temperature for 200 minutes and processed in a manner similar to Example 32 to give 1.4 mg of the above titled compound. The product was in good accord with the compound obtained in Example 32 in the data of TLC, IR and NMR.

EXAMPLE 59

Preparation of 3-[2-[1-(2-dimethylaminoethyl)-1H-tetrazol-5-yl]thio]acetamido-lankone 8,14-diacetate In 1 ml of N,N-dimethylformamide was dissolved 55.0 mg of 3-chloroacetamido-lankone 8,14-diacetate. To the solution were added 17.3 mg of [1-(2-dimethylaminoethyl)-1H-tetrazol-5-yl]thiol, 8.09 μl of pyridine and 16.6 mg of potassium iodide, and the mixture was stirred at 50° C. for 3 hours. to which was added, after cooling, water, followed by extracting with ethyl acetate and by drying over MgSO$_4$. The solvent was distilled off, and the residue was subjected to a silica gel column chromatography, eluting with a mixture of ethyl acetate and methanol (5:1). The desired fractions were combined and concentrated to give 59.6 mg of the above titled compound.

NMR (90 MHz, CDCl$_3$)δ: 1.27 (d, J=7 Hz, 17-Me), 1.30 (s, 2-Me), 1.53 (s, 11-Me), 1.84 (s, 5-Me), 2.01 and 2.03 (each s, 8-OAc, 14-OAc) 2.1~2.6 (m, 9-H$_2$, 15-H$_2$, 17-H), 2.25 (s, NMe$_2$), 2.75 (t, J=6 Hz, CH$_2$NMe$_2$), 3.88 and 4.08 (ABq, J=15 Hz, SCH$_2$CO), 4.35 (t, J=6 Hz, tetrazole-CH$_2$), ~4.4 (m, 16-H), 4.63 (d, J=11 Hz, 4-H), 5.05 (m, 8-H), 5.2~6.1 (m, 3-H, 6-H, 7-H, 10-H, 13-H, 14-H), 6.25 (d, J=15 Hz, 12-H), 7.58 (d, J=10 Hz, NH).

IR (KBr): 3440, 1724, 1704, 1618, 1366, 1236, 1014 cm$^{-1}$.

EXAMPLE 60

Preparation of 3-[2-(4-methyl-4H-1,2,4-triazol-3-yl)thio]acetamido-lankone 8,14-diacetate Employing (4-methyl-4H-1,2,4-triazol-3-yl)thiol, the reaction was carried out in a manner similar to Example 59 to obtain the above titled compound in a yield of 48%.

NMR (90 MHz, CDCl$_3$)δ: 1.26 (d, J=7 Hz, 17-Me), 1.35 (s, 2-Me), 1.51 (s, 11-Me), 1.82 (s, 5-Me), 2.00 and 2.04 (each s, 8-OAc, 14-OAc), 2.1~2.6 (m, 9-H$_2$15-H$_2$, 17-H), 3.58 (s, triazole-Me), 3.76 and 4.05 (ABq, J=15 Hz, SCH$_2$CO), 4.35 (m, 16-H), 4.61 (d, J=11 Hz, 4-H), 5.05 (m, 8-H), 5.2~5.9 (m, 3-H, 6-H, 7-H, 10-H, 13-H, 14-H), 6.25 (d, J=15 Hz, 12-H), 7.76 (d, J=9 Hz, NH), 8.13 (s, triazole-H).

IR (KBR): 1732, 1712(sh.), 1666, 1508, 1370, 1244, 1020, 960 cm$^{-1}$.

EXAMPLE 61

Preparation of 3-[2-(4-pyridyl)thio]acetamido-lankone 8,14-diacetate

Employing 4-pyridyl thiol, the reaction was carried out proceed in a manner similar to Example 59 to obtain the above titled compound in a yield of 57%.

NMR (90 MHz, CDCl$_3$)δ: 1.09 (s, 2-Me), 1.26 (d, J=7 Hz, 17-Me), 1.53 (s, 11-Me), 1.87 (s, 5-Me), 2.00 and 2.04 (each s, 8-OAc, 14-OAc), 2.1~2.7 (m, 9-H$_2$, 15-H$_2$, 17-H), 3.57 and 3.80 (ABq, J=17 Hz, SCH$_2$CO), 4.33 (m, 16-H), 4.54 (d, J=11 Hz, 4-H), 5.05 (m, 8-H), 5.2~5.9 (m, 3-H, 6-H, 7-H, 10-H, 13-H, 14-H), 6.24 (d, J=15 Hz, 12-H), 7.14 and 8.39 (ABq, J=6 Hz, pyridine-H$_4$), 7.80 (d, J=9 Hz, NH).

IR (KBr): 1730, 1710, 1670, 1574, 1498, 1370, 1240, 1018, 960 cm$^{-1}$.

EXAMPLE 62

Preparation of 3-[(4-carboxy-3-hydroxy-1,2-thiazol-5-yl)thio]acetamido-lankone 8,14-diacetate In 1 ml of N,N-dimethylformamide was dissolved 55.0 mg of 3-chloroacetamido-lankone 8,14-diacetate. To the solution were added 24.3 mg of (4-carboxy-3-hydroxy-1,2-thiazol-5-yl)thio trisodium salt and 16.6 mg of potassium iodide. The mixture was stirred at 60° C. for 30 minutes. N,N-dimethylformamide was distilled off under reduced pressure. To the residue was added chloroform, which was washed with 1N hydrochloric acid, followed by drying over MgSO$_4$. The chloroform was the distilled off, and the residue was subjected to separation by means of reversed phase TLC Plates: manufactured by Merck, Art. No. 15424, 10×10 cm, 2 plates, developing solvent:methanol-water (5:1)) to obtain 33.2 mg of the above titled compound.

IR (KBr): 1728, 1660, 1368, 1236, 1018, 958 cm$^{-1}$.

EXAMPLE 63

Preparation of 3-[2-(5-methoxymethyl-1,3,4-thiadiazol-2-yl)thio]acetamido-lankone 8,14-diacetate Employing (5-methoxymethyl-1,3,4-thiadiazol-5-yl)thiol, the reaction was carried out in a manner similar to Example 59 to obtain the above titled compound in a yield of 41%.

NMR (90 MHz, CDCl$_3$)δ: 1.25 (d, J=7 Hz, 17-Me), 1.34 (s, 2-Me), 1.53 (s, 11-Me), 1.84 (s, 5-Me), 1.99 and 2.03 (each s, 8-OAc, 14-OAc), 2.1~2.6 (m, 9-H$_2$, 15-H$_2$, 17-H), 3.42 (s, CH$_2$OCH$_3$), 3.97 (s, COCH$_2$S), 4.35 (m, 16-H), 4.67 (d, J=11 Hz, 4-H), 4.77 (s, CH$_2$OCH$_3$), 5.05 (m, 8-H), 5.2~5.9 (m, 3H, 6-H, 7-H, 10-H, 13-H, 14-H), 6.25 (d, J=15 Hz, 12-H), 7.73 (d, J=9 Hz, NH).

IR (KBr): 1728, 1710, 1674, 1366, 1240, 1018, 960 cm$^{-1}$.

EXAMPLE 64

Preparation of 3-[2-(5-methanesulfonylmethyl-1,3,4-thiadiazol-2-yl)thio]acetamido-lankone 8,14-diacetate Employing (5-methanesulfonyl-1,3,4-thiadiazol-2-yl)thio, the reaction was carried out in a manner similar to Example 59 to obtain the above titled compound in a yield of 55%.

NMR (90 MHz, CDCl$_3$)δ: 1.24 (d, J=7 Hz, 17-Me), 1.29 (s, 2-Me), 1.51 (s, 11-Me), 1.83 (s, 5-Me), 2.00 and 2.03 (each s, 8-OAc, 14-OAc), 2.1~2.6 (m, 9-H$_2$, 15-H$_2$, 17-H), 2.97 (s, CH$_3$SO$_2$), 4.01 (s, COCH$_2$S), 4.36 (m, 16-H), 4.60 (d, J=11 Hz, 4-H), 4.70 (s, CH$_2$SO$_2$), 5.05 (m, 8-H), 5.2~5.85 (m, 3-H, 6-H, 7-H, 10-H, 13-H, 14-H), 6.25 (d, J=15 Hz, 12-H), 7.62 (d, J=10 Hz, NH).

IR (KBr): 1726, 1708(sh.), 1660, 1362, 1312, 1240, 1140 cm$^{-1}$.

EXAMPLE 65

Preparation of 3-[2-[1-(2-hydroxyethyl)-1H-tetrazol-5-yl]thio]acetamido-lankone 8,14-diacetate Employing [1-(2-hydroxyethyl)-1H-tetrazol-5-yl]thiol, the reaction was carried out in a manner similar to Example 59 to obtain the above titled compound in a yield of 70%.

NMR (90 MHz, CDCl$_3$)δ: 1.23 (d, J=7 Hz, 17-Me), 1.30 (s, 2-Me), 1.50 (s, 11-Me), 1.80 (s, 5-Me), 2.00 and 2.03 (each s, 8-OAc, 14-OAc), 2.1~2.6 (m, 9-H$_2$, 15-H$_2$, 17-H), 3.88 and 4.10 (ABq, J=15 Hz, COCH$_2$S), ~4.0 (m, CH$_2$CH$_2$OH), ~4.4 (m, CH$_2$CH$_2$OH), 4.58 (d, J=11 Hz, 4-H), 5.0 (m, 8-H), 5.2~5.8 (m, 3-H, 6-H, 7-H, 10-H, 13-H, 14-H), 6.25 (d, J=15 Hz, 12-H), 7.50 (d, J=10 Hz, NH).

IR (KBR): 1724, 1706, 1656, 1366, 1240, 1016, 956 cm$^{-1}$.

EXAMPLE 66

Preparation of 3-(2-aminothiazol-4-yl)acetamido-lankone 8,14-diacetate

In 5 ml of tetrahydrofuran was dissolved 108.5 mg of 3-(2-chloroacetylaminothiazol-4-yl)acetamido-lankone 8,14-diacetate. To the solution were added 5 ml of water and 20.3 mg of sodium N-methyldithiocarbamate, and the mixture was stirred at room temperature for 90 minutes, followed by extraction with ethyl acetate. The extract was washed with saline, then dried over MgSO$_4$. The residue was subjected to separation by means of preparative TLC Plates: manufactured by Merck, Art. No. 5715, 20×20 cm, two plates, developing solvent:tetrahydrofuran-chloroform (1:1)) to obtain 34.5 mg of the title compound.

N M R (90 MHz, CDCl$_3$-DMSO-d$_6$(3:1))δ:1.25(d, J=7 Hz, 17-Me), 1.31(s, 2-Me), 1.50(s, 11-Me), 1.79(s, 5-Me), 1.99 and 2.02 (each s, 8-OAc, 14-OAc), 2.1~2.7(m, 9-H$_2$,15-H$_2$, 17-H), 3.39(thiazole-CH$_2$), 4.52(m,. 16-H), 4.73(d, J=11 Hz, 5.02(m, 8-H), 5.2~5.8(m, 3-H, 6-H, 7-H, 10-H, 13-H, 14-H), 6.22(s, thiazole-5-H), 6.29(d, J=15 Hz, 12-H), 6.32(br. s, NH$_2$), 7.70(d, J=9 Hz, NH).

I R (KBr): 1730, 1710, 1658, 1514, 1368, 1240 cm$^{-1}$.

EXAMPLE 67

Preparation of 3-[D(−)-2-amino-phenyl acetamido]-lankone 8,14-diacetate

In 15 ml of ethyl acetate was dissolved 330.6 mg of 3-[D(−)-2-(2,2,2-trichloroethoxycarbonylamino)-phenylacetamido]-lankone8,14-diacetate. To the solution were added 2.8 ml of acetic acid and 1.25 g of zinc powder, and the mixture was stirred at room temperature overnight. Precipitates were filtered off using a filter aid. The filtrate was washed with saline and dried over MgSO$_4$. The solvent was distilled off, and the residue was subjected to a silica gel chromatography (2.5×38 cm), followed by elution with chloroform-acetone (9:1) then with chloroform-acetone (2:1). The desired fractions were combined and concentrated to obtain 85.0 mg of the above titled compound.

N M R (90 MHz, CDCl$_3$)δ:123(s, 2-Me), 1.27(d, J=6.5 Hz, 17-Me), 1.53(s, 11-Me), 1.84(s, 5-Me), 2.00 and 2.03 (each s, 8-OAc, 14-OAc), 2.1~2.6(m, 9-H$_2$, 15-H$_2$, 17-H), 4.37(m, 16-H), 4.68(d, J=11 Hz, 4-H), 5.07(m, 8-H), 5.2~5.9(m, 3-H, 6-H, 7-H, 10-H, 13-H, 14-H, C$_6$H$_5$CH), 6.28(d, J=15 Hz, 12-H), 7.32(br. s, C$_6$H$_5$), 7.83(br. d, J=10 Hz, NH).

I R (KBr): 3415, 1735, 1715, 1675, 1500, 1370, 1250, 1025, 965, 750 cm$^{-1}$.

EXAMPLE 68

Preparation of 3-(2-carboxy-phenylacetamido)-lankone8,14-diacetate

In 1.5 ml of dichloromethane was dissolved 38.3 mg of 3-[2-(2,2,2-trichloroethoxycarbonyl)-phenylacetamido]-lankone8,14-diacetate. To the solution were added 50 μl of acetic acid and 43 mg of zinc powder, and the mixture was stirred at room temperature, to which were supplemented, two hours later and five hours later, 50 μl each portion of acetic acid and 42 mg each portion of zinc powder. Eight hours later, precipitates were filtered off using a filter aid, The filtrate was washed with dichloromethane, which was washed with dilute aqueous solution of sodium hydrogencarbonate and water in sequence, then dried over MgSO$_4$. Dichloromethane was distilled off. The residue was subjected to separation by means of preparative TLC Plate: manufactured by Merck, Art. No. 5715, 20×20 cm, two plates, developing solvent: chloroform-methanol (4:1)) to obtain 10.6 mg of the title compound.

N M R (90 MHz, CDCl$_3$)δ:1.15~1.35(m, 17-Me, 2-Me), 1.50(s, 11-Me), 1.83(s, 5-Me), 1.98 and 2.02 (each s, 8-OAc, 14-OAc), 2.25~2.6(m, 9-H$_2$, 15-H$_2$, 17-H), 4.3~4.45(m, 16-H), 4.47 and 4.50 (each s, C$_6$H$_5$CH), 4.60(br. d, J=11 Hz, 4-H), 5.06(m, 8-H), 5.25~5.9(m, 3-H, 6-H, 7-H, 10-H, 13-H, 14-H), 6.25(d, J=15 Hz, 12-H), 7.37(s, C$_6$H$_5$), 7.65(d, J=10 Hz, NH), 9.7(br., -COOH).

I R (KBr): 3400, 2930, 1730, 1710, 1670, 1370, 1300, 1250, 1235, 1015, 960 cm$^{-1}$.

EXAMPLE 69

Preparation of 3-(2-acetoxyacrylamido)-lankone8,14-diacetate

In 1 ml of dichloromethane was dissolved 54.3 mg of lankacidin C 8,14-diacetate. To the solution were added 13.9 μl of triethylamine, 18.9 μl of acetic anhydride and 12.2 mg of 4-(N,N-dimethylamino)pyridine. The mixture was stirred at room temperature for 9 hours, which was left standing overnight at room temperature. To the resultant was added dichloromethane, followed by washing with 2 ml of 0.5N hydrochloric acid and saline in sequence then drying over MgSO$_4$. Dichloromethane was distilled off, and the residue was subjected to separation by means of preparation TLC Plates: manufactured by Merck, Art. No. 5715, 20×20 cm, two plates, developing solvent: a mixture of ethyl acetate and chloroform (1:4) to obtain 13.9 mg of the title compound.

N M R (90 MHz, CDCl$_3$)δ:1.29(d, J=7 Hz, 17-Me), 1.38(s, 2-Me), 1.54(s, 11-Me), 1.89(s, 5-Me), 2.02 and 2.04 (each s, 8-OAc, 14-OAc), 2.2~2.7(m, 9-H$_2$, 15-H$_2$, 17-H), 2.33(s, 2'-OAc), 4.39(m, 16-H), 4.67(d, J=11 Hz, 4-H), 5.07(m, 8-H), 5.2~6.2(m, 3-H, 6-H, 7-H, 10-H, 13-H, 14-H, =CH$_2$), 6.27(d, J=15 Hz, 12-H), 7.35(d, J=10 Hz, NH).

I R (KBr): 1738, 1712, 1372, 1244, 1172, 1022 cm$^{-1}$.

EXAMPLE 70

Preparation of 3-(2-t-butoxycarbonyloxyacrylamido)-lankone8,14-diacetate

In 20 ml of dichloromethane was dissolved 1.086 g of lankacidin C 8,14-diacetate. The solution was cooled to −30° C.~−20° C. To the solution were added 0.278 ml of triethylamine, 0.918 ml of di-t-butyl bicarbonate and 244 mg of 4-(N,N-dimethylamino)pyridine, and the mixture was stirred for 8.5 hours, to which was added dichloromethane, followed by washing with 40 ml of 0.5N hydrochloric acid and with saline in sequence and dried over MgSO$_4$. The dichloromethane was distilled off and the residue was subjected to a column chromatography on 250 g of silica gel, followed by eluting with a mixture of ethyl acetate and chloroform (1:4). The eluate was fractionated by 20 g each portion. The 49th~78th fractions were combined and concentrated to leave crystals, to which was added hexane, followed by drying to obtain 747.6 mg of the above titled compound, m.p. 199°–201° C. (decomp.)

N M R (90 MHz, CDCl$_3$)δ:1.30(d, J=7 Hz, 17-Me), 1.40(s, 2-Me), 1.53(s, Bu$^t$, 11-Me), 1.90(s, 5-Me), 2.01 and 2.03 (each s, 8-OAc, 14-OAc), 2.2~2.7(m, 9-H$_2$, 15-H$_2$, 17-H), 4.40(m, 16-H), 4.72(d, J=11 Hz, 4-H), 5.2~6.1(m, 3-H, 6-H, 7-H, 10-H, 13-H, 14-H, =CH$_2$), 6.28(d, J=15 Hz, 12-H), 7.35(d, J=10 Hz, NH).

IR (KBr): 3400, 1748, 1728, 1706, 1504, 1368, 1240, 1146 cm$^{-1}$.

[α]$_D^{23.5}$ −169.4° (c=0.595, CHCl$_3$).

Mass m/e: 643(M$^+$), 543(M$^+$-101(COOBu$^t$)), 483(M$^+$-101-60(AcOH)), 440(M$^+$-101-60-44 (CO$_2$)), 423(M$^+$-101-60-60), 380(M$^+$-101-60-60-44).

EXAMPLE 71

Preparation of (i) 3-(2-t-butoxycarbonyloxyacrylamido)-lankone 14-acetate-8-t-butylcarbonate and (ii) 3-(2-t-butoxycarbonyloxyacrylamido)-lankone 14-acetate In 1 ml of dichloromethane was dissolved 50.1 mg of lankacidin A. The solution was cooled with ice-water, to which were added 13.9 μl of triethylamine, 45.9 μl of di-t-butyl bicarbonate and 12.2 mg of 4-(N,N-dimethylamino)pyridine, followed by stirring for 55 minutes. To the mixture was added dichloromethane, which was washed with 2 ml of 0.5N hydrochloric acid and with saline in sequence and dried over MgSO$_4$. The discholromethane was distilled off and the residue was subjected to separation by means of preparative TLC Plates: manufactured by Merck, Art. No. 5715, 20×20 cm, two plates, developing solvent:ethyl acetate-hexane (2:1)) to obtain 14.3 mg of the above titled compound (i) and 17.4 mg of the above titled compound (ii).

Compound (i):
NMR (90 MHZ, CDCl$_3$)δ:1.29(d, J=7 Hz, 17-Me), 1.39(s, 2-Me), 1.46(s, 8-OCOOBu$^t$), 1.52(s, 11-Me, 2'-OCOOBu$^t$), 1.88(s, 5-Me), 2.01(s, OAc), 2.2~2.7(m, 9-H$_2$15-H$_2$, 17-H), 4.39(m, 16-H), 4.69(d, J=11 Hz, 4-H), 4.86(m, 8-H), 5.2~6.1(m, 3-H, 6-H, 7-H, 10-H, 13-H, 14-H, =CH$_2$), 7.34(d, J=9 Hz, NH).

IR (KBr): 1758(sh.), 1738, 1710, 1368, 1276, 1252, 1146 cm$^{-1}$.

Compound (ii):
NMR (90 MHz, CDCl$_3$)δ: 1.28(d, J=7 Hz, 17-Me), 1.39(s, 2-Me), 1.53(s, 11-Me, Bu$^t$), 1.89(s, 5-Me), 2.01(s, OAc), 2,2~2.6(m, 9-H$_2$, 15-H$_2$, 17-H), ~4.1(m, 8-H), 4.40(m, 16-H), 4.66(d, J=11 Hz, 4-H), 5.2~6.1(m, 3-H, 6-H, 7-H, 10-H, 13-H, 14-H, =CH$_2$), 6.26(d, J=14 Hz, 12-H), 7.36(d, J=9 Hz, NH).

IR (KBr): 1756, 1734(sh.), 1708, 1642, 1508, 1372, 1244, 1146 cm$^{-1}$.

EXAMPLE 72

Preparation of 3-(2-acetoxyacrylamido)-lankone 8,14-bis(2,2,2-trichloroethyl)carbonate In 6 ml of pyridine was dissolved 810 mg of lankacidin C 8,14-bis(2,2,2-trichloroethyl)carbonate, and the solution was cooled with ice-water, to which were added 122 mg of 4-(N,N-dimethylamino)pyridine and 3 ml of acetic anhydride. The mixture was stirred for 3 hours and poured into ice-water, followed by extraction with ethyl acetate. The extract was washed with 1N hydrochloric acid and aqueous NaCl solution in sequence, followed by drying over MgSO$_4$. The solvent was distilled off, and the residue was subjected to a column chromatography on 130 g of silica gel, eluting with a mixture of ethyl acetate and hexane (1:1). The eluate was fractionated by 10 g each portion. The 23th~26th fractions were combined and concentrated to obtain 267.1 mg of the above titled compound.

NMR (90 MHz, CDCl$_3$)δ: 1.31(d, J=7 Hz, 17-Me), 1.40(s, 2-Me), 1.57(s, 11-Me), 2.33(s, OAc), 2.2~2.7(m, 9-H$_2$, 15-H$_2$, 17-H), 4.45(m, 16-H), ~4.7(m, 4-H), 4.75(s, CCl$_3$CH$_2$×2), ~5.0(m, 8-H), 5.2~6.4(m, 3-H, 6-H, 7-H, 10-H, 13-H, 14-H), 5.37 & 6.02(each d, J=2 Hz, =CH$_2$), 6.35(d, J=15 Hz, 12-H), 7.35(d, J=9 Hz, NH).

IR (KBr): 1750, 1704, 1680, 1374, 1240, 1164, 810 cm$^{-1}$.

EXAMPLE 73

Preparation of 3-(2-(L)-iodopropionamido)-lankone 8,14-diacetate and 3-(2-(D)-iodopropionamido)-lankone 8,14-diacetate In 5 ml of acetone was dissolved in 230.7 mg of bis[3-(2-(D)-hydroxy-propionamido)lankone 8,14-diacetate-2'(O)yl]sulfone. To the solution was added 300 mg of sodium iodode, which was refluxed for 22.5 hours. Acetone was distilled off. To the residue was added ethyl acetate, which was washed with water and with aqueous NaCl solution in sequence, followed by drying over Na$_2$SO$_4$. From the resultant was distilled off ethyl acetate. The residue was subjected to a silica gel column chromatography, eluting with first ethyl acetate-benzene (1:2) then with ethyl acetate-benzene (2:1). Desired fractions were combined and concentrated to obtain 59.2 mg of the titled compound (2'-(L)compound) and 35.7 mg of the titled compound (2'-(D) compound).

2'-(L)compound:
NMR (90 MHz, CDCl$_3$)δ: 1.31(d, 3H, J=7 Hz), 1.47(s, 3H), 1.54(s, 3H), 1.87(s, 3H), 1.95(d, 3H, J=8 Hz), 2.01(s, 3H), 2.03(s, 3H), 2.20~2.55(m, 5H), 4.30~4.80(m, 3H), 4.90~5.88(m, 7H), 6.27(d, 1H, J=15 Hz), 7.02(d, 1H, J=10 Hz).

IR (KBr): 1735, 1715, 1670, 1240 cm$^{-1}$.

2'-(D)compound:
NMR (90 MHz, CDCl$_3$)δ: 1.31(d, 3H, J=7 Hz), 1.42(s, 3H), 1.54(s, 3H), 1.87(s, 3H), 1.95(d, 3H, J=6 Hz), 2.01(s, 3H), 2.04(s, 3H), 2.20~2.55(m, 5H), 4.25~4.80(m, 3H), 4.90~5.87(m, 7H), 6.27(d, 1H, J=14 Hz), 7.10(d, 1H, J=10 Hz).

IR (KBr): 1740, 1715, 1680, 1240 cm$^{-1}$.

EXAMPLE 74

Preparation of 3-(2-(DL)-p-toluenesulfonyloxypropionamido)-lankone 8,14-diacetate In 1 ml of pyridine was dissolved 273.8 mg of 3-(2-(DL)-lankone 8,14-diacetate. To the solution was added, under cooling with ice-water, 104.9 mg of p-toluenesulfonyl chloride. The mixture was stirred for 15 minutes, which was further stirred at room temperature for 21 hours, to which was added 133.5 mg of p-toluenesulfonyl chloride, followed by stirring for further 2 hours. To the resultant was added ice-water, which was extracted with ethyl acetate. The extract was washed with 1N hydrochloric acid then with aqueous NaCl solution in sequence, followed by drying over Na$_2$SO$_4$. The solvent was distilled off. The residue was subjected to a silica gel column chromatography, eluting with ethyl acetate-benzene (1:2). Desired fractions were combined and concentrated to obtain 198.9 mg of the titled compound.

NMR (90 MHz, CDCl$_3$)δ: 1.23~1.50(m, 6H), 1.54(s, 3H), 1.70~1.90(m, 6H), 2.02(s, 3H), 2.03(s, 3H), 2.20~2.60(m, 5H), 4.30~5.90(m, 10H), 6.30(d, 1H, J=14 Hz), 7.30~7.94(m, 5H).

IR (KBr): 1740, 1720, 1685, 1245 cm$^{-1}$.

EXAMPLE 75

Preparation of 3-(2-(L)-iodopropionamido)-lankone 8,14-diacetate and 3-(2-(D)-iodopropionamido)-lankone 8,14-diacetate In 5 ml of acetone was dissolved 199 mg of 3-(2-(DL)-p-toluenesulfonyloxyproionamido)-lankone 8,14-diacetate. To the solution was added 127.8 mg of sodium iodide, and the mixture was refluxed for 3.5 hours, followed by distilling off the acetone. To the residue was added ethyl acetate, which was washed with water and with aqueous NaCl solution in sequence, followed by drying over $Na_2SO_4$ The solvent was distilled off, and the residue was subjected to a silica gel column chromatography, eluting with a mixture of ethyl acetate and benzene (1:2). Desired fractions were combined and concentrated to obtain 111.9 mg of the titled compound (2'-(L)compound) and 62.4 mg of the titled compound (2'-(D)compound). These compounds are respectively in good accord with those obtained in Example 73 in the data of TLC, IR and NMR.

EXAMPLE 76

Preparation of 3-(2-(DL)-methanesulfonyloxypropionamido)lankone 8,14-diacetate

In 2 ml of dichloromethane was dissolved in 1.09 g of 3-(2-(DL)-hydroxypropionamido)-lankone 8,14-diacetate. To the solution were added, under ice-cooling, 0.32 ml of pyridine and 0.31 ml of methanesulfonyl chloride, and the mixture was stirred for 15 minutes. The resultant was stirred for further one hour at room temperature, to which was added ice-water, followed by extraction with ethyl acetate. The organic layer was washed with 1N-hydrochloric acid then with aqueous NaCl solution in sequence, followed by drying over $Na_2SO_4$. The solvent was distilled off, and the residue was subjected to a silica gel column chromatography, eluting with ethyl acetate-benzene (1:1). Desired fractions were combined and concentrated to obtain 998 mg of the titled compound.

NMR (90 MHz, $CDCl_3$)δ: 1.25~1.66(m, 12H), 1.87(s, 3H), 2.02(s, 3H), 2.03(s, 3H), 2.16~2.60(m, 5H), 3.03(s, 1H), 3.18(s, 2H), 4.30~4.56(m, 1H), 4.70(d, 1H, J=10 Hz), 4.90~5.90(m, 8H), 6.26(d, 1H, J=15 Hz), 7.43~7.70(m, 1H).

IR (KBr): 1740, 1715, 1690, 1240 $cm^{-1}$.

EXAMPLE 77

Preparation of 3-(2-(L)-iodopropionamido)-lankone 8,14-diacetate and 3-(2-(D)-iodopropionamido)-lankone 8,14-diacetate Employing 4.4 g of 3-(2-(DL)-methanesulfonyloxypropionamido)-lankone 8,14-diacetate, the reaction was carried out to proceed to obtain 2.8 g of the titled compound (2'-(L)compound) and 1.5 g of the titled compound (2'-(D)compound). These products are in good accord with those obtained in Example 73 in the data of TLC, IR and NMR.

EXAMPLE 78

Preparation of 3-(2-(DL)-trimethylsilyloxypropionamido)-lankone 8,14-diacetate

In 1 ml of dichloromethane was dissolved 109.1 mg of 3-(2-(DL)-hydroxypropionamido)-lankone 8,14-diacetate. To the solution was added 33.5 μl of triethylamine and 30.5 μl of chlorotrimethylsilane, and the mxiture was stirred at room temperature for 20 minutes. To the resultant was added ice-water, which was subjected to extraction with dichloromethane, followed by drying over $Na_2SO_4$ and distilling off the solvent. The residue was subjected to a silica gel column chromatography, eluting with a mixture of ethyl acetate and hexane (1:1). Desired fractions were combined and concentrated to obtain 117 mg of the titled compound.

NMR (90 MHz, $CDCl_3$)δ: 0.21(s, 3.6H), 0.26(s, 5.4H), 1.25~1.50(m, 9H), 1.59(s, 3H), 1.92(s, 3H), 2.06(s, 3H), 2.08(s, 3H), 2.20~2.65(m, 5H)00, 4.10~5.90(m, 10H), 6.33(d, 1H, J=15 Hz), 7.75~8.06(m, 1H).

IR (KBr): 1740, 1710, 1680, 1240 $cm^{-1}$.

EXAMPLE 79

Preparation of 3-(2-phenylthiopropionamido)-lankone 8,14-diacetate

In 0.1 ml of pyridine was dissolved 54.6 mg of 3-(2-(DL)-hydroxypropionamido)-lankone 8,14-diacetate. To the solution were added 74 μl of tributyl phosphine and 65.5 mg of diphenyl disulfide, and the mixture was stirred at room temperature for 19 hours, which was subjected to a silica gel column chromatography, eluting with a mixture of ethyl acetate and benzene (1:2) to obtain 40.8 mg of the titled compound.

NMR (90 MHz, $CDCl_3$)δ: 1.25~1.86(m, 15H), 2.01(s, 3H), 2.06(s, 3H), 2.15~2.60(m, 5H), 3.66~4.02(m, 1H), 4.20~4.55(m, 2H), 4.90~5.83(m, 7H), 6.26(d, 1H, J=14 Hz), 7.12~7.45(m, 5H), 7.56~7.80(m, 1H).

IR (KBr): 1735, 1715, 1675, 1240 $cm^{-1}$.

EXAMPLE 80

Preparation of 3-(2-(DL)-phenylthiopropionamido)-lankone 8,14-diacetate

To 2 ml of ethanol was added 168 mg of sodium hydride (60% purity) and 0.43 ml of thiophenol, and the mixture was cooled with ice-water, to which was added dropwise, while stirring, 2.18 g of 3-(2-(DL)-methane sulfonyloxypropionamido)-lankone 8,14-diacetate dissolved in 14 ml of tetrahydrofuran. The whole mixture was stirred at room temperature for 2 hours, to which was added aqueous NaCl solution, followed by extraction with ethyl acetate. The organic layer was washed with aqueous NaCl solution and dried over $Na_2SO_4$. The solvent was distilled off, and the residue was subjected to a silica gel column chromatography, eluting with a mixture of ethyl acetate and hexane (1:1). The desired fractions were combined and concentrated to obtain 1.785 g of the above titled compound. This product was in good accord with the compound obtained in Example 79 in the data of TLC, IR and NMR.

EXAMPLE 81

Preparation of 3-(2-(DL)-methanesulfonyloxypropionamido)-lankone 8,14-ditrimethylsilylether In a mixture of 10 ml of tetrahydrofuran and 10 ml of methanol was dissolved 1.38 g of lankacidin C 8,14-ditrimethylsilylether. To the solution was added, while stirring under ice-cooling, 25.9 mg of sodium borohydride, and the mixture was stirred for 10 minutes at the same temperature. The solvent was distilled off to leave crude 3-(2-(DL)-hydroxypropionamido)-lankone 8,14-ditrimethylsilylether, whcih was dissolved in 7 ml of pyridine. To the solution was added dropwise, while stirring at 0° C., 0.53 ml of methanesulfonyl chloride. The mixture was further stirred for 70 minutes, which was poured into ice-water, followed by extraction with ethyl acetate. The organic layer was dried over $Na_2SO_4$. The solvent was distilled off, and the residue was subjected to a silica gel column chromatography, eluting with a mixture of ethyl acetate and benzene (1:2). Desired fractions were combined and concentrated to obtain 330 mg of the above titled compound.

NMR (90 MHz, $CDCl_3$)δ: 0.10(s, 18H), 1.2~1.7(m, 12H), 1.87(s, 3H), 2.1~2.6(m, 5H), 3.14 and 3.17 (each s, 3H), 3.8~4.45(m, 4H), 4.9~6.1(m, 8-H), 7.53(d, 1H, J=10 Hz).

IR (KBr): 1750, 1710, 1515, 1360, 1260, 1175 $cm^{-1}$.

EXAMPLE 82

Preparation of (3-(2-(L)-iodopropionamido)-lankone 8,14-ditrimethylsilylether and 3-(2-(D)-iodopropionamido)-lankone 8,14-ditrimethylsilylether In 2 ml of acetone was dissolved 136.8 mg of 3-(2-(DL)-methanesulfonyloxypropionamido)-lankone 8,14-ditrimethylsilylether. To the solution was added 111 mg of sodium iodide, and the mixture was refluxed for 4 hours. After cooling, precipitates were filtered off, and the filtrate was concentrated. The concentrate was subjected to a silica gel column chromatography, eluting with ethyl acetate-hexane (1:2). Desired fractions were combined and concentrated to obtain 61.8 mg of the above titled compound (2'-(L-compound) and 42.7 mg of the above titled compound (2'-(D)compound).

2'-(L)compound:

NMR (90 MHz, $CDCl_3$)δ: 0.01(s, 18H), 1.25(d, 3H, J=7 Hz), 1.49(s, 3H), 1.52(s, 3H), 1.88(s, 3H), 1.96(d, 3H, J=7 Hz), 2.10~2.70(m, 5H), 3.80~4.70(m, 5H), 5.10~5.80(m, 5H), 6.00(d, 1H, J=15 Hz), 7.03(d, 1H, J=10 Hz).

IR (KBr): 1760, 1720, 1675, 1255, 1070, 845 $cm^{-1}$.

2'-(D)compound:

NMR (90 MHz, $CDCl_3$)δ: 0.01(s, 18H), 1.25(d, 3H, J=7 Hz), 1.42(s, 3H), 1.53(s, 3H), 1.87(s, 3H), 1.92(d, 3H, J=7 Hz), 2.05~2.60(m, 5H), 3.85~4.70(m, 5H), 5.12~5.85(m, 5H), 6.00(d, 1H, J=15 Hz), 7.15(d, 1H, J=10 Hz).

IR (KBr): 1755, 1715, 1675, 1255, 1045, 845 $cm^{-1}$.

EXAMPLE 83

Preparation of 3-(2-trimethylsilyloxyacrylamido)-lankone 8,14-diacetate

In 4 ml of dichloromethane was dissolved 1.08 g of lankacidin C 8,14-diacetate. To the solution were added 0.42 ml of triethylamine and 0.32 ml of chlorotrimethylsilane, and the mixture was stirred at room temperature for 2 hours. Resultant precipitate were filtered off. To the filtrate was added dichloromethane, which was washed with cold water and substantially with aqueous NaCl solution, followed by drying over $Na_2SO_4$. The solvent was distilled off, and the residue was dissolved in 2 ml of dichloromethane. To the solution was added 20 ml of petroleum ether to obtain 1.17 g of the above titled compound as needles, m.p. 190°-191.5° C.

NMR (90 MHz, $CDCl_3$)δ: 0.30(s, $SiMe_3$), 1.30(d, J=7 Hz, 17-Me), 1.39(s, 2-Me), 1.55(s, 11-Me), 1.90(s, 5-Me), 2.02 and 2.04(each s, OAc×2), 2.2~2.6(m, 9-$H_2$, 15-$H_2$, 17-H), 4.40(m, 16-H), 4.59 and 5.50(each d, J=2 Hz, 3'-$H_2$), 4.71(d, J=11 Hz, 4-H), 5.07(m, 8-H), 5.2~5.9(m, 3-H, 6-H, 7-H, 10-H, 13-H, 14-H), 6.28(d, J=15 Hz, 12-H), 7.88(d, J=10 Hz, NH).

IR (KBr): 3410, 1741, 1712, 1496, 1374, 1250, 856 $cm^{-1}$.

$[\alpha]_D^{26}$ −201.0° (c=0.505, $CHCl_3$).

EXAMPLE 84

Preparation of 3-(3-bromo-2-oxopropionamido)-lankone 8,14-diacetate

In 20 ml of dichloromethane was dissolved 1.23 g of 3-(2-trimethylsiloxyacrylamido)-lankone 8,14-diacetate. To the solution was added little by little 0.427 g of N-bromosuccinimide, followed by stirring for 10 minutes. To the resultant mixture was added 20 ml of dichloromethane. The mixture was washed with water and with aqueous NaCl solution in sequence, followed by drying over $Na_2SO_4$. Dichloromethane was distilled off, and the residue was subjected to chromatography on silica gel inactivated with 10% of water, eluting with ethyl acetate-hexane (1:2) then with ethyl acetate-hexane (2:3). Desired fractions were combined and concentrated to obtain 622.8 mg of the above titled compound.

NMR (90 MHz, $CDCl_3$)δ: 1.31(d, 3H, J=7 Hz), 1.38(s, 3H), 1.53(s, 3H), 1.88(s, 3H), 2.01(s, 3H), 2,03(s, 3H), 2.15~2.55(m, 5H), 4.36(d, 1H, J=14 Hz), 4.54(d, 1H, J=14 Hz), 4.70(d, 1H, J=11 Hz), 4.93~5.83(m, 7H), 6.27(d, 1H, J=15 Hz), 8.10(d, 1H, J=10 Hz).

IR (KBr): 1740, 1720, 1700, 1245 $cm^{-1}$.

EXAMPLE 85

Preparation of 3-(2-(DL)-methanesulfonyloxypropionamide)-lankone 8,14-bis(dimethyl-t-butylsilylether)

Employing 13.8 g of lankacidin C 8,14-bis(dimethyl-t-butylsilylether), the reaction was allowed to proceed in a manner similar to Example 81 to obtain 7.5 g of the above titled compound, m.p. 207°-208° C.(chloroform-petroleum ether).

NMR (90 MHz, $CDCl_3$)δ: 0.00(s, 6H), 0.04(s, 6H), 0.85(s, 9H), 0.88(s, 9H), 1.20(d, 3H, J=6 Hz), 1.40(s, 3H), 1.50(s, 3H), 1.54~1.67(m, 3H), 1.89(s, 3H), 2.05~2.60(m, 5H), 3.04 and 3.08(each s, 3H), 3.80~4.70(m, 4H), 4.95~5.89(m, 6H), 6.00(d, 1H, J=15 Hz), 7.59(d, 1H, J=10 Hz ).

IR (KBr): 1745, 1710, 1060 $cm^{-1}$.

$[\alpha]_D^{23}$ −111.9° (c=0.52, $CHCl_3$).

EXAMPLE 86

Preparation of 3-(2-(L)-iodopropionamido)-lankone 8,14-bis(dimethyl-t-butylsilylether) and 3-(2-(D)-iodopropionamido)-lankone 8,14-bis(dimethyl-t-butylsilylether)

Employing 1.536 g of 3-(2-(DL)-methanesulfonyloxyproionamido)-lankone, 8,14-bis(dimethyl-t-butylsilylether), the reaction was carried out in a manner similar to Example 82 to obtain 951 mg of the above titled compound (2'-(L)compound) and 501 mg of the above titled compound (2'-(D)compound).

2'-(L)compound, m.p. 175° C. (decomp.)(ethyl acetate-hexane):

NMR (90 MHz, $CDCl_3$)δ: 0.00(s, 12H), 0.83(s, 9H), 0.85(s, 9H), 1.25(d, 3H, J=6 Hz), 1.48(s, 3H), 1.52(s, 3H), 1.85(s, 3H), 1.96(d, 3H, J=7 Hz), 2.05~2.50(m, 5H), 3.80~4.70(m, 5H), 5.00~5.80(m, 5H), 6.00(d, 1H, J=15 Hz), 7.06(d, 1H, J=10 Hz).

IR (KBr): 1745, 1715, 1675, 1065 $cm^{-1}$.

$[\alpha]_D^{23}$ −105.7° (c=0.525, CHCl$_3$)

2′-(D)compound, m.p. 185° C. (decomp.)(ethyl acetate-hexane):

NMR (90 MHz, CDCl$_3$)δ: 0.03(s, 12H), 0.85(s, 9H), 0.87(s, 9H), 1.24(d, 3H, J=7 Hz), 1.40(s, 3H), 1.54(s, 3H), 1.87(s, 3H), 1.98(d, 3H, J=7 Hz), 2.00~2.60(m, 5H), 3.90~4.75(m, 5H), 5.15~5.86(m, 5H), 6.00(d, 1H, J=15 Hz), 7.20(d, 1H, J=9 Hz).

IR (KBr): 1745, 1705, 1675, 1065 cm$^{-1}$.

$[\alpha]_D^{23}$ −73.6° (c=0.0525, CHCl$_3$)

EXAMPLE 87

Preparation of 3-(2-(DL)-benzenesulfinylpropionamido)-lankone 8,14-diacetate

In 6 ml of dichloromethane was dissolved 1.60 g of 3-(2-(DL)-phenylthiopropionamido)-lankone 8,14-diacetate, and the solution was cooled with ice-water, to which was added 649.3 mg of m-chloroperbenzoic acid. The mixture was stirred for 30 minutes, to which was further added 61.8 mg of m-chloroperbenzoic acid, and the whole mixture was stirred for 15 minutes. The resultant precipitates were filtered off, and the filtrate was washed with an aqueous solution of sodium hydrogencarbonate then with aqueous NaCl solution, followed by drying over Na$_2$SO$_4$. Then, the dichloromethane was distilled off, and the residue was subjected to a silica gel column chromatography, eluting with ethyl acetate-hexane (2:1) then with ethyl acetate. Desired fractions were combined and concentrated to obtain 1.39 g of the above titled compound.

NMR (90 MHz, CDCl$_3$)δ: 1.20~1.90(m, 15H), 2.01(s, 3H), 2.08(s, 3H), 2.16~2.60(m, 5H), 3.26~3.70(m, 1H), 4.26~4.56(m, 1H), 4.70(d, 1H, J=11 Hz), 4.93~5.90(m, 7H), 6.26(d, 1H, J=14 Hz), 7.20~7.72(m, 6H).

IR (KBr): 1735, 1715, 1670 cm$^{-1}$.

EXAMPLE 88

Preparation of 3-(2-(DL)-benzenesulfinylpropionamido)-lankone 8,14-diacetate and 3-(2-(DL)-benzenesulfonylpropionamido)-lankone 8,14-diacetate Employing 238.7 mg of 3-(2-(DL)-phenylthiopropionamido)-lankone 8,14-diacetate and 127 mg of m-chloroperbenzoic acid, the reaction was allowed to proceed in a manner similar to Example 87 to obtain 199.2 mg of the above titled compound (sulfoxide compound) (this product was in good accord with that obtained in Example 87 in the data of TLC, NMR and IR) and 50 mg of the above titled compound (sulfone compound). Solfone compound:

NMR (90 MHz, CDCl$_3$)δ: 1.25~1.90(m, 15H), 2.00~2.15(m, 6H), 2.19~2.60(m, 5H), 3.73~4.03(m, 1H), 4.30~4.60(m, 1H), 4.63~4.90(m, 1H), 4.92~5.90(m, 7H), 6.30(d, 1H, J=15 Hz), 7.23~7.90(m, 6H).

IR (KBr): 1740, 1725, 1715, 1680, 1240 cm$^{-1}$.

EXAMPLE 89

Preparation of 3-acrylamido-lankone 8,14-diacetate

A mixture of 1.10 g of 3-(2-(DL)-benzenesulfinylpropionamido)lankone 8,14-diacetate and 1.0 ml of trimethylphosphite was refluxed in 30 ml of xylene for 30 minutes. Xylene was distilled off, and the residue was subjected to a silica gel column chromatography, eluting with a mixture of ethyl acetate and hexane (2:1) then with ethyl acetate. Desired fractions were combined and concentrated to obtain 402.9 mg of the above titled compound.

NMR (90 MHz, CDCl$_3$)α: 1.30(d, 3H, J=7Hz), 1.41(s, 3H), 1.55(s, 3H), 1.90(s, 3H), 2.01(s, 3H), 2.03(s, 3H), 2.20~2.55(m, 5H), 4.25~4.50(m, 1H), 4.70(d, 1H, J=10 Hz), 4.93~5.93(m, 8H), 6.13~6.40(m, 2H), 6.72(d, 1H, J=10 Hz).

IR (KBr): 1740, 1720, 1680, 1240 cm$^{-1}$.

EXAMPLE 90

Preparation of 3-(2-(DL)-N-methylthiocarbamoylthiopropionamido)-lankone, 8,14-diacetate In 1.5 ml of tetrahydrofuran was dissolved 98.3 mg of 3-(2-(L)-iodopropionamido)-lankone 8,14-diacetate. To the solution was added 21.3 mg of sodium N-methyldithiocarbamate dissolved in 0.5 ml of water. The mixture was stirred at room temperature for 40 minutes, followed by extraction with ethyl acetate. The extract was washed with aqueous NaCl solution, then dried over Na$_2$SO$_4$. The solvent was distilled off, and the residue was subjected to a silica gel column chromatography, eluting with a mixture of ethyl acetate and benzene (1:2). Desired fractions were combined and concentrated to obtain 83.3 mg of the above titled compound.

NMR (90 MHz, CDCl$_3$)δ: 1.28(d, 3H, J=7 Hz), 1.39(s, 3H), 1.51(d, 3H, J=8 Hz), 1.52(s, 3H), 1.85(s, 3H), 2.25~2.55(m, 5H), 3.16(s, 1.5H), 3.22(s, 1.5H), 4.27~4.78(m, 3H), 4.90~5.90(m, 7H), 6.26(d, 1H, J=15 Hz), 7.50(d, 1H, J=10 Hz), 8.60 (br.s, 1H).

EXAMPLE 91

Preparation of 3-[2-(L)-(benzothiazol-2-yl)thio-propionamido]-lankone 8,14-diacetate and 3-[2-(D)-(benzothiazol-2-yl)thio-propionamido]-lankone, 8,14-diacetate A mixture of 31.2 mg of 3-(2(DL)-methanesulfonyloxypropionamido)-lankone 8,14-diacetate and 10.4 mg of 2-mercaptobenzothiazol sodium was subjected to reflux for 3.5 hours in 0.5 ml of tetrahydrofuran. To the resultant mixture was added, after cooling, ethyl acetate, which was washed with water and aqueous NaCl solution in sequence, followed by drying over Na$_2$SO$_4$. The solvent was distilled off, and the residue was subjected to separation by means of preparative TLC Plates: manufactured by Merck, Art. No. 5715, 20×20 cm, developing solvent: ethyl acetate-hexane (1:1)) to obtain 13.4 mg of the above titled compound (2′-(L)compound) and 7.8 mg of the above titled compound (2′-(D)compound). 2′-(L)compound, m.p. 178°–180° C.(AcOEt-Et$_2$O):

NMR (90 MHz, CDCl$_3$)δ: 1.14(s, 3H), 1.16(d, 3H, J=7 Hz), 1.51(s, 3H), 1.61(d, 3H, J=7 Hz), 1.86(s, 3H), 2.00(s, 3H), 2.05(s, 3H), 2.10~2.55(m, 5H), 4.15~4.40(m, 1H), 4.50~4.80(m, 2H), 4.90–5.80(m, 7H), 6.23(d, 1H, J=15 Hz), 7.17~8.10(m, 5H).

IR (KBr): 1740, 1715, 1680, 1245 cm$^{-1}$.

2′-(D)compound, m.p. 151°–152° C.(AcOEt-Et$_2$O):

NMR (90 MHz, CDCl$_3$)δ: 1.27(d, 3H, J=7 Hz), 1.34(s, 3H), 1.49(s, 3H), 1.61(d, 3H, J=8 Hz), 1.81(s, 3H), 2.00(s, 3H), 2.03(s, 3H), 2.15~2.55(m, 5H), 4.33(br.d., 2H, J=12 Hz), 4.65(q, 1H, J=8 Hz), 4.80~5.80(m, 7H), 6.20(d, 1H, J=14 Hz). 7.20~8.20(m, 5H).

IR (KBr): 1735, 1715, 1665, 1240 cm$^{-1}$.

EXAMPLE 92

Preparation of
3-[2-(L)-(benzothiazol-2-yl)thio-propionamido]-lankone 8,14-diacetate and
3-[2-(D)-(benzothiazol-2-yl)thio-propionamido]-lankone 8,14-diacetate In 1 ml of tetrahydrofuran was dissolved 65.6 mg of 3-(2-(L)-iodopropioamido)-lankone 8,14-diacetate. To the solution was added 28.4 mg of 2-mercaptobenzothiazole sodium. The mixture was stirred at room temperature for 40 minutes. To the resultant mixture was added ethyl acetate, which was washed with water and with aqueous saline solution in sequence, followed by drying over $Na_2SO_4$. The solvent was distilled off and the residue was subjected to a silica gel column chromatography, eluting with a mixture of ethyl acetate and hexane (1:1). Desired fractions were combined and concentrated to obtain 3.7 mg of the above titled compound (2'-(L)compound) and 57.4 mg of the above titled compound (2'-(D)compound). These products were in good accord with those obtained in Example 91 in the data of TLC, NMR and IR.

EXAMPLE 93

Preparation of
3-[2-(L)-(benzothiazol-2-yl)thio-propionamido]-lankone 8,14-diacetate and
3-[2-(D)-(benzothiazol-2-yl)thio-propionamido]-lankone 8,14-diacetate Employing 65.6 mg of 3-(2-(D)-iodopropionamido)-lankone 8,14-diacetate, the reaction was allowed to proceed in a manner similar to Example 92 to obtain 61.4 mg of the above titled compound (2'-(L)-compound) and 5.8 mg of the above titled compound (2'-(D)-compound). These products are in good accord with those obtained in Example 91 in the data of TLC, NMR and IR.

EXAMPLE 94

Preparation of
3-[2-(L)-(benzoxazol-2-yl)thio-propionamido]-lankone 8,14-diacetate and
3-[2-(D)-(benzoxazol-2-yl)thio-propionamido]-lankone 8,14-diacetate In 1 ml of tetrahydrofuran was dissolved 22.7 mg of 2-mercaptobenzoxazole. To the solution was added 6 mg of sodium hydride (ca. 60%), and the mixture was stirred for 5 minutes, to which was added 65.6 mg of 3-(2-(L)-iodopropionamido)-lankone 8,14-diacetate, followed by stirring for further 30 minutes. To the resultant mixture was added ethyl acetate, which was washed with water and aqueous NaCl solution in sequence, followed by drying over $Na_2SO_4$. The solvent was distilled off, and the residue was subjected to separation by means of preparative TLC Plates: manufactured by Merck, Art. No. 5715, 20×20 cm, developing solvent: ethyl acetate-benzene (1:2)) to give 5.1 mg of the above titled compound (2'-(L)compound) and 52.1 mg of the above titled compound (2'-(D)compound).

2'-(L)compound, m.p. 188°-190° C.(AcOEt-Et$_2$O):
NMR (90 MHz, CDCl$_3$)δ: 1.16(d, 3H, J=6 Hz), 1.19(s, 3H), 1.52(s, 3H), 1.63(d, 3H, J=8 Hz), 1.86(s, 3H), 2.00(s, 3H), 2.06(s, 3H), 2.10~2.55(m, 5H), 4.30(dt, 1H, J=12 Hz and 3 Hz), 4.46(q, 1H, J=8 Hz), 4.66(s, 1H, J=12 Hz), 4.90~5.80(m, 7H), 6.25(d, 1H, J=15 Hz), 7.10~7.70(m, 4H), 7.93(d, 1H, J=10 Hz). IR (KBr): 1740, 1715, 1680, 1240 cm$^{-1}$.

2'-(D)compound, m.p. 191°-192° C. (AcOEt-Et$_2$O):
NMR (90 MHz, CDCl$_3$)δ: 1.25(d, 3H, J=6 Hz), 1.35(s, 3H), 1.50(s, 3H), 1.65(d, 3H, J=7 Hz), 1.88(s, 3H), 2.00(s, 3H), 2.03(s, 3H), 2.13~2.53 (m, 5H), 4.25~4.63(m, 3H), 4.80~5.80(m, 7H), 6.20(d, 1H, J=15 Hz), 7.10~7.76(m, 4H), 8.09(d, 1H, J=10 Hz).
IR (KBr): 1740, 1715, 1665, 1245 cm$^{-1}$.

EXAMPLE 95

Preparation of
3-[2-(L)-(benzoxazol-2-yl)thio-propionamido]-lankone 8,14-diacetate and
3-[2-(D)-(benzoxazol-2-yl)thio-propionamido]-lankone 8,14-diacetate Employing 65.6 mg of 3-(2-(D)-iodopropioamido)-lankone 8,14-diacetate, the reaction was allowed to proceed in a manner similar to Example 94 to give 45.8 mg of the above titled compound (2'-(L)compound) and 9.1 mg of the above titled compound (2'-(D)compound). These products were in good accord with those obtained in Example 94 in the data of TLC, IR and NMR.

EXAMPLE 96

Preparation of
3-[2-(D)-(benzoimidazol-2-yl)thio-propionamido]-lankone 8,14-diacetate Employing 22.5 mg of 2-mercaptobenzoimidazole and 65.6 mg of 3-(2-(L)-iodopropionamido)-lankone 8,14-diacetate, the reaction was carried out in a manner similar to Example 94 to obtain 41.5 mg of the above titled compound, m.p. 158°-160° C. (AcOEt-Et$_2$O).
NMR (90 MHz, CDCl$_3$)δ: 1.29(d, 3H, J=7 Hz), 1.36(s, 3H), 1.48(s, 3H), 1.57(d, 3H, J=8 Hz), 1.80(s, 3H), 2.00(s, 3H), 2.03(s, 3H), 2.15~2.55(m, 5H), 4.15~4.53(m, 3H), 4.82~5.80(m, 7H), 6.20(d, 1H, J=15 Hz), 7.10~7.85(m, 4H), 8.10(d, 1H, J=10 Hz), 10.40(br, s, 1H).
IR (KBr): 1740, 1715, 1670, 1240 cm$^{-1}$.

EXAMPLE 97

Preparation of 3-[2-(L)-(benzoimidazol-2-yl) thio-propionamido]-lankone, 8,14-diacetate Employing 22.5 mg of 2-mercaptobenzoimidazole and 65.6 mg of 3-(2-(D)-iodopropionamido)-lankone 8,14-diacetate, the reaction was allowed to proceed in a manner similar to Example 94 to obtain 43.0 mg of the above titled compound, m.p. 156°-57° C. (Et$_2$O-petroleum ether).
NMR (90 MHz, CDCl$_3$)δ: 1.10(s, 3H), 1.22 (d, 3H, J=7 Hz), 1.50(s, 3H), 1.57(d, 3H, J=8 Hz), 1.86(s, 3H), 2.01(s, 3H), 2.04(s, 3H), 2.05~2.55(m, 5H), 4.10~4.43(m, 2H), 4.65(d, 1H, J=11 Hz), 4.90~5.80(m, 7H), 6.20(d, 1H, J=15 Hz), 7.00~7.80(m, 4H), 8.01(d, 1H, J=10 Hz), 11.05(br, s, 1H).
IR (KBr): 1730, 1715, 1660, 1240 cm$^{-1}$.

EXAMPLE 98

Preparation of
3-[2-(D)-(benzothiazol-2-yl)thio-propioamido]-lankone

In 1 ml of tetrahydrofuran was dissolved 61.8 mg of 3-(2-(L)-iodopropionamido)-lankone 8,14-ditrimethylsilylether. To the solution was added ;b 25.1 mg of 2-mercaptobenzothiazole sodium, and the mixture was stirred for 30 minutes, to which was added 0.3 ml of 1N hydrochloric acid, which was subjected, after stirring for further 10 minutes, to extraction with ethyl acetate. The extract was washed with water, aqueous solution of sodium hydrogencarbonate and aqueous NaCl solution, in sequence, followed by drying over $Na_2SO_4$. The solvent was distilled off, and the residue was subjected to a silica gel column chromatography, eluting with ethyl acetate. Desired fractions were combined and concentrated to obtain 52.0 mg of the above titled compound.

NMR (90 MHz, $CDCl_3$)δ: 1.30(s, 3H), 1.45 (s, 3H), 1.60(d, 3H, J=7 Hz), 1.80(s, 3H), 2.00~2.60(m, 5H), 3.80~4.50(m, 4H), 4.65(q, 1H, J=7 Hz), 5.05~5.85(m, 5H), 6.06(d, 1H, J=16 Hz), 7.15~8.15(m, 5H).

IR (KBr): 3400(br.), 1750, 1710, 1670 $cm^{-1}$.

EXAMPLE 99

Preparation of 3-(2-(D)-(benzothiazol-2-yl)thio-propionamido]-lankone 8,14-bis(dimethyl-t-butylsilylether)

Employing 120 mg of 3-(2-(L)-iodopropionamido)-lankone 8,14-bis(dimethyl-t-butylsilylether), the reaction was allowed to proceed in a manner similar to Example 92 to obtain 114.4 mg of the above titled compound.

NMR (90 MHz, $CDCl_3$)δ: 0.00(s, 12H), 0.80(s, 9H), 0.83(s, 9H), 1.13(d, 3H, J=7 Hz), 1.26(s, 3H), 1.43(s, 3H), 1.59(d, 3H, J=7 Hz), 1.79(s, 3H), 1.95~2.60(m, 5H), 3.70~4.80(m, 5H), 5.00~5.80(m, 5H), 5.90(d, 1H, J=15 Hz), 7.15~8.10(m, 5H).

IR (KBr): 1755, 1710, 1680, 1060 $cm^{-1}$.

$[\alpha]_D^{24}$ −91.7°(c=0.605, $CHCl_3$).

EXAMPLE 100

Preparation of 3-[2-(L)-(benzothiazol-2-yl)thio-propioamido]-lankone 8,14-bis(dimethyl-t-butylsilylether) and 3-[2-(D)-(benzothiazol-2-yl)thiopropioamido]-lankone 8,14-bis(dimethyl-t-butylsilylether)

Employing 120 mg of 3-(2-(D)-iodopropionamido)-lankone 8,14-bis(dimethyl-t-butylsilylether), the reaction was allowed to proceed in a manner similar to Example 92 to obtain 114.3 mg of the above titled compound (2'-(L)compound) and 12.2 mg of the above titled compound (2'-(D)compound) (this product was in good accord with that obtained in Example 99 in the data of TLC, IR and NMR).

2'-(L)compound, m.p. 192°-194° C. ($CHCl_3$-petroleum ether):

NMR (90 MHz, $CDCl_3$)δ: −0.06(s, 3H), 0.00(s, 9H), 0.78(s, 9H), 0.86(s, 9H), 1.01(d, 3H, H=7 Hz), 1.07(s, 3H), 1.45(s, 3H), 1.58(d, 3J, J=7 Hz), 1.83(s, 3H), 1.95~2.60(m, 5H), 3.80~4.80 (m, 5H), 5.00~5.80(m, 5H), 5.93(d, 1H, J=15 Hz), 7.09~8.15(m, 5H).

IR (KBr): 1745, 1715, 1685, 1070 $cm^{-1}$.

$[\alpha]_D^{24}$ −183.8° (c=0.475, $CHCl_3$)

EXAMPLE 101

Preparation of 3-[2-(L)-(benzoxazol-2-yl)thio-propionamido]-lankone 8,14-bis(dimethyl-t-butylsilylether) and 3-[2-(D)-(benzoxazol-2-yl)thio-propionamido]-lankone 8,14-bis(dimethyl-t-butylsilylether)

Employing 120 mg of 3-(2-(L)-iodopropionamido)-lankone 8,14-bis(dimethyl-t-butylsilylether), the reaction was allowed to proceed in a manner similar to Example 94 to obtain 22.7 mg of the above titled compound (2'-(L)compound) and 98.7 mg of the above titled compound (2'-(D)compound). 2'-(L)compound, m.p. 198°-199° C. ($CHCl_3$-petroleum ether):

NMR (90 MHz, $CDCl_3$)δ: −0.04(s, 3H), 0.00(s, 9H), 0.79(s, 9H), 0.83(s, 9H), 1.06(d, 3H), J=7 Hz), 1.13(s, 3H), 1.48(s, 3H), 1.62(d, 3H, J=7 Hz), 1.84(s, 3H), 1.95~2.60(m, 5H), 3.80~4.70(m, 5H), 5.05~5.80(m, 5H), 5.92(d, 1H, J=15 Hz), 7.10~7.70(m, 4H), 7.90(d, 1H, J=10 Hz).

IR (KBr): 1755, 1710, 1680, 1060 $cm^{-1}$.

$[\alpha]_D^{25}$ −175.7° (c=0.56, $CHCl_3$).

2'-(D)compound, m.p. 192°-192° C. ($CHCl_3$-petroleum ether):

NMR (90 MHz, $CDCl_3$)δ: 0.00(s, 3H), 0.01(s, 6H), 0.02(s, 3H), 0.83(s, 9H), 0.85(s, 9H), 1.16(d, 3H, J=7 Hz), 1.33(s, 3H), 1.46(s, 3H), 1.67(d, 3H, J=7 Hz), 1.84(s, 3H), 2.00~2.60(m, 5H), 3.75~4.65(m, 5H), 5.00~5.80(m, 5H), 5.96(d, 1H, J=16 Hz), 7.10~7.80(m, 4H), 8.10(d, 1H, J=10 Hz).

IR (KBr): 1755, 1705, 1660, 1065 $cm^{-1}$.

$[\alpha]_D^{24}$ ÷57.2° (c=0.465, $CHCl_3$).

EXAMPLE 102

Preparation of 3-[2-(L)-(benzoxazol-2-yl)thio-propionamido]lankone, 8,14-bis(dimethyl-t-butylsilylether) and 3-[2-(D)-(benzoxasol-2-yl)thio-propionamido]-lankone, 8,14-bis (dimethyl-t-butylsilylether)

Employing 120 mg of 3-(2-(D)-iodopropionamido)-lankone 8,14-bis(dimethyl-t-butylsilylether), the reaction was allowed to proceed in a manner similar to Example 94 to obtain 101.4 mg of the above titled compound (2'-(L)compound) and 20.9 mg of the above titled compound (2'-(D)compound). These products were in good accord with those obtained in Example 101 in the data of TLC, IR and NMR.

EXAMPLE 103

Preparation of 3-[2-(D)-(benzoimidazol-2-yl) thio-propionamido]-lankone 8,14-bis(dimethyl-t-butylsilylether)

Employing 33.8 mg of 2-mercaptobenzoimidazole and 120 mg of 3-(2-(L)-iodopropionamido)-lankone 8,14-bis(dimethyl-t-butylsilylether), the reaction was allowed to proceed in a manner similar to Example 94 to obtain 86.5 mg of the above titled compound, m.p. 175°-176° C. (AcOEt).

NMR (90 MHz, $CDCl_3$)δ: 0.00(s, 9H), 0.03(s, 3H), 0.83(s, 18H), 1.18(d, 3H, J=6 Hz), 1.33(s, 3H), 1.46(s, 3H), 1.56(d, 3H, J=7 Hz), 1.81(s, 3H), 2.00~2.65(m, 5H), 3.75~4.60(m, 5H), 5.00~5.80(m, 5H), 5.90(d, 1H, J=15 Hz), 7.05~7.28(, 2H), 7.36~7.62(m, 2H), 8.03(d, 1H, J=9 Hz), 8.15(br, s, 1H). IR (KBr): 1750, 1710, 1660, 1065 $cm^{-1}$.

$[\alpha]_D^{25}$=45.4° (c;32 0.485, $CDCl_3$).

EXAMPLE 104

Preparation of 3-[2-(L)-(benzoimidazol-2-yl)thio-propionamido]-lankone 8,14-bis(dimethyl-t-butylsilylether)

Employing 33.8 mg of 2-mercaptobenzoimidazole and 120 mg of 3-(2-(D)-iodopropionamido)-lankone, 8,14-bis (dimethyl-t-butysilylether), the reaction was allowed to proceed in a manner similar to Example 94 to obtain 69.2 mg of the above titled compound, m.p. 200° C. (decomp.) (AcOEt).

NMR (90 MHz, CDCl$_3$)δ: 0.00(s, 12H), 0.79(s, 9H), 0.82(s, 9H), 1.01(s, 3H), 1.09(d, 3H, J=7 Hz), 1.46(s, 3H9, 1.54(d, 3H, J=7 Hz), 1.83(s, 3H), 1.90~2.70(m, 5H), 3.80~4.75(m, 5H), 4.95~5.75(m, 5H), 5.90(d, 1H, J=15 Hz), 6.96~7.25(m, 2H), 7.33~7.65(m, 2H), 7.96(d, 1H, J=10 Hz), 8.16(br, s, 1H).

IR (KBr): 1745, 1715, 1660, 1065 cm$^{-1}$.

[α]$_D^{25}$ −189.5° (c=0.465, CHCl$_3$).

EXAMPLE 105

Preparation of
3-[2-(D)-(2-pyridylthio)propionamido]-lankone 8,14-bis(dimethyl-t-butylsilylether)

Employing 25.5 mg of 2-mercaptopyridine and 120.5 mg of 3-(2-(L)-iodopropionamido)-lankone 8,14-bis(-dimethyl-t-butylsilylether), the reaction was allowed to proceed in a manner similar to Example 94 to obtain 46.4 mg of the above titled compound, m.p. 190°–191° C. (CHCl$_3$-petroleum ether).

NMR (90 MHz, CDCl$_3$)δ: 0.00(s, 3H), 0.03(s, 9H), 0.77(s, 9H), 0.80(s, 9H), 1.13(d, 3H, J=6 Hz), 1.18(s, 3H), 1.44(s, 3H), 1.50(d, 3H, J=7 Hz), 1.77(s, 3H), 1.90~2.55(m, 5H), 3.75~4.65(m, 5H), 5.00~5.80(m, 5H), 5.90(d, 1H, J=15 Hz), 6.84~7.63(m, 3H), 8.13(d, 1H, J=10 Hz), 8.43~8.55(m, 1H).

IR (KBr): 1755, 1720, 1675, 1065 cm$^{-1}$.

[α]$_D^{24}$ ÷15.5° (c=0.54, CHCl$_3$).

EXAMPLE 106

Preparation of
3-[2-(L)-(2-pyridylthio)propionamido]-lankone 8,14-bis(dimethyl-t-butylsilylether)

Employing 25.6 mg of 2-mercaptopyridine and 120.1 mg of 3-(D)-iodopropionamido)-lankone 8,14-bis(-dimethyl-t-butylsilylether), the reaction was allowed to proceed in a manner similar to Example 94 to obtain 99.1 mg of the above titled compound, m.p. 221°–222° C. (AcOEt-hexane).

NMR (90 MHz, CDCl$_3$)δ: 0.02(s, 3H), 0.02(s, 9H), 0.82(s, 9H), 0.86(s, 9H), 1.10(d, 3H, J=6 Hz), 1.12(s, 3H), 1.49(s, 3H), 1.55(d, 3H, J=7 Hz), 1.85(s, 3H), 2.00~2.60(m, 5H), 3.85~4.64(m, 5H), 5.05~5.80(m, 5H), 5.92(d, 1H, J=15 Hz), 6.85~7.60(m, 3H), 8.02(d, 1H, J=10 Hz), 8.43~8.56(m, 1H).

IR (KBr): 1745, 1715, 1680, 1065 cm$^{-1}$.

[α]$_D^{25}$ −163.2° (c=0.53, CHCl$_3$).

EXAMPLE 107

Preparation of
3-[2-(D)-(benzothiazol-2-yl)thio-1-thioxo]propylamino-lankone 8,14-bis(dimethyl-t-butylsilylether)

In 4 ml of pyridine was dissolved 662.4 mg of 3-[2-(D)-(benzothiazol-2-yl)thio-propionamido]-lankone 8,14-bis(dimethyl-t-butylsilylether). To the solution was added 0.4 g of phosphorus pentasulfide, and the mixture was stirred at 90° C. for 6 hours. Pyridine was distilled off, and the residue was subjected to a silica gel column chromatography, eluting with a mixture of ethyl acetate and hexane (:5). Desired fractions were combined and concentrated, and the concentrate was subjected to separation by means of preparative TLC plates; manufacturee by Merck, Art. No. 5715, 20×20 cm, developing solvent: ethyl acetate-hexane (1:5) to obtain 42.5 mg of the above titled compound.

NMR (90 MHz, CDCl$_3$)δ: 0.00(s, 3H), 0.03(s, 9H), 0.83(s, 9H), 0.88(s, 9H), 1.15(d, 3H, J=7 Hz), 1.19(s, 3H), 1.31(d, 3H, J=7 Hz), 1.50(s, 3H), 1.94(s, 3H), 2.00~2.50(m, 5H), 3.80~4.70(m, 5H), 4.95~6.40(m, 6H), 7.15~8.00(m, 4H), 9.66(d, 1H, J=9 Hz).

IR (KBr): 1760, 1715, 1260, 1065 cm$^{-1}$.

EXAMPLE 108

Preparation of 3-(2-(D)-azidopropionamido)-lankone 8,14-bis(dimethyl-t-butylsilylether)

In 15 ml of N,N-dimethylformamide was dissolved 1.0 g of 3-(2-(L)-iodopropionamido)-lankone 8,14-bis(-dimethyl-t-butylsilylether). To the solution was added 122 mg of sodium azide. The mixture was stirred at 0° C. for 1 hour, then at room temperature for 30 minutes, which was poured into ice-water. Resultant precipitates were collected by filtration and dissolved in ethyl acetate. The organic layer was separated from the aqueous layer and dried over Na$_2$SO$_4$. The ethyl acetate solution was concetrated, and to the concentrate were added chloroform and petroleum ether to obtain 603.3 mg of the above titled a silica-gel column chromatography, eluting with a mixture of ethyl acetate and hexane (1:3) to give further 167.4 mg of the above titled compound, m.p. 197°–198° C. (CHCl$_3$-petroleum ether).

NMR (90 MHz, CDCl$_3$)δ: 0.00(s, 3H), 0.03(s, 9H), 0.85(s, 9H), 0.88(s, 9H), 1.22(d, 3H, J=7 Hz), 1.38(s, 3H), 1.46(d, 3H, J=7 Hz), 1.53(s, 3H), 1.73(s, 3H), 1.95~2.55(m, 5H), 3.75~4.65(m, 5H), 5.00~5.75(m, 5H), 5.90(d, 1H, J=15 Hz), 7.40(d, 1H, J=10 Hz).

IR (KBr): 2140, 1750, 1710, 1680, 1060 cm$^{-1}$.

[α]$_D^{24}$ −128.4° (c=0.54, CHCl$_3$).

EXAMPLE 109

Preparation of 3-(2-(L)-azidopropionamido)-lankone 8,14-bis(dimethyl-t-butylsilylether)

Employing 400.4 mg of 3-(2-(D)-iodopropionamido)-lankone 8,14-bis(dimethyl-t-butylsilylether), the reaction was allowed to proceed in a manner similar to Example 108 (purification by means of reprecipitation was not conducted) to obtain 300.3 mg of the above titled compound.

NMR (90 MHz, CDCl$_3$)δ: 0.00(s, 3H), 0.03(s, 6H), 0.05(s, 3H), 0.73(s, 9H), 0.75(s, 9H), 1.12(d, 3H, J=7 Hz), 1.25(s, 3H), 1.39(s, 3H), 1.43(d, 3H, J=7 Hz), 1.75(s, 3H), 2.00~2.55(m, 5H), 3.80~4.65(m, 5H), 5.00~5.80(m, 5H), 5.90(d, 1H, J=15 Hz), 7.45(d, 1H, J=10 Hz).

IR (KBr): 2110, 1755, 1715, 1680, 1065 cm$^{-1}$.

[α]$_D^{25}$ −88.3° (c=0.48, CHCl$_3$).

EXAMPLE 110

Preparation of 3-(2(D)-aminopropionamido)-lankone 8,14-bis(dimethyl-t-butylsilylether)

To 71.9 mg of 3-(2-(D)-azidopropionamido)-lankone 8,14-bis(dimethyl-t-butylsilylether) were added 0.5 ml of methanol and 0.5 ml of dichloromethane. To the mixture were added 20.1 μl of 1,3-propanedithiol and 27.9 μl of triethylamine. The whole mixture was stirred at room temperature overnight. The solvent was distilled off, and the residue was subjected to separation by means of preparative TLC Plates: manufactured by Merck, Art. No. 5715, 20×20 cm, developing solvent: acetone-benzene (1:1) to give 30.5 mg of the above titled compound, m.p. 165°–166° C. (AcOEt-petroleum ether).

IR (KBr): 1710, 1250, 1060, 834 cm$^{-1}$.

EXAMPLE 111

Preparation of 3-(2-(D)-aminopropionamido)-lankone 8,14-bis(dimethyl-t-butylsilylether)

In 2 ml of benzene was dissolved 71.5 mg of 3-(2-(D)-azidopropionamido)-lankone 8,14-bis(dimethyl-t-butylsilylether). To the solution was added 35.1 mg of a Lindlar catalyst, and the mixture was stirred at room temperature for 19 hours under hydrogen atmosphere, during which 35 mg each portion of the Lindlar catalyst was added five times. The catalyst was filtered off, and the filtrate was subjected to a silica gel column chromatography, eluting with acetone-benzene (2:3). Desired fractions were combined and concentrated to obtain 71.3 mg of the above titled compound. This product was in good accord with that obtained in Example 110 in the data of TLC, IR and NMR.

EXAMPLE 112

Preparation of 3-(2-(L)-aminopropionamido)-lankone 8,14-bis(dimethyl-t-butylsilylether)

Employing 71.7 mg of 3-(2-(L)-azidopropionamido)-lankone 8,14-bis(dimethyl-t-butylsilylether), the reaction was allowed to proceed in a manner similar to Example 111 to obtain 28.8 mg of the above titled compound.

IR (KBr): 1716, 1256, 1068, 840 cm$^{-1}$.

EXAMPLE 113

Preparation of 3-(2-(D)-acetylaminopropionamido)-lankone 8,14-bis(dimethyl-t-butylsilylether)

In 1 ml of pyridine was dissolved 65.4 mg of 3-(2-(D)-aminopropionamido)-lankone 8,14-bis(dimethyl-t-butylsilylether). To the solution was added, under cooling with ice-water, 0.5 ml of acetic anhydride, which was stirred at the same temperature for 22 minutes. The solvent was distilled off, and the residue was subjected to separation by means of preparative TLC Plates: manufactured by Merck, Art. No. 5715, 20×20 cm, developing solvent: acetone-benzene (1:3) to obtain 63.5 mg of the above titled compound, m.p. 207°–209° C. (CHCl$_3$-petroleum ether).

NMR (90 MHz, CDCl$_3$)δ: 0.00(s, 3H), 0.01(s, 9H), 0.90(s, 9H), 0.92(s, 9H), 1.28(d, 3H, J=6 Hz), 1.42(s, 3H), 1.47(d, 3H, J=7 Hz), 1.59(s, 3H), 1.91(s, 3H), 2.04(s, 3H), 2.05~2.70(m, 5H), 3.95~4.75(m, 5H), 5.10~5.90(m, 5H), 6.00(d, 1H, J=15 Hz), 6.43(d, 1H, J=6 Hz), 7.09(d, 1H, J=10 Hz).

IR (KBr): 3430, 1745, 1710, 1680, 1660, 1060 cm$^{-1}$.

$[\alpha]_D^{24}$ −112.8° (c=0.485, CHCl$_3$).

EXAMPLE 114

Preparation of 3-(2-(L)-acetylaminopropionamide)-lankone 8,14-bis(dimethyl-t-butylsilyl ether) p Employing 28.6 mg of 3-(2-(L)-aminopropionamido)-lankone, 8,14-bis(dimethyl-t-butylsilylether), the reaction was allowed to proceed in a manner similar to Example 113 to obtain 27.1 ml of the above titled compound.

NMR (90 MHz, CDCl$_3$)δ: 0.00(s, 3H), 0.03 (s, 3H), 0.83(s, 9H), 0.85(s, 9H), 1.20(d, 3H, J=6 Hz), 1.31(d, 3H, J=7 Hz), 1.36 (s, 3H), 1.51(s, 3H), 1.85(s, 3H), 2.00(s, 3H), 2.05~2.63(m, 5H), 3.85~4.70(m, 5H), 5.10~5.83(m, 5H), 6.00(d, 1H, 15 Hz), 6.31(d, 1H, J=7 Hz), 7.10(d, 1H, J=10 Hz).

IR (KBr): 3450, 1755, 1715, 1680, 1660, 1065 cm$^{-1}$.

EXAMPLE 115

Preparation of 3-(2-(L)-azidopropionamido)-lankone 8,14-diacetate

Employing 983.7 mg of 3-(2-(D)-iodopropionamido)-lankone 8,14-diacetate, the reaction was allowed to proceed in a manner similar to Example 108 to obtain 745.7 mg of the above titled compound.

NMR (90 MHz, CDCl$_3$)δ: 1.30(d, 3H, J=7 Hz), 1.38(s,3H), 1.53(d, 3H, J=7 Hz), 1.54(s, 3H), 1.87(s, 3H), 2.01(s, 3N), 2.04(s, 3H), 2.20~2.60(m, 5H), 4.11(q, 1H, J=7 Hz), 4.40(dt, 1H, J=12 Hz and 3Hz), 4.68(d, 1H, J=11 Hz), 4.93~5.85(m, 7H), 6.27(d, 1H, J=15 Hz), 7.50(d, 1H, J=10 Hz).

IR (KBr): 2120, 1740, 1715, 1695, 1240 cm$^{-1}$.

$[\alpha]_D^{25}$ −161.8° (c=1.05, CHCl$_3$).

EXAMPLE 116

Preparation of 3-(2-(D)-azidopropionamido)-lankone 8,14-diacetate

Employing 1.311 g of 3-(2-(L)-iodopropionamido)-lankone 8,14-diacetate, the reaction was allowed to proceed in a manner similar to Example 108 to obtain 1.0205 g of the above titled compound, m.p. 193° C. (decomp.) (AcOEt-Et$_2$O).

NMR (90 MHz, CDCl$_3$)δ: 1.31(d, 3H, J=7 Hz), 1.38(s, 3H), 1.46(d, 3H, J=7 Hz), 1.54(s, 3H), 1.87(s, 3H), 2.02(s, 3H), 2.04(s, 3H), 2.20~2.60 (m, 5H), 4.09(q, 1H, J=7 Hz), 4.40(dt, 1H, J=12 Hz and 3 Hz), 4.67(d, 1H, J=11 Hz), 4.93~5.84(m, 7H), 6.28(d, 1H, J=15 Hz), 7.50(d, 1H, J=10 Hz).

IR (KBr): 2120, 1735, 1715, 1685, 1240 cm$^{-1}$.

$[\alpha]_D^{25}$ −180.0° (c=0.55, CHCl$_3$)

EXAMPLE 117

Preparation of 3-(2-(D)-aminopropionamido)-lankone 8,14-diacetate

Employing 540.4 mg of 3-(2-(D)-azidopropionamido)lankone 8,14-diacetate, the reaction was allowed to proceed in a manner similar to Example 111 to obtain 465.2 mg of the above titled compound, m.p. 162°–163° C. (AcOEt-Et$_2$O).

NMR (90 MHz, CDCl$_3$)δ: 1.25(d, 3H, J=7 Hz), 1.27(d, 3H, J=7 Hz), 1.35(s, 3H), 1.52(s, 3H), 1.56(s, 2H), 1.86(s, 3H), 1.98(s, 3H), 2.00(s, 3H), 2.15~2.55(m, 5H), 3.45(q, 1H, J=7 Hz), 4.33(dt, 1H, J=12 Hz and 3 Hz), 4.70(d, 1H, J=11 Hz), 4.92~5.83(m, 7H), 6.26(d, 1H, J=15 Hz), 8.06(d, 1H, J=10 Hz).

IR (KBr): 1735, 1720, 1670, 1240 cm$^{-1}$.

$[\alpha]_D^{24}$ −238.3° (c=0.46, CHCl$_3$).

EXAMPLE 118

Preparation of 3-(2-(L)-aminopropionamido)-lankone 8,14-diacetate

Employing 525.6 mg of 3-(2-(L)-azidopropionamido)lankone 8,14-diacetate, the reaction was allowed to proceed in a manner similar to Example 111 to obtain 333.1 mg of the above titled compound, m.p. 149°–150° C. (AcOEt).

NMR (90 MHz, CDCl$_3$)δ: 1.30(d, 3H, J=7 Hz), 1.33(d, 3H, J=7 Hz), 1.38(s, 3H), 1.55(s, 3H), 1.64(s, 2H), 2.01(s, 3H), 2.03(s, 3H), 2.20~2.55(m, 5H), 3.461 (q, 1H, J=7 Hz), 4.39(dt, 1H, J=12 Hz and 3 Hz), 4.72(d, 1H, J=11 Hz), 4.93~5.85(m, 7H), 6.27(d, 1H, J=15 Hz), 8.15(d, 1H, J=10 Hz).

IR (KBr): 1735, 1715, 1670, 1250 cm$^{-1}$.

$[\alpha]_D^{25}$ −231.1° (c=0.505, CHCl$_3$).

EXAMPLE 119

Preparation of 3-(2-(D)-acetylaminopropionamide)-lankone 8,14-diacetate

Employing 97.5 mg of 3-(21 -(D)-aminopropionamido)-lankone 8,14-diacetate, the reaction was allowed to proceed in a manner similar to Example 113 to obtain 101.1 mg of the above titled compound, m.p. 173°–174° C. (AcOEt-Et$_2$O).

NMR (90 MHz, CDCl$_3$)δ: 1.28(d, 3H, J=7 Hz), 1.37(d, 3H, J=7 Hz), 1.37(s, 3H), 1.54(s, 3H), 1.82(s, 3H), 2.02(s, 6H), 2.04(s, 3H), 2.20~2.60(m, 5H), 4.26~4.75(m, 3H), 4.90~5.85(m, 7H), 6.23(d, 1H, J=7 Hz), 6.26(d, 1H, J=15 Hz), 7.10(d, 1H, J=10 Hz).

IR (KBr): 1735, 1715, 1660, 1245 cm$^{-1}$.

$[\alpha]_D^{25}$ −167.0° (c=0.525, CHCl$_3$).

EXAMPLE 120

Preparation of 3-(2-(L)-acetylaminopropionamido)-lankone 8,14-diacetate

Employing 109.3 mg of 3-(2-(L)-aminopropionamide)-lankone 8,14-diacetate, the reaction was allowed to proceed in a manner similar to Example 113 to obtain 122.8 mg of the compound.

NMR (90 MHZ, CDCl$_3$)δ: 1.28(d, 6H, J=7 Hz), 1.38(s, 3H), 1.53(s, 3H), 1.84(s, 3H), 1.93(s, 3H), 2.00(s, 3H), 2.031 (s, 3H), 2.15~2.60(m, 5H), 4.25~4.70(m, 3H), 4.91~5.85(m, 7H), 6.26(d, 1H, J=15 Hz), 6.74(d, 1H, J=7 Hz), 7.13(d, 1H, J=10 Hz).

IR (KBr): 1740, 1715, 1665, 1240 cm$^{-1}$.

$[\alpha]_D^{24}$ −207.0° (c=0.56, CHCl$_3$).

EXAMPLE 121

Prepqration of 3-(2-(D)-propionylaminopropionamido)-lankone 8,14-diacetate

Employing 109.1 mg of 3-(2-(D)-aminopropionamido)-lankone 8,14-diacetate and propionic anhydride, the reaction was allowed to proceed in a manner similar to Example 113 to obtain 115.2 mg of the above titled compound, m.p. 188°–189° C. (AcOEt).

NMR (90 MHz, CDCl$_3$)δ: 1.15(t, 3H, J=7 Hz), 1.28(d, 3H, J=7 Hz), 1.37(d, 3H, J=7 Hz), 1.37(s, 3H), 1.53(s, 3H), 1.86(s, 3H), 2.01(s, 3H), 2.03(s, 3H), 2.13~2.55(m, 7H), 4.27~4.75(m, 3H), 4.91~5.85(m, 7H), 6.14(d, 1H, J=8 Hz), 6.23(d, 1H, J=15 Hz), 7.12(d, 1H, J=10 Hz).

IR (KBr): 1740, 1715, 1665, 1245 cm$^{-1}$.

$[\alpha]_D^{25}$ −154.1° (c=0.56, CHCl$_3$).

EXAMPLE 122

Preparation of 3-(2-(L)-propionylaminopropionamido)-lankone 8,14-diacetate

Employing 108.9 mg of 3-(2-(L)-aminopropionamide)-lankone 8,14-diacetate and pripionic anhydride, the reaction was allowed to proceed in a manner similar to Example 113 to obtain 122.3 mg of the above titled compound.

NMR (90 MHz, CDCl$_3$)δ: 1.13(t, 3H, J=7 Hz), 1.28(d, 6H, J=7 Hz), 1.38(s, 3H), 1.53(s, 3H), 1.85(s, 3H), 2.00(s, 3H), 2.03(s, 3H), 2.10~2.60(m, 7H). 4.30~4.80(m, 3H), 4.93~5.85(m, 7H), 6.27(d, 1H, J=15 Hz), 6.52(d, 1H, J=8 Hz), 7.15(d, 1H, J=10 Hz).

IR (KBr): 1740, 1720, 1670, 1245 cm$^{-1}$.

$[\alpha]_D^{25}$ −209.2° (c=0.545, CHCl$_3$).

EXAMPLE 123

Preparation of 3-(2-(D)-n-butyrylaminopropionamido)-lankone 8,14-diacetate

Employing 109.1 mg of 3-(2-(D)-aminopropionamido)-lankone 8,14-diacetate and n-butyric anhydride, the reaction was allowed to proceed in a manner similar to Example 113 to obtain 119.7 mg of the above titled compound, m.p. 188°–189° C. (AcOEt).

NMR (90 MHz, CDCl$_3$)δ: 0.92(t, 3H, J=7 Hz), 1.27(d, 3H, J=7 Hz), 1.34(d, 3H, J=7 Hz), 1.37(s, 3H), 1.50~1.85(m, 2H), 1.53(s, 3H), 1.86(s, 3H), 2.01(s, 3H), 2.03~2.55(m, 7H), 2.04(s, 3H), 4.25~4.75(m, 3H), 4.90~5.50(m, 7H), 6.06(d, 1H, J=7 Hz), 6.25(d, 1H, J=15 Hz), 7.10(d, 1H, J=10 Hz).

IR (KBr): 1740, 1715, 1665, 1245 cm$^{-1}$.

$[\alpha]_D^{25}$ −155.7° (c=0.535, CHCl$_3$)

EXAMPLE 124

Preparation of 3-(2-(L)-n-bityrylaminopropionamido)-lankone 8,14-diacetate

Employing 109.4 mg of 3-(2-(L)-aminopropionamido)-lankone 8,14-diacetate and n-butyric anhydride, the reaction was allowed to proceed in a manner similar to Example 113 to obtain 128.1 mg of the above titled compound.

NMR (90 MHz, CDCl$_3$)δ: 0.91(t, 3H, J=7 Hz), 1.29(d, 6H, J=7 Hz), 1.38(s, 3H), 1.50~1.90(m, 2H), 1.54(s, 3H), 1.86(s, 3H), 2.00~2.55(m, 7H), 2.01(s, 3H), 2.03(s, 3H), 4.27~4.74(m, 3H), 4.91~5.85(m, 7H), 6.23(d, 1H, J=8 Hz), 6.25(d, 1H, J=15 Hz), 7.05(d, 1H, J=10 Hz).

IR (KBr): 1740, 1715, 1665, 1240 cm$^{-1}$.

$[\alpha]_D^{25}$ −192.2° (c=0.475, CHCl$_3$).

EXAMPLE 125

Preparation of 3-(2-(D)-benzyloxycarbonylaminopropionamido)-lankone 8,14-diacetate In 2 ml of benzene was dissolved 109.3 mg of 3-(2-(D)-aminopropionamido)-lankone 8,14-diacetate. To the solution were added, while stirring under cooling with ice-water, 31.4 μl of carbobenzoxy chloride and 22 μl of 10N aqueous solution of sodium hydroxide dropwise simultaneously. The mixture was stirred for 5 minutes at room temperature, which was extracted with ethyl acetate. The extract was washed with aqueous NaCl solution, followed by drying over Na$_2$SO$_4$. The solvent was distilled off, and the residue was subjected to a silica gel column chromatography, eluting with ethyl acetate. Desired fractions were combined and concentrated to give 114.4 mg of the above titled compound, m.p. 185°–186° C. (AcOEt).

NMR (90MHz, CDCl$_3$), δ: 1.26(d, 3H, J=7 Hz), 1.33(s, 3H), 1.36(d, 3H, J=7 Hz), 1.52(s, 3H), 1.84(s, 3H), 2.00(s, 3H), 2.02(s, 3H), 2.13~2.55(m, 5H), 4.16(q, 1H, J=7 Hz), 4.20~4.50(m, 1H), 4.63(d, 1H, J=11 Hz), 4.90~5.85(m, 9H), 6.23(d, 1H, J=15 Hz), 7.16(d, 1H, J=10 Hz), 7.31(s, 5H).

IR (KBr): 1735, 1715, 1250 cm$^{-1}$.
[α]$_D^{25}$ −151.1° (c=0.47, CHCl$_3$).

EXAMPLE 126

Preparation of 3-(2-(L)-benzyloxycarbonylaminopropionamido)-lankone 8,14-diacetate Employing 109.1 mg of 3-(2-(L)-aminopropionamido)-lankone 8,14-diacetate and dichloromethane as a solvent, the reaction was allowed to proceed in a manner similar to Example 125 to obtain 133.8 mg of the above titled compound.

NMR (90 MHz, CDCl$_3$)δ: 1.26(d, 3H, J=7 Hz), 1.32(d, 3H, J=7 Hz), 1.34(s, 3H), 1.53(s, 3H), 1.84(s, 3H), 2.01(s, 3H), 2.03(s, 3H), 2.15~2.50(m, 5H), 4.15(q, 1H, J=7 Hz), 4.25~4.50(m, 1H), 4.65(d, 1H, J=11 Hz), 4.90~5.80(m, 9H), 6.26(d, 1H, J=15 Hz), 7.11(d, 1H, J=10 Hz), 7.30(s, 5H).

IR (KBr): 1735, 1720, 1245 cm$^{-1}$.
[α]$_D^{25}$ −175.2° (c=0.52, CHCl$_3$).

EXAMPLE 127

Preparation of 3-(2-(D)-p-toluenesulfonylaminopropionamido)lankone 8,14-diacetate In 1 ml of pyridine was dissolved 109.2 mg of 3-(2-(D)-aminopropionamido)-lankone 8,14-diacetate. To the solution was added 46.6 mg of p-toluenesulfonyl chloride, and the mixture was stirred for 30 minutes. The pyridine was distilled off. To the residue was added ethyl acetate, which was washed with water, 1N hydrochloric acid and aqueous NaCl solution in sequence, followed by drying over Na$_2$SO$_4$. The solvent was distilled off, and the residue was subjected to a silica gel column chromatography, eluting with ethyl acetate—hexane (2:1). Desired fractions were combined and concentrated to give 89.4 mg of the above titled compound, m.p. 193°–194° C. (AcOEt).

NMR (90 MHz, CDCl$_3$)δ: 1.25(d, 3H, J=7 Hz), 1.27(d, 3H, J=7 Hz), 1.36(s, 3H), 1.79(s, 3H), 2.00(s, 3H), 2.03(s, 3H), 2.15~2.55(m, 5H), 2.35(s, 3H), 3.75(quintet, 1H, J=7 Hz), 4.26~4.70(m, 2H), 4.90–5.85(m, 7H), 6.25(d, 1H, J=15 Hz), 7.20(d, 2H, J=8 Hz), 7.40(d, 1H, J=10 Hz), 7.68(d, 2H, J=8 Hz).

IR (KBr): 1730, 1715, 1240 cm$^{-1}$.
[α]$_D^{25}$ −138.3° (c=0.475, CHCl$_3$).

EXAMPLE 128

Preparation of 3-(2-(L)-p-toluenesulfonylaminopropionamido)-lankone 8,14-diacetate Employing 109.4 mg of 3-(2-(L)-aminopropionamido)-lankone 8,14-diacetate, the reaction was allowed to proceed in a manner similar to Example 127 to obtain 94.2 mg of the above titled compound, m.p. 174°–175° C. (AcOEt).

NMR (90 MHz, CDCl$_3$)δ: 1.21(s, 3H), 1.25(d, 3H, J=7 Hz), 1.29(d, 3H, J=7 Hz), 1.52(s, 3H), 1.82(s, 3H), 2.01(s, 3H), 2.03(s, 3H), 2.15~2.55(m, 5H), 2.38(s, 3H), 3.78(quintet, 1H, J=7 Hz), 4.25~4.65(m, 2H), 4.90~5.85(m, 7H), 6.24(d, 1H, J=15 Hz), 7.06(d, 1H, J=10 Hz), 7.24(d, 2H, J=8 Hz), 7.73(d, 2H, J=8 Hz).

IR (KBr): 1740, 1715, 1245 cm$^{-1}$.
[α]$_D^{25}$ −205.9° (c=0.49, CHCl$_3$).

EXAMPLE 129

Preparation of 3-(2-(D)-diphenylphosphinothioylaminopropionamido)-lankone 8,14-diacetate In 0.5 ml of chloroform was dissolved 108.4 mg of 3-(2-(D)-aminopropionamido)-lankone 8, 14-diacetate. To the solution was added 83.7 μl of triethylamine. To the mixture was added dropwise a solution of 102.1 mg of diphenylphosphinothioyl chloride in 0.5 ml of chloroform, which was stirred for 1 hour. To the resultant was added ethyl acetate. The mixture was washed with 1N hydrochloric acid, water, aqueous solution of sodium hydrogencarbonate and aqueous NaCl solution in sequence, followed by drying over Na$_2$SO$_4$. The solvent was distilled off, and the residue was subjected to a silica gel column chromatography, eluting with ethyl acetate—hexane (1:1). Desired fractions were combined and concentrated to give 96.0 mg of the above titled compound.

NMR (90 MHz, CDCl$_3$)δ: 1.28(d, 3H, J=7 Hz), 1.36(s, 3H), 1.38(d, 3H, J=7 Hz), 1.54(s, 3H), 1.86(s, 3H), 2.01(s, 3H), 2.03(s, 3H), 2.15~2.55(m, 5H), 3.41(dd, 1H, J=6 Hz and 9 Hz), 3.70~4.20(m, 1H), 4.30~4.55(m, 1H), 4.67(d, 1H, J=8 Hz), 4.90~5.85(m, 7H), 6.27(d, 1H, J=5 Hz), 7.20~7.60(m, 7H), 7.70~8.15(m, 4H).

IR (KBr): 1735, 1715, 1680, 1240 cm$^{-1}$.
[α]$_D^{26}$ −131.4° (c=0.455, CHCl$_3$).

EXAMPLE 130

Preparation of 3-(2-(L)-diphenylphosphinothioylaminopropionamido)-lankone 8,14-diacetate Employing 109.2 mg of 3-(2-(L)-aminopropionamido)-lankone 8,14-diacetate, the reaction was allowed to proceed ina manner similar to Example 129 to obtain 102.1 mg of the above titled compound.

NMR (90 MHz, CDCl$_3$)δ: 1.30(d, 3H, J=7 Hz), 1.33(d, 3H, J=7 Hz), 1.38(s, 3H), 1.53(s, 3H), 1.85(s, 3H), 2.01(s, 3H), 2.04(s, 3H), 2.15~2.55(m, 5H), 3.43(dd, 1H, J=5 Hz and 9 Hz), 3.65~4.20(m, 1H), 4.25~4.50(m, 1H), 4.65(d, 1H, J=10 Hz), 4.90~5.85(m, 7H), 6.25(d, 1H, J=15 Hz), 7.16(d, 1H, J=10 Hz), 7.27~7.56(m, 6H), 7.70~8.15(m, 4H).

IR (KBr): 1740, 1715, 1680, 1240 cm$^{-1}$.
[α]$_D^{26}$ −161.5° (c=0.48, CHCl$_3$).

EXAMPLE 131

Preparation of 3-(2-(D)-ethylthiopropionamido)-lankone 8,14-diacetate

Employing 164.3 mg of 3-(2-(L)-iodopropionamido)-lankone 8,14-diacetate and ethanthiol, the reaction was allowed to proceed in a manner similar to Example 94 to obtain 99.5 mg of the above titled compound, m.p. 183°–184° C. (AcOEt-Et$_2$O).

NMR (90 MHz, CDCl$_3$)δ: 1.21(t, 3H, J=7 Hz), 1.32(d, 3H, J=7 Hz), 1.38(d, 3H, J=7 Hz), 1.39(s, 3H), 1.56(s, 3H), 1.79(s, 3H), 2.03(s, 3H), 2.05(s, 3H), 2.20~2.70(m, 7H), 3.42(q, 1H, J=7 Hz), 4.42(dt, 1H, J=3 Hz and 12 Hz), 4.70(br.d, 1H, J=11 Hz), 4.94~5.86(m, 7H), 6.28(d, 1H, J=15 Hz), 7.71(d, 1H, J=10 Hz).

IR (KBr): 1740, 1710, 1675, 1245 cm$^{-1}$.
[α]$_D^{22}$ −150.0° (c=0.48, CHCl$_3$)

EXAMPLE 132

Preparation of 3-(2-(L)-ethylthioprionamido)-lankone 8,14-diacetate

Employing 164.9 mg 3-(2-(D)-iodopropionamido)-lankone 8,14-diacetate and ethanethiol, the reaction was allowed to proceed in a manner similar to Example 94 to obtain 93.1 mg of the above titled compound, m.p. 178°-179° C. (Et$_2$O).

NMR (90 MHZ, CDCl$_3$)δ: 1.20(t, 3H, J=7 Hz), 1.32(d, 3H, J=7 Hz), 1.40(s, 3H), 1.46(d, 3H, J=7 Hz), 1.54(s, 3H), 1.88(s, 3H), 2.02(s, 3H), 2.04(s, 3H), 2.16~2.60(m, 7H), 2.39(dt, 1H, J=3 Hz and 12 Hz), 3.36(q, 1H, J=7 Hz), 4.70(br.d, 1H, J=11 Hz), 4.93~5.84(m, 7H), 6.26(d, 1H, J=15 Hz), 7.76(d, 1H, J=10 Hz).

IR (KBr): 1740, 1710, 1675, 1240 cm$^{-1}$.

$[\alpha]_D^{22}$ −213.7° (c=0.49, CHCl$_3$).

EXAMPLE 133

Preparation of 3-[3-(benzothiazol-2-yl)thio-2-oxopropionamido]-lankone 8-acetate In 1 ml of tetrahydrofuran was dissolved 187.0 mg of 3-(3-bromo-2-oxopropionamido)-lankone 8,14-diacetate. To the solution was added 69.1 mg of 2-mercaptobenzothiazole sodium at 0° C., and the mixture was stirred for 15 minutes at the same temperature, to which was added ethyl acetate, followed by washing with water and aqueous NaCl solution. The resultant was dried over Na$_2$SO$_4$, then the solvent was distilled off, and the residue was subjected to a silica gel column chromatography, eluting with ethyl acetate-hexane (1:1) then with ethyl acetate-hexane (2:1). Desired fractions were combined and concentrated to give 80.1 mg of a crude 9,14-diacetate compound, which was dissolved in 5 ml of tetrahydrofuran. To the solution were added 10 ml of methanol and 30 ml of an aqueous solution containing 1.4 g of the enzyme prepared in Reference Example 11, and the mixture was stirred for 40 minutes. The resultant mixture was subjected to extraction with 60 ml of chloroform. The organic layer was washed with aqueous NaCl solution, then dried over Na$_2$SO$_4$. The solvent was distilled off, and the residue was subjected to separation by means of reversed phase preparative TLC. Plates: manufactured by Merck Art. No. 15424, 10×20 cm, developing solvent: methanol-water (4:1) to obtain 25.1 mg of the above titled compound.

NMR (90 MHz, CDCl$_3$) δ: 1.23(d, 3H, J=7 Hz), 1.41(s, 3H), 1.56(s, 3H), 1.67(br.s, 1H), 1.96(s, 3H), 2.07(s, 3H), 2.15~2.60(m, 5H), 4.15~4.76(m, 5H), 4.90~5.92(m, 6H), 6.13(d, 1H, J=15 Hz), 7.20~7.92(m, 4H), 8.23(d, 1H, J=10 Hz).

IR (KBr):3400, 1735, 1710, 1260 cm$^{-1}$.

$[\alpha]_D^{24}$ −112.1° (c=0.14, EtOH).

EXAMPLE 134

Preparation of 3-[3-(benzoxazol-2-yl)thio-2-oxopropionamido]-lankone 8,14-diacetate From 307.4 mg of 3-(2-trimethylsilyloxyacrylamido)-lankone 8,14-diacetate was prepared 3-(3-bromo-2-oxopropionamido)-lankone 8,14-diacetate. On the other hand, 113.7 mg of 2-mercaptobenzoxazole was dissolved in 1 ml of tetrahydrofuran. To the solution mixture was added dropwise 2 ml of sodium hydride (60% purity), and the mixture was stirred for 5 minutes. To the resultant was added dropwise 2 ml of tetrahydrofuran containing the 3′-bromo compound prepared as above. The mixture was stirred for 15 minutes, diluted with ethyl acetate and washed with water and aqueous saline solution in sequence. The resultant solution was dried over Na$_2$SO$_4$, then the solvent was distilled off. The residue was subjected to a silica gel column chromatography, eluting with ethyl acetate-hexane (1:1). Desired fractions were combined and concentrated to obtain 168.1 mg of the above titled compound.

NMR (90 MHz, CDCl$_3$) δ: 1.37(d, 1H, J=7 Hz), 1.41(s, 3H), 1.55(s, 3H), 1.93(s, 3H), 2.03(s, 3H), 2.05(s, 3H), 2.2~2.6(m, 5H), 4.50(m, 1H), 4.65(s, 2H), 4.70(d, 1H, J=11 Hz), 5.05(m, 1H), 5.2~5.9(m, 6H), 6.28(d, 1H, J=15 Hz), 7.15~7.6(m, 4H), 8.09(d, 1H, J=10 Hz).

IR (KBr): 1735, 1715, 1695, 1505, 1245 cm$^{-1}$.

EXAMPLE 135

Preparation of 3-[3-(pyridine-2-yl)thio-2-oxopropionamido]-lankone 8-acetate

In 4 ml of tetrahydrofuran was dissolved 54.0 mg of 2-mercaptopyridine, to which was added under cooling with ice-water 19.5 mg of sodium hydride (60% in an oil), followed by stirring for 5 minutes. To the mixture was added 249.1 mg of 3-(3-bromo-2-oxopropionamido)-lankone 8,14-diacetate, which was stirred for further 10 minutes. To this was added ethyl acetate, which was washed with water and aqueous NaCl solution in sequence, then dried over Na$_2$SO$_4$. The solvent was distilled off, and the residue was subjected to a silica gel column chromatography, eluting with a mixture of ethyl acetate and hexane (1:1). Desired fractions were combined and concentrated to give 123.7 mg of crude 8,14-diacetate. The crude product was dissolved in 5 ml of methanol, to which was added 40 ml of an aqueous solution of 2.5 g of the enzyme prepared in Reference Example 11. The mixture was stirred for 30 minutes and subjected to extraction with chloroform. The extract was washed with aqueous NaCl solution, then dried over Na$_2$SO$_4$. The solvent was distilled off, and the residue was subjected to a column chromatography on silica gel inactivated with 10% of water, eluting with ethyl acetate-hexane (2:1). Desired fractions were combined and concentrated to obtain 73.6 mg of the above titled compound, m.p. 145°-146° C. (Et$_2$O).

NMR (90 MHz, CDCl$_3$) δ: 1.23(d, 3H, J=7 Hz), 1.41(s, 3H), 1.55(s, 3H), 1.72(br.s, 1H), 1.93(s, 3H), 2.05(s, 3H), 2.15~2.55(m, 5H), 4.15~4.80(m, 5H), 4.93~5.91(m, 6H), 6.15(d, 1H, J=15 Hz), 6.84~7.55(m, 3H), 7.99~8.20(m, 2H).

IR (KBr): 3400, 1730, 1710, 1690, 1260 cm$^{-1}$.

$[\alpha]_D^{23.5}$ −136.8° (c=0.345, EtOH).

In a manner similar to the above, sodium salt of thiol was allowed to react with 3-(3-bromo-2-oxopropionamido)lankone 8,14-diacetate to give 3′-substituted thio-8,14-diacetate, which was subjected to hydrolysis with the enzyme prepared in Reference Example 11 to obtain 3-(3-substituted thio-2-oxopropionamido)-lankone 8-acetate shown by Examples 136~139.

EXAMPLE 136

Preparation of 3-(3-phenylthio-2-oxopropionamido)-lankone 8-acetate

Overall yield: 8% m.p.: 164°-165° C. (AcOEt)

NMR (90 MHz, CDCl$_3$) δ: 1.25(d, 3H, J=7 Hz), 1.34(s, 3H), 1.58(s, 3H), 1.63(br.s, 1H), 1.90(s, 3H), 2.05(s, 3H), 2.15~2.55(m, 5H), 4.01(d, 1H, J=14 Hz), 4.18(d, 1H, J=14 Hz), 4.20~4.56(m, 2H), 4.68(br.d, 1H, J=11 Hz), 4.93~5.91(m, 6H), 6.13(d, 1H, J=15 Hz), 7.15~7.50(m, 5H), 8.30(d, 1H, J=10 Hz).

IR (KBr): 3400, 1730, 1710, 1690, 1260 cm$^{-1}$.

$[\alpha]_D^{23}$ −117.4° (c=0.155, EtOH).

EXAMPLE 137

Preparation of 3-(3-ethylthio-2-oxopropionamido)-lankone 8-acetate

Overall yield: 14% m.p.: 191° C. (decomp.) (Et$_2$O)

NMR (90 MHz, CDCl$_3$) δ: 1.21(t, 3H, J=7 Hz), 1.25(d, 3H, J=7 Hz), 1.39(s, 3H), 1.55(s, 3H), 1.82(br.s, 1H), 1.89(s, 3H), 2.04(s, 3H), 2.15~2.63(m, 7H), 3.55(d, 1H, J=13 Hz), 3.69(d, 1H, J=13 Hz), 4.20~4.55(m, 2H), 4.72(br.d, 1H, J=11 Hz), 4.92~5.91(m, 6H), 6.13(d, 1H, J=15 Hz), 8.08(d, 1H, J=10 Hz).

IR (KBr): 3400, 1730, 1710, 1680, 1260 cm$^{-1}$.

$[\alpha]_D^{24}$ −162.6° (c=0.115, EtOH).

EXAMPLE 138

Preparation of 3-[3-[1-(2-dimethylaminoethyl)-1H-tetrazol-5-yl]thio-2-oxopropionamido]-lankone-8-acetate Overall yield: 20%

(Hexamethylphosphoramide (HMPA) was used as the solvent for 3'-thioation and the reaction was conducted at room temperature).

NMR (90 MHz, CDCl$_3$) δ: 1.23(d, 3H, J=7 Hz), 1.40(s, 3H), 1.54(s, 3H), 1.89(s, 3H), ~2.0 (br.s, 1H), 2.04(s, 3H), 2.25(s, 6H), 2.15~2.55(m, 5H), 2.75(t, 2H, J=6 Hz), 4.15~4.80(m, 7H), 4.93~5.90(m, 6H), 6.15(d, 1H, J=15 Hz), 8.06(d, 1H, J=10 Hz).

IR (KBr): 3400, 1735, 1710, 1260 cm$^{-1}$.

$[\alpha]_D^{24}$ −121.8° (c=0.385, EtOH).

EXAMPLE 139

Pewparation of 3-[3-(1-methyl-1H-1,3,4-triazol-2-yl)thio-2-oxopropionamido]lankone 8-acetone Overall yield: 11%

(Ethanol-tetrahydrofuran was employed as the solvent for 3'-thioation.)

NMR (90 MHz, CDCl$_3$) δ: 1.23(d, 3H, J=7 Hz), 1.40(s, 3H), 1.54(s, 3H), 1.88(s, 3H), 2.04(s, 3H), ~2.1(br.s, 1H), 2.15~2.55(m, 5H), 3.64(s, 3H), 4.16~4.70(m, 5H), 4.92~5.90(m, 6H), 6.12(d, 1H, J=15 Hz), 8.05(d, 1H, J=10 Hz), 8.10(s, 1H).

IR (KBr): 3400, 1740, 1715, 1265 cm$^{-1}$.

$[\alpha]_D^{23}$ −132.1° (c=0.215, EtOH).

EXAMPLE 140

Preparation of 3-(2-aminothiazol-4-yl)carboxamido-lankone 8,14-diacetate

In 5 ml of N,N-dimethylformamide was dissolved 499.5 mg of 3-(3-bromo-2-oxopropionamido)-lankone 8,14-diacetate, To this was added 74.0 mg of thiourea. The mixture was stirred for 1.5 hour dilute with ethyl acetate. The resultant mixture was washed with an aqueous solution of sodium hydrogencarbonate and aqueous saline solution in sequence, followed by drying over Na$_2$SO$_4$. The solvent was then distilled off, and the residue was subjected to a silica gel column chromatography, eluting with ethyl acetate-hexane (2:1). Desired fractions were combined and concentrated to obtain 263.0 mg of the above titled compound, m.p. 206° C. (decomp.)(AcOEt).

NMR (90 MHz, CDCl$_3$-DMSO-d$_6$) δ: 1.25(d, 3H, J=7 Hz), 1.39(s, 3H), 1.51(s, 3H), 1.82(s, 3H), 1.99(s, 3H), 2.01(s, 3H), 2.15~2.60(m, 5H), 4.53~5.80(m, 9H), 6.30(d, 1H, J=15 Hz), 6.93(br.s, 2H), 7.94(s, 1H), 8.05(d, 1H, J=10 Hz).

IR (KBr): 3400, 1735, 1715, 1245 cm$^{-1}$.

$[\alpha]_D^{24}$ −84.9° (c=0.485, EtOH).

EXAMPLE 141

Preparation of 3-[3-(pyridine-2-yl)thio-2-hydroxyiminopropionamido]-lankone 8,14-diacetate In 1 ml of methanol was dissolved 66.0 mg of 3-[3-(pyridin-2-yl)thio-2-oxopropionamido]-lankone 8,14-diacetate. To the solution were added 8.0 mg of hydroxylamine.hydrochloride and 8.9 μl of pyridine, and the mixture was stirred. Pyridine was supplemented (9 μl) after 30 minutes, (30 μl) after 70 minutes, and hydroxylamine.hydrochloride was supplemented (7.7 mg) after 170 minutes, and the whole mixture was stirred for 4 hours in total. To this was added ethyl acetate, which was washed with water and aqueous NaCl solution in sequence, followed by drying over Na$_2$SO$_4$. The solvent was distilled off, and the residue was subjected to separation by means of TLC (Plates: manufactured by Merck, Art. 5715, 20×20 cm, developing solvent: ethyl acetate-hexane (1:1)) to obtain 47.3 mg of the above titled compound.

NMR (90 MHz, CDCl$_3$) δ: 1.26(d, 3H, J=7 Hz), 1.37(s, 3H), 1.52(s, 3H), 1.88(s, 3H), 2.00(s, 3H), 2.03(s, 3H), 2.15~2.55(m, 5H), 4.20(s, 2H), 4.25~4.50(m, 1H), 4.70(br. d, 1H, J=10 Hz), 4.90~5.95(m, 7H), 6.25(d, 1H, J=15 Hz), 6.93~7.66(m, 3H), 8.01(br. d, 1H, J=10 Hz), 8.40(m, 1H).

IR (KBr): 3400, 1735, 1710, 1675, 1240 cm$^{-1}$.

$[\alpha]_D^{21}$ −112.8° (c=0.54, CHCl$_3$)

EXAMPLE 142

Preparation of 3-[3-(pyridin-2-yl)thio-2-methoxyiminopropionamido]-lankone 8,14-diacetate Employing 65.9 mg of 3-[3-(pyridin-2-yl)thio-2-oxopropionamido]-lankone 8,14-diacetate and O-methylhydroxylamine.hydrochloride, the reaction was allowed to proceed in a manner similar to Example 141 to give 40.8 mg of the above titled compound, m.p. 175°-177° C. (Et$_2$O).

NMR (90 MHz, CDCl$_3$) δ: 1.30(d, 3H, J=7 Hz), 1.39(s, 3H), 1.55(s, 3H), 1.89(s, 3H), 2.03(s, 3H), 2.05(s, 3H), 2.15~2.55(m, 5H), 4.03(s, 3H), 4.27(s, 2H), 4.30~4.53(m, 1H), 4.73(br. d, 1H, J=11 Hz), 4.95~5.85(m, 7H), 6.27(d, 1H, J=15 Hz), 6.86~7.55(m, 3H), 7.68(br. d, 1H, J=10 Hz), 8.88(m, 1H).

IR (KBr): 1735, 1710, 1680, 1240 cm$^{-1}$.

$[\alpha]_D^{22}$ −108.9° (c=0.485, CHCl$_3$).

EXAMPLE 143

Preparation of
3-[3-(pyridin-2-yl)thio-2-(L)-hydroxypropionamido]-lankone 8,14-diacetate and
3-[3-(pyridin-2-yl)thio-2-(D)-hydroxypropionamido]-lankone 8,14-diacetate In 10 ml of methanol was dissolved 580.4 mg of 3-[3-(pyridin-2-yl)thio-2-oxopropionamido]-lankone 8,14-diacetate. To the solution was added dropwise with stirring 0.5 ml of a methanol solution containing 10.4 mg of sodium borohydride, and the mixture was stirred for 15 minutes. The solvent was distilled off, and the residue was subjected to a silica gel column chromatography, eluting with a mixture of ethyl acetate and hexane (2:1). Desired fractions were combined and concentrated to give 409.6 mg of the above titled compound (2'-(DL)compound). 52.2 mg of this product was subjected to separation by means of TLC (Plates: manufactured by Merck, Art. No. 5715, 20×20 cm, developing solvent: ethyl acetate-hexane (1:2)) to obtain 23.4 mg of the above titled compound (2'-(L)compound) and 21.5 mg of the above titled compound (2'-(D)compound).

2'-(L)compound:
NMR (90 MHz, CDCl$_3$) δ: 1.26(d, 3H, J=7 Hz), 1.36(s, 3H), 1.54(s, 3H), 1.90(s, 3H), 2.01(s, 3H), 2.04(s, 3H), 2.15~2.55(m, 5H), 2.56(d, 2H, J=4 Hz), 4.22~4.55(m, 2H), 4.73(br. d, 1H, J=11 Hz), 4.93~5.84(m, 7H), 6.26(d, 1H, J=15 Hz), 7.00~7.80(m, 3H), 8.16(br. d, 1H, J=10 Hz), 8.40(m, 1H), ~7.80(br. s, 1H).
IR (KBr): 3400, 1735, 1715, 1680, 1245 cm$^{-1}$.
$[\alpha]_D^{22.5}$ −229.1° (c=0.485, CHCl$_3$)

2'-(D)compound:
NMR (90 MHz, CDCl$_3$) δ: 1.27(d, 3H, J=7 Hz), 1.42(s, 3H), 1.53(s, 3H), 1.89(s, 3H), 2.02(s, 3H), 2.04(s, 3H), 2.15~2.55(m, 5H), 3.40(dd, 1H, J=5 Hz and 15 Hz), 3.56(dd, 1H, J=4 Hz and 15 Hz), 4.27~4.58(m, 2H), 4.72(br. d, 1H, J=11 Hz), 4.90~5.85(m, 7H), 6.23(d, 1H, J=15 Hz), 6.99~7.66(m, 3H), 7.16(br. d, 1H, J=10 Hz), 8.37(m, 1H), ~7.90(br. s, 1H).
IR (KBr): 3400, 1735, 1715, 1670, 1240 cm$^{-1}$.
$[\alpha]_D^{22.5}$ +14.5° (c=0.47, CHCl$_3$).

EXAMPLE 144

Preparation of
3-(3-bromo-2-methoxyiminopropionamido)-lankone 8,14-diacetate

Using 62.8 mg of 3-(3-bromo-2-oxopropionamido)-lankone 8,14-diacetate and O-methyl-hydroxylamine.hydrochloride, the reaction was allowed to proceed in a manner similar to Example 141 to obtain 5.9 mg of the above titled compound.
NMR (90 MHz, CDCl$_3$) δ: 1.31(d, 3H, J=7 Hz), 1.41(s, 3H), 1.54(s, 3H), 1.89(s, 3H), 2.01(s, 3H), 2.03(s, 3H), 2.20~2.55(m, 5H), 4.02~4.55(m, 4H), 4.72(br. d, 1H, J=10 Hz), 4.93~5.81(m, 7H), 6.25(d, 1H, J=15 Hz), 7.83(br. d, 1H, J=10 Hz).
IR (KBr): 1735, 1710, 1240 cm$^{-1}$.
Mass m/e: 652(M$^+$+2), 650(M$^+$).

EXAMPLE 145

Preparation of
3-(3-phenylthio-2-(L)-hydroxypropionamido)-lankone 8,14-diacetate and
3-(3-phenylthio-2-(D)-hydroxypropionamido)-lankone 8,14-diacetate Employing 429.2 mg of 3-(3-phenylthio-2-oxopropionamido)-lankone 8,14-diacetate, the reaction was allowed to proceed in a manner similar to Example 143 to obtain 112.3 mg of the above titled compound (2'-(L)compound) and 84.1 mg of the above titled compound (2'-(D)compound).

2'-(L)compound:
NMR (90 MHz, CDCl$_3$) δ: 1.23(d, 3H, J=7 Hz), 1.36(s, 3H), 1.53(s, 3H), 1.67(br. s, 1H), 1.86(s, 3H), 2.01(s, 3H), 2.03(s, 3H), 2.15~2.55(m, 5H), 2.96~3.65(m, 2H), 4.00~4.50(m, 2H), 4.68(br. d, 1H, J=11 Hz), 4.90~5.85(m, 7H), 6.26(d, 1H, J=15 Hz), 7.15~7.46(m, 5H), 7.84(br. d, 1H, J=10 Hz).
IR (KBr): 3420, 1740, 1715, 1245 cm$^{-1}$.
$[\alpha]_D^{21}$ −204.7° (c=0.53, CHCl$_3$).

2'-(D)compound, m.p. 177°−178° (AcOEt-Et$_2$O):
NMR (90 MHz, CDCl$_3$) δ: 1.28(d, 3H, J=7 Hz), 1.37(s, 3H), 1.54(s, 3H), 1.86(s, 3H), ~2.0(br. s, 1H), 2.02(s, 3H), 2.05(s, 3H), 2.15~2.55(m, 5H), 2.99(dd, 1H, J=9 Hz and 15 Hz), 3.55(dd, 1H, J=4 Hz and 15 Hz), 4.05~4.52(m, 2H), 4.70(br. d, 1H, J=11 Hz), 4.96~5.85 (m, 7H), 6.26(d, 1H, J=15 Hz), 7.12~7.50(m, 5H), 7.87(br. d, 1H, J=10 Hz).
IR (KBr): 3420, 1740, 1715, 1670, 1245 cm$^{-1}$.
$[\alpha]_D^{21}$ −165.5° (c=0.475, CHCl$_3$)

EXAMPLE 146

Preparation of 3-(2-oxo-1-thioxopropylamino)-lankone 14-acetate 8-diethylphosphate In 0.5 ml of pyridine were reacted with stirring 96.3 mg of lankacidin A 8-diethylphosphate and 15.1 mg of phosphorus pentasulfide at 50° C. for 19 hours. The pyridine was distilled off. To the residue was added dichloromethane and insolubles were removed by filtration. The filtrate was concentrated and subjected to separation by means of TLC (Plates: manufactured by Merck, Art. No. 5715, 20×20 cm, two plates, developing solvent: ethyl acetate:hexane (1:1)) to obtain 10.2 mg of the above titled compound.
NMR (90 MHz, CDCl$_3$) δ: 1.20~1.45(m, 12H), 1.55(s, 3H), 1.97(s, 3H), 2.02(s, 3H), 2.20~2.65(m, 5H), 2.65(s, 3H), 3.89~4.27(m, 4H), 4.32~4.82(m, 3H), 5.20~6.36(m, 7H), 10.01(br. d, 1H, J=10 Hz).
IR (KBr): 1740, 1715, 1270, 1245, 1015 cm$^{-1}$.

EXAMPLE 147

Preparation of
3-(2-(DL)-hydroxypropionamido)-lankone 14-acetate 8-diethylphosphate Employing 956.7 mg of lankacidin A diethylphosphate, the reaction was allowed to proceed in a manner similar to Example 143 to obtain 817.1 mg of the above titled compound.
NMR (90 MHz, CDCl$_3$) δ: 1.20~1.50 (m, 15H), 1.55 (s, 3H), 1.88 (s, 3H), 2.02 (s, 3H), ~2.0 (br. s, 1H), 2.15~2.70 (m, 5H), 3.85~4.85 (m, 8H), 5.20~5.90 (m, 6H), 6.26 (d, 1H, J=15 Hz), 7.67 (br. d, ~0.5H, J=10 Hz), 7.78 (br.d, ~0.5 H, J=10 Hz).
IR (KBr): 3400, 1740, 1715, 1675, 1245, 1010 cm$^{-1}$.

EXAMPLE 148

Preparation of
3-(2-(DL)-n-octanoyloxypropionamido)-lankone
14-acetate 8-diethylphosphate In 0.5 ml of pyridine was dissolved 64.8 mg of 3-(2-(DL)-hydroxypropionamido)-lankone-14-acetate-8-diethylphosphate. To the solution was added dropwise while stirring under cooling with ice-water 0.1 ml of n-octanoyl chloride, followed by stirring for further 15 minutes. To the resultant was added ice-water, and the mixture was subjected to extraction with ethyl acetate. The extract was washed with 1N hydrochloric acid, aqueous NaCl solution, aqueous solution of sodium hydrogencarbonate and aqueous NaCl solution in sequence, followed by drying over $Na_2SO_4$. The solvent was distilled off, and the residue was subjected to a silica gel column chromatography, eluting with chloroform-ethyl acetate (2:1). Desired fractions were combined and concentrated to obtain 77.0 mg of the above titled compound.

NMR (90 MHz, $CDCl_3$) δ: 0.87 (~t, 3H), 1.15~2.75 (m, 29H), 1.55 (s, 3H), 1.89 (s, 3H), 2.02 (s, 3H), 3.90~4.85 (m, 7H), 5.10~5.90 (m, 7H), 6.25 (d, 1H, J=15 Hz), 7.29 (br.d, ~0.5H, J=10 Hz), 7.45 (br.d, ~0.5H, J=10 Hz).

IR (KBr): 2940, ~1720 (br.), 1260 (br.), ~1000 (br.) $cm^{-1}$.

EXAMPLE 149

Preparation of 8-dehydroxy-8-iodolankacidin A

In 50 ml of N,N-dimethylformamide was dissolved 5.01 g of lankacidin A. To the solution was added 1.82 ml of pyridine and 1.72 ml of methanesulfonyl chloride, and the mixture was stirred for one hour. To the resultant was added 3.735 g of potassium iodide, which was stirred at 60° C. for 20 minutes then poured into 500 ml of ice-water, followed by extraction of ethyl acetate (250 ml×2). The extract was washed with water and dried over $MgSO_4$. The solvent was distilled off, and the residue was subjected to a column chromatography on 100 g of silica gel, eluting with ethyl acetate-chloroform (1:10). Desired fractions were combined and concentrated. To the concentrate was added a small volume of ether to cause crystallization, to which was added ether-petroleum ether (1:2), followed by filtration to collect the crystals. The crystals were washed with the same solvent system then dried to obtain 2.3431 g of the above titled compound. This product was revealed to be a mixture of three components by means of NMR at 400 MHz.

NMR (90 MHz, $CDCl_3$) δ: (data of only the principal component are given) 1.28 (d, J=7 Hz, 17-Me), 1.37 (s, 2-Me), 1.51 (s, 11-Me), 1.88 (s, 5-Me), 2.00 (s, OAc), 2.2~2.6 (m, 3H, 15-Hz, 17H), 2.43 (s, $COCOCH_3$), ~2.8 (m, 2H, 9-H$_2$), ~4.3 (m, 16-H, 8-H), 4.68 (d, J=11 Hz, 4-H), 5.1~6.0 (m, 6H, 3-H, 6-H, 7-H, 10-H, 13-H, 14-H), 6.23 (d, J=15 Hz, 12-H), 8.05 (d, J=10 Hz, NH).

IR (KBr): 3380, 1740, 1708, 1690, 1510, 1358, 1224, 1136, 948 $cm^{-1}$.

Mass m/e: 552 (M+-59(AcO)), 484 (M+-127(I)), 483 (M+-128(HI)), 424 (M+-127-60(AcOH)), 423 (M+-128-60).

EXAMPLE 150

Preparation of 8-dehydroxy-8-azidolankacidin A

In 50 ml of N,N-dimethylformamide was dissolved 3.055 g of 8-dehydroxy-8-iodo-lankacidin A. To the solution was added 390 mg of sodium azide, and the mixture was stirred for 80 minutes. The resultant mixture was poured into ice-water to which was added sodium chloride, followed by extraction with ethyl acetate and drying over $MgSO_4$. The solvent was distilled off, and the residue was subjected to a column chromatography on 120 g of silica gel, eluting with ethyl acetate-hexane (1:1). Eluate was fractionated by 13 g each portion, and the 19th~31st fractions were combined and concentrated, to which was added a small volume of ether to cause crystallisation, followed by addition of ether-petroleum ether (1:2). The mixture was subjected to filtration to collect the crystals, which were washed with the same solvent system, followed by drying to obtain 1.3184 g of the above titled compound.

NMR (90 MHz, $CDCl_3$) δ: 1.32 (d, J=7 Hz, 17-Me), 1.37 (s, 2-Me), 1.49 (s, 11-Me), 1.89 (s, 5-Me), 2.01 (s, OAc), 2.2~2.8 (m, 15-H$_2$, 9-H$_2$, 17-H), 2.44 (s, $COCOCH_3$), 4.43 (m, 16-H), ~4.6 (m, 8-H), 4.77 (d, J=11 Hz, 4-H), 5.2~6.1 (m, 3-H, 6-H, 7-H, 10-H, 13-H, 14-H), 6.25 and 6.32 and 6.35 (each 1H, each d, ca. 2:3:1, J=15 Hz, 12-H), 8.09 (d, J=9 Hz, NH).

IR (KBr): 2100, 1728, 1706, 1688, 1502, 1352, 1232, 1134 $cm^{-1}$.

EXAMPLE 151

Preparation of
8-dehydroxy-8-[[1-(2-dimethylaminoethyl)-1H-tetrazol-5-yl]thio]-lankacidin A In 10 ml of hexamethylphosphoramide were dissolved 208 mg of [1-(2-dimethylaminoethyl)-1H-tetrazol-5-yl]thiol and 44.0 mg of sodium hydride (60% in oil) under heating. To the solution, after cooling, was added 611 mg of 8-dehydroxy-8-iodo-lankacidin A, and the mixture was stirred at room temperature for 14 hours, to which was added aqueous NaCl solution, followed by extraction with ethyl acetate. The extract was dried over $MgSO_4$. The solvent was distilled off, and the residue was subjected to a column chromatography on 300 g of silica gel, eluting with ethyl acetate-ethanol (10:1). Desired fractions were combined and concentrated to obtain 273.9 mg of the above titled compound (isomer of low polarity: presumed as β compound at 8-position) and 113.9 mg of the above titled compound (isomer of high polarity: presumed as α compound at 8-position).

β compound at 8-position:
NMR (90 MHz, $CDCl_3$) δ: 1.33 (d, J=7 Hz, 17-Me), 1.37 (s, 2-Me), 1.52 (s, 11-Me), 1.88 (s, 5-Me), 2.01 (s, OAc), 2.1~2.5 (m, 3H, 15-H$_2$, 17-H), 2.25 (s, NMe$_2$), 2.43 (s, $COCOCH_3$), 2.5~2.9 (m, 2H, 9-H$_2$), 2.73 (t, J=7 Hz, $CH_2NMe_2$), 4.30 (t, J=7 Hz, tetrazole-CH$_2$), ~4.4 (m, 16-H), 4.72 (d, J=11 Hz, 4-H), 4.95 (m, 8-H), 5.3~5.9 (m, 3-H, 7-H, 10-H, 13-H, 14-H), 6.35 (d, J=15 Hz, 12H), 8.07 (d, J=10 Hz, NH).

IR (KBr): 1728, 1708, 1688, 1356, 1240 $cm^{-1}$.

α compound at 8-position:
NMR (90 MHz, $CDCl_3$) δ: 1.31 (d, J=7 Hz, 17-Me), 1.37 (s, 2-Me), 1.55 (s, 11-Me), 1.85 (s, 5-Me), 2.01 (s, OAc), 2.1~2.5 (m, 15-H$_2$, 17-H), 2.24 (s, NMe$_2$), 2.43 (s, $COCOCH_3$), 2.5~2.8 (m, 9-H$_2$), 2.73 (t, J=7 Hz, $CH_2NMe_2$), 4.30 (t, J=7 Hz, tetrazole-CH$_2$), ~4.3 (m, 16-H, 8-H), 4.70 (d, J=11 Hz, 4-H), 5.2~5.9 (m, 3-H, 6-H, 7-H, 10-H, 13-H, 14-H), 6.29 (d, J=15 Hz, 12-H), 8.06 (d, J=10 Hz, NH).

IR (KBr): 1728, 1708, 1688, 1356, 1240 cm$^{-1}$.

In a manner similar to the above, sodium salt of thiol was allowed to react with 8-dehydroxy-8-iodo-lankacidin to give 8-dehydroxy-8-substituted-thio-lankacidin A in Examples 152~161.

EXAMPLE 152

Preparation of 8-dehydroxy-8-(4-pyridylthio)-lankacidin A

Employing N,N-dimethylformamide-tetrahydrofuran (1:2) as the reaction solvent, the reaction was allowed to proceed at 0° C. for 4 hours. The yield was 58%.

NMR (90 MHz, CDCl$_3$)δ: 1.30(d, J=7 Hz, 17-Me), 1.41 (s, 2-Me), 1.53 (s, 11-Me), 1.92 (s, 5-Me), 2.01 (s, OAc), 2.1~2.5 (m, 15-H$_2$, 17-H), 2.41 (s, COCOCH$_3$), 2.5~2.8 (m, 9-H$_2$), ~4.4 (m, 16-H, 8-H), 4.70 (d, J=11 Hz, 4-H), 5.3~6.25 (m, 3-H, 6-H, 7-H, 10-H, 13-H, 14-H), 6.35 (d, J=15 Hz, 12-H), ~7.1 (br., pyridine-H$_2$), 8.05 (d, J=9 Hz, NH), ~8.1 (br., pyridine-H$_2$).

IR (KBr): 1724, 1708, 1682, 1572, 1354, 1236 cm$^{-1}$.

Mass m/e: 594 (M$^+$), 550 (M$^+$-44 (CO$_2$)), 534 (M$^+$-60 (AcOH)), 490 (M$^+$-44-60), 483 (M$^+$-111

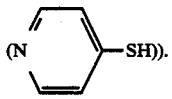

EXAMPLE 153

Preparation of 8-dehydroxy-8-[[1-(3-dimethylaminopropyl)-1H-tetrazol-5-yl]thio-lankacidin A 8-β-compound (supposed): The yield was 50%.

NMR (90 MHz, CDCl$_3$)δ: 1.33 (d, J=7 Hz, 17-Me), 1.38 (s, 2-Me), 1.53 (s, 11-Me), 1.89 (s, 5-Me), 2.02 (s, OAc), 1.8~2.9 (m, CH$_2$CH$_2$N, 15-H$_2$, 17-H, 9-H$_2$), 2.20 (s, NMe$_2$), 2.44 (s, COCOCH$_3$), 4.27 (, J=7 Hz, tetrazole-CH$_2$), ~4.4 (m,. 16-H), 4.72 (d, J=11 Hz, 4-H), 4.98 (m, 8-H), 5.3~5.9 (m, 3-H, 6-H, 7-H, 10-H, 13-H, 14-H), 6.35 (d, J=15 Hz, 12-H), 8.05 (d, J=10 Hz, NH).

IR (KBr): 1726, 1706, 1682, 1498, 1356, 1234, 950 cm$^{-1}$.

8-α-compound (supposed): The yield was 14%.

NMR (90 MHz, CDCl$_3$)δ: (data different from those of 8-β-compound) 1.31 (d, J=7 Hz, 17-Me), 1.85 (s, 5-Me), 2.18 (s, NMe$_2$), 6.31 (d, J=15 Hz, 12-H).

IR (KBr): 1726, 1706, 1682, 1498, 1356, 1234, 950 cm$^{-1}$.

EXAMPLE 154

Preparation of 8-dehydroxy-8-(1-methyl-1H-tetrazol-5-yl)thio-lankacidin A

Employing N,N-dimethylformamide as the reaction solvent, the reaction was allowed to proceed at 0° C.~5° C. overnight. The yield was 44%.

NMR (90 MHz, CDCl$_3$)δ: 1.31 (d, J=6.5 Hz, 17-Me), 1.37 (s, 2-Me), 1.54 (s, 11-Me), 1.89 (s, 5-Me), 2.02 (s, OAc) 2.25~2.85 (m, 9-H$_2$, 15-H$_2$, 17-H), 2.43 (s, COCOCH$_3$), 3.90 (s, tetrazole-CH$_3$), 4.44 (m, 16-H), 4.72 (d, J=11 Hz, 4-H), 4.97 (br., 8-H), 5.3~5.9 (m, 3-H, 6-H, 7-H, 10-H, 13-H, 14-H), 6.35 (d, J=15 Hz, 12-H), 8.06 (d, J=10 Hz, NH).

IR (KBr): 3400, 2950, 1730, 1715, 1690, 1500, 1450, 1360, 1240, 1170, 1140, 1015, 955, 750 cm$^{-1}$.

EXAMPLE 155

Preparation of 8-dehydroxy-8-(5-methyl-1,3,4-thiazol-2-yl)thio-lankacidin A

The reaction was allowed to proceed at room temperature for one hour. The yield was 37%.

NMR (90 MHz, CDCl$_3$)δ: 1.32 (d, 6.5 Hz, 17-Me), 1.47 (s, 2-Me), 1.52 (s, 11-Me), 1.90 (s, 5-Me), 2.01 (s, OAc), 2.2~2.8 (m, 9-H$_2$, 15-H$_2$17-H), 2.43 (s, COCOCH$_3$), 2.68 (s, thiazole-CH$_3$), 4.43 (m, 16-H), 4.72 (d, J=11 Hz, 4-H), 4.83 (m, 8-H), 5.3~6.15 (m, 3-H, 6-H, 7-H, 10-H, 13-H, 14-H), 6.35 (d, J=15 Hz, 12-H), 8.07 (d, J=10 Hz, NH).

IR (KBr): 3385, 2930, 1730, 1710, 1685, 1500, 1445 (sh.), 1430, 1355, 1230, 1135, 1055, 1010, 950 cm$^{-1}$.

EXAMPLE 156

Preparation of 8-dehydroxy-8-phenylthio-lankacidin A

Employing N,N-dimethylformamide as the reaction solvent, the reaction was allowed to proceed at 0° C. for 30 minutes, then at room temperature for 45 minutes. The yield was 12%.

NMR (90 MHz, CDCl$_3$)δ: 1.33 (d, J=6 Hz, 17-Me), 1.36 (s, 2-Me), 1.50 (s, 11-Me), 1.89 (s, 5-Me), 2.02 (s, OAc), 2.2~2.8 (m, 9-H$_2$, 15-H$_2$, 17-H), 2.43 (s, COCOCH$_3$), 4.22 (m, 8-H), 4.31 (m, 16-H), 4.73 (d, J=11 Hz, 4-H), 5.3~6.25 (m, 3-H, 6-H, 6-H, 7-H, 10-H, 13-H, 14-H), 6.48 (d, J=15 Hz, 12-H), 7.1~7.35 (m, C$_6$H$_5$), 8.06 (d, J=10 Hz, NH).

IR (KBr): 3490, 2930, 1750 (sh.), 1730, 1710, 1685, 1500, 1360, 1235, 1160 (sh.), 1140, 1010, 950, 740 cm$^{-1}$.

EXAMPLE 157

Preparation of 8-dehydroxy-8-[5-(2-dimethylaminoethyl)-1,3,4-thiadiazol-2-yl]thio-lankacidin A The reaction was allowed to proceed at 0° C. for 3 hours.

8-β-compound (supposed): The yield was 12%.

NMR (90 MHz, CDCl$_3$)δ: 1.32 (d, J=6.5 Hz, 17-Me), 1.37 (s, 2-Me), 1.52 (s, 11-Me), 1.90 (s, 5-Me), 2.03 (s, OAc), 2.27 (s, NMe$_2$), 2.43 (s, COCOCH$_3$), 2.2~2.8 (m, 9-H$_2$, 15-H$_2$, 17-H), 2.59 (t, J=6.5 Hz, CH$_2$NMe$_2$), 3.14 (t, J=6.5 Hz, thiazole-CH$_2$), 4.42 (m, 16-H), 4.76 (d, J=11 Hz, 4-H), 4.86 (m, 8-H), 5.3~6.1 (m, 3-H, 6-H, 7-H, 10-H, 13-H, 14-H), 6.34 (d, J=15 Hz, 12-H), 8.05 (d, J=10 Hz, NH).

IR (KBr): 3380, 2940, 1745, 1705, 1685, 1500, 1450, 1375, 1360, 1260, 1160, 1140, 1055, 1010, 960, 745 cm$^{-1}$.

8-α-compound (supposed): The yield was 2%.

NMR (90 MHz, CDCl$_3$)δ: 1.30 (d, J=6.5 Hz, 17-Me), 1.37 (s, 2-Me), 1.55 (s, 11-Me), 1.87 (s, 5-Me), 2.02 (s, OAc), 2.27 (s, NMe$_2$), 2.43 (s, COCOCH$_3$), 2.2~2.8 (m, 9-H$_2$, 15-H$_2$, 17-H), 2.61 (t, J=6.5 Hz, —CH$_2$NMe$_2$), 3.16 (t, J=6.5 Hz, thiazole-CH$_2$), 4.06 (m, 8-H), 4.41 (m, 16-H), 4.68 (d, J=11 Hz, 4-H), 5.25~6.0 (m, 3-H, 6-H, 7-H, 10-H, 13-H, 14-H), 6.28 (d, J=15 Hz, 12-H), 8.05 (d, J=10 Hz, NH).

IR (KBr): 3400, 2925, 2860, 1730, 1705, 1680, 1495, 1450, 1365, 1230, 1135, 1055, 1010, 950 cm$^{-1}$.

EXAMPLE 158

Preparation of 8-dehydroxy-8-(4,5-dimethyl-thiazol-2-yl)thio-lankacidin A

Employing N,N-dimethylformamide as the reaction solvent, the reaction was allowed to proceed at 0° C. for one hour then at room temperature for one hour. The yield was 17%.

NMR (90 MHz, CDCl$_3$)δ: 1.32 (d, J=6.5 Hz, 17-Me), 1.38 (s, 2-Me), 1.51 (s, 11-Me), 1.90 (s, 5-Me), 2.03 (s, OAc), 2.26 (s, thiazole-CH$_3$×2), 2.44 (s, COCOCH$_3$), 2.2~2.7 (m, 9-H$_2$, 15-H$_2$, 17-H), 4.42 (m, 16-H), 4.62 (m, 8-H), 4.73 (d, J=11 Hz, 4-H), 5.3~5.9 (m, 3-H, 7-H, 10-H, 13-H, 14-H), 60.5 (d, J=15 Hz, 6-H), 6.37 (d, J=15 Hz, 12-H), 8.06 (d, J=10 Hz, NH).

IR (KBr): 3380, 2930, 1730, 1710, 1685, 1500, 1440, 1430(sh.), 1365(sh.), 1355, 1230, 1160, 1135, 1010, 950 cm$^{-1}$.

EXAMPLE 159

Preparation of 8-dehydroxy-8-(4,5-dimethyl-oxazol-2-yl)thio-lankacidin A

Employing N,N-dimethylformamide as the reaction solvent, the reaction was allowed to proceed at 0° C. for one hour. The yield was 12%.

NMR (90 MHz, CDCl$_3$)δ: 1.33(d, J=6.5 Hz, 17-Me), 1.38(s, 2-Me),1.52(s, 11-Me), 1.89(s, 5-Me), 2.03(s, 6H, OAc, oxazole-CH$_3$), 2.18(s, oxazole-CH$_3$) 2.2~2.75(m, 9-H$_2$, 15-H$_2$, 17H), 2.44(s, COCOCH$_3$), 4.42(m, 16-H), 4.56(m, 8-H), 4.74(d, J=10 Hz, 4-H), 5.3~6.05(m, 3-H, 6-H, 7-H, 10-H, 13-H, 14-H), 6.35(d, J=15 Hz, 12-H), 8.05(d, H=10 Hz, NH).

IR (KBr): 3400(br.), 2930, 1730, 1710, 1690, 1500, 1360, 1235, 1140, 1020, 955 cm$^{31\ 1}$.

EXAMPLE 160

Preparation of 8-dehydroxy-8-(1-dimethylamino-1H-tetrazol-5-yl)thio-lankacidin A Employing N,N-dimethylformamide as the reaction solvent, the reaction was allowed to proceed at room temperature for 3 hours. The yield was 45%. m.p.: 144°-146° C. (decomp.) (CHCl$_3$-Et$_2$O-hexane)

NMR (90 MHz, CDCl$_3$)δ: 1.32(d, J=6.5 HZ, 17-Me), 1.37(s, 2-Me), 1.53(s, 11 Me), 1.90(s, 5-Me), 2.01(s, OAc), 2.2~2.85(m, 9-H$_2$, 15-H$_2$, 17-H), 2.43(s, COCOCH$_3$), 2.94(s, NMe$_2$), 4.43(m, 16-H), 4.69(d, J=11 Hz, 4-H), 4.95(m, 8-H), 5.3~5.9(m, 3-H, 6-H, 7-H, 10-H, 13-H, 14-H), 6.32(d, J=15 Hz, 12-H), 8.02(d, J=10 Hz, NH).

IR (KBr): 3400, 2980, 2940, 1730, 1710, 1685, 1500, 1440, 1350, 1230, 1155, 1135, 1065, 1010, 950, 745 cm$^{-1}$.

EXAMPLE 161

Preparation of 8-dehydroxy-8-(1-ethyl-1H-1,2,4-triazol-3-yl)thio-lankacidin A

Employing N,N-dimethylformamide as the reaction solvent, the reaction was allowed to proceed under ice-cooling for 3 hours. The yield was 42%.

NMR (90 MHz, CDCl$_3$)δ: 1.33(d, J=6.5 Hz, 17-Me), 1.37(s, 2-Me), 1.47(t, J=7.5 Hz, NCH$_2$CH$_3$), 1.52(s, 11-Me), 1.88(s, 5-Me), 2.02(s, OAC), 2.2~ 2.75(m, 9-H$_2$, 15-H$_2$, 17-H), 2.43(s, COCOCH$_3$), 4.13 (q, J=7.5 Hz, NCH$_2$CH$_3$), 4.44(m, 16-H), 4.73(d, J= 10 Hz, 4-H), 4.73(m, 8-H), 5.3~5.95(m, 3-H, 6-H, 7-H, 10-H, 13-H, 14-H), 6.37(d, J=15 Hz, 12-H), 7.95 (s, triazole-H), 8.05(d, J=10 Hz, NH).

IR (KBr): 3380, 2975, 2925, 1720, 1700, 1680, 1490, 1435, 1350, 1230, 1130, 1050, 1005, 945 cm$^{-1}$.

EXAMPLE 162

Preparation of lankacidin C 8-(2,2,2-trichloroethylcarbonate)

In 20 ml of tetrahydrofuran was dissolved 135.3 mg of lankacidin A 8-(2,2,2-trichloroethylcarbonate), to which was added 20 ml of methanol. To the mixture was added 40 ml of aqueous solution containing 2.7 g of the enzyme prepared in Reference Example 11, followed by stirring at room temperature for 50 minutes. The resultant mixture was subjected to extraction with 80 ml of chloroform. The chloroform layer was washed with aqueous NaCl solution and was dried over MgSO$_4$. Chloroform was distilled off. To the residue was added a small volume of ether, and the mixture was left standing to cause crystallization, to which was added ether-petroleum ether (1:1). The crystals were collected by filtration, followed by drying to obtain 82.9 mg of the above titled compound, m.p. 209°–211° C. (decomp.).

NMR (90 MHz, CDCl$_3$)δ: 1.28(d, J=7 Hz, 17-Me), 1.38(s, 2-Me), 1.57(s, 11-Me), 1.91(s, 5-Me), 2.2~2.7(m, 9-H$_2$, 15-H$_2$, 17-H), 2.43(s, COCOCH$_3$), ~4.4(m, 16-H, 14-H), ~4.7(m, 4-H), 4.73(s, CCl$_3$CH$_2$), 4.97(m, 8-H), 5.15~5.95(m, 3-H, 6-H, 7-H, 10-H, 13-H), 6.18(d, J=15 Hz, 12-H), 8.07 (d, J=10 Hz, NH).

IR (KBr): 1748, 1704, 1674(sh.), 1376, 1244, 954 cm$^{-1}$.

$[\alpha]_D^{25}$ −183.8° (c=0.495, CHCl$_3$).

In a manner similar to the above, 14-acetate was subjected to deacetylation with an enzyme giving the corresponding 14-hydroxy compounds of the following Examples 163~221.

EXAMPLE 163

Preparation of 3-(2-oxo-1-thioxopropylamino)-lankone 8-acetate

The yield was 94%. m.p.: 201°–203° C.

NMR (90 MHz, CDCl$_3$)δ: 1.27(d, J=7 Hz, 17-Me), 1.41(s, 2-Me), 1.56(s, 11-Me), 1.95(s, 5-Me), 2.03(s, OAc), 2.2~2.6(m, 9-H$_2$, 15-H$_2$, 17-H), 2.63(s, CSCOCH$_3$), 3.72(m, 14-OH), 4.32(m, 14-H), 4.43(m, 16-H), 4.69(d, J=11 Hz, 4-H), 5.04(m, 8-H), 5.2~6.15(m, 3-H, 6-H, 7-H, 10-H, 13-H), 6.15 (d, J=15 Hz, 12-H), 9.98(d, J=10 Hz, NH).

IR (KBr): 3330, 1740, 1708, 1494, 1378, 1350, 1262, 1210, 1026, 964 cm$^{-1}$.

$[\alpha]_D^{25}$ −409.1° (c=0.47, CHCl$_3$).

EXAMPLE 164

3-(2-Oxo-1-thioxopropylamino)-lankone 8-(2,2,2-trichloroethylcarbonate)

The reaction was allowed to proceed at room temperature for 45 minutes, then at 37° C. for 200 minutes, followed by purification by means of a silica gel column. The yield was 80%,. m.p.: 177°–179° C.

NMR (90 MHz, CDCl$_3$)δ: 1.28(d, J=7 Hz, 17-Me), 1.39(s, 2-Me), 1.57(s, 11-Me), 1.96(s, 5-Me), 2.2~2.7(m, 9-H$_2$, 15-H$_2$, 17-H), 2.64(s, CSCOCH$_3$), ~4.4(m, 16-H, 14-H), ~4.7(m, 4-H), 4.73(s, CCl$_3$CH$_2$), 4.96(m, 8-H), 5.2~6.15(m, 3-H, 6-H, 7-H, 10-H, 13-H), 6.17(d, J=15 Hz, 12-H), 9.98 (d, J=10 Hz, NH).

IR (KBr): 1752, 1706, 1378, 1248, 1208, 960 cm$^{-1}$.

$[\alpha]_D^{25}$ −321.8° (c=0.485, CHCL$_3$).

EXAMPLE 165

3-(2-(L)-hydroxy-1-thioxopropylamino)-lankone 8-acetate

The yield was 61%. m.p.: 213°-214° C. (decomp.)

NMR (90 MHz, CDCL$_3$-DMSO-d$_6$(4:1))δ: 1.25(d, J=7 Hz, 17-Me), 1.37(s, 2-Me), 1.48(d, J=7 Hz, 2'-Me), 1.53(s, 11-Me), 1.92(s, 5-Me), 2.01(s, OAc), 2.1~2.7(m, 9-H$_2$, 15-H$_2$, 17-H), 4.1~4.6(m, 2'-H, 14-H), ~4.5(m, 16-H), 4.78(d, J=11 Hz, 4-H), 4.99(m, 8-H), 5.15~6.35(m 3-H, 6-H, 7-H, 10-H, 13-H), 6.13(d, J=15 Hz, 12-H), 9.77(d, J=10 Hz, NH).

IR (KBr): 1730, 1710, 1500, 1372, 1260, 1064, 1020, 996, 964 cm$^{-1}$.

$[\alpha]_D^{25}$ −366.0° (c=0.52, CHCl$_3$)

EXAMPLE 166

3-(2-(D)-hydroxy-1-thioxopropylamino)-lankone 8-acetate

The yield was 81%. m.p.: 156°-158° C. (decomp.)

NMR (90 MHz, CDCL$_3$-DMSO-d$_6$(4:1))δ: 1.25(d, J=7 Hz, 17-Me), 1.40(d, J=7 Hz, 2'-Me), 1.41(s, 2-Me), 1.55(s, 11-Me), 1.93(s, 5-Me), 2.02(s, OAc), 2.1~2.7(m, 9-H$_2$, 15-H$_2$, 17-H), 4.1~4.7(m, 2'-H, 14-H, 16-H), 4.75(d, J=11 Hz, 4-H), 5.03(m, 8-H), 5.1~6.3(m, 3-H, 6-H, 7-H, 10-H, 13-H), 6.14(d, J=15 Hz, 12-H), 9.85(d, J=10 Hz, NH).

IR(KBr): 3520, 3300, 1730, 1702, 1498, 1374, 1260(sh.), 1248, 1064, 958 cm$^{-1}$.

$[\alpha]_D^{25}$ −272.6° (c=0.53, CHCL$_3$).

EXAMPLE 167

3-[2-[1-(2-dimethylaminoethyl)-1H-tetrazol-5-yl]thio]acetamido-lankone 8-acetate Employing the enzyme in 40 times as much (weight) of 14-acetate, the reaction was allowed to proceed at 37° C. for 4.5 hours then at room temperature for 14 hours, followed by purification by means of TLC. The yield was 15%.

NMR (90 MHz, CDCl$_3$)δ: 1.22(d, J=7 Hz, 17-Me), 1.29(s, 2-Me), 1.53(s, 11-Me), 1.84(s, 5-Me), 2.03(s, OAc), 2.1~2.6(m, 9-H$_2$, 15-H$_2$, 17-H), 2.24(s, NMe$_2$), 2.73(t, J=7 Hz, CH$_2$NMe$_2$), 3.84 and 4.04(ABq, J=15 Hz, SCH$_2$CO), ~4.3(m, 16-H, 14-H), 4.31(t, J=7 Hz, tetrazole-CH$_2$), 4.59(d, J=11 Hz, 4-H), 5.05(m, 8-H), 5.2~5.9(m, 3-H, 6-H, 7-H, 10-H, 13-H), 6.13(d, J=15 Hz, 12-H), 7.56(d, J= 9 Hz, NH).

IR (KBr): 1728, 1702, 1666, 1620, 1366, 1250, 1012, 954 cm$^{-1}$.

EXAMPLE 168

3-[2-(4-methyl-4H-1,2,4-triazol-3-yl)thio]acetamido-lankone 8-acetate

The reaction was allowed to proceed at 37° C. for 15 hours, followed by purification by means of TLC. The yield was 18%.

NMR (90 MHz, CDCL$_3$)δ: 1.27(d, J=7 Hz, 17-Me), 1.35(s, 2-Me), 1.53(s, 11-Me), 1.83(s, 5-Me), 2.04(s, OAc), 2.1~2.6(m, 9-H$_2$, 15-H$_2$, 17-H), 3.57(s, triazole-CH$_3$), 3.74 and 4.02 (ABq, J=15 Hz, SCH$_2$CO), ~4.4(m, 16-H, 14-H), 4.59(d, J=10 Hz, 4-H), ~5.05(m, 8-H), 5.2~6.0(m, 3-H, 6-H, 7-H, 10-H, 13-H), 6.12(d, J=15 Hz, 12-H), 6.95(s, triazole-H), 7.74(d, J=10 Hz, NH).

IR (KBr): 1730, 1708, 1660, 1508, 1370, 1250, 1020, 960 cm$^{-1}$.

EXAMPLE 169

3-[2-(4-pyridyl)thio]acetamido-lankone 8-acetate

The reaction was allowed to proceed at 37° C. for 15.5 hours, followed by purification by means of TLC. The yield was 42%.

NMR (90 MHz, CDCl$_3$)δ: 1.10(s, 2-Me), 1.18(d, J=7 Hz, 2-Me), 1.52(s, 11-Me), 1.86(s, 5-Me), 2.04(s, OAc), 2.1~2.6(m, 9-H$_2$, 15-H$_2$, 17-H), 3.57 and 3.78(ABq, J=17 Hz, SCH$_2$CO), ~4.3(m, 16-H, 14-H), 4.50(d, J=12 Hz, 4-H), 5.05(m, 8-H), 5.2~5.9(m, 3-H, 6-H, 7-H, 10-H, 13-H), 6.12(d, J=15 Hz, 12-H), 7.14(d, J=6 Hz, pyridine-H$_2$), 7.81(d, J=10 Hz, NH) 8.38(m, pyridine-H$_2$).

IR(KBr): 1726, 1702, 1652, 1578, 1498, 1370, 1252, 1014, 960$^{-1}$.

EXAMPLE 170

3-(2-Difluoromethylthio)acetamido-lankone 8-acetate

Purification was conducted by means of TLC. The yield was 49%.

NMR (90 MHz, CDCl$_3$)δ: 1.25(d, J=7 Hz, 17-Me), 1.38(s, 2-Me), 1.53(s, 11-Me), 1.87(s, 5-Me), 2.03(s, OAc), 2.1~2.6(m, 9-H$_2$, 15-H$_2$, 17-H), 3.47(s, SCH$_2$CO), ~4.4(m, 16-H, 14-H), 4.67(d, J=11 Hz, 4-H), 5.05(m, 8-H), 5.2~5.9(m, 3-H, 6-H, 7-H, 10-H, 13-H), 6.15(d, J=15 Hz, 12-H), 6.87(t, J=56 Hz, CHF$_2$), 7.58(d, J=10 Hz, NH).

IR (KBr): 1732, 1706, 1664, 1502, 1372, 1254, 1060, 1020, 960 cm$^{-1}$.

EXAMPLE 171

3-[2-(5-methanesulfonylmethyl-1,3,4-thiadiazol-2-yl)thio]acetamido-lankone 8-acetate The reaction was allowed to proceed at 37° C. for 20 hours, followed by purification by means of TLC. The yield was 26%.

NMR (90 MHz, CDCl$_3$)δ: 1.20(d, J=7 Hz, 17-Me), 1.30(s, 2-Me), 1.53(s, 11-Me), 1.83(s, 5-Me), 2.04(s, OAc), 2.1~2.6(m, 9-H$_2$, 15-H$_2$, 17-H), 2.99(s, SO$_2$CH$_3$), 4.02(s, SCH$_2$CO), ~4.4(m, 14-H, 16-H), 4.62(d, J=11 Hz, 4-H), 4.70(s, thiadiazole-CH$_2$), 5.05(m, 8-H), 5.2~5.9(m, 3-H, 6-H, 7-H, 10-H, 13-H), 6.13(d, J=15 Hz, 12-H), 7.62(d, J=10 Hz, NH).

IR (KBr): 1728, 1710, 1664, 1368, 1312, 1260, 1140, 964 cm$^{-1}$.

EXAMPLE 172

3-[2-[1-(2-hydroxyethyl)-1H-tetrazol-5-yl]thio]acetamido-lankone 8-acetate

The reaction was allowed to proceed at 37° C. for 16 hours, followed by purification by means of TLC. The yield of 19%.

NMR (90 MHz, CDCl$_3$)δ: 1.22(d, J=7 Hz, 17-Me), 1.32(s, 2-Me), 1.53(s, 11-Me), 1.82(s, 5-Me), 2.04(s, OAc), 2.1~2.6(m, 9-H$_2$, 15-H$_2$, 17-H), 3.88 and 4.12(ABq, J=15 Hz, SCH$_2$CO), 18 4.1(m, CH$_2$CH$_2$OH), ~4.4(m, 14-H, 16-H, tetrazole-CH$_2$), 4.55(d, J=12 Hz, 4-H), 5.03(m, 8-H), 5.2~5.9(m, 3-H, 6-H, 7-H, 10-H, 13-H), 6.15(d, J=15 Hz, 12-H), 7.52(d, J=10 Hz, NH).

IR (KBr): 1730, 1708, 1662, 1372, 1252, 1060, 1018, 960 cm$^{-1}$.

EXAMPLE 173

3-[2-(2-Aminothiazol-4-yl)acetamido]lankone 8-acetate

The reaction was allowed to proceed at 37° C. for 7.5 hours, followed by purification by means of TLC. The yield was 30%.

NMR (90 MHz, CDCl$_3$)δ: 1.53(d, J=7 Hz, 17-Me), 1.30(s, 2-Me), 1.53(s, 11-Me), 1.85(s, 5-Me), 2.03(s, OAc), 2.1∼2.6(m, 9-H$_2$, 15-H$_2$, 17-H), 3.45(s, thiazole-CH$_2$), 4.37(m, 14-H, 16-H), 4.65(d, J=12 Hz, 4-H), 5.05(m, 8-H), 5.2∼5.9(m, 3-H, 6-H, 10-H, 13-H), 6.13(d, J=15 Hz, 12-H), 6.28(s, thiazole-H), 7.18(d, J=10 Hz, NH), IR (KBr): 1736, 1710, 1630, 1512, 1260, 1246 cm$^{-1}$.

EXAMPLE 174

8-Dehydroxy-8-iodo-lankacidin C:

Purification was conducted by means of silica-gel column. The yield was 75%. m.p.: 150° C. (decomp.)

NMR (90 MHz, CDCl$_3$)δ: 1.23(d, J=7 Hz, 17-Me), 1.40(s, 2-Me), 1.51 and 1.54(each s, 3H, 11-Me), 1.88(s, 5-Me), 2.1∼2.4(m, 3H, 15-H$_2$, 17-H), 2.43(s, COCOCH$_3$), 2.5∼3.0(m, 2H, 9-H$_2$), ∼4.3(m, 3H, 16-H, 8-H, 4-H), 4.63(d, J=11 Hz, 4-H), 5.0∼6.0(m, 5H, 3-H, 6-H, 7-H, 10-H, 13-H), 6.12 and 6.22 (each d, 1H, J=15 Hz, 12-H), 8.07(d, J=9Hz, NH), IR (KBr): 3560, 3410, 1700, 1676, 1494, 1358, 1262, 1138, 1000, 960 cm$^{-1}$.

EXAMPLE 175

8-Dehydroxy-8-[[1-(2-dimethylaminoethyl)-1H-tetrazol-5-yl]thio]-lankacidin C (8-β compound)

The reaction was allowed to proceed at 37° C. for 20 hours, followed by purification by means of a silica gel column chromatography. The yield was 29%.

NMR (90 MHz, CDCl$_3$)δ: 1.28(d, J=7 Hz, 17-Me), 1.38(s, 2-Me), 1.53(s, 11-Me), 1.88(s, 5-Me), 2.26(s, NMe$_2$), ∼2.3(m, 15-H$_2$, 17-H), 2.75(t, J=7 Hz, CH$_2$NMe$_2$), ∼2.75(m, 9-H$_2$), 4.31(t, J=7 Hz, tetrazole-CH$_2$), ∼4.4(m, 14-H, 16-H), 4.72(d, J=11 Hz, 4-H), 4.93(m, 8-H), 5.25∼6.0(m, 3-H, 6-H, 7-H, 10-H, 13-H), 6.22(d, J=15 Hz, 12-H), 8.08(d, J=10 Hz, NH), IR (KBr): 1740, 1708, 1686, 1502, 1452, 1386, 1358, 1258 cm$^{-1}$.

EXAMPLE 176

8-Dehydroxy-8-[[1-(2-dimethylaminoethyl)-1H-tetrazol-5-yl]thio]-lankacidin C (8-α compound The reaction was allowed to proceed at 37° C. for 3 hours, then at room temperature for 14 hours, followed by purification by means of a silica gel column chromatography. The yield was 52%.

NMR (90 MHz, CDCl$_3$)δ: 1.25(d, J=7 Hz, 17-Me), 1.37(5,2-Me), 1.55(s, 11-Me), 1.84(s, 5-Me), 2.23(s, NMe$_2$), ∼2.3(m, 15-H$_2$, 17-H), 2.43(s, COCOCH$_3$), 2.73(t, J=7 Hz, CH$_2$NMe$_2$), 18 2.8(m, 9-H$_2$), 4.30(t, J=7 Hz, tetrazole-CH$_2$), ∼4.3(m, 14-H, 8-H), ∼4.4(m, 16-H), 5.2∼6.0(m, 3-H, 6-H, 7-H, 10-H, 13-H), 6.17(d, J=15 Hz, 12-H), 8.07(d, J=10 Hz, NH), IR (KBr): 1740, 1706, 1682, 1500, 1448, 1386, 1356, 1258 cm$^{-1}$.

EXAMPLE 177

8-Dehydroxy-8-[[1-(3-dimethylaminopropyl)1H-tetrazol-5-yl]thio]-lankacidin C (8-β compound)

The reaction was allowed to proceed at room temperature for 22.5 hours, followed by purification by means of silica gel column chromatography. The yield was 63%.

NMR (90 MHz, CDCl$_3$)δ:1.28(d, J=7 Hz, 17-Me), 1.38(s, 2-Me), 1.53(s, 11-Me), 1.88(s, 5-Me), 1.9∼2.8(m, CH$_2$CH$_2$NMe$_2$, 15-H$_2$, 17-H, 9-H$_2$), 2.20(s, NMe$_2$), 2.44(s, COCOCH$_3$), 4.28(t, J=7 Hz, tetrazole-CH$_2$), ∼4.45(m, 16-H, 14-H), 4.73 (d, J=11 Hz, 4-H), 4.94(m, 8-H), 5.2∼6.0(m, 3-H), 6-H, 7-H, 10-H, 13-H), 6.21(d, J=15 Hz, 12-H), 8.07 (d, J=10 Hz, NH).

IR (KBr): 3380, 1742, 1706, 1686, 1500, 1450, 1384, 1356, 1258 cm$^{-1}$.

EXAMPLE 178

8-Dehydroxy-8-[[1-(3-dimethylaminopropyl)-1H-tetrazol-5-yl]thio]-lankacidin (8-α compound)

The reaction was allowed to proceed at room temperature for 5 hours, followed by purification by means of silica gel column chromatography. The yield was 65%.

NMR (90 MHz, CDCl$_3$) δ: 1.26(d, J=7 Hz, 17-Me), 1.38(s, 2-Me), 1.53(s, 11-Me), 1.88(s, 5-Me), 1.9∼2.8(m, CH$_2$CH$_2$NME$_2$, 15-H$_2$, 17-H, 9-H$_2$), 2.19(s, NMe$_2$), 2.44(s, COCOCH$_3$), 4.28(t, J=7 Hz, tetrazole-CH$_2$), ∼4.45(m, 16-H, 14-H) 4.73(d, J=11 Hz, 4-H), 4.94(m, 8-H), 5.2∼6.0(m, 3-H, 6-H, 7-H, 10-H, 13-H), 6.17(d, J=15 Hz, 12-H), 8.07(d, J=10 Hz, NH).

IR (KBr): 3380, 1742, 1706, 1686, 1500, 1450, 1384, 1356, 1258 cm$^{-1}$.

EXAMPLE 179

8-Dehydroxy-8-azido-lankacidin C

Purification was conducted by means of silica gel column chromatography. The yield was 82%.

NMR (90 MHz, CDCl$_3$) δ: 1.26(d, J=7 Hz, 17-Me), 1.38(s, 2-Me), 1.49(s, 11-Me), 1.89(s, 5-Me), 2.1∼2.8(m, 15-H$_2$, 9-H$_2$, 17-H), 2.44(s, COCOCH$_3$), 4.0∼5.0(m, 16-H, 8-H, 14-H, 4-H), 5.1∼6.0(m, 3-H, 6-H, 7-H, 10-H, 13-H), 6.14 and 6.19 and 6.23(each d, 1H, Ca 2:3:1, J=15 Hz, 12-H), 8.08(d, J=10 Hz, NH).

IR (KBr): 2110, 1744, 1708, 1686, 1504, 1354, 1256, 962 cm$^{-1}$.

EXAMPLE 180

8-Dehydroxy-8-chloro-lankacidin C

Purification was conducted by means of silica gel column chromatography. The yield was 91%.

NMR (90 MHz, DMSO-d$_6$-CDCl$_3$ (1:1)) δ: 1.22(d, J=7 Hz, 17-Me), 1.32(s, 2-Me), 1.50(s, 11-Me), 1.79(s, 5-Me), 1.95∼2.8(m, 15-H$_2$, 17-H, 9-H$_2$), 2.38(s, COCOCH$_3$), 4.22(m, 8-H, 14-H), ∼4.6(m, 16-H), 4.82(d, J=11 Hz, 4-H), 5.1∼5.8(m, 3-H, 6-H, 7-H, 10-H, 13-H), 6.10(d, J=15 Hz, 12-H), 8.04(d, J=9 Hz, NH).

IR (KBr): 3410, 1702, 1674, 1488, 1352, 1260, 1134, 998, 960 cm$^{-1}$.

EXAMPLE 181

3-(2-(L)-azidopropionamido)-lankone 8-acetate

Purification was conducted by means of silica gel column chromatography. The yield was 91%. m.p.: 202° C. (decomp.)(AcOEt-Et$_2$O)

NMR (90 MHz, CDCl$_3$) δ: 1.25(d, 3H, J=7 Hz), 1.37(s, 3H), 1.52(d, 3H, J=7 Hz), 1.53(s, 3H), 1.70~1.85(m, 1H), 1.86(s, 3H), 2.04(s, 3H), 2.15~2.55(m, 5H), 4.00(q, 1H, J=7 Hz), 4.10~4.75(m, 3H), 4.90~5.90(m, 7H), 6.12(d, 1H, J=15 Hz), 7.47(d, 1H, J=10 Hz).

IR (KBr): 3410, 2140, 1740, 1710, 1660, 1250 cm$^{-1}$.

$[α]_D^{25}$ −167.5° (c=0.48, CHCl$_3$).

EXAMPLE 182

3-(2-(D)-azidopropionamido)-lankone 8-acetate

Purification was conducted by means of silica gel column chromatography. The yield was 88%. m.p.: 195°–196° C. (AcOEt-Et$_2$O)

NMR (90 MHz, CDCl$_3$) δ: 1.26(d, 3H, J=7 Hz), 1.40(s, 3H), 1.45(d, 3H, J=7 Hz), 1.55(s, 3H), 1.70~1.85(m, 1H), 1.87(s, 3H), 2.05(s, 3H), 2.18~2.60(m, 5H), 4.08(q, 1H, J=7 Hz), 4.20~4.72(m, 3H), 4.90~5.90(m, 7H), 6.13(d, 1H, J=15 Hz), 7.48(d, 1H, J=10 Hz).

IR (KBr): 3400, 2110, 1760, 1740, 1715, 1660, 1260 cm$^{-1}$.

$[α]_D^{25}$ −197.0° (c=0.495, CHCl$_3$).

EXAMPLE 183

3-(2-(L)-acetylaminopropionamido)-lankone 8-acetate

Employing the enzyme in an amount of 30 times as much (weight) of 14-acetate, the reaction was allowed to proceed at 37° C. for 4.5 hours, followed by purification by means of silica gel chromatography. The yield was 36%.

NMR (90 MHz, CDCl$_3$) δ: 1.23(d, 3H, J=7 Hz), 1.29(d, 3H, J=7 Hz), 1.39(s, 3H), 1.53(s, 3H), 1.85(s, 3H), 1.99(s, 3H), 2.04(s, 3H), 2.00~2.60(m, 6H), 4.20~4.75(m, 3H), 4.90~5.90(m, 7H), 6.13(d, 1H, J=15 Hz), 6.39(d, 1H, J=7 Hz), 7.06(d, 1H, J=10 Hz).

IR (KBr): 3400, 1740, 1715, 1665, 1255 cm$^{-1}$.

$[α]_D^{26}$ −172.8° (c=0.125, EtOH)

EXAMPLE 184

3-(2-(D)-acetylaminopropionamido)-lankone 8-acetate

The reaction was allowed to proceed at room temperature for 7 hours, followed by purification by means of silica gel column chromatography. The yield was 68%. m.p.: 192°–193° C. (MeOH)

NMR (90 MHz, CDCl$_3$) δ: 1.23(d, 3H, J=7 Hz), 1.38(d, 3H, J=7 Hz), 1.38(s, 3H), 1.54(s, 3H), 1.62(s, 1H), 1.86(s, 3H), 2.01(s, 3H), 2.04(s, 3H), 2.15~2.55(m, 5H), 4.20~4.70(m, 3H), 4.91~5.91(m, 7H), 6.10(d, 1H, J=7 Hz), 6.13(d, 1H, J=15 Hz), 7.06(d, 1H, J=10 Hz).

IR (KBr): 3450, 1730, 1710, 1660, 1255 cm$^{-1}$.

$[α]_D^{26}$ −140.4° (c=0.535, EtOH).

EXAMPLE 185

3-(2-(L)-butyrylaminopropionamido)-lankone 8-acetate

Purification was conducted by means of silica gel column chromatography. The yield was 98%.

NMR (90 MHz, CDCl$_3$) δ: 0.91(t, 3H, J=7 Hz), 1.23(d, 3H, J=7 Hz), 1.29(d, 3H, J=7 Hz), 1.38(s, 3H), 1.54(s, 3H), 1.45~1.90(m, 2H), 1.86(s, 3H), 2.04(s, 3H), 2.06~2.60(m, 8H), 4.20~4.76(m, 4H), 4.90~5.90(m, 7H), 6.13(d, 1H, J=15 Hz), 6.35(d, 1H, J=8 Hz), 7.08(d, 1H, J=10 Hz).

IR (KBr): 3400, 1740, 1715, 1660, 1255 cm$^{-1}$.

$[α]_D^{25}$ −177.8° (c=0.445, EtOH).

EXAMPLE 186

3-(2-(D)-butyrylaminopropionamido)-lankone 8-acetate

Purification was conducted by means of silica gel column chromatography. The yield was quantitative. m.p.: 199°–200° C. (AcOEt)

NMR (90 MHz, CDCl$_3$) δ: 0.91(t, 3H, J=7 Hz), 1.22(d, 3H, J=7 Hz), 1.38(s, 3H), 1.39(d, 3H, J=7 Hz), 1.54(s, 3H), 1.50~1.90(m, 3H), 1.86(s, 3H), 2.04(s, 3H), 2.10~2.55(m, 7H), 4.15~4.72(m, 4H), 4.90~5.90(m, 7H), 6.11(d, 1H, J=8 Hz), 6.13(d, 1H, 15 Hz), 7.10(d, 1H, J=10 Hz).

IR (KBr): 3400, 1730, 1710, 1645, 1260 cm$^{-1}$.

$[α]_D^{25}$ −130.2° (c=0.5, EtOH).

EXAMPLE 187

3-(2-(L)-benzyloxycarbonylaminopropionamido)-lankone 8-acetate

The reaction was allowed to proceed at room temperature overnight, followed by purification by means of TLC. The yield was 51%.

NMR (90 MHz, CDCl$_3$) δ: 1.24(s, 3H), 1.30(d, 3H, J=7 Hz), 1.31(d, 3H, J=7 Hz), 1.54(s, 3H), 1.76(br. s, 2H), 1.86(s, 3H), 2.04(s, 3H), 2.10~2.55(m, 5H), 4.04~4.70(m, 4H), 4.90~5.90(m, 7H), 5.10(s, 2H), 6.10(d, 1H, J=15 Hz), 7.05(d, 1H, J=10 Hz), 7.31(s, 5H).

IR (KBr): 3420, 1730, 1715, 1250 cm$^{-1}$.

$[α]_D^{25}$ −125.2° (c=0.735, EtOH).

EXAMPLE 188

3-(2-(D)-benzoyloxycarbonylaminopropionamido)-lankone 8-acetate

The reaction was allowed to proceed at room temperature overnight. The yield was 100%. m.p.: 191°–192° C. (AcOEt)

NMR (90 MHz, CDCl$_3$) δ: 1.23(d, 3H, J=7 Hz), 1.35(s, 3H), 1.39(d, 3H, J=7 Hz), 1.54(s, 3H), 1.64(s, 2H), 1.86(s, 3H), 2.04(s, 3H), 2.15~2.50(m, 5H), 4.06~4.70(m, 4H), 4.90~5.90(m, 7H), 5.11(s, 2H), 6.10(d, 1H, J=15 Hz), 7.13(d, 1H, J=10 Hz), 7.33(s, 5H).

IR (KBr): 3370, 1730, 1710, 1645, 1245 cm$^{-1}$.

$[α]_D^{25}$ −130.3° (c=0.495, EtOH).

EXAMPLE 189

3-(2-(L)-p-toluenesulfonylaminopropionamido)-lankone 8-acetate

Employing the enzyme in an amount of 60 times as much (weight) of 14-acetate, the reaction was allowed to proceed at room temperature for 24 hours, followed by separation by means of TLC. The yield was 48%. m.p.: 182°–183° C. (AcOEt)

NMR (90 MHz, CDCl$_3$) δ: 1.23(d, 6H, J=7 Hz), 1.26(s, 3H), 1.52(s, 3H), 1.81(s, 3H), 1.90(br. s, 2H), 2.04(s, 3H), 2.10~2.55(m, 5H), 2.38(s, 3H), 3.78(quintet, 1H, J=7 Hz), 4.15~4.65(m, 3H), 4.90~5.90(m, 7H), 6.13(d, 1H, J=15 Hz), 7.10~7.40(m, 3H), 7.73(d, 2H, J=8 Hz).

IR (KBr): 3400, 1740, 1715, 1670, 1260 cm$^{-1}$.

$[α]_D^{25}$ −164.2° (c=0.095, EtOH).

EXAMPLE 190

3-(2-(D)-p-toluenesulfonylaminopropionamido)-lankone 8-acetate

Employing the enzyme in an amount of 40 times as much (weight) of 14-acetate, the reaction was allowed to proceed at room temperature for 21 hours, followed by purification by means of silica gel column chromatography. The yield was 82%. m.p.: 198°–199° C. (AcOEt)

NMR (90 MHz, CDCl$_3$-(CD$_3$)$_2$C=O) δ: 1.22(d, 3H, J=7 Hz), 1.26(d, 3H, J=7 Hz), 1.39(s, 3H), 1.54(s, 3H), 1.81(s, 3H), 2.14(s, 3H), 2.10~2.55(m, 5H), 2.39(s, 3H), 2.52(s, 1H), 3.32(d, 1H, J=4 Hz), 3.76(quintet, 1H, J=7 Hz), 4.10~4.76(m, 3H), 4.90~5.90(m, 7H), 6.14(d, 1H, J=15 Hz), 6.35(d, 1H, J=7 Hz), 7.27(d, 2H, J=8 Hz), 7.72(d, 2H, J=8 Hz).

IR (KBr): 3420, 1730, 1715, 1660, 1260 cm$^{-1}$.
[α]$_D^{25}$ −119.5° (c=0.4, EtOH).

EXAMPLE 191

3-(2-(L)-diphenylphosphinothioylaminopropionamido)-lankone 8-acetate

Employing the enzyme in an amount of 40 times as much (weight) of 14-acetate, the reaction was allowed to proceed at room temperature for 28 hours, followed by separation by means fo TLC. The yield was 40%.

NMR (90 MHz, CDCl$_3$) δ: 1.23(d, 3H, J=7 Hz), 1.28(d, 3H, J=7 Hz), 1.34(s, 3H), 1.53(s, 3H), 1.84(s, 3H), 1.95(br. s, 1H), 2.04(s, 3H), 2.10~2.55(m, 5H), 3.50(dd, 1H, J=5 Hz and 9 Hz), 3.70~4.70(m, 4H), 4.90~5.90(m, 7H), 6.14(d, 1H, J=15 Hz), 7.17(d, 1H, J=10 Hz), 7.30~7.55(m, 6H), 7.70~8.15(m, 4H).

IR (KBr): 3400, 1740, 1710, 1665, 1255 cm$^{-1}$.
[α]$_D^{25}$ −117.9° (c=0.655. EtOH).

EXAMPLE 192

3-(2-(D)-diphenylphosphinothioylaminopropionamido)-lankone 8-acetate

Employing the enzyme in an amount of 40 times as much (weight) of 14-acetate, the reaction was allowed to proceed at room temperature for 17 hours. The yield was 74%.

NMR (90 MHz, DMSO-d$_6$) δ: 1.22(d, 3H, J=7 Hz), 1.26(d, 3H, J=7 Hz), 1.32(s, 3H), 1.55(s, 3H), 1.70(s, 3H), 2.00(s, 3H), 2.20~2.60(m, 6H), 3.60~5.90(m, 12-H), 6.13(d, 1H, J=15 Hz), 7.35~7.66(m, 6H), 7.66~8.13(m, 5H).

IR (KBr): 3390, 1740, 1710, 1650, 1255 cm$^{-1}$.
[α]$_D^{24}$ −97.0° (c=0.44, DMF)

EXAMPLE 193

3-[3-(Benzoxazol-2-yl)thio-2-oxopropionamido]-lankone 8-acetate

Purification was conducted column chromatography on silica gel inactivated with 10% of water, followed by further purification by the use of reversed pahse TLC plates. The yield was 44%.

NMR (90 MHz, CDCl$_3$) δ: 1.23(d, 3H, J=7 Hz), 1.41(s, 3H), 1.56(s, 3H), 1.65(br. s, 1H), 1.92(s, 3H), 2.06(s, 3H), 2.15~2.55(m, 5H), 4.10~4.80(m, 4H), 4.95~5.92(m, 6H), 6.12(d, 1H, J=15 Hz), 7.15~7.60(m, 4H), 8.10(d, 1H, J=10 Hz).

IR (KBr): 3490, 1725, 1700, 1680, 1235 cm$^{-1}$.
[α]$_D^{25}$ −114.3° (c=0.2275, CHCl$_3$)

EXAMPLE 194

3-(2-Aminothiazol-4-yl)carboxamido-lankone 8-acetate

Purification was conducted by means of silica gel column chromatography. The yield was 97%. m.p.: 182°–184° C. (CHCl$_3$).

NMR (90 MHz, CDCl$_3$) δ: 1.25(d, 3H, J=7 Hz), 1.43(s, 3H), 1.55(s, 3H), 1.75(br. s, 1H), 1.90(s, 3H), 2.04(s, 3H), 2.15~2.50(m, 5H), 4.20~5.92(m, 11H), 6.13(d, 1H, J=15 Hz), 7.32(s, 1H), 8.10(d, 1H, J=10 Hz).

IR (KBr): 3400, 1730, 1715, 1655, 1250 cm$^{-1}$.
[α]$_D^{24.5}$ −77.7° (c=0.44, EtOH).

EXAMPLE 195

3-(2-(D)-ethylthiopropionamido)-lankone 8-acetate

Purification was conducted by means of TLC. The yield was 87%.

NMR (90 MHz, CDCl$_3$) δ: 1.22(t, 3H, J=7 Hz), 1.28(d, 3H, J=7 Hz), 1.39(d, 3H, J=7 Hz), 1.40(s, 3H), 1.54(s, 3H), 1.86(s, 3H), 2.03(s, 3H), ~2.1(br. s, 1H), 2.15~2.67(m, 7H), 3.38(q, 1H, J=7 Hz), 4.20~4.83(m, 3H), 4.92~5.93(m, 6H), 6.15(d, 1H, J=15 Hz), 7.73(d, 1H, J=10 Hz).

IR (KBr): 3420, 1740, 1715, 1670, 1255 cm$^{-1}$.
[α]$_D^{24}$ −135.4° (c=0.435, EtOH).

EXAMPLE 196

3-(2-(L)-ethylthiopropionamido)-lankone 8-acetate

Purification was conducted by means of TLC. The yield was 68%. m.p.: 179°–180° C. (Et$_2$O)

NMR (90 MHz, CDCl$_3$) δ: 1.20(t, 3H, J=7 Hz), 1.25(d, 3H, J=7 Hz), 1.39(s, 3H), 1.47(d, 3H, J=7 Hz), 1.54(s, 3H), 1.88(s, 3H), 2.04(s, 3H), 2.16~2.60(m, 7H), 3.36(q, 1H, J=7 Hz), 4.20~4.80(m, 3H), 4.94~5.93(m, 6H), 6.16(d, 1H, J=15 Hz), 7.80(d, 1H, J=10 Hz).

IR (KBr): 3420, 1740, 1715, 1670, 1255 cm$^{-1}$.
[α]$_D^{24}$ −193.3° (c=0.36, EtOH)

EXAMPLE 197

3-[3-(pyridin-2-yl)thio-2-hydroxyiminopropionamido]-lankone 8-acetate

Purification was conducted by means of silica gel column chromatography. The yield was 73%.

NMR (90 MHz, CDCl$_3$) δ: 1.22(d, 3H, J=7 Hz), 1.39(s, 3H), 1.54(s, 3H), 1.89(s, 3H), ~2.0(br. s, 1H), 2.05(s, 3H), 2.15~2.55(m, 5H), 4.22(s, 2H), 4.15~4.56(m, 2H), 4.72(br. d, 1H, J=10 Hz), 4.90~5.93(m, 6H), 6.15(d, 1H, J=15 Hz), 6.95~7.65(m, 3H), 8.01(br. d, 1H, J=10 Hz), 8.40(m, 1H), ~11.5(br. s, 1H).

IR (KBr): 3400, 1740, 1710, 1670, 1260 cm$^{-1}$.
[α]$_D^{21}$ −120.0° (c=0.365, EtOH).

EXAMPLE 198

3-[3-(pyridine-2-yl)thio-2-methoxyiminopropionamido]-lankone 8-acetate

Purification was conducted by means of silica gel column chromatography. The yield was 78%.

NMR (90 MHz, CDCl$_3$) δ: 1.23(d, 3H, J=7 Hz), 1.38(s, 3H), 1.55(s, 3H), 1.66(br. s, 1H), 1.89(s, 3H), 2.05(s, 3H), 2.15~2.55(m, 5H), 4.03(s, 3H), 4.26(s, 2H), 4.20~4.55(m, 2H), 4.72(br. d, 1H, J=11 Hz), 4.93~5.92(m, 6H), 6.15(d, 1H, J=15 Hz), 6.85~7.55(m, 3H), 7.76(br. d, 1H, J=10 Hz), 8.38(m, 1H).

IR (KBr): 3400, 1740, 1715, 1680, 1260 cm$^{-1}$.

[α]$_D^{22}$ −163.1° (c=0.065, EtOH)

EXAMPLE 199

3-[3-(pyridin-2-yl)thio-2-(L)-hydroxypropionamido]-lankone 8-acetate

Employing 2'-(DL) compound, separation of the product was conducted by means of TLC. The yield was 31%.

NMR (90 MHz, CDCl$_3$) δ: 1.21(d, 3H, J=7 Hz), 1.36(s, 3H), 1.55(s, 3H), 1.90(s, 3H), 2.15(s, 3H), ~1.7(br. s, 2H), 2.15~2.55(m, 5H), 3.57(d, 2H, J=4 Hz), 4.16~4.56(m, 3H), 4.75(br. d, 1H, J=11 Hz), 4.95~5.95(m, 6H), 6.16(d, 1H, J=15 Hz), 7.02~7.70(m, 3H), 8.19(br. d, 1H, J=10 Hz), 8.45(m, 1H).

IR (KBr): 3400, 1740, 1710, 1670, 1260 cm$^{-1}$.

[α]$_D^{21}$ −213.6° (c=0.11, EtOH).

EXAMPLE 200

3-[3-(pyridin-2-yl)thio-2-(D)-hydroxypropionamido]-lankone 8-acetate

Employing 2'-(DL) compound, separation of the product was conducted by means of TLC. The yield was 33%.

NMR (90 MHz, CDCl$_3$) δ: 1.23(d, 3H, J=7 Hz), 1.42(s, 3H), 1.55(s, 3H), ~1.80(br.s, 2H), 1.89(s, 3H), 2.05(s, 3H), 2.15~2.55(m, 5H), 3.30~3.70(m, 2H), 4.15~4.58(m, 3H), 4.72(br.d, 1H, J=11 Hz), 4.95~5.95(m, 6H), 6.14(d, 1H, J=15 Hz), 7.00~7.70(m, 3H), 8.16(br.d, 1H, J=10 Hz), 8.40 (m, 1H).

IR (KBr): 3400, 1740, 1710, 1670, 1255 cm$^{-1}$.

[α]$_D^{21}$ −64.3° (c=0.185, EtOH).

EXAMPLE 201

Lankacidin C 8-dibenzylphosphate

The reaction was allowed to proceed at room temperature, followed by purification by means of silica gel column chromatography. The yield was 68%. m.p.: 194° C. (decomp.) (AcOEt)

NMR (90 MHz), CDCl$_3$) δ: 1.24(d, 3H, J=7 Hz), 1.37(s, 3H), 1.49(s, 3H), 1.83 (s, 3H), 2.15~2.65(m, 6H), 2.45(s, 3H), 4.15~4.80(m, 4H), 4.97(d, 2H, J=8 Hz), 5.01(d, 2H, J=8 Hz), 5.05~5.90(m, 5H), 6.10(d, 1H, J=15 Hz), 7.29(s, 5H), 7.31(s, 5H), 8.11(br.d, 1H, J=10 Hz).

IR (KBr): 3425, 1755, 1715, 1695, 1265, 1000 cm$^{-1}$.

[α]$_D^{25}$ −157.6° (c=0.49, CHCl$_3$).

EXAMPLE 202

Lancadin C 8-diethylphosphate

The reaction was allowed to proceed at 35° C. for one hour, followed by purification by means of silica gel column chromatography. The yield was 79%. m.p.: 194° C. (decomp.) (AcOEt-Et$_2$O)

NMR (90 MHz, CDCl$_3$) δ: 1.20~1.40(m, 12H), 1.54(s, 3H), 1.79(br.s, 1H), 1.90(s, 3H), 2.20~2.70(m, 5H), 2.45(s, 3H), 2.87~4.80(m, 8H), 5.15~5.93(m, 5H), 6.13(d, 1H, J=15 Hz), 8.09 (br.d, 1H, J=10 Hz).

IR (KBr): 3400, 1745, 1710, 1680, 1260, 1005 cm$^{-1}$.

[α]$_D^{21}$ −193.7° (c=0.46, EtOH).

EXAMPLE 203

Lankacidin C 8-dimethylphosphate

Purification was conducted by means of silica gel column chromatography. The yield was 95%. m.p.: 173° C. (decomp.) (AcOEt)

NMR (90 MHz, CDCl$_3$) δ: 1.26(d, 3H, J=7 Hz), 1.37(s, 3H), 1.54(s, 3H), 1.90(s, 3H), 2.15~2.70(m, 5H), 2.45(s, 3H), 2.84 (br.s, 1H), 3.69(d, 3H, J=12 Hz), 3.74(d, 3H, J=12 Hz), 4.20~4.85(m, 4H), 5.15~5.98(m, 5H), 6.13(d, 1H, J=15 Hz), 8.15 (br.d, 1H, J=10 Hz).

IR (KBr): 3410, 1755, 1715, 1690, 1265, 1015 cm$^{-1}$.

[α]$_D^{24}$ −222.0° (c=0.5, CHCl$_3$).

EXAMPLE 204

3-(2-Oxo-1-thioxopropylamino)-lankone 8-diethylphosphate

The reaction was allowed to proceed at 37° C. for two hours, followed by purification by means of silica gel column chromatography. The yield was 89%.

NMR (90 MHz, CDCl$_3$) δ: 1.20~1.45(m, 12H), 1.56(s, 3H), 1.96(s, 3H), 2.05(br.s, 1H), 2.16~2.65 (m, 5H), 2.65(s, 3H), 3.88~4.80(m, 8H), 5.15~6.25(m, 6H), 10.01(br.d, 1H, J=10 Hz).

IR (KBr): 3420, 1755, 1710, 1265, 1010 cm$^{-1}$.

[α]$_D^{24}$ −303.0° (c=0.1, EtOH).

EXAMPLE 205

3-(2-(DL)-n-octanoyloxypropionamido)lankone 8-diethylphosphate

The reaction was allowed to proceed at room temperature for two hours, then at 30° C. overnight, followed by purification by means of TLC. The yield was 64%.

NMR (90 MHz, CDCl$_3$) δ: 0.87(~t, 3H), 1.15~1.95(m, 34H), 2.10~2.70(m, 8H), 3.85~4.80(m, 8H), 5.05~5.95(m, 6H), 6.12(d, 1H, J=15 Hz), 7.30(br.d, ~0.5H, J=10 Hz), 7.45 (br.d, ~0.5H, J=10 Hz).

IR (KBr): 3430, 2945, 1750, 1710, 1685, 1265, 1035, 1010 cm$^{-1}$.

EXAMPLE 206

3-(2-(DL)-hydroxypropionamido)-lankone 8-diethylphosphate

Purification was conducted by means of silica gel column chromatography. The yield was 85%.

NMR (90 MHz, CDCl$_3$) δ: 1.15~1.50(m, 15H), 1.54(s, 3H), 1.88(s, 3H), 2.10~2.68(m, 6H), 3.49(br.s, 1H), 3.88~4.80(m, 9H), 5.15~5.95(m, 5H), 6.13(d, 1H, J=15 Hz), 7.57(br.d, ~0.5H, J=10 Hz). 7.73(br.d, ~0.5H, J=10 Hz).

IR (KBr): 3420, 1750, 1715, 1655, 1265, 1040, 1010 cm$^{-1}$.

EXAMPLE 207

3-Cyclohexylcarboxamido-lankone 8-acetate

The reaction was allowed to proceed at room temperature overnight, followed by purification by means of TLC. The yield was 25%. m.p.: 169°-172° C.

NMR (90 MHz, CDCl$_3$) δ: 1.23(d, J=7 Hz, 17-Me), 1.37(s, 2-Me), 1.54(s, 11-Me), 1.87(s, 5-Me), 1.2~2.0(m, cyclohexyl-CH$_2$×5), 2.04 (s, OAc), 2.2~2.6(m, 9-H$_2$, 15-H$_2$, 17-H, cyclohexyl-CH), 4.3~4.5(m, 14-H, 16-H), 4.64(d, J=11 Hz, 4-H), 5.06(m, 8H), 5.15~5.95 (m, 3-H, 6H, 7-H, 10H, 13-H), 6.16(d, J=15 Hz, 12-H), 6.60(d, J=10 Hz, NH).

IR (KBr): 3450, 2930, 1735, 1705, 1650, 1495, 1450, 1370, 1245, 1015, 960, 745 cm$^{-1}$.

EXAMPLE 208

3-(2-Thienyl)acetamido-lankone 8-acetate

The reaction was allowed to proceed at room temperature overnight, followed by purification by means of TLC. The yield was 43%. m.p.: 187°–189° C. (decomp.)

NMR (90 MHz, CDCl$_3$) δ: 1.18(d, J=6.5 Hz, 17-Me), 1.30(s, 2-Me), 1.53(s, 11-Me), 1.87(s, 5-Me), 1.74(br.s, OH), 2.04(s, OAc), 2.15~2.55(m, 9-H$_2$, 15-H$_2$, 17-H), 3.75(s, thiophen-CH$_2$), 4.15~4.45(m, 14-H, 16-H), 4.58(d, J=11 Hz, 4-H), 5.03 (m, 8-H), 5.15~5.9(m, 3H, 6-H, 7-H, 10-H, 13-H), 6.11(d, J=15 Hz, 12-H), 6.79(d, J=10 Hz, NH), 6.95~ 7.1(m, 2H, thiophen-H$_2$), 7.2~7.3(m, 1H, thiophen-H).

IR (KBr): 3430(sh.), 3390, 1735, 1710, 1650, 1375, 1265, 1240, 1020, 965 cm$^{-1}$.

EXAMPLE 209

3-[D(−)-2-(4-ethyl-2,3-dioxo-1-piperazinecarboxamido)phenylacetamido]-lankone 8-acetate The reaction was allowed to proceed at room temperature overnight, followed by purification by means of TLC. The yield was 24%. m.p.: 166°–169° C.

NMR (90 MHz, CDCl$_3$) δ: 1.01(s, 2-Me),1.16(d, J=7 Hz, 17-Me), 1.20(t, J=7.5 Hz, CH$_2$CH$_3$), 1.52(s, 11-Me), 1.71(br.s, OH), 1.84(s, 5-Me), 2.05(s, OAc), 2.1~2.55(m, 9-H$_2$, 15-H$_2$, 17-H), 3.53(q, J=7.5 Hz, CH$_2$CH$_3$), 3.4~3.7 and 3.95~4.15 (each m, each 2H, piperazine-H$_4$), 4.15~4.45(m, 14-H, 16H), 4.64(d, J=11 Hz, 4-H), 5.06(m, 8-H), 5.25~5.9(m, 3-H, 6-H, 7-H, 10-H, 13-H, C$_6$H$_5$CH), 6.14(d, J=15 Hz, 12H), 6.93(d, J=10 Hz, 3-NH), 7.38(br.s, C$_6$H$_5$), 9.93(d, J=6 Hz,

IR (KBr): 3420(br.), 1710, 1680, 1500, 1370, 1250, 1185, 1015, 960 cm$^{-1}$.

EXAMPLE 210

3-[D(−)-2-(2,2,2-trichloroethoxycarbonylamino)-phenylacetamido]-lankone 8-acetate The reaction was allowed to proceed at 33° C. for 20 hours, followed by purification by means of TLC. The yield was 25%. m.p.: 147°–150° C.

NMR (90 MHz, CDCl$_3$) δ: 0.85(s, 2-Me), 1.17(d, J=6.5 Hz, 17-Me), 1.52(s, 11-Me), 1.59(s, OH), 1.87(s, 5-Me), 2.04(s, OAc), 2.15~2.55(m, 9-H$_2$, 15-H$_2$, 17-H), 4.15~4.55(m, 14-H, 16-H), 4.63 (d, J=11 Hz, 4H), 4.57 and 4.73(ABq, J=12 Hz, CCl$_3$CH$_2$), 4.9~5.2(m, 8-H, C$_6$H$_5$CH), 5.3~5.9(m, 3-H, 6-H, 7-H, 10-H, 13-H), 6.12(d, J=15 Hz, 12-H), 6.47 (br.d, J=7 Hz, NHCOO), 6.91(br, J=10 Hz, 3-N H), 7.37(br. s, C$_6$H$_5$).

IR (KBr): 3415 (br.), 1735, 1710, 1630, 1495, 1370, 1250, 1060, 1020, 960, 745, 720, 695 cm$^{-1}$.

EXAMPLE 211

3-[D(−)-2-aminophenylacetamido]-lankone 8-acetate

The reaction was allowed to proceed at 30°–35° C. for 22 hours, followed by purification by means of TLC. The yield was 27%. m.p.: 135°–137° C.

NMR (90 MHz, CDCl$_3$) δ: 1.21(s, 2-Me), 1.21(d, J=6.5 Hz, 17-Me), 1.53(s, 11-Me), 1.83(s, 5-Me), 1.7~2.01(br., OH, NH$_2$), 2.03(s, OAc), 2.15~2.45(m, 9-H$_2$, 15-H$_2$, 17-H), 4.25~4.5(m, 14-H, 16-H), 4.68(d, J=11 Hz, 4-H), 5.07(m, 8-H), 5.2~5.9(m, 3-H, 6-H, 7-H, 10-H, 13-H, C$_6$H$_5$CH), 6.15(d, J=15 Hz, 12-H), 7.31(s, C$_6$H$_5$), 7.79(br.d, J=10 Hz, NH).

IR (KBr): 3400(br.), 1735, 1705, 1670, 1490, 1370, 1245, 1020, 960 cm$^{-1}$.

EXAMPLE 212

Lankacidin C 8-(2-methoxyethoxymethylether)

Purification was conducted by means of silica gel column chromatography. The yield was 99%. m.p.: 168°–170° C. (CHCl$_3$-hexane)

NMR (90 MHz, CDCl$_3$) δ: 1.25(d, J=6.5 Hz, 17-Me), 1.34(s, 2-Me), 1.47(s, 11-Me), 1.89(s, 5-Me), 2.2~2.55(m, 9-H$_2$, 15-H$_2$17-H), 2.45(s, COCOCH$_3$), 3.35(s, CH$_2$CH$_2$OCH$_3$), 3.45~3.8(m, CH$_2$CH$_2$OCH$_3$), 4.01(m, 8-H), 4.3~4.55(m, 14-H, 16-H), 4.66(d, J=11 Hz, 4-H), 4.71(s, OCH$_2$O), 5.2~5.95(m, 3-H, 6-H, 7-H, 10-H, 13-H), 6.16(d, J=15 Hz, 12-H), 8.07(d, J=10 Hz, NH).

IR (KBr): 3470, 3375, 2940, 2890, 1745, 1705, 1670, 1515, 1505(sh.), 1450, 1350, 1255, 1130, 1100, 1085, 1060, 1035, 1015, 980, 960 cm$^{-1}$.

EXAMPLE 213

Lankacidin C 8-methoxymethylether

Purification was conducted by means of silica gel column chromatography. The yield was 77%. m.p.: 197°–199° C. (decomp.) (CHCl$_3$-Et$_2$O).

NMR (90 MHz, CDCl$_3$) δ: 1.23(d, J=6.5 Hz, 17-Me), 1.36(s, 2-Me), 1.48(s, 11-Me), 1.51(s, OH), 1.90(s, 5-Me), 2.2~2.55(m, 9-H$_2$, 15-H$_2$, 17-H), 2.43(s, COCOCH$_3$), 3.32(s, CH$_2$OCH$_3$), 3.96(m, 8-H), 4.25~4.55(m, 14-H, 16-H), 4.57 and 4.64(ABq, J=10 Hz, CH$_2$OCH$_3$), 4.65 (d, J=11 Hz, 4-H), 5.2~5.9(m, 3-H, 6-H, 7-H, 10-H, 13H), 6.15(d, J=15 Hz, 12-H), 8.06(d, J=10 Hz, NH).

IR (KBr): 3450, 3375, 2930, 1745, 1725(sh.), 1705, 1670, 1505, 1350, 1250, 1220, 1140, 1090, 1060, 1020, 960 cm$^{-1}$.

EXAMPLE 214

8-Dehydroxy-8-(1-methyl-1H-tetrazol-5-yl) thio-lankacidin C

The reaction was allowed to proceed at room temperature for 20 hours, followed by purification by means of a silica gel column chromatography. The yield was 74%. m.p.: 182°–184° C. (CHCl$_3$-Et$_2$O)

NMR (90 MHz, CDCl$_3$) δ: 1.27(d, J=6.5 Hz, 17-Me), 1.37(s, 2-Me), 1.53(s, 11-Me), 1.90(s, 5-Me), 2.2~2.85(m, 9-H$_2$, 15-H$_2$, 17-H), 2.44(s, COCOCH$_3$), 3.91(s, tetrazole-CH$_3$), 4.25~4.5(m, 14H), 4.47(m, 16-H), 4.72(d, J=10 Hz, 4-H), 4.85~5.05(m, 8-H), 5.3~6.0(m, 3-H, 6-H, 7-H, 10-H, 13-H), 6.22(d, J=15.5 Hz, 12-H), 8.07(d, J=11 Hz, NH).

IR (KBr): 3410, 1745, 1705, 1665, 1605, 1380, 1350, 1250, 1160, 1150, 1130, 1055, 1010, 960 cm$^{-1}$.

EXAMPLE 215

8-Dehydroxy-8-(5-methyl-1,3,4-thiadiazolyl)thio-lankacidin C

The reaction was allowed to proceed at room temperature overnight, followed by purification by means of TLC. The yield was 85%. m.p.: 142°–144° C. (CHCl$_3$-Et$_2$O-C$_6$H$_{14}$)

NMR (90 MHz, CDCl$_3$) δ: 1.27(d, J=6.5 Hz, 17-Me), 1.37(s, 2-Me), 1.50(s, 11-Me), 1.90(s, 5-Me), 2.2~2.8(m,

9H$_2$, 15-H$_2$, 17-H), 2.44(s, COCOCH$_3$), 2.66(s, thiadiazole-CH$_3$), 4.25~4.6(m, 14-H, 16-H), 4.71(d, J=11 Hz, 4-H), 4.7~4.9(m, 8-H), 5.3~6.1(m, 3-H, 6-H, 7-H, 10-H, 13-H), 6.22(d, J=15 Hz, 12-H), 8.07(d, J=10 Hz, NH).

IR (KBr): 3450(br.), 1735, 1700, 1675, 1490, 1370, 1350, 1250, 1130, 1050, 955 cm$^{-1}$.

EXAMPLE 216

8-Dehydroxy-8-phenylthio-lankacidin C

The reaction was allowed to proceed at room temperature overnight, followed by purification by means of TLC. The yield was 70%.

NMR (90 MHz, CDCl$_3$) δ: 1.27(d, J=6.5 Hz, 17-Me), 1.37(s, 2-Me), 1.52(s, 11-Me), 1.64(br., OH), 1.92(s, 5-Me), 2.2~2.7(m, 9-H$_2$, 15-H$_2$, 17-H), 2.45(s, COCOCH$_3$), 4.2~4.6(m, 8-H, 14-H, 16-H), 4.74(d, J=11 Hz, 4-H), 5.3~5.6(m, 3-H, 7-H, 10-H, 13-KH), 6.15(d, J=15 Hz, 6-H), 6.28(d, J=15 Hz, 12-H), 7.15~7.45(m, C$_6$H$_5$), 8.10(d, J=10 Hz, NH).

IR (KBr): 3400, 2930, 1750, 1710, 1680, 1505, 1455, 1440, 1360, 1260, 1225, 1160, 1140, 1060, 1005, 965, 745 cm$^{-1}$.

EXAMPLE 217

8-Dehydroxy-8-[5-(2-dimethylaminoethyl)-1,3,4-thiadiazol-2-yl]thio-lankacidin C

The reaction was allowed to proceed at room temperature overnight, followed by purification by means of TLC. The yield was 47%.

NMR (90 MHz, CDCl$_3$) δ: 1.26(d, J=6.5 Hz, 17-Me), 1.37(s, 2-Me), 1.52(s, 11-Me), 1.89(s, 5-Me), 2.07(br., OH), 2.26(s, NMe$_2$), 2.2~2.8(m, 9-H$_2$, 15-H$_2$, 17-H), 2.43(s, COCOCH$_3$), 2.60(t, J=6.5 Hz, CH$_2$NMe$_2$), 3.15(t, J=6.5 Hz, thiadiazole-CH$_2$)4.2~4.55(m, 14-H, 16-H), 4.70(d, J=11 Hz, 4-H), 4.78(m, 8-H), 5.3~6.1(m, 3-H, 6-H, 7-H, 10-H, 13-H), 6.22(d, J=15 Hz, 12-H), 8.06(d, J=10 Hz, NH).

IR (KBr): 3380, 2940, 1745, 1705, 1685, 1500, 1450, 1375, 1360, 1260, 1160, 1140, 1055, 1010, 960, 745 cm$^{-1}$.

EXAMPLE 218

8-Dehydroxy-8-(4,5-dimethylthiazol-2-yl)thio-lankacidin C

Purification was conducted by means of TLC. The yield was 61%.

NMR (90 MHz, CDCl$_3$)δ: 1.27(d, J=6.5 Hz, 17-Me), 1.37(s, 2-Me), 1.51(s, 11-Me), 1.7~1.9 (br., OH), 1.89(s, 5-Me), 2.2~2.75(m, 9-H$_2$15-H$_2$, 17-H), 2.25(s, thiazole-CH$_3$×2), 2.43(s, COCOCH$_3$), 4.3~4.6(m, 8-H, 14-H, 16-H), 4.73(d, J=11 Hz, 4-H), 5.3~5.95(m, 3-H, 7-H, 10-H, 13-H), 6.03(d, J=15 Hz, 6-H), 6.22(d, J=15 Hz, 12-H), 8.06(d, J=10 Hz, NH).

IR (KBr): 3380, 2910, 1740, 1700, 1680, 1490, 1360(sh.), 1350, 1250, 1155, 1125, 1050, 1005, 955 cm$^{-1}$.

EXAMPLE 219

8-Dehydroxy-8-(4,5-dimethyloxazol-2-yl)thio-lankacidin C

Purification was conducted by means of TLC. The yield was 64%.

NMR (90 MHz, CDCl$_3$)δ: 1.26(d, J=6.5 Hz, 17-Me), 1.37(s, 2-Me), 1.51(s, 11-Me), 1.76(br. s, OH), 1.88(s, 5-Me), 2.01 and 2.17(each s, oxazole —CH$_3$×2), 2.2~2.75(m, 9-H$_2$, 15-H$_2$, 17-H), 2.43 (s, COCOCH$_3$), 4.2~4.55(m, 14-H, 16-H), 4.65(m, 8-H), 4.72(d, J=10 Hz, 4-H), 5.3~6.05(m, 3-H, 6-H, 7-H, 10-H, 13-H), 6.22(d, J=15 Hz, 12-H), 8.05(d, J=10 Hz, NH).

IR (KBr): 3400, 2930, 1750, 1710, 1690, 1500, 1450, 1360, 1260, 1225, 1185, 1165, 1140, 1060, 1010, 965, 745 cm$^{-1}$.

EXAMPLE 220

8-Dehydroxy-8-(1-dimethylamino-1H-tetrazol-5-yl)thio-lankacidin C

The reaction was allowed to proceed at room temperature for 5.5 hours. The yield was 78%.

NMR (90 MHz, CDCl$_3$)δ: 1.27(d, J=6.5 Hz, 17-Me), 1.38(s, 2-Me), 1.54(s, 11-Me), 1.90(s, 5-Me), ~2.0(br., OH), 2.2~2.85(m, 9-H$_2$, 15-H$_2$, 17-H), 2.44(s, COCOCH$_3$), 2.95(s, NMe), 4.2~4.55(m, 14-H, 16-H), 4.72(d, J=11 Hz, 4-H), 4.93(m, 8-H), 5.3~6.0(m, 3-H, 6-H, 7-H, 10-H, 13-H), 6.23(d, J=15 Hz, 12-H), 8.07(d, J=10 Hz, NH).

IR (KBr): 3390, 2980, 2930, 1745, 1710, 1685, 1500, 1440, 1380, 1355, 1250, 1220, 1160, 1135, 1055, 1010, 960, 745 cm$^{-1}$.

EXAMPLE 221

8-Dehydroxy-8-(1-ethyl-1H-1,2,4-triazol-3-yl)thio-lankacidin C

Purification was conducted by means of TLC, The yield was 81%. m.p.: 139°–141° C. (decomp.) (CHCl$_3$-Et$_2$O-C$_6$H$_{14}$)

NMR (90 MHz, CDCl$_3$)δ: 1.27(d, J=6.5 Hz, 17-Me), 1.37(s, 2-Me), 1.46(t, J=7.5 Hz, CH$_2$CH$_3$), 1.52(s, 11-Me), 1.87(s, 5-Me), 2.2~2.75(m, 9-H$_2$, 15-H$_2$, 17-H, OH), 2.43(s, COCOCH$_3$), 4.13(q, J=7.5 Hz, CH$_2$CH$_3$), 4.3~4.6(m, 14-H, 16-H), 4.73(d, J=10 Hz, 4-H), 4.73(m, 8-H), 5.3~6.1(m, 3-H, 6-H, 7-H, 10-H, 13-H), 6.23(d, J=15 Hz, 12-H), 7.97(s, triazole-H), 8.07(d, J=10 Hz, NH).

IR (KBr): 3390, 2980, 2925, 1740, 1700, 1680, 1495, 1445, 1350, 1255, 1130, 1055, 1005, 955 cm$^{-1}$.

EXAMPLE 222

Preparation of 3-(2-(L)-aminopropionamido)-lankone 8-acetate

In 3 ml of acetone was dissolved 81.4 mg of 3-(2-(L)-azidopropionamido)-lankone 8-acetate. To the solution was added 82 mg of Lindlar catalyst. The mixture was stirred for 1.5 hour under hydrogen atmosphere. Acetone was distilled off. To the residue were added 2 ml of ethanol and 40 mg of Lindlar catalyst. The mixture was stirred for 2.5 hours under hydrogen atmosphere, which was subjected to filtration by the use of a filter aid (celite). The filtrate was concentrated and subjected to a silica gel column chromatography, eluting with ethyl acetate-methanol (6:1). Desired fractions were combined and concentrated to obtain 63.6 mg of the above titled compound, m.p. 178°–179° C. (AcOEt).

NMR (90 MHZ, CDCl$_3$)δ: 1.24(d, 3H, J=7 Hz), 1.33(d, 3H, J=7 Hz), 1.37(s, 3H), 1.55(s, 3H), 1.76(br. s, 3H), 1.88(s, 3H), 2.04(s, 3H), 2.15~2.53(m, 5H), 3.47(q, 1H, J=7 Hz), 4.10~4.80(m, 3H), 4.95~5.93(m, 7H), 6.15(d, 1H, J=15 Hz), 8.18 (d, 1H, J=10 Hz).

IR (KBr): 3400, 1735, 1710, 1660, 1260 cm$^{-1}$.

[α]$_D^{25}$ −212.9° (c=0.465, EtOH)

EXAMPLE 223

Preparation of 3-(2-(D)-aminopropionamido)-lankone 8-acetate

In 2 ml of dichloromethane was dissolved 101.0 mg of 3-(2-(D)-azidopropionamido)-lankone 8-acetate. To the solution was added 102 mg of Lindlar catalyst, and the mixture was stirred under hydrogen atmosphere for 160 minutes. To the resultant were supplemented 0.5 ml of ethanol and 200 mg of Lindlar catalyst, and the mixture was stirred for further one hour under hydrogen atmosphere. The catalyst was filtered off, and the filtrate was concentrated. The concentrate was subjected to a silica gel column chromatography, eluting with ethyl acetate-methanol (6:1). Desired fractions were combined and concentrated to give 85.4 mg of the above titled compound, m.p. 169° C. (decomp.) (AcOEt).

NMR (90 MHz, $CDCl_3$)$\delta$: 1.23(d, 3H, J=7 Hz), 1.29(d, 3H, J=7 Hz), 1.38(s, 3H), 1.55(s, 3H), 1.82(s, 3H), 2.04(s, 3H), 2.12(s, 3H), 2.10~2.60 (m, 5H), 3.49(q, 1H, J=7 Hz), 4.15~4.80(m, 3H), 4.90~5.91(m, 7H), 6.13(d, 1H, J=15 Hz), 7.99(d, 1H, J=10 Hz).

IR (KBr): 3410, 1730, 1710, 1655, 1250 $cm^{-1}$.

$[\alpha]_D^{25}$ −145.5° (c=0.53, EtOH).

EXAMPLE 224

Preparation of 3-phenoxyacetamido-lankone

In 1.25 ml of dichloromethane was dissolved 54.5 mg of 3-phenoxyacetamido-lankone 8,14-bis(2,2,2-trichloroethylcarbonate). To the solution were added 0.125 ml of acetic acid and 109 mg of zinc powder. To the mixture were supplemented 109 mg of zinc powder after 190 minutes and 1 ml of dichloromethane after 265 minutes. The stirring was conducted for 385 minutes in total. The resultant was subjected to filtration by the use of a filter aid (celite) to eliminate the precipitates. The filtrate was washed well with ethyl acetate, followed by concentration. The concentrate was subjected to separation by means of TLC (Plates: manufactured by Merck, Art. No. 5715, 20×20 cm, two plates, developing solvent: tetrahydrofuran-chloroform (1:1)) to thereby obtain 17.1 mg of the above titled compound.

NMR (90 MHz, $CDCl_3$)$\delta$: 1.23(d, J=7 Hz, 17-H), 1.30(s, 2-Me), 1.53(s, 11-Me), 1.90(s, 5-Me), 2.1~2.5(m, 9-$H_2$, 15-$H_2$, 17-H), 4.07(m, 8-H), ~4.4(m, 14-H, 16-H), 4.43(s, $COCH_2O$), 4.64(d, J=10 Hz, 4-H), 5.1~5.9(m, 3-H, 6-H, 7-H, 10-H, 13-H), 6.13(d, J=15 Hz, 12-H), ~6.95 and ~7.3(m, $C_6H_5$), 7.85(d, J=9 Hz, NH).

IR (KBr): 1742, 1704, 1668, 1506, 1488, 1256, 1008, 960 $cm^{-1}$.

EXAMPLE 225

Preparation of 3-phenoxyacetamido-lankone 14-acetate

Employing 144.8 mg of 3-phenoxyacetamido-lankone 14-acetate 8-(2,2,2-trichloroethyl carbonate), the reaction was allowed to proceed in a manner similar to Example 224 to obtain 59.6 mg of the above titled compound, m.p. 128° C. ($CHCl_3$).

NMR (90 MHz, $CDCl_3$)$\delta$: 1.27(d, J=7 Hz, 17-Me), 1.30(s, 2-Me), 1.53(s, 11-Me), 1.90(s, 5-Me), 2.01(s, OAc), 2.15~2.7(m, 9$H_2$, 15-$H_2$, 17-H), ~4.1(m, 8-H), 4.37(m, 16-H), 4.43(s, $COCH_2O$), 4.65(d, J=11 Hz, 4-H), 5.2~5.85(m, 3-H, 6-H, 7-H, 10-H, 13-H, 14-H), 6.26(d, J=15 Hz, 12-H), ~7.0 and ~7.3(m, $C_6H_5$), 7.87(d, J=10 Hz, NH).

IR (KBr): 1728, 1706, 1674, 1504, 1488, 1236, 1008 $cm^{-1}$.

EXAMPLE 226

Preparation of 3-(2-acetoxyacrylamido)-lankone

Employing 200.3 mg of 3-(2-acetoxyacrylamido)-lankone 8,14-bis(2,2,2-trichloroethyl carbonate), the reaction was allowed to proceed in a manner similar to Example 224 to obtain 36.5 mg of the above titled compound.

NMR (90 MHz, $CDCl_3$)$\delta$: 1.22(d, J=7 Hz, 17-Me), ~1.40(s, 2-Me), 1.54(s, 11-Me), 1.89(s, 5-Me), 2.2~2.7(m, 9-$H_2$, 15-$H_2$, 17-H), 2.32(s, OAc), ~4.06(m, 8-H), ~4.4(m, 14-H, 16-H), 4.62(d, J=10 Hz, 4-H), 5.2~5.9(m, 3-H, 6-H, 7-H, 10-H, 13-H), 5.35 and 6.01(d, J=2 Hz, =$CH_2$), 6.13(d, J=15 Hz, 12-H), 7.41(d, J=10 Hz, NH).

IR (KBr): 1744, 1704, 1500, 1253, 1163, 1012 $cm^{-1}$.

EXAMPLE 227

Preparation of 3-[(2-carboxy)-phenylacetamido]-lankone

Employing 73.2 mg of 3-[2-(2,2,2-trichloroethoxycarbonyl)-phenylacetamido]-lankone 8,14-bis(2,2,2-trichloroethyl carbonate), the reaction was allowed to proceed in a manner similar to Example 224 to obtain 21.7 mg of the above titled compound.

NMR (90 MHz, $CD_3OD$)$\delta$: 0.92(d, J=6.5 Hz, 17-Me), 0.93(s, 2-Me), 1.21(s, 11-Me), 1.49(s, 5-Me), 1.8~2.3(m, 9$H_2$, 15-$H_2$, 17-H), 3.71(m, 8-H), 3.95~4.6(m, 4-H, 14-H, 16-H), 4.95~5.5(m, 3-H, 6-H, 7-H, 10-H, 13-H), 5.89(d, J=15 Hz, 12-H), 6.9~7.1 and 7.2~7.4(m, $C_6H_5$).

IR (KBr): 3420, 1740, 1710, 1650, 1510, 1370, 1255, 1010, 960 $cm^{-1}$.

EXAMPLE 228

Preparation of 3-[2-(D)-(benzothiazol-2-yl)thio-1-thioxo]propylamino-lankone

In 1 ml of tetrahydrofuran was dissolved 42.4 mg of 3-[2-(D)-(benzothiazol-2-yl)thio-1-thioxo]propylamino-lankone, 8,14-bis(dimethyl-t-butylsilylether). To the solution was added 0.15 ml of 2N hydrochloric acid. The mixture was stirred for 2.5 hours, followed by concentration. The concentrate was subjected to separation by means of TLC (Plates: manufactured by Merck, Art. No. 5715, 20×20 cm, developing solvent: ethyl acetate-hexane (2:1)) to obtain 19. mg of the above titled compound.

NMR (90 MHz, $CDCl_3$)$\delta$: 1.16(d, 3H, J=7 Hz), 1.21(s, 3H), 1.51(s, 3H), 1.78(d, 3H, J=7 Hz), 1.80(br. s, 2H), 1.90(s, 3H), 2.10~2.50(m, 5H), 3.80~4.60(m, 4H), 4.95~6.35(m, 7H), 7.15~8.00 (m, 4H), 9.65(d, 1H, J=10 Hz).

IR (KBr): 3430, 1750, 1710, 1260 $cm^{-1}$.

$[\alpha]_D^{25}$ −271.6° (c=0.44, $CHCl_3$).

EXAMPLE 229

Preparation of 3-[2-(L)-(benzothiazol-2-yl)thio-propylamido]-lankone

In 1.5 ml of tetrahydrofuran was dissolved 99.7 mg of 3-[2-(L)-(benzothiazol-2-yl)thio-propionamido]-lankone 8,14-bis(dimethyl-t-butylsilylether). To the solution was added 0.36 ml of 2N hydrochloric acid, and the mixture was stirred for 2 hours, followed by extraction with ethyl acetate. The extract was washed with water, aqueous solution sodium hydrogencarbonate and aqueous saline solution in sequence. The resultant was dried over Na$_2$SO$_4$, then concentrated. The concentrate was subjected to purification by means of TLC (Plates: manufactured by Merck, Art. No. 5715, 20×20 cm, developing solvent: ethyl acetate) to obtain 53.6 mg of the above titled compound, m.p. 139°–140° C. (AcOEt-petroleum ether).

NMR (90 MHz, CDCl$_3$)δ: 1.08(d, 3H, J=6 Hz), 1.01(s, 3H), 1.50(s, 3H), 1.60(d, 3H, J=7 Hz), 1.86(s, 3H), 2.00~2.60(m, 7H), 3.85~4.80(m, 5H), 5.10~5.90(m, 5H), 6.10(d, 1H, J=15 Hz), 7.15~8.10(m, 5H).

IR (KBr): 3400, 1745, 1710, 1665 cm$^{-1}$.
$[\alpha]_D^{24}$ −267.0° (c=0.525, MeOH).

Employing corresponding 8,14-bis(dimethyl-t-butylsilyl ether, the reaction was allowed to proceed in a manner similar to the above, compounds of Example 230~Example 237.

EXAMPLE 230

3-[2-(D)-(benzoxazol-2-yl)thio-propionamido]-lankone

The yield was 78%.

NMR (90 MHz, CDCl$_3$)δ: 1.16(d, 3H, J=7 Hz), 1.32(s, 3H), 1.47(s, 3H), 1.63(d, 3H, J=7 Hz), 1.82(s, 3H), 2.05~2.80(m, 7H), 3.80~4.65(m, 5H), 5.05~5.90(m, 5H), 6.06(d, 1H, J=15 Hz), 7.10~7.80(m, 4H), 8.10(d, 1H, J=10 Hz).

IR (KBr): 3400, 1745, 1710, 1670 cm$^{-1}$.
$[\alpha]_D^{24}$ −48.6° (c=0.51, EtOH).

EXAMPLE 231

3-[2-(L)-(benzoxazol-2-yl)thio-propionamido]-lankone

The yield was 71%. m.p.: 142°–144° C. (AcOEt)

NMR (90 MHz, CD$_3$COCD$_3$)δ: 1.05(d, 3H, J=7 Hz), 1.01(s, 3H), 1.50(s, 3H), 1.62(d, 3H, J=7 Hz), 1.82(s, 3H), 2.00~2.60(m, 5H), 2.76(s, 2H), 4.00~4.85(m, 5H), 5.10~5.80(m, 5H), 6.18 (d, 1H, J=15 Hz), 7.20~7.70(m, 4H), 7.83(d, 1H, J=11 Hz).

IR (KBr): 3400, 1745, 1715, 1660 cm$^{-1}$.
$[\alpha]_D^{24}$ −226.5° (c=0.54, EtOH).

EXAMPLE 232

3-[2-(D)-(benzoimidazol-2-yl)thio-propionamido]-lankone

The yield was 64%.

NMR (90 MHz, CD$_3$COCD$_3$)δ: 1.23(d, 3H, J=6 Hz), 1.36(s, 3H), 1.46(s, 3H), 1.55(d, 3H, J=7 Hz), 1.76(s, 3H), 1.95~2.65(m, 5H), 2.93(br. s, 2H), 3.70~4.75(m, 5H), 5.00~5.80(m, 5H), 6.10 (d, 1H, J=15 Hz), 7.00~7.25(m, 2H), 7.35~7.70(m, 2H), 8.48(d, 1H, J=10 Hz), 11.50(br. s, 1H),

IR (KBr): 3400, 1750, 1710, 1665 cm$^{-1}$.

EXAMPLE 233

3-[2-(L)-(benzoimidazol-2-yl)thio-propionamido]-lankone

The yield was 41%.

NMR (90 MHz, CD$_3$COCD$_3$)δ:1.03(d, 3H, J=7 Hz), 1.04(s, 3H), 1.50(s, 3H), 1.53(d, 3H, J=7 Hz), 1.82(s, 3H), 2.00~2.70(m, 5H), 2.80(s, 2H), 3.70~4.90(m, 5H), 5.15~5.80(m, 5H), 6.15d, 1H, J=15 Hz), 7.00~7.22(M, 2H), 7.23~7.80(m, 2H), 8.28(d, 1H, J=10 Hz), 11.53(br.s, 1H).

IR (KBr): 3400, 1740, 1710, 1660 cm$^{-1}$.
$[\alpha]_D^{24}$ −163.3° (c=0.40, EtOH).

EXAMPLE 234

3-[2-(D)-(pyridin-2-yl)thio-propionamido]lankone

The yield was 61%.

NMR (90 MHz, CDCl$_3$)δ:1.20(d, 3H, J=7 Hz) 1.25(s, 3H), 1.50(s, 3H), 1.52(d, 3H, J=7 Hz), 1.72(br.s, 2H), 183(s, 3H), 2.05~2.50(m, 5H), 3.84~4.60(m, 5H), 5.10~5.90(M, 5H), 6.10(d, 1H, J=15 Hz), 6.90~7.60(M, 3H), 8.26(d, 1H, J=10 Hz), 8.45~8.60(m, 1H).

IR (Neat): 3400(br.), 1740, 1710, 1660 cm$^{-1}$.
$[\alpha]_D^{24}$ +12.1° (c=0.77, EtOH).

EXAMPLE 235

3-[2-(L)-(pyridin-2-yl)thio-propionamido]lankone

The yield was 59%. m.p.: 187° C. (decomp.) (AcOEt-C$_6$H$_{14}$)

NMR (90 MHz, DMSO-d$_6$)δ: 1.10 (s, 3H), 1.14 (d, 3H, J=6 Hz), 1.45 (s, 3H), 1.46 (d, 3H, J=7 Hz), 1.95~2.50 (m, 5H), 3.85~4.90 (m, 6H), 5.00~5.75 (m, 5H), 6.08 (d, 1H, J=15 Hz), 6.95~7.70 (m, 3H), 8.03 (d, 1H, J=10 Hz), 8.45~8.55 (m, 1H).

IR (KBr): 3400(br.), 1750, 1715, 1660 cm$^{-1}$.
$[\alpha]_D^{25}$ −252.6° (c=0.53, EtOH).

EXAMPLE 236

3-(2-(D)-azidopropionamido)-lankone

The yield was 68%. m.p.: 186°–188° C. (decomp.) (AcOEt)

NMR (90 MHz, CDCL$_3$)δ: 1.25 (d, 3H, J=6 Hz), 1.38 (s, 3H), 1.46 (d, 3H, J=7 Hz), 1.52 (s, 3H), 1.85 (s, 3H), 2.10~2.80 (m, 7H), 3.90~4.75 (m, 5H), 5.10~5.90 (m, 5H), 6.13 (d, 1H, J=15 Hz), 7.51 (d, 1H, J=10 Hz).

IR (CHCl$_3$): 3400, 2120, 1740, 1710, 1680 cm$^{-1}$.
$[\alpha]_D^{24.5}$ −220.4° (c=0.55, EtOH).

EXAMPLE 237

3-(2-(L)-azidopropionamido)lankone

The yield was 60%. m.p.: 192°–194° C. (decomp.) (AcOEt)

NMR (90 MHz, CDCl$_3$)δ: 1.25 (d, 3H, J=6 Hz), 1.3 (s, 3H), 1.53 (d, 3H, J=7 Hz), 1.54 (s, 3H), 1.89 (s, 5H), 2.10~2.65 (m, 5H), 3.90~4.75 (m, 5H), 5.10~5.90 (m, 5H), 6.15 (d, 1H, J=15 Hz), 7.50 (d, 1H, J=10 Hz).

IR (KBr): 3350 (br.), 2130, 1755, 1710, 1655 cm$^{-1}$.
$[\alpha]_D^{23.5}$ −175.3° (c=0.45, EtOH).

EXAMPLE 238

Preparation of lankacidin A 8-dihydrodiene phosphate

In 0.5 ml of dichloromethane was dissolved 76.3 mg of lankacidin A 8-dibenzylphosphate. To the solution was added 33.0 μl of trimethylsilyl bromide under nitrogen atmosphere, and the mixture was stirred for 20 minutes, followed by concentration. The resultant was subjected to separation by the use of reversed phase TLC plates (manufactured by Merck, Art. No. 15424, 10×20 cm, developing solvent: methanol-water-tetrahydrofuran (10:10:1)) to obtain 36.9 mg of the above titled compound.

NMR (90 MHz, DMSO-d$_6$-CDCl$_3$-D$_2$O)δ:1.25 (d, 3H, J=6 Hz), 1.34 (s, 3H), 1.48 (s, 3H), 1.80 (s, 3H), 1.98 (s, 3H) 2.15~2.65 (m, 5H), 2.39 (s, 3H), 4.45~4.90 (m, 3H), 5.05~5.80 (m, 6H), 6.30 (d, 1H, J=15 Hz), 8.10 (br.d, 1H, J=10 Hz).

IR (KBr): 3400, 1735, 1715, 1695, 1245, 1015 cm$^{-1}$.

EXAMPLE 239

Preparation of Lankacidin A 8-formate

In 2.5 ml of N,N-dimethylforamamide was dissolved 251 mg of Lankacidin A. To the solution were added while stirring 89 mg of pyridine and 126 mg of methanesulfonyl chloride, successively. The mixture was stirred for 1.5 hour, to which was added ethyl acetate, followed by washing with an aqueous NaCl solution. The resultant was dried over $MgSO_4$, then the solvent was distilled off to give 294 mg of a yellow crystalle solid substance, which was recrystallized from chloroform-ether-hexane to obtain 152 mg of the above-titled compound as pale yellow crystals, m.p. 214°–215° C. (decomp.).

NMR (90 MHz, $CDCl_3$)δ: 1.31 (3H, d, J=6.5 Hz), 1.37 (3H, s), 1.56 (3H, s), 1.90 (3H, s), 2.01 (3H, s), 2.2~2.6 (5H, m), 4.41 (1H, m), 4.71 (1H, d, J=10 Hz), 5.17 (1H, m), 5.25~5.9 (6H, m), 6.29 (1H, J=15 Hz), 8.03 (1H, s), 8.08 (1H, d, J=10 Hz).

IR (KBr): 3410, 2930, 1720 (sh.), 1705, 1685, 1495, 1440, 1370, 1350, 1310, 1260, 1240 (sh.), 1230, 1170, 1135, 1015, 965, 940, 860, 810 $cm^{-1}$.

EXAMPLE 240

Preparation of Lankacidin A 8-chloromethyl carbonate

In 150 ml of dichloromethane was dissolved 13.0 g of Lankacidin A, to which were added dropwise under ice-cooling while stirring 7.1 g of chloromethyl chloroformate (containing about 15% dichloromethyl chloroformate) then 4.5 g of pyridine dissolved in dichloromethane (40 ml), followed by stirring for 30 minutes at room temperature. To the resultant was added 200 ml of chloroform, which was washed with water (100 ml×2), 0.1N HCl (100 ml), water (100 ml), dilute aqueous solution of sodium hydrogencarbonate (100 ml), and water (100 ml) in sequence. The resultant was dried on $MgSO_4$, then the solvent was distilled off. The residue was subjected to a column chromatography with 300 g of silica gel, followed by elution with chloroform-ethyl acetate (20:1, then 15:1). The eluate containing the above-titled compound was divided into three groups in order of elution. Each group was concentrated to obtain the above-titled compound as a foam.

To Fr. 3 obtained as above was added ether (ca. 70 ml), which was left standing, then crystals precipitated out. The crystals were collected by filtration and dried to obtain 609 mg of the above titled compound in a pure state, m.p. 195°–196° C. (decomp.).

NMR (90 MHz, $CDCL_3$)δ: 1.30 (3H, d, J=6.5 Hz), 1.37 (3H, s), 1.55 (3H, s), 1.90 (3H, s), 2.03 (3H, s), 2.2~2.65 (5H, m), 2.44 (3H, s), 4.40 (1H, m), 4.72 (1H, d, J=10 Hz), 4.95 (1H, m), 5.2~5.85 (8H, m), 6.27 (1H, d, J=14.5 Hz), 8.06 (1H, d, J=10 Hz).

IR (KBr): 3400, 1760, 1710, 1680, 1510, 1440, 1355, 1235, 1155, 1130, 1100, 1020, 940 $cm^{-1}$.

EXAMPLE 241

Preparation of Lankacidin A 8-methylthiomethylether

In 10 ml of 1,2-dichloroethane was dissolved 501 mg of Lankacidin A, to which were added 0.261 ml of di-iso-propylethylamine and 0.126 l ml of chloromethyl methylsulfide. The mixture was stirred for 19 hours under reflux. When cooled, to this was then added dichlorometane, followed by washing with an aqueous NaCl solution and drying on $MgSO_4$. The solvent was distilled off. The residue was subjected to a silica gel (100 g) column chromatography, eluting with ethyl acetate-chloroform (1:4). The eluate was fractionated by 15 g portions each. The fractions of 26th~37th were combined and concentrated to obtain 161.9 mg of the above titled compound as white crystals, m.p. 175°–177° C.

NMR (90 MHz, $CDCl_3$)δ: 1.31 (3H, d, J=7 Hz), 1.38 (3H, s), 1.54 (3H, s), 1.92 (3H, s), 2.02 (3H, s), 2.13 (3H, s), 2.2~2.6 (5H, m), 2.44 (3H, s), 4.11 (1H, m), 4.41 (1H, m), 4.50 and 4.72 (2H, ABq, J=12 Hz), 4.70 (1H, d, J=11 Hz), 5.25~5.9 (6H, m), 6.28 (1H, d, J~15 Hz), 8.09 (1H, d).

IR (KBr): 1720 (sh.), 1706 (sh.), 1686 (sh.), 1354, 1238, 1050, 954 $cm^{-1}$.

EXAMPLE 242

Preparation of Lankacidin A 8-iodomethyl carbonate

In 120 ml of acetonitrile was dissolved the crude Lankacidin A 8-chloromethyl carbonate (8.2 g of Fr. 1+5.5 g of Fr. 2). To the solution was added 11.2 g of sodium iodide. The mixture was stirred at 50°~60° C. for 3 hours, to which was added 1.5 l of ethyl acetate, followed by washing with 300 ml of water containing 19.3 g of $NA_2S_2O_3$, 200 ml of water and 200 ml of aqueous Nacl solution in sequence and drying over $MgSO_4$. The solvent was then distilled off, and the residue was subjected to a silica gel (320 g) column chromatography, eluting with chloroform-ethyl acetate (30:1, then 20:1). The fractions containing the above titled compound was concentrated to obtain 13.8 g of yellow foamy substance, to which was added ether (ca. 100 ml). The mixture was left standing, then crystals separated out, which were collected by filtration and dried to obtain 9.5 g of the above titled compound. This compound was found to contain about 5% of 8-chloromethyl carbonate and 8-dichloromethyl carbonate. In the subsequent working examples, this compound was used without further purification. Melting point: 147°–149° C. (decomp.)

NMR (90 MHz, $CDCl_3$)δ: 1.31 (3H, d, J=6.5 Hz), 1.37 (3H, s), 1.54 (3H, s), 1.90 (3H, s), 2.01 (3H, s), 2.2~2.65 (5H, m), 2.44 (3H, s), 4.41 (1H, m), 4.71 (1H, d, J=10 Hz), 4.96 (1H, m), 5.22~6.0 (6H, m), 5.91 (2H, s), 6.27 (1H, d, J=15 Hz), 8.06 (1H, d, J=9 Hz).

IR (KBr): 3400, 1760, 1680, 1510, 1360, 1280, 1235, 1220, 1160, 1135, 1070, 1020, 930 $cm^{-1}$.

EXAMPLE 243

Preparation of 8-dehydroxy-8-acetylaminolankacidin C (1) In a mixture of 100 ml of tetrahydrofuran and 50 ml of methanol was dissolved 3.6 g of 8-dehydroxy-8-azidolankacidin A. To the solution was added 120 mg of sodium borohydride at −20° C. while stirring, which was stirred for further 20 minutes. To the resultant was added 0.24 l ml of acetic acid, then the solvent was distilled off. The residue was dissolved in 400 ml of ethyl acetate, which was washed with water, a 5% aqueous solution of sodium hydrogen carbonate, a saturated aqueous soltuion of ammonium chloride and a saturated aqueous NaCl solution, followed by drying over $MgSO_4$. The solvent was then distilled off, and the residue was subjected to a silica gel (250 g) column chromatography, eluting with ethyl acetate-chloroform (1:4, then 1:1), to obtain 729 mg of 8-dehydroxy-8-azido-lankacidinol A [2'-(L)-isomer] and 1.29 g of 8-dehydroxy-8-azido-lankacidinol A [2'-(D)-isomer]. 2'-(L)-isomer:

NMR (90 MHz, CDCl₃)δ: 1.30 (3H, d, J=6 Hz), 1.38 (3H, d, J=6 Hz), 1.40 (3H, s), 1.50 (3H, s), 1.88 (3H, s), 2.03 (3H, s), 2.2~2.7 (5H, m), 4.0~4.7 (4H, m), 4.75 (1H, d, J=10.5 Hz), 5.2~6.0 (6H, m), 6.32 (1H, d, J=15 Hz), 7.65 (1H, d, J=10.5 Hz).

IR (KBr): 3380, 3250, 2930, 2940, 2100, 1730, 1705, 1640, 1520 cm⁻¹.

2'-(D)-isomer:

NMR (90 MHz, CDCl₃)δ: 1.30 (3H, d, J=6 Hz), 1.39 (3H, d, J=6 Hz), 1.40 (3H, s), 1.49 (3H, s), 1.87 (3H, s), 2.03 (3H, s), 2.2~2.8 (5H, m), 4.0~4.7 (4H, m), 4.76 (1H, d, J=10.5 Hz), 5.3~6.0 (6H, m), 6.32 (1H, d, J=15 Hz), 7.53 (1H, d, J=10.5 Hz).

IR (KBr): 3400, 2990, 2940, 2100, 1730, 1705, 1640, 1500 cm⁻¹.

(2) In 15 ml of N,N-dimethylformamide was dissolved 1.20 g of 8-dehydroxy-8-azido-lankacidinol A[2'-(D)-isomer]. To the solution were added 0.32 g of imidazole and 0.69 g of t-butyldimethylsilyl chloride, and the mixture was stirred for 14 hours, to which was added 200 ml of ethyl acetate, followed by washing with water, 1N HCl, water, 5% aqueous solution of sodium hydrogencarbonate, water and saturated aqueous NaCl solution, in sequence, and by drying over MgSO₄. The solvent was then distilled off, and the residue was subjected to a silica gel (260 g) column chromatography. Elution was conducted with ethyl acetate-chloroform (1:20) to give 1.22 g of 8-dehydroxy-8-azido-O(2')-t-butyldimethylsilyl-lankacidinol A[2'-(D)-isomer].

NMR (90 MHz, CDCl₃)δ: 1.00 (9H, s), 1.20~1.34 (6H, d,×3), 1.38 (3H, s), 1.90 (3H, s), 2.03 (3H, s), 2.2~2.8 (5H, m), 4.0~4.71 (3H, m), 4.78 (1H, d, J=10.5 Hz), 5.2~6.2 (6H, m), 6.29 and 6.33 (1H, each d, J=15 Hz), 7.75 (1H, d, J=9 Hz).

IR (KBr): 3400, 2930, 2850, 2100, 1730, 1710, 1670, 1490 cm⁻¹.

(3) In a mixture of 20 ml of acetone and 10 ml of acetic acid was dissolved 1.20 g of 8-dehydroxy-8-azido-O(2')-t-butyldimethylsilyl-lankacidinol A[2'-(D)-isomer]. To the solution was added 2.0 g of zinc powder, and the mixture was stirred for 20 minutes. The isolubles were filtered off, and the filtrate was concentrated. The concentrate was dissolved in 300 ml of a mixture of tetrahydrofuran-ethyl acetate (1:4), followed by washing with water, 5% aqueous solution of sodium hydrogencarbonate, water, saturated aqueous solution of ammonium chloride and saturated aqueous saline solution, in sequence. The resultant was then dried over MgSO₄, the the solvent was distilled off. The residue was subjected to a silica gel (90 g) column chromatography, eluting with methanol-chloroform (1:20) to obtain 492 mg of 8-dehydroxy-8-amino-O(2')-t-butyldimethylsilyl-lankacidinol A[2'-(D)-isomer].

NMR (90 MHz, CDCl₃)δ: 1.00 (9H, s), 1.29 (3H, d, J=7.5 Hz), 1.32 (3H, d, J=7.5 Hz), 1.38 (3H, s), 1.53 (3H, s), 1.88 (3H, s), 2.00 (3H, s), 2.1~3.0 (7H, m), 4.00 (1H, br.s), 4.25 (1H, q, J=6.8 Hz), 4.3~4.5 (1H, m), 4.75 (1H, d, J=9 Hz), 5.2~6.2 (6H, m), 6.33 (1H, d, J=15 Hz), 7.73 (1H, d, J=10.5 Hz).

IR (KBr): 3410, 2940, 2860, 1730, 1710, 1670, 1500 cm⁻¹.

(4) In 3 ml of pyridine was dissolved 470 mg of 8-dehydroxy-8-amino-O(2')-t-butyldimethylsilyl-lankacidinol A[2'-(D)-isomer]. To the solution was added 2 ml of acetic anhydride, and the mixture was stirred for one hour, which was then concentrated. The concentrate was dissolved in 200 ml of ethyl acetate, and the solution was washed with 1N HCl, water, 5% aqueous solution of sodium hydrogencarbonate, water and saturated aqueous saline solution in sequence, followed by drying over MgSO₄. The solvent was distilled off to obtain 429 mg of 8-dehydroxy-8-acetylamino-O(2')-t-butyldimethylsilyl-lankacidinol A[2'-(D)-isomer].

NMR (90 MHz, CDCl₃)δ: 1.00 (9H, s), 1.29 (3H, d, J=7.5 Hz), 1.32 (3H, d, J=7.5 Hz), 1.38 (3H, s), 1.53 (3H, s), 1.89 (3H, s), 2.03 (6H, s), 2.2~2.9 (5H, m), 4.23 (1H, q, J=6.8 Hz), 4.40 (1H, dt, J=3 and 12 Hz), 4.70 (1H, d, J=12 Hz), 4.7~5.0 (1H, m), 5.2~6.0 (7H, m), 6.28 (1H, d, J=15 Hz), 7.73 (1H, d, J=11 Hz).

IR (KBr): 3410, 2860, 1730, 1710, 1660, 1500 cm⁻¹.

(5) In 5 ml of tetrahydrofuran was dissolved 200 mg of 8-acetylamino-O(2')-t-butyldimethylsilyl-lankacidinol A[2'-(D)-isomer]. To the solution was added 5 ml of 2N HCl, and the mixture was stirred for 3 hours, to which was added 60 ml of ethyl acetate, followed by washing with water, 5% aqueous solution of sodium hydrogencarbonate, water and saturated aqueous NaCl solution, in sequence, then by drying over MgSO₄. The solvent was distilled off. The residue was subjected to a silica gel (28 g) column chromatography, eluting with methanol-chloroform (1:20, then 1:10) to obtain 56 mg of 8-dehydroxy-8-acetylamino-lankacidinol A [2'-(D)-isomer].

NMR (90 MHz, CDCl₃)δ: 1.27 (3H, d, J=6 Hz), 1.31 (3H, d, J=7 Hz), 1.40 (3H, s), 1.51 (3H, s), 1.83 (3H, s), 2.03 (6H, s), 2.2~2.7 (5H, m), 4.1~4.3 (1H, m), 4.40 (1H, dt, J=3 and 15 Hz), 4.65 (1H, d, J=12 Hz), 4.7~5.0 (1H, m), 5.3~6.2 (7H, m), 6.30 (1H, d, J=15 Hz), 7.61 (1H, d, J=7 Hz).

(6) In 0.5 ml of dimethyl sulfoxide was dissolved 56 mg of 8-dehydroxy-8-acetylamino-lankacidinol A[2'-(D)-isomer]. To the solution was added 0.5 ml of acetic anhydride, which was stirred for 30 hours. To the mixture was added 60 ml of ethyl acetate, followed by washing with water, 5% aqueous solution of sodium hydrogencarbonate, water and saturated aqueous saline solution, in sequence, then by drying on MgSO₄. The solvent was distilled off, and the residue was subjected to a silica gel (35 g) column chromatography, eluting with methanol-chloroform (1:20) to obtain 46 mg of 8-dehydroxy-8-acetylamino-lankacidin A.

NMR (90 MHz, CDCl₃)δ: 1.30 (3H, d, J=6 Hz), 1.38 (3H, s), 1.52 (3H, s), 1.88 (3H, s), 1.98 (3H, s), 2.01 (3H, s), 2.2~2.7 (5H, m), 2.45 (3H, s), 4.43 (1H, dt, J=3 and 12 Hz), 4.67 (1H, d, J=10.5 Hz), 4.7~5.0 (1H, m), 5.2~6.0 (7H, m), 6.31 (1H, d, J=15 Hz), 8.02 (1H, d, J=10.5 Hz).

IR (KBr): 3380, 2990, 2940, 1720 (sh.), 1710, 1660, 1510 cm⁻¹.

(7) In a mixture of 5 ml of tetrahydrofuran and 5 ml of methanol was dissolved 46 mg of 8-dehydroxy-8-acetylaminolankacidin A, to which added a solution of 1.0 g of the esterase prepared in Reference Example 11 in 10 ml of water, and the mixture as stirred for 2.5 hours. The resultant was extracted with 20 ml of chloroform. The organic layer was washed with saturated aqueous saline solution, followed by drying over MgSO₄. The solvent was distilled off, and the residue was subjected to a silica gel (30 g) column chromatography, eluting with methanol-chloroform (1:20) to obtain 27 g of the above titled compound.

NMR (90 MHz, CDCl₃)δ: 1.27 (3H, d, J=6 Hz), 1.38 (3H, s), 1.52 (3H, s), 1.90 (3H, s), 2.00 (3H, s), 2.2~2.6 (5H, m), 2.45 (3H, s), 4.1~4.6 (2H, m), 4.65 (1H, d,

J=10.5 Hz), 4.7~5.0 (1H, m), 5.2~6.0 (6H, m), 6.18 (1H, d, J=15 Hz), 8.05 (1H, d, J=10.5 Hz).

IR (KBr): 3380, 2980, 2925, 1715, 1700, 1670, 1510 cm$^{-1}$.

EXAMPLE 244

Preparation of 8-dehydroxy-8-p-toluenesulfonylamino-lankacidin C (1) In 6 ml dichloromethane was dissolved 180 mg of 8-dehydroxy-8-amino-O(2')-t-butyldimethylsilyl-lankacidinol A [2'-(D)-isomer], to which were added 36 mg of pyridine and 57 mg of p-toluenesulfonyl chloride, and the mixture was stirred for 18 hours. To the resultant was added 70 ml of ethyl acetate, which was washed with 5% aqueous solution of sodium hydorgencarbonate, water, 1N HCl and saturated aqueous saline solution, followed by drying over MgSO$_4$. The solvent was distilled off, and the residue was subjected to a silica gel (70 g) column chromatography. Elution was conducted with methanol-chloroform (1:20) to obtain 143 mg of 8-dehydroxy-8-p-toluenesulfonylamino-O(2')-t-butyldimethylsilyl-lankacidinol A[2'-(D)-isomer].

NMR (90 MHz, CDCl$_3$)δ: 1.00 (9H, s), 1.28 (3H, d, J=6 Hz), 1.33 (3H, s), 1.39 (3H, d, J=7 Hz), 1.46 (3H, s), 1.75 (3H, s), 2.01 (3H, s), 2.2~2.7 (5H, m), 2.40 (3H, s), 4.1~4.5 (3H, m), 4.69 (1H, d, J=10.5 Hz), 5.2~5.9 (7H, m), 6.32 (1H, d, J=15 Hz), 7.1~7.3 (2H, m), 7.6~7.8 (3H, m).

IR (KBr): 3420, 2940, 2850, 1740, 1710, 1680, 1500 cm$^{-1}$.

(2) Employing 8-dehydroxy-8-p-toluenesulfonylamino-O(2')-t-butyldimethylsilyl-lankacidinol A[2'-(D)-isomer], reactions were allowed to proceed in manners similar to those in Example 244 (5) et seq. to obtain the following compounds.

8-Dehydroxy-8-p-toluenesulfonylamino-lankacidinol A[2'-(D)-isomer]:

NMR (90 MHz, CDCl$_3$)δ: 1.30 (3H, d, J=6 Hz), 1.40 (3H, s), 1.42 (3H, d, J=7 Hz), 1.44 (3H, s), 1.78 (3H, s), 2.02 (3H, s), 2.2~2.7 (5H, m), 2.40 (3H, s), 4.1~4.4 (2H, m), 4.68 (1H, d, J=10.5 Hz), 5.2~5.6 (8H, m), 6.35 (1H, d, J=15 Hz), 7.2~7.5 (3H, m), 7.4~7.9 (2H, m).

IR (KBr): 3400, 2940, 1730 (sh.), 1625 cm$^{-1}$.

8-Dehydroxy-8-p-toluenesulfonylamino-lankacidin A:

NMR (90 MHz, CDCl$_3$)δ: 1.28 (3H, d, J=6 Hz), 1.33 (3H, s), 1.43 (3H, s), 1.70 (3H, s), 2.01 (3H, s), 2.40 (3H, s), 2.50 (3H, s), 4.37 (1H, dt, J=3 and 12 Hz), 4.65 (1H, d, J=10.5 Hz), 5.2~6.2 (8H, m), 6.83 (1H, d, J=15 Hz), 7.2~7.4 (2H, m), 7.6~8.1 (3H, m).

8-Dehydroxy-8-p-toluenesulfonylamino-lankacidin C:

NMR (90 MHz, CDCl$_3$)δ: 1.25 (3H, d, J=6 Hz), 1.33 (3H, s), 1.43 (3H, s), 1.71 (3H, s), 2.1~2.7 (5H, m), 2.40 (3H, s), 2.48 (3H, s), 4.1~4.6 (2H, m), 4.62 (1H, d, J=10.5 Hz), 5.1~6.0 (7H, m), 6.28 (1H, d, J=15 Hz), 7.2~7.4 (2H, m), 7.6~7.8 (2H, m), 7.95 (1H, d, J=10.5 Hz).

IR (KBr): 3400, 2910, 1740, 1705, 1680, 1500 cm$^{-1}$.

EXAMPLE 245

Preparation of lankacidin A 8-chloroacetate

In 250 ml of N,N-dimethylacetamide was dissolved 20 g of lankacidin A, to which was added dropwise while stirring 5 ml of chloroacetyl chloride. The mixture was stirred at room temperature for 2.5 hours, to which was added 1 l of ethyl acetate. The mixture was washed with water, 5% aqueous solution of sodium hydrogencarbonate, 1N HCl, water and saturated aqueous NaCl solution, in sequence, followed by drying over MgSO$_4$. The solvent was distilled off. To the residue was added 200 ml of isopropyl ether. The mixture was left standing, then crystals separated out. The crystals were collected by filtration, followed by drying to obtain 21.8 g of the above titled compound, m.p. 192°-198° C. (decomp.).

NMR (90 MHz, CDCl$_3$)δ: 1.30 (3H, d, J=6 Hz), 1.38 (3H, s), 1.56 (3H, s), 1.90 (3H, s), 2.02 (3H, s), 2.44 (3H, s), 2.2~2.7 (5H, m), 4.03 (2H, s), 4.42 (1H, dt, J=3 and 12 Hz), 4.72 (1H, d, J=10.5 Hz), 5.0~5.9 (7H, m), 6.28 (1H, d, J=15 Hz), 8.07 (1H, d, J=10.5 Hz).

IR (KBr): 3400, 2960, 2870, 1740, 1710, 1510 cm$^{-1}$.

EXAMPLE 246

Preparation of lankacidin A 8-phenyl carbonate

In 5 ml pyridine was dissolved 501 mg of lankacidin A. To the solution was added dropwise 0.188 ml of phenyl chloroformate under ice-cooling while stirring. The mixture was stirred at the same temperature for 5 minutes, then at room temperature for 75 minutes. To the resultant was added ice-water, which was subjected to extraction with ethyl acetate. The extract solution was washed with 1N HCl and aqueous saline solution in sequence, which was dried on MgSO$_4$, followed by distilling off the solvent. To the residue was added ether, whereupon crystallization occurred. To this was added ether - petroleum ether (1:1), then the crystals were collected by filtration, followed by drying to obtain 473.9 mg of the above titled compound, m.p. 220°-222° C. (decomp.).

NMR (90 MHz, CDCl$_3$)δ: 1.32 (3H, d, J=7 Hz), 1.40 (3H, s), 1.59 (3H, s), 1.95 (3H, s), 2.04 (3H, s), 2.2~2.8 (5H, m), 2.47 (3H, s), 4.43 (1H, m), 4.75 (1H, d, J=11 Hz), 5.03 (1H, m), 5.2~6.0 (6H, m), 6.32 (1H, d, J=15 Hz), 7.1~7.55 (5H, m), 8.10 (1H, d, J=10 Hz).

IR (KBr): 1740, 1706, 1684, 1354, 1240, 1208, 952 cm$^{-1}$.

In a manner similar to tht of this Example 246, the following compounds were obtained.

EXAMPLE 247

Lankacidinol A 8-methylcarbonate, m.p. 215°-216° C. (decomp.)

NMR (90 MHz, CDCl$_3$)δ: 1.32 (3H, d, J=7 Hz), 1.39 (3H, s), 1.56 (3H, s), 1.91 (3H, s), 2.04 (3H, s), 2.2~2.6 (5H, m), 3.78 (3H, s), 4.44 (1H, m), 4.74 (4H, d, J=11 Hz), 4.93 (1H, m), 5.2~5.9 (6H, m), 6.31 (1H, d, J=15 Hz), 8.09 (1H, d, J=10 Hz).

IR (KBr): 1740, 1706, 1684, 1500, 1440, 1356, 1260, 948 cm$^{-1}$.

EXAMPLE 248

Lankacidin A 8-pentachlorophenylcarbonate, m.p. 185°-187° C. (decomp.)

NMR (90 MHz, CDCl$_3$)δ: 1.31 (3H, d, J=7 Hz), 1.38 (3H, s), 1.59 (3H, s), 1.94 (3H, s), 2.03 (3H, s), 2.15~2.8 (5H, m), 2.46 (3H, s), 4.43 (1H, m), 4.75 (1H, d, J=11 Hz), 5.05 (1H, m), 5.2~5.95 (6H, m), 6.30 (1H, d, J=15 Hz), 8.10 (1H, d, J=10 Hz).

IR (KBr): 1780 (sh.), 1756, 1710, 1688, 1360, 1240 cm$^1$.

EXAMPLE 249

Preparation of lankacidin A 8-azidoacetate

In 10 ml of N, N-dimethylformamide was dissolved 200 mg of lankacidin A 8-iodoacetate. To the solution was added 40 mg of sodium azide, and the mixture as stirred at room temperature for one hour. To the resultant mixture was added 50 ml of ethyl acetate, followed by washing with water, 1N HCl, water and saturated aqueous saline solution, then dried on $MgSO_4$. The solvent was distilled off, and the residue was subjected to a silica gel (70 g) column chromatography, eluting with ethyl acetate - chloroform (1:20 then 1:10) to obtain 110 mg of the above titled compound, m.p. 186°–191° C. (decomp.).

NMR (90 MHz, $CDCl_3$)δ: 1.32 (3H, d, J=6 Hz), 1.40 (3H, s), 1.57 (3H, s), 1.92 (3H, s), 2.03 (3H, s), 2.1~2.7 (5H, m), 2.47 (3H, s), 3.87 (2H, s), 4.43 (1H, dt, J=3 and 12 Hz), 4.74 (1H, d, J=10.5 Hz), 5.0~5.9 (7H, m), 6.32 (1H, d, J=15 Hz), 8.10 (1H, d, J=10.5 Hz).

IR (KBr): 3400, 2100, 1735, 1710, 1685, 1500 $cm^{-1}$.

EXAMPLE 250

Preparation of 3-(2'-methoxyiminopropionamido)-lankone 14-acetate 8-iodoacetate In 20 ml of tetrahydrofuran was dissolved 500 mg of lankacidin A 8-iodoacetate. To the solution was added 190 mg of O-methyl-hydroxylamine hydrochloride and 320 mg of sodium carbonate, and the mixture was stirred at room temperature for 21 hours. To the resultant mixture was added 100 ml of ethyl acetate, which was washed with water, saturated aqueous solution of ammonium chloride, water and saturated aqueous saline solution, in sequence, followed by drying over $MgSO_4$. The solvent was distilled off, and the residue was subjected to a silica gel (70 g) column chromatography, eluting with hexane - ethyl acetate (2:1) to obtain 390 mg of the above titled compound, m.p. 138°–141° C.

NMR (90 MHz, $CDCl_3$)δ: 1.3 (3H, d, J=6 Hz), 1.41 (3H, s), 1.57 (3H, s), 1.90 (3H, s), 2.00 (3H, s), 2.03 (3H, s), 2.1~2.7 (5H, m), 3.68 (2H, s), 4.03 (3H, s), 4.40 (1H, dt, J=3 and 12 Hz), 4.76 (1H, d, J=10.5 Hz), 4.9~5.9 (7H, m), 6.30 (1H, d, J=15 Hz), 7.89 (1H, d, J=10.5 Hz).

IR (KBr): 3400, 2940, 1725, 1670, 1500 $cm^{-1}$.

EXAMPLE 251

Preparation of of lankacidin A 8-iodoacetate

In 300 ml of acetonitrile was dissolved 10 g of lankacidin A 8-chloroacetate. To the solution was added 10 g of sodium iodide, and the mixture was stirred at 55° C. for 18 hours. The acetonitrile was distilled off. To the residue was added 600 ml of ethyl acetate, which was washed with water, aqueous solution of sodium thiosulfate, water and saturated aqueous NaCl solution, in sequence, followed by drying on $MgSO_4$. The solvent was distilled of. To the residue was added 110 ml of ether, whereupon crystals precipitated out. The crystals were collected by filtration and dried to give 8.9 g of the above tiltled compound, m.p. 191°–197° C. (decomp.).

NMR (90 MHz, $CDCl_3$)δ: 1.30 (3H, d, J=6 Hz), 1.38 (3H, s), 1.57 (3H, s), 1.90 (3H, s), 2.03 (3H, s), 2.1~2.7 (5H, m), 2.46 (3H, s), 3.67 (2H, s), 4.40 (1H, dt, J=3 and 12 Hz), 4.71 (1H, d, J=10.5 Hz), 4.9~5.9 (7H, m), 6.28 (1H, d, J=15 Hz), 8.08 (1H, d, J=10.5 Hz).

IR (KBr): 3400, 2940, 1725, 1675, 1500 $cm^{-1}$.

EXAMPLE 252

Preparation of lankacidin A 8-N-phenylcarbamate

In 6 ml of dichloromethane was dissolved 300.6 mg of lankacidin A. To the solution were added 180 mg of zinc chloride and 0.131 mg of phenyl isocyanate. The mixture was stirred at room temperature for 19 hours. To the resultant mixture was added dichlromethane, and insolubles were removed by decantation. The liquid portion was concentrated and subjected to a silica gel (75 g) column chromatography, eluting with ethyl acetate - chloroform (1:10). The eluate was fractionated by 20 g each portion. The 34th ~the 43rd fractions were combined and concentrated to leave crystals, to which was added ether, then the crystals were collected by filtration, washed with ether and dried to obtain 121.1 mg of the above titled compound as white crystals, m.p. 231°14 232° C. (decomp.).

NMR (90 MHz, $CDCl_3$)δ: 1.31 (3H, d, J=7 Hz), 1.37 (3H, s), 1.55 (3H, s), 1.89 (3H, s), 2.02 (3H, s), 2.2~2.6 (5H, m), 2.44 (3H, s), 4.40 (1H, m), 4.70 (1H, d, J=11 Hz), 5.05 (1H, m), 5.25~5.9 (6H, m), 6.28 (1H, d, J=15 Hz), 6.73 (1H, br.s), 6.9~7.5 (5H, m), 8.05 (1H, d, J=10 Hz).

IR (KBr): 1724 (sh.), 1706, 1682, 1514, 1438, 1236 (sh.), 1220 $cm^{-1}$.

Employing lankacidin A as the starting material, reactions were conducted in a manner similar to that of Example 252 to obtain compounds shown in Table 1.

TABLE 1

8-position($R^3$) derivatives of Lankacidin A

| Example No. | $R^3$ | Yield (%) | m.p. (°C.) | NMR: 11-Me, $COCOCH_3$, 8-H, others | IR(carbonyl region) |
|---|---|---|---|---|---|
| 253 | MeNHCOO— | 29.9 | — | 1.53(s),2.44(s),4.98 (m),2.77(d,J=5Hz NHMe) | 1720(sh),1708, 1684(sh) |
| 254 | PrNHCOO— | 62.9 | — | 1.53(s),2.43(s),4.98 (m),0.89(t,J=7Hz, $CH_3CH_2CH_2$) | 1720(sh),1708, 1684(sh) |
| 255 | $EtOCOCH_2NHCOO$— | 20.7 | — | 1.53(s),2.43(s),4.98 (m),1.26(t,J=7Hz,$CH_3$ $CH_2$) | 1726,1706,1688 (sh) |
| 256 | $ClCH_2CH_2NHCOO$— | 26.5 | — | 1.54(s),2.44(s),5.00 (m)~3.55(4H,m,NH$CH_2$ $CH_2Cl$) | 1720,1700,1680 (sh) |
| 257 | BuBHCOO— | 77 | — | 1.53(s),2.44(s),4.98 (m),0.90(t,J=7Hz,$CH_3$ | 1720(sh),1706, 1685(sh) |

TABLE 1-continued 8-position($R^3$) derivatives of Lankacidin A

| Example No. | $R^3$ | Yield (%) | m.p. (°C.) | NMR: 11-Me, COCO$\underline{C}H_3$, 8-H, others | IR(carbonyl region) |
|---|---|---|---|---|---|
| 258 | tBuNHCOO— | 81.4 | — | (CH$_2$)$_3$)<br>1.53(s),2.45(s),4.93 (m),1.31(s,tBu) | 1720(sh),1708 1685(sh) |
| 259 | Cy—NHCOO— | 81.5 | — | 1.53(s),2.43(s),4.93 (m), ~3.4(br cyclohexylmethine | 1720(sh),1704, 1685(sh) |
| 260 | iPrNHCOO— | 99.4 | — | 1.56(s),2.43(s),4.95 (m),1.13(d,J=7Hz, Me$_2$) | 1720(sh),1704, 1680(sh) |
| 261 | EtNHCOO— | 74.8 | — | 1.54(s),2.46(s),4.98 (m),1.12(t,J=7Hz,C$\underline{H}_3$ CH$_2$) | 1720(sh),1708, 1686(sh), |

EXAMPLE 262

Preparation of O(8)-morpholinocarbonyl lankacidin A

In 6 ml of dichloromethane was dissolved 476.1 mg of lankacidin A 8-pentachlorophenyl carbonate. To the solution was added 0.104 ml of morpholine, and the mixture was stirred at room temperature for 2 hours. To the resultant mixture was added dichloromethane and the solution was washed with water then dried on MgSO$_4$. The solvent was distilled off, and the residue was subjected to a silica gel (100 g) column chromatography, eluting with ethyl acetate - chloroform (1:4) then with ethyl acetate - chloroform (1:1). The eluate was concentrated. To the concentrate was added a small volume of ether to cause crystallization, to which was added ether - petroleum ether (1:1), followed by collecting the crystals and drying to obtain 313.0 mg of the above titled compound as white crystals, m.p. 223°–225° C. (decomp.).

NMR (90 MHz, CDCl$_3$)δ: 1.31 (3H, d, J=7 Hz), 1.38 (3H, s), 1.56 (3H, s), 1.91 (3H, s), 2.03 (3H, s), 2.2~2.7 (5H, m), 2.46 (3H, s), ~3.6 (8H, m), 4.43 (1H, m), 4.71 (1H, d, J=11 Hz), 5.02 (1H, m), 5.25~5.9 (6H, m), 6.32 (1H, d, J=15 Hz), 8.07 (1H, d, J=10 Hz).

IR (KBr): 1750 (sh.), 1730 (sh.), 1710, 1695, 1426, 1360, 1238, 1132, 954 cm$^{-1}$.

Employing lankacidin A 8-pentachlorophenyl carbonate as the starting material, reactions were conducted in a manner similar to that of Example 262 to obtain compounds shown in Table 2.

TABLE 2

8-position($R^3$) derivatives of Lankacidin A

| Example No. | $R^3$ | Yield (%) | m.p. (°C.) | NMR: 11-Me, COCO$\underline{C}H_3$, 8-H, others | IR(carbonyl region) |
|---|---|---|---|---|---|
| 263 | H-Pipe-COO— | 53.7 | — | 1.56(s), 2.46(s), 5.01 (m), ~2.3(br, piperadine-NH) | 1750(sh) |
| 264 | Me$_2$N(CH$_2$)$_2$NHCOO— | 47.4 | 179–181 (dec) | 1.54(s), 2.45(s), 4.97 (m),2.27(s,NMe$_2$) | 1750,(sh),1722 (s),1708,1688 (sh) |
| 265 | 2-Py-Pipe-COO— | 76.1 | 212–213 (dec) | 1.56(s),2.44(s),5.03 (m),6.63,7.50,8.18 (each m,Py) | 1750,(sh),1728 (sh),1705,1690 (sh) |
| 266 | NH$_2$COO— | 58.5 | 216–218 (dec) | 1.54(s),2.45(s),4.97 (m)4.77(s,CONH$_2$) | 1724(sh),1710, 1682(sh) |
| 267 | MePipe-(CH$_2$)$_2$NHCOO— | 57.9 | 149–151 | 1.53(s),2.43(s),4.97 (m),2.26(s,N-Me) | 1720(sh),1706, 1682(sh) |
| 268 | Me$_2$N(CH$_2$)$_2$-Pipe-COO— | 70.0 | — | 1.54(s),2.43(s),5.00 (m),2.29(s,NMe$_2$) | 1720(sh),1702 1686(sh) |
| 269 | 3-Py-CH$_2$NHCOO— | 66.1 | — | 1.55(s),2.46(s),5.01 (m) | 1720(sh),1706, 1688(sh) |
| 270 | Me-Pipe-COO— | 59.1 | 210–212 (dec) | 1.56(s),2.46(s),5.01 (m),2.30(s,N-Me) | 1700(sh),1688 |
| 271 | HO(CH$_2$)$_2$-Pipe-COO— | 77.5 | 173–175 (dec) | 1.55(s),2.45(s),4.99 (m),3.62(t,J = 6Hz,CH C$\underline{H}_2$OH) | 1726,1706, 1688(sh) |
| 272 | 3-Py(CH$_2$)$_2$NHCOO— | 70.4 | 142–144 | 1.52(s),2.44(s),4.95 (m),3.57(dt,J = 6 & 6 Hz,NHC$\underline{H}_2$CH$_2$) | 1722(sh),1708, 1688(sh) |
| 273 | 2-Py-CH$_2$NHCOO— | 53.8 | 192–194 | 1.53(s),2.44(s),5.01 (m),4.47(d,J = 5Hz, NHC$\underline{H}_2$) | 1720(sh),1708 1688(sh) |
| 274 | 4-Py-CH$_2$NHCOO— | 68.4 | 222–224 (dec) | 1.53(s),2.45(s),5.01 (m),4.36(d,J = 6Hz, NHC$\underline{H}_2$) | 1706,1690(sh) |
| 275 | Piri-4-Piri-COO— | 70.3 | 201–203 (dec) | 1.54(s),2.44(s),4.98 (m),0.8–2.1,2.5–3.38~ 4.2(m,piperidine-H) | 1720(sh),1700 (sh),1682 |
| 276 | PhCH$_2$-Pipe-COO— | 67.9 | 215–217 (dec) | 1.54(s),2.45(s),4.99 (m),3.50(s,C$\underline{H}_2$Ph) | 1720(sh),1700, (sh),1688 |
| 277 | 4-Py-Pipe-COO— | 46.8 | 175–177 | 1.54(s),2.43(s),5.01 (m),6.55–6.75 & 8.15– 8.45(Py-H) | 1740(sh),1705, 1685 |
| 278 | Mor-COCH$_2$-Pipe-COO— | 84.7 | 183–185 | 1.55(s),2.45(s),4.99 | 1728(sh),1708 |

TABLE 2-continued

| | 8-position($R^3$) derivatives of Lankacidin A | | | | |
|---|---|---|---|---|---|
| Example No. | $R^3$ | Yield (%) | m.p. (°C.) | NMR: 11-Me, COCOC$\underline{H}_3$, 8-H, others | IR(carbonyl region) |
| 279 | Pyr-COCH$_2$Pipe-COO— | 85.3 | 217–219 (dec) | (m),31.8(s,NCH$_2$CO) 1.55(s),2.45(s),5.00 (m),3.12(s,NCH$_2$CO) | (sh),1686,1640 1726,1708(sh), 1688,1640 |
| 280 | iPrNHCOCH$_2$Pipe-COO— | 72.4 | — | 1.54(s),2.45(s),4.99 (m),2.97(s,NCH$_2$CO) | 1724(sh),1702 (sh),1682 |
| 281 | 3-Py-NH(CH$_2$)$_2$NHCOO— | 32.6 | 134–136 | 1.53(s),2.45(s),4.97 (m),3.43(br,s,NC$\underline{H}_2$ C$\underline{H}_2$N) | 1720(sh),1705, 1685 |
| 282 | 2-PyCH$_2$-Pipe-COO— | 54.4 | 195–197 (dec) | 1.53(s),2.45(s),4.98 (m),3.65(s,Py-CH$_2$) | 1745(sh),1725 (sh),1705(sh), 1685 |

EXAMPLE 283

Preparation of lankacidin A 8-(1-methyl-1H-tetrazol-5-yl)thioacetate

In 2 ml of N,N-dimethylformamide was dissolved 200 mg of 1-methyl-1H-tetrazol-5-thiol. To the solution was added 24 mg of sodium hydride (60%), which was stirred at room temperature for 10 minutes. To the mixture was added dropwise 500 mg of lankacidin A 8-chloroacetate dissolved in 2 ml of N,N-dimethylformamide, taking 5 minutes. The mixture was stirred for forther 30 minutes. To the resultant mixture was added 50 ml of ethyl acetate, and the mixture was washed with water, 1N HCl, water and saturated aqueous saline solution, in sequence, followed by drying over MgSO$_4$. The solvent was distilled off, and the residue was subjected to a silica gel (60 g) column chromatography, eluting with ethyl acetate - chloroform (1:4 then 1:2) to obtain 560 mg of the above titled compound, m.p. 131°–139° C.

NMR (90 MHz, CDCl$_3$)δ: 1.31 (3H, d, J=6 Hz), 1.40 (3H, s), 1.57 (3H, s), 1.92 (3H, s), 2.03 (3H, s), 2.2~2.7 (5H, m), 2.47 (3H, s), 3.97 (3H, s), 4.13 (2H, s), 4.43 (1H, dt, J=3 and 12 Hz), 4.72 (1H, d, J=10.5 Hz), 4.9~5.9 (7H, m), 6.28 (1H, d, J=15 Hz), 8.08 (1H, d, J=10.5 Hz).

IR (KBr): 3400, 2990, 2940, 1730, 1710, 1685, 1500 cm$^{-1}$.

Employing lankacidin A 8-chloroacetate as the starting material, reactions were conducted in a manner similar to that of Example 283 to obtain compounds shown in Table 3.

TABLE 3

| | 8-position($R^3$) derivatives of Lankacidin A | | | | |
|---|---|---|---|---|---|
| Example No. | $R^3$ | Yield (%) | m.p. (°C.) | NMR: 11-Me, COCOC$\underline{H}_3$, 8-H, others | IR(carbonyl region) |
| 284 | TeEn-SCH$_2$COO— | 78 | — | 1.53(s),5.06(m),4.10 (s,SCH$_2$CO) | 1740,1715, 1690 |
| 285 | TeEo-SCH$_2$COO— | 66 | — | 1.53(s),2.45(s),5.06 (m),4.13(s,SCH$_2$CO) | 1735,1710 |
| 286 | ThMe-SCH$_2$COO— | 59 | — | 1.53(s),2.47(s),5.13 (m),4.13(s,SCH$_2$CO) | 1730,1710,1690 |
| 287 | ThPe-SCH$_2$COO— | 74 | — | 1.56(s),2.47(s),5.11 (m),4.08(s,SCH$_2$CO) | 1725,1705,1680 |
| 288 | Me$_2$(CH$_2$)$_2$SCH$_2$COO— | 52 | — | 1.55(s),2.44(s),5.10 (m),3.23(s,SCH$_2$CO) | 1730,1715, 1690 |
| 289 | Et$_2$N(CH$_2$)$_2$SCH$_2$COO— | 28 | — | 1.57(s),2.48(s),5.10 (m),3.27(s,SCH$_2$CO) | 1730,1710, 1685 |

EXAMPLE 290

Preparation of lankacidin A 8-diethylaminoacetate

In 30 ml of tetrahydrofuran was dissolved 1.0 g of lankacidin A 8-iodoacetate. To the solution was added 0.5 ml of diethylamine, and the mixture was stirred for 1.5 hour, to which was added 200 ml of ethyl acetate, followed by washing with water and saturated aqueous saline solution in sequence, then by drying over MgSO$_4$. The solvent was distilled off, and the residue was subjected to a silica gel (75 g) column chromatography. Elution was conducted with ethyl acetate - chloroform (1:1) to obtain 800 mg of the above titled compound, m.p. 183° C.

NMR (90 MHz, CDCl$_3$)δ: 1.02 (6H, t, J=7 Hz), 1.30 (3H, d, J=6 Hz), 1.35 (3H, s), 1.88 (3H, s), 2.00 (3H, s), 2.1~2.7 (5H, m), 2.43 (3H, s), 2.63 (4H, q, J=7 Hz), 3.30 (2H, s), 4.40 (1H, dt, J=3 and 12 Hz), 4.69 (1H, d, J=10.5 Hz), 5.0~5.9 (7H, m), 6.28 (1H, d, J=15 Hz), 8.07 (1H, d, J=10.5 Hz).

IR (KBr): 3400, 2975, 2940, 1730, 1710, 1685, 1505 cm$^{-1}$.

Employing lankacidin A 8-iodoacetate as the starting material, reactions were conducted in a manner similar to that of Example 290 to obtain compounds shown in Table 4.

TABLE 4

| | 8-position($R^3$) derivatives of Lankacidin A | | | | |
|---|---|---|---|---|---|
| Example No. | $R^3$ | Yield (%) | m.p. (°C.) | NMR: 11-Me, COCOC$\underline{H}_3$, 8-H, others | IR(carbonyl region) |
| 291 | Me$_2$NCH$_2$COO— | 82 | 191–193 (dec) | 1.53(s),2.42(s),5.15 (m),3.15(br.s,NCH$_2$CO) | 1730,1710,1605 |

TABLE 4-continued

8-position(R³) derivatives of Lankacidin A

| Example No. | R³ | Yield (%) | m.p. (°C.) | NMR: 11-Me, COCOCH₃, 8-H, others | IR(carbonyl region) |
|---|---|---|---|---|---|
| 292 | Me-Pipe-CH₂COO— | 70 | — | 1.53(s),2.28(s),5.12 (m),3.19(br.s,NCH₂CO) | 1730,1710,1685 |
| 293 | 2-Py-Pipe-CH₂COO— | 83 | — | 1.56(s),2.45(s),5.13 (m),3.27(s,NCH₂CO) | 1720,1710,1685 |
| 294 | Cl(CH₂)₂NHCH₂COO— | 22 | — | 1.54(s),2.43(s),5.12 (m),3.43(s,NCH₂CO) | 1735(sh),1710, 1685 |
| 295 | F(CH₂)₂NHCH₂COO— | 60 | — | 1.55(s),2.45(s),5.12 (m),3.45(br.s,NCH₂CO) | 1730,1710,1605 |
| 296 | PrNHCH₂COO— | 62 | — | 1.50(s),2.47(s),5.13 (m),3.40(br.s,NCH₂CO) | 1710,1690 |
| 297 | iPr₂NCH₂COO— | 39 | — | 1.55(s),2.45(s),5.10 (m),3.23(s,NCH₂CO) | 1710,1690 |
| 298 | HO(CH₂)₂NHCH₂COO— | 40 | — | 1.55(s),2.45(s),5.12 (m),3.42(br.s,NCH₂CO) | 1705,1690(sh) |
| 299 | iPrNHCH₂COO— | 76 | — | 1.56(s),2.45(s),5.13 (m),3.40(s,NCH₂CO) | 1730,1710,1685, 1600 |
| 300 | Mor-CH₂COO— | 48 | — | 1.55(s),2.43(s),5.12 (m),3.18(s,NCH₂CO) | 1710,1680 |
| 301 | MeNH(CH₂)₃NHCH₂COO— | 17 | — | 1.55(s),2.45(br.s), 2.9–3.7(m,NCH₂CO) | 1730,1710,1680 |
| 302 | M-Py-Pipe-CH₂COO— | 21 | — | 1.54(s),2.44(s),5.14 (m),3.27(br.s,NCH₂CO) | 1730,1710,1600 |

EXAMPLE 303

Preparation of 8-dehydroxy-8-[[1-(2-hydroxyethyl)-1H-tetrazol-5-yl]thio]lankacidin A In 4 ml of N,N-dimethylformaide were dissolved 100 mg of 8-dehydroxy-8-iodolankacidin and 70.0 mg of 1-(2-hydroxyethyl)-1H-tetrazole-5-thiol. To the solution was added 16.0 mg of sodium hydride, and the mixture was stirred for 5 hours, to which was added ice-water, followed by extraction with ethyl acetate. The organic layer was dried over MgSO₄. The solvent was distilled off, and the residue was purified by means of a silica gel column chromatography to obtain 79.8 mg of the above titled compound (an isomer of low polarity: presumed as 8-β compound) and 6.1 mg of the above titled compound (an isomer of high polarity: presumed as 8-α compound).

8-β compound:
NMR (90 MHz, CDCl₃)δ: 1.33(3H, d, J=6.5 Hz), 1.39(3H, s), 1.53(3H, s), 1.89(3H, s), 2.02 (3H, s), 2.2~2.8(5H, m), 2.44(3H, s), 4.0~4.2(2H, m), 4.36(2H, t, J=5 Hz), 4.43(1H, m), 4.72(1H, d, J=11 Hz), 4.9~5.05(1H, m), 5.3~5.9(6H, m), 6.35 (1H, d, J=15 Hz), 8.06(1H, d, J=10 Hz).

IR (KBr): 3480, 2430, 1725, 1705, 1680, 1510, 1490, 1450, 1380, 1355, 1235, 1135, 1055, 1010, 950, 740 cm⁻¹.

8-α compound:
NMR (90 MHz, CDCl₃)δ: 1.30(3H, d, J=6.5 Hz), 1.37(3H, s), 1.55(3H, s), 1.85(3H, s), 2.02 (3H, s), 2.2~2.8(5H, m), 2.44(3H, s), 3.95~4.2(3H, m), 4.3~4.55(3H, m), 4.73(1H, d, J=11 Hz), 5.25~5.9(6H, m), 6.29(1H, d, J=14 Hz), 8.06(1H, d, J=9 Hz).

Employing 8-dehydroxy-8-iodolankacidin A as the starting compound, reactions were conducted in a manner similar to that of Example 303 to obtain compounds shown in Table 5.

TABLE 5

8-position(R³) derivatives of Lankacidin A

| Example No. | R³ | | Yield (%) | m.p. (°C.) | NMR: 11-Me, COCOCH₃, 8-H, others | IR(carbonyl region) |
|---|---|---|---|---|---|---|
| 304 | ThMe—S— | | 34.5 | — | 1.51(s),2.42(s),~ 4.9(m),3.40(s,OMe) | 1725,1705,1680 |
| 305A | ThSm—S— | (β form) | 28.5 | — | 1.53(s),2.48(s),4.89 (m),2.94(s,SO₂Me) | 1720,1705,1680 |
| 305B | ThSm—S— | (α form) | 4.1 | — | 1.60(s),2.45(s),4.0 ~4.15(m),2.94(s, SO₂Me) | 1730,1710,1685 |
| 306 | ThOh—S— | | 6.5 | — | 1.54(s),2.44(s),4.7 ~4.9(m),3.88(s, CH₂CO) | 1730,1710,1690 (sh),1610 |
| 307 | ThPe—S— | | 41.4 | — | 1.53(s),2.43(s),4.80 (m),1.32(t,J=7.5Hz, CH₂CH₃) | 1730,1710,1690 |

EXAMPLE 308

Preparation of lankacidin A 8-[(2-dimethylaminoethyl)thio]methyl carbonate and lankacidin A 8-[S-(2-dimethylaminoethyl)]thiocarbonate To 22 ml of methanol was added 178 mg of sodium hydride (60%). To the solution was added, after an exothermic reaction and foaming finished, 316 mg of 2-dimethylaminoethane thiol. hydrochloride, then the mixture was stirred for 10 minutes. To the resultant mixture was added 1.46 g of lankacidin A 8-iodomethyl carbonate obtained in Example 242, and the mixture was stirred for further one hour. To the resultant was added 500 ml of ethyl acetate, which was washed with aqueous saline solution (100 ml×3), followed by drying on MgSO₄. The solvent was distilled off, and the residue was subjected to a silica gel (300 g) column chromatography. Elution was conducted with methanol-ethyl acetate (1:20) to obtain 698.5 mg of the above titled compound (methyl carbonate compound) and 83.4 mg of the above titled compound (thiocarbonate compound). Methyl carbonate compound, m.p. 99°–101° C. (decomp.):

NMR (90 MHz, CDCl$_3$)δ: 1.31(3H, d, J=6.5 Hz), 1.37(3H, s), 1.55(3H, s), 1.90(3H, s), 2.02 (2H, s), 2.2~2.65(7H, m), 2.26(6H, s), 2.45(3H, s), 2.75~2.9(2H, m), 4.40(1H, m), 4.72(1H, d, J=11 Hz), 4.93(1H, m), 5.21(2H, s), 5.2~5.85(6H, m), 6.29(1H, d, J=15 Hz), 8.07(1H, d, J=10 Hz).

IR (KBr): 3380, 2940, 1740, 1705, 1685, 1500, 1450, 1355, 1330, 1230, 1135, 1010, 960, 925 cm$^{-1}$.

Thiocarbonate compound, m.p. 190°–191° C. (decomp.):

NMR (90 MHz, CDCl$_3$)δ: 1.31(3H, d, J=6.5 Hz), 1.38(3H, s), 1.55(3H, s), 1.90(3H, s), 2.03 (3H, s), 2.27(6H, s), 2.2~2.65(7H, m), 2.45(3H, s), 2.9~3.05(2H, m), 4.40(1H, m), 4.70(1H, d, J=11 Hz), 5.13(1H, m), 5.2~5.85(6H, m), 6.28(1H, d, J=15 Hz), 8.06(1H, d, J=10 Hz).

IR (KBr): 3390, 2935, 1725, 1705, 1685, 1500, 1450, 1355, 1235, 1135, 1010, 940 cm$^{-1}$.

Employing lankacidin A 8-iodomethyl carbonate as the starting compound, reactions were conducted in a manner similar to that of Example 308 to obtain compound shown in Table 6.

62.3 mg of the above titled compound as an oily product.

NMR (90 MHz, CDCl$_3$)δ: 1.30(3H, d, J=7 Hz), 1.36(3H, s), 1.53(3H, s), 1.88(3H, s), 2.00(3H, s), 2.15~2.6(5H, m), 2.27(6H, s), 2.43(3H, s), 2.80(2H, t, J=6 Hz), ~3.45(4H, m), 4.32(2H, t, J=6 Hz), ~4.4(1H, m), 4.70(1H, d, J=11 Hz), 4.93(1H, m), 5.2~5.9(7H, m), 6.28(1H, d, J=15 Hz)8.04(1H, d, J=10 Hz).

IR (KBr): 1724(sh.), 1710, 1686(sh.), 1500, 1356, 1242, 1136 cm$^{-1}$.

EXAMPLE 317

Preparation of lankacidin A
8-(3,4-dihydro-2H-pyran-2-carbonyloxy)methyl carbonate In 5 ml of N,N-dimethylacetamide was suspended 97.5 mg of sodium 3,4-dihydro-2H-pyran-2-carboxylate. To the suspension was added 342.5 mg of lankacidin A 8-iodomethyl carbonate, which was stirred for one hour. To the mixture was added 200 ml of ethyl acetate, followed by washing with an aqueous saline solution (50 ml×4) then by drying over MgSO$_4$. The solvent was distilled off, and the residue was subjected to a silica gel (180 g) column chromatography, eluting with ethyl acetate-chloroform (1:10) to obtain 305.8 mg of the above titled compound.

NMR (90 MHz, CDCl$_3$)δ: 1.31(3H, d, J=6.5 Hz), 1.40(3H, s), 1.56(3H, s), 1.92(3H, s), 2.04 (7H, br.s),

TABLE 6

| | 8-position (R$^3$) derivatives of Lankacidin A | | | | |
|---|---|---|---|---|---|
| Example No. | R$^3$ | Yield (%) | m.p. (°C.) | NMR: 11-Me,COCOCH$_3$, 8-H,others | IR (carbonyl region) |
| 309 | TeEn-SCH$_2$OCOO— | 85.5 | — | 1.54(s),2.44(s), 4.92(m),5.77(s, OCH$_2$S) | 1750,1710,1680 |
| 310 | TeM-S—CH$_2$OCOO— | 85.9 | 212–213 (dec) | 1.54(s),2.44(s),4.96 (m),5.81(s,OCH$_2$S) | 1765,1725,1710 1690 |
| 311A | ThMe—SCH$_2$OCOO— | 63.8 | — | 1.54(s),2.44(s),4.95 (m),5.77(s,OCH$_2$S) | 1750,1730(sh), 1705,1680 |
| 311B | ThMe—SCOO— | 10.8 | — | 1.56(s),2.46(s),5.19 (m),3.47(s,OMe) | 1730,1710,1685 |
| 312 | Ph-SCH$_2$OCOO— | 84.4 | — | 1.54(s),2.44(s),4.93 (m),5.43(s,OCH$_2$S) | 1740,1705,1680 |
| 313 | Et-SCH$_2$OCOO— | 75.2 | — | 1.54(s),2.44(s), 4.94(m),5.20(s, OCH$_2$S) | 1740,1710,1685 |
| 314A | AcNH(CH$_2$)$_2$SCH$_2$OCOO— | 87.7 | — | 1.55(s),2.46(s),4.94 (m),5.22(s,OCH$_2$S) | 1735,1710,1680, |
| 314B | AcNH(CH$_2$)$_2$SCOO— | — | 161–163 | 1.56(s),2.47(s),5.13 (m), | 1730(sh),1710, 1680 |

EXAMPLE 315

Preparation of lankacidin A
8-N-[2-[[1-(2-dimethylaminoethyl)-1H-tetrazol-5-yl]thio]ethyl]carbamate In 2 ml of N,N-dimethylformamide was dissolved 121.3 mg of lankacidin A 8-N-(chloroethyl)carbamate. To the solution were added 34.6 mg of 1-(2-dimethylaminoethyl)-1H-tetrazol-5-thiol, 33.2 mg of potassium iodide and 0.0162 ml of pyridine. The mixture was stirred at 60° C. for one hour, at 80° C. for one hour and at 100° C. for 3 hours. The solvent was distilled off under reduced pressure. To the residue was added chloroform (small volume) and ethyl acetate, which washed with and aqueous NaCl solution, followed by drying on MgSO$_4$. The solvent was distilled off, and the residue was subjected to a silica gel (25 g) column chromatography, eluting with ethanol-ethyl acetate (1:10) to obtain 2.2~2.65(5H, m), 2.47(3H, s), 4.43(1H, m), 4.5~4.65(1H, m), 4.72(1H, d, J=11 Hz), 4.7~4.85(1H, m), 4.95(1H, m), 5.25~5.9(6H, m), 5.84 (2H, s), 6.30(1H, d, J=15 Hz), 6.42(1H, d, J=6 Hz), 8.11(1H, d, J=10 Hz).

IR (KBr): 1750, 1730(sh.), 1710, 1685, 1500, 1360, 1240, 1150, 1070, 1010, 940 cm$^{-1}$.

EXAMPLE 319

Preparation of lankacidin A
8-(4-dimethylamino)butyrate

In 30 ml of dichloromethane was dissolved 500 mg of lankacidin A. To the solution were added 481.3 mg of 4-(dimethylamino)butyrate.hydrochloride, 353.5 mg of triethylamine, 1.09 g of dicyclohexyl carbodiimide and 318 mg of zinc chloride, and the mixture was stirred for 1.5 hour. To the mixture were further added 160 mg of 4-(dimethylamino)butyrate.hydrochloride, 117 mg of triethylamine, 363 mg of dicyclohexylcarbodiimide and 106 mg of zinc chloride. The resultant mixture was stirred for further one hour, subjected to filtration. The solid portion was washed with 100 ml of chloroform. The filtrate and the washing were combined and washed with water (100 ml×3), followed by drying over MgSO$_4$. The solvent was distilled off, and the residue was subjected to a silica gel (180 g) column chromatography, eluting with methanol-chloroform (1:25 then 1:8) to obtain 251.7 mg of the above titled compound as a white powdery product.

NMR (90 MHz, CDCl$_3$)δ: 1.30(3H, d, J=7 Hz), 1.37(3H, s), 1.54(3H, s), 1.90(3H, s), 1.7~1.95(2H, m), 2.02(3H, s), 2.24(6H, s), 2.2~2.55 (9H, m), 2.44(3H, s), 4.40(1H, m), 4.70(1H, d, J=11 Hz), 5.07(1H, m), 5.25~5.9(6H, m), 6.29(1H, d, J=15 Hz), 8.07(1H, d, J=10 Hz).

IR (KBr): 3400, 2940, 1725, 1710, 1690, 1500, 1360, 1230, 1160, 1135, 1015, 960 cm$^{-1}$.

EXAMPLE 322

Preparation of lankacidin A 8-N-(3-carboxypropyl)carbamate

To 37.5 ml of methanol was added 72 mg of sodium hydride (60%). To the mixture were added, after foaming and exothermic reaction finished, 201 mg of 4-aminobutyric acid and 342 mg of lankacidin A 8-iodomethyl carbonate, followed by stirring for 1.5 hour. The resultant was concentrated, to which was added 100 ml of chloroform. The mixture was washed with dilute phosphoric acid and water in sequence, followed by drying over MgSO$_4$. The solvent was distilled off, and the residue was subjected to a silica gel (100 g) column chromatography, eluting with methanol-chloroform (1:20 then 1:10) to obtain 231 mg of the above titled compound, m.p. 179°-181° C. (decomp.).

NMR (90 MHz, CDCl$_3$)δ: 1.30(3H, d, J=6.5 Hz), 1.37(3H, s), 1.53(3H, s), 1.89(3H, s), 1.85~2.1(2H, m), 2.02(3H, s), 2.2~2.6(7H, m), 2.45 (1H, s), 3.23(2H, dd, J=6.5 and 6.5 Hz), 4.41(1H, m), 4.69(1H, d, J=11 Hz), 4.8~5.2(2H, m), 5.3~5.9(6H, m), 6.28(1H, d, J=15 Hz), 8.07(1H, d, J=10 Hz).

IR (KBr): 3380, 2940, 1730(sh.), 1710, 1690(sh.), 1510, 1360, 1230, 1160, 1135, 1010, 960 cm$^{-1}$.

A reaction similar to that in Example 315 gave the compound of Example 316, a reaction similar to that in Example 317 gave the compound of Example 318, a reaction similar to that in Example 319 gave the compound of Example 320 and the compound of Example 321, and a reaction similar to that in Example 322 gave the compound of Example 323, as shown in Table 7, respectively.

TABLE 7

8-position (R$^3$) derivatives of Lankacidin A

| Example No. | R$^3$ | Yield (%) | m.p. (°C.) | NMR: 11-Me,COCOCH$_3$, 8-H,others | IR (carbonyl region) |
|---|---|---|---|---|---|
| 316 | TePn-S(CH$_2$)$_2$NHCOO— | 35.6 | — | 1.53(s),2.43(s),4.96 (m),2.23(s,NMe$_2$) | 1720(sh),1706, 1684(sh) |
| 318 | AcNHCH$_2$COOCH$_2$OCOO— | 52.0 | 190-192 (dec) | 1.55(s),2.45(s),4.95 (m),5.79(s,OCH$_2$O) | 1750,1730,1710, 1690 |
| 320 | AcMeNCH$_2$COO— | 22.7 | 192-195 (dec) | 1.53(s),2.43(s),5.08 (m),2.10(s,NAc) | 1740,1705,1680 1650 |
| 321 | Me$_2$N(CH$_2$)$_2$COO— | 55.9 | 177-179 (dec) | 1.55(s),2.44(s),5.08 (m),2.23(s,NMe$_2$) | 1730,1715,1690, |
| 323 | L—Ala—COO— | 33.9 | 168-171 (dec) | 1.54(s),2.46(s),4.98 (m),1.44(d,J=7Hz, CHCH$_3$) | 1725(sh),1710, 1690(sh) |

EXAMPLE 324

Preparation of lankacidin C 8-N-methyl carbamate

In a mixture of 24.3 ml of tetrahydrofuran and 24.3 ml of methanol was dissolved 135.5 mg of lankacidin A 8-N-methyl carbamate, to which was added a solution of 2.2 g of the esterase prepared in Reference Example 11 in 48.6 ml of water. The whole mixture was stirred for one hour, and then subjected to extraction with 47.2 ml of chloroform. The organic layer was washed with an aqueous NaCl solution and dried over MgSO$_4$. The solvent was distilled off. The residue was subjected to a silica gel (25 g) column chromatography, eluting with ethyl acetate. The eluate was fractionated by 5 g each. The 12th~17th fractions were combined and subjected to distillation to obtain 77.4 mg of the above titled compound.

NMR (90 MHz, CDCl$_3$)δ: 1.26(3H, d, J=7 Hz), 1.37(3H, s), 1.54(3H, s), 1.89(3H, s), 2.2~2.6(5H, m), 2.44(3H, s), 2.77(3H, d, J=5 Hz), ~4.3 (1H, m), 4.42(1H, m), 4.69(1H, d, J=11 Hz), ~4.7 (1H, m), 5.2~5.95(5H, m), 6.17(3H, d, J=15 Hz), 8.06(1H, d, J=10 Hz).

IR (KBr): 1720(sh.), 1704, 1682(sh.), 1500, 1254, 1130, 960 cm$^{-1}$.

Employing corresponding lankacidin A 8-derivatives as starting compounds, reactions similar to that in Example 324 gave the compounds shown in Table 8, excepting Example 404 where the compound obtained in Example 250 was employed as the starting material.

TABLE 8

8-position(R$^3$) derivatives of Lankacidin C

| Example No. | R$^3$ | Yield (%) | m.p. (°C.) | NMR: 11-Me, COCOCH$_3$, 8-H, others | IR(carbonyl region) |
|---|---|---|---|---|---|
| 325 | TeEo—S— | 57.3 | — | 1.56(s),2.44(s),4.8—4.95(m),4.36(t,J=5 Hz,tetrazole-CH$_2$) | 1745,1710,1685 |
| 326 | ThMe—S— | 82.7 | 126-128 | 1.53(s),2.43(s),~4.9 (m),3.42(s,OMe) | 1740,1700,1680 |
| 327 | ThSm—S— | 70.1 | 151-152 | 1.54(s),2.44(s),4.87 (m),4.68(s,CH$_2$SO$_2$) | 1735,1705,1680 |

TABLE 8-continued 8-position($R^3$) derivatives of Lankacidin C

| Example No. | $R^3$ | Yield (%) | m.p. (°C.) | NMR: 11-Me, COCOCH$_3$, 8-H, others | IR(carbonyl region) |
|---|---|---|---|---|---|
| 328 | ThOh—S— | 16.3 | — | 1.66(s),2.56(s),~4.95(m),3.99(s,CH$_2$COO) | 1745,1710,1680, 1605 |
| 329 | ThPe—S— | 87.0 | 88–91 | 1.52(s),2.43(s),N.A. 1.31(t,J=7.5Hz, CH$_3$CH$_2$×2) | 1740,1705,1680 |
| 330 | PhNHCOO— | 64 | — | 1.54(s),2.43(s),4.05 (m),6.9–7.5(m,C$_6$H$_5$) | 1720(sh),1706, 1680(sh) |
| 331 | PrNHCOO— | 80 | — | 1.54(s),2.44(s),4.96 (m),0.90(t,J=7Hz, CH$_3$CH$_2$)$_2$) | 1720(sh),1704, 1684(sh) |
| 332 | HCOO | 44.8 | 193–195 (dec) | 1.54()s),2.43(s),5.15 (m),8.03(s,CHO) | 1750(sh),1725 (sh),1710,1690 (sh) |
| 333 | ClCH$_2$OCOO— | 87.9 | 186–188 | 1.55(s),2.43(s),4.95 (m),~5.95(m,CH$_2$Cl) | 1760,1750(sh), 1705,1680 |
| 334 | CH$_3$SCH$_2$O— | 78 | 211–213 (dec) | 1.54(s),2.44(s),4.10 (m),2.13(s,SMe) | 1742,1704,1668 |
| 335 | EtOCOCH$_2$NHCOO— | 49 | 218–220 (dec) | 1.55(s),2.45(s),4.99 (m),3.92(d,J=6Hz, COCH$_2$N) | 1740,1720(sh), 1700,1680(sh) |
| 336 | Cl(CH$_2$)$_2$NHCOO— | 65 | — | 1.54(s),2.45(s),4.95 (m),~3.54(m,CH$_2$CH$_2$ Cl) | 1740(sh),1706, 1680 |
| 337 | TeEn—SCH$_2$OCOO— | 67.5 | 163–165 (dec) | 1.54(s),2.44(s),4.91 (m),2.24(s,NMe$_2$) | 1745,1705,1680 |
| 338 | ICH$_2$OCOO— | 88.4 | 156–158 (dec) | 1.56(s),2.45(s),4.95 (m),5.95(s,CH$_2$I) | 1750,1700,1670 |
| 339 | TeM—SCH$_2$OCOO— | 97 | 136–138 (dec) | 1.54(s),2.44(s),4.93 (m),3.93(s,NMe) | 1745,1705,1685 |
| 340 | Me$_2$N(CH$_2$)$_2$OCOO— | 74.6 | 151–154 (dec) | 1.55(s),2.45(s),4.92 (m),2.23(s,NMe$_2$) | 1745,1705,1680 |
| 341 | TeEn—S(CH$_2$)$_2$NHCOO— | 85 | — | 1.53(s),2.44(s),4.92 (m),2.27(s,NMe$_2$) | 1740(sh),1720 (sh),1706,1688 (sh) |
| 342 | TePn—S(CH$_2$)$_2$NHCOO— | 59 | — | 1.54(s),2.45(s),4.95 (m),2.23(s,NMe$_2$) | 1740(sh),1720 (sh),1704,1685 (sh) |
| 343 | Me$_2$N(CH$_2$)$_2$SCOO— | 52.6 | — | 1.54(s),2.44(s),5.11 (m),2.25(s,NMe$_2$) | 1750,1700,1690 (sh) |
| 344 | ThMe—SCH$_2$OCOO— | 88.8 | — | 1.56(s),2.47(s),4.95 (m),3.48(s,OMe) | 1750,1710,1685 |
| 345 | ClCH$_2$OCOO— | 81 | — | 1.57(s),2.45(s),5.11 (m),4.03(s,ClCH$_2$) | 1730,1700,1665 |
| 346 | BuNHCOO— | 69 | 212 (dec) | 1.54(s),2.44(s),4.94 (m),0.90(t,J=7Hz, CH$_3$(CH$_2$)$_4$) | 1746,1706,1684 |
| 347 | tBuNHCOO— | 57 | 198 (dec) | 1.53(s),2.43(s),4.91 (m),1.29(s,tBu) | 1740(sh),1720 (sh),1706,1685 |
| 348 | Cy—NHCOO— | 65 | 179–181 (dec) | 1.50(s),2.41(s),4.90 (m),0.8~2.1(m,Cy—CH$_2$) | 1744,1706,1680, 1624,1680 |
| 349 | PhSCH$_2$OCOO— | 68.2 | 184–185 | 1.56(s),2.43(s),4.92 (m),5.43(s,SCH$_2$O) | 1710,1680 |
| 350 | EtSCH$_2$OCOO— | 59.1 | — | 1.56(s),2.45(s),4.93 (m),5.22(s,SCH$_2$O) | 1750,1710,1685 |
| 351 | TeM—SCH$_2$COO— | 74 | — | 1.55(s),2.45(s),5.09 (m),3.98(s,NMe) | 1740,1705,1680 |
| 352 | TeEn—SCH$_2$COO— | 86 | — | 1.55(s),2.47(s),5.01 | 1740,1705,1685 |
| 353 | TeEo—SCH$_2$COO— | 82 | — | 1.53(s),2.43(s),5.02 (m),4.10(s,SCH$_2$CO) | 1730,1705,1680 |
| 354 | ThMe—SCH$_2$COO— | 70 | — | 1.53(s),2.43(s),5.03 (m),3.43(s,OMe) | 1730,1705,1685 |
| 355 | iPrNHCOO— | 58 | 208–210 | 1.51(s),2.43(s),4.91 (m),1.12(d,Me$_2$CH) | 1736(sh),1704, 1688 |
| 356 | EtNHCOO— | 65 | 201–203 (dec) | 1.54(s),2.46(s),4.97 (m),1.12(t,J=7Hz, CH$_3$CH$_2$) | 1740(sh),1704, 1680(sh) |
| 357 | PhOCOO— | 69 | 217–219 | 1.55(s),2.43(s),5.00 (m),7.1~7.5(m,C$_6$H$_5$) | 1750,1708,1676 |
| 358 | MeOCOO— | 75 | 201–202 (dec) | 1.55(s),2.45(s), 4.92(m),3.77(s,MeO) | 1742.1706,1678, |
| 359 | Pyn—COOCH$_2$OCOO— | 71.9 | 119–122 | 1.59(s),2.45(s),4.94 (m),5.82(s,OCH$_2$) | 1750,1710,1685 |
| 360 | AcNHCH$_2$COOCH$_2$OCOO— | 55.8 | — | 1.56(s),2.47(s),4.95 (m),5.81(s,OCH$_2$O) | 1750,1710,1680 |
| 361 | ThPe—SCH$_2$COO— | 69 | — | 1.53(s),2.46(s),5.09 (m),4.08(s,SCH$_2$CO) | 1735,1705,1680 |
| 362 | Me$_2$N(CH$_2$)$_2$SCH$_2$COO— | — | — | 1.54(s),2.43(s),5.10 | 1710,1685 |

TABLE 8-continued

8-position($R^3$) derivatives of Lankacidin C

| Example No. | $R^3$ | Yield (%) | m.p. (°C.) | NMR: 11-Me, COCOCH$_3$, 8-H, others | IR(carbonyl region) |
|---|---|---|---|---|---|
| 363 | Et$_2$N(CH$_2$)$_2$SCH$_2$COO— | 50 | — | 1.55(s),2.45(s),5.09 (m),3.25(s,SCH$_2$CO) (m),3.25(s,SCH$_2$CO) | 1725(sh),1705, 1690 1690 |
| 364 | Mor-COO— | 67 | — | 1. 56(s),2.47(s),5.01 (m),~3.55(m,Mor-CH$_2$) | 1740(sh),1700, 1685(sh) |
| 365 | H-Pipe-COO— | 64 | — | 1.53(s),2.43(s),4.97 (m),2.80(br.s,C$\underline{H}_2$NH CH$_2$) | 1740,1700, 1688(sh) |
| 366 | Me$_2$N(CH$_2$)$_2$NHCOO— | 62 | — | 1.52(s),2.43(s),4.94 (m),2.20(s,Me$_2$N) | 1748,1706, 1688 |
| 367 | 2-Py-Pipe—COO— | 65 | — | 1.55(s),2.42(s),5.01 (m),3.55(s,Pipe-CH$_2$) | 1740,1700,1682 (sh) |
| 368 | NH$_2$COO— | 69 | >300 | 1.51(s),2.42(s),4.89 (m),5.86(s,NH$_2$) | 1706,1682(sh) |
| 369 | Me-Pipe(CH$_2$)$_2$NHCOO— | 69 | 171–173 (dec) | 1.55(s),2.47(s),4.99 (m),2.27(s,NMe) | 1740,1702,1684 (sh) |
| 370 | L-Ala-COO— | 23.8 | — | 1.44(s),2.33(s),4.83 (m),1.30(d,J=7Hz-MeCH) | 1740(sh),1705, 1690(sh) |
| 371 | HO$_2$C(CH$_2$)$_3$NHCOO— | 85.9 | — | 1.54(s),2.42(s),4.98 (m),3.05–3.35(m, NHC$\underline{H}_2$) | 1730(sh),1705, 1680(sh) |
| 372 | AcMeNCH$_2$COO— | 73.6 | 217–219 (dec) | 1.55(s),2.45(s),5.09 (m),2.02&2.11(each s,1:4,NAc) | 1745,1710, 1690,1630 |
| 373 | Me$_2$NCH$_2$COO— | 75 | 204–208 (dec) | 1.53(s),2.43(s),5.15 (m),2.23(s,NMe$_2$) | 1740,1720(sh), 1705,1675 |
| 374 | Et$_2$NCH$_2$COO— | 73 | 193–196 (dec) | 1.55(s),2.45(s),5.14 (m),3.30(s,NCH$_2$CO) | 1740(sh),1705, 1685 |
| 375 | Me-Pipe-CH$_2$COO— | 45 | — | 1.55(s),2.45(s),5.12 (m),3.20(br.s,NCH$_2$ CO) | 1740,1705,1605 |
| 376 | Me$_2$N(CH$_2$)$_2$-Pipe-COO— | 57 | — | 1.54(s),2.44(s),4.98 (m),2.23(s,NMe$_2$) | 1742,1700,1686 (sh) |
| 377 | 3-Py-CH$_2$NHCOO— | 70 | 193–195 | 1.49(s),2.38(s),5.12 (m),4.23(d,J=6Hz, NCH$_2$) | 1740(sh),1708 1682(sh) |
| 378 | Me-Pipe-COO— | 79 | 201–203 (dec) | 1.54(s),2.44(s),4.99 (m),2.27(s,NMe) | 1744,1700,1688 (sh) |
| 379 | AcNH(CH$_2$)$_2$SCOO— | 75.9 | 175–178 | 1.54(s),2.44(s),5.11 (m),1.94(s,AcN) | 1750,1710, 1690 |
| 380 | AcNH(CH$_2$)$_2$SCH$_2$OCOO— | 19.5 | 108–110 | 1.55(s),2.44(s),4.92 (m),1.97(s,AcN) | 1740,1710,1670 |
| 381 | Me$_2$N (CH$_2$)$_2$COO— | 41.8 | 184–186 (dec) | 1.54(s),2.44(s),5.08 (m),2.23(s,NMe$_2$) | 1720,1710,1685 |
| 382 | Me$_2$N—(CH$_2$)$_3$COO— | 71.3 | 163–165 | 1.55(s),2.44(s),5.07 (m),2.24(s,NMe$_2$) | 1725,1710,1690 |
| 383 | 2-Py-Pipe-CH$_2$COO— | 64 | — | 1.57(s),2.47(s),5.12 (m),3.27(br.s,-CH$_2$ COO) | 1740(sh),1705, 1680 |
| 384 | Cl(CH$_2$)$_2$NHCH$_2$COO— | 59 | — | 1.56(s),2.46(s),5.12 (m),3.45(br.s,NCH$_2$ CO) | 1730,1700,1680 |
| 385 | F(CH$_2$)$_2$NHCH$_2$COO— | 72 | — | 1.56(s),2.45(s),5.12 (m),3.46(br.s,NCH$_2$CO) | 1730,1700,1680 |
| 386 | HO(CH$_2$)$_2$-Pipe-COO— | 84 | 210–212 | 1.56(s),2.45(s),5.00 (m),3.63(t,J=6Hz, CH$_2$CH$_2$O) | 1740,1702,1686 (sh) |
| 387 | 2-Py-(CH$_2$)$_2$NHCOO— | 65 | — | 1.50(s),2.40(s),4.90 (m),2.93(t,J=7Hz, PyCH$_2$CH$_2$) (DM) | 1746(sh),1708, 1682(sh) |
| 388 | 2-Py-CH$_2$NHCOO— | 70 | 192–194 (dec) | 1.54(s),2.45(s),5.01 (m),4.47(d,J=6Hz, NHCH$_2$) | 1740(sh),1704, 1684(sh) |
| 389 | 4-Py-CH$_2$NHCOO— | 76 | 215–217 (dec) | 1.51(s),2.42(s),4.95 (m),4.27(d,J=6Hz, NCH$_2$) | 1740(sh),1718 (sh),1704,1674 |
| 390 | Piri-4-Piri-COO— | 74 | 206–207 (dec) | 1.53(s),2.43(s),4.97 (m),0.8–2.1,2.1–2.9, ~4.2(each m,Pipe-CH$_2$) | 1738,1688 |
| 391 | PhCH$_2$Pipe-COO— | 62 | — | 1.54(s),2.44(s),4.97 (m),3.50(s,PhCH$_2$N) | 1740,1700,1685 |
| 392 | 4-Py-Pipe-COO— | 54.7 | 180–182 (dec) | 1.55(s),2.44(s),5.01 (m),3.25–3.7(m,Pipe-CH$_2$) | 1710,1685 |
| 393 | PrNHCH$_2$COO— | 51 | — | 1.57(s),2.47(s),5.09 (m),0.90(t,J=7Hz, CH$_3$(CH$_2$)$_2$) | 1705,1685 |
| 394 | N$_3$CH$_2$COO— | 59 | — | 1.57(s),2.47(s),5.17 | 1730,1705,1675 |

TABLE 8-continued 8-position(R³) derivatives of Lankacidin C

| Example No. | R³ | Yield (%) | m.p. (°C.) | NMR: 11-Me, COCOCH₃, 8-H, others | IR(carbonyl region) |
|---|---|---|---|---|---|
| 395 | iPr₂NCH₂COO— | 80 | — | (m),3.87(s,N₃CH₂) 1.55(s),2.45(s),5.10 (m),1.00(s,Me₂CH×2) | 1740,1705,1685 |
| 396 | HO(CH₂)₂NHCH₂COO— | 39 | — | 1.55(s),2.43(s),5.11 (m),3.43(br.s,NCH₂ CO) | 1735,1705 |
| 397 | Mor-COCH₂-Pipe-COO— | 69 | 220–222 (dec) | 1.55(s),2.45(s),5.00 (m),3.18(s,COCH₂N) | 1740,1692,1636 |
| 398 | Pyr-COCH₂-Pipe-COO— | 73 | 222–224 (dec) | 1.54(s),2.45(s),4.98 (m),3.11(s,COCH₂N) | 1730(sh),1690 (br.),1620 |
| 399 | iPrNHCOCH₂-Pipe-COO— | 62 | 166–168 | 1.55(s),2.45(s),4.99 (m),2.97(s,COCH₂N) | 1698(sh),1672, 1650(sh) |
| 400 | 2-Py-NH(CH₂)₂NHCOO— | 39.6 | 138–140 | 1.56(s),2.44(s),4.95 (m),3.41(br.s, N(CH₂)₂N) | 1750,1705(sh), 1690 |
| 401 | 2-Py-CH₂-Pipe-COO— | 54.7 | 216–218 (dec) | 1.53(s),2.43(s),4.97 (m),3.65(s,CH₂N) | 1750,1705(sh), 1690 |
| 402 | iPrNHCH₂COO— | 65 | — | 1.55(s),2.44(s),5.09 (m),3.38(br.s,NCH₂ CO) | 1730,1700 |
| 403 | Mor-CH₂COO— | 71 | — | 1.55(s),2.45(s),5.10 (m),3.20(s,NCH₂CO) | 1735,1700,1660 |
| 404 | ICH₂COO— R¹:*¹ | 79 | — | 1.57(s), —,5.06 (m),3.68(s,ICH₂) | 1725,1710,1675 |
| 405 | MeNH(CH₂)₃NHCH₂COO— | 27 | — | 1.55(s),2.45(s),5.09 (m),2.33(br.s,MeN) | 1740,1705 |
| 406 | ICH₂COO— | 46 | — | 1.57(s),2.45(s),5.09 (m),3.67(s,ICH₂) | 1725,1710,1675 |
| 407 | 4-Py-Pipe-CH₂COO— | 50 | — | 1.53(s),2.44(s),5.10 (m),3.27(br.s,CH₂CO) | 1740,1705,1600 |

R¹: *¹ =3-CH₃C(=NOCH₃)CONH

EXAMPLE 408

Preparation of O(8)-(4-methylpiperazino) carbonyl lankacidin A hydrochloride

In 6.4 ml of tetrahydrofuran was dissolved 200 mg of O(8)-(4-methylpiperazino)carbonyl lankacidin A. To the solution was added 0.139 ml of 1N HCl, which was left standing for 10 minutes. The solvent was distilled off. The residual glassy substance was treated with ether, and pulverized. The powdery product was collected by filtration and dried to obtain 203.7 mg of the above titled compound.

NMR (90 MHz, CDCl₃)δ: 1.31(3H, d, J=7 Hz), 1.38(3H, s), 1.55(3H, s), 1.90(3H, s), 2.02 (3H, s), 2.1~2.65(5H, m), 2.44(3H, s), 2.83(3H, s), 3.15(4H, br.), 4.0(4H, br.), 4.43(1H, m), 4.72(1H, d, J=11 Hz), 5.00(1H, m), 5.2~5.9(6H, m), 6.28(1H, d, J=15 Hz), 8.07(1H, d, J=10 Hz).

IR (KBr): 1740(sh.), 1720(sh.), 1700, 1460 (sh.), 1420, 1254, 962 cm⁻¹.

Employing as starting materials free amino compounds of corresponding lankacidin A or C derivatives, reactions similar to that in Example 408 were conducted to obtain the respective hydrochloride shown in Table 9.

TABLE 9

Hydrochloride of Lankacidin Derivative

| Example No. | R³ | R⁴ | Yield (%) | m.p. (°C.) | NMR: 11-Me, COCOCH₃, 8-H,(CDCl₃)others | IR (KBr) (carbonyl region) |
|---|---|---|---|---|---|---|
| 409 | Me—Pipe-COO— | OH | 99 | — | 1.54(s),2.43(s),4.98 (m),2.83(s,NMe) (DM) | 1734(sh),1696, 1680(sh) |
| 410 | Me₂NCH₂COO— | OAc | 107 | 156–163 (dec) | 1.57(s),2.45(s),5.10 (m),3.00(br,s,NMe₂) | 1730,1705 |
| 411 | Me₂NCH₂COO— | OH | 94 | 182–195 (dec) | 1.53(s),2.43(s),5.09 (m),3.00(br,s,NMe₂) | 1740,1705 |
| 412 | Et₂NCH₂COO— | OAc | 94 | 154–160 (dec) | 1.57(s),2.47(s),5.11 (m),3.92(br,s,NCH₂CO) | 1740,1705 |
| 413 | Et₂NCH₂COO— | OH | 98 | 159–171 (dec) | 1.57(s),2.45(s),5.08 (m),3.90(br,s,NCH₂CO) | 1740,1700 |
| 414 | 2-Py-Pipe-COO— | OAc | 99 | — | 1.57(s),2.46(s),5.03 (m),3.77&3,90(each br,s,Pipe-CH₂) | 1720(sh),1700, 1682(sh),1632, 1602 |
| 415 | 2-Py-Pipe-COO— | OH | 94 | 214 (dec) | 1.55(s),2.44(s),5.00 (m),3.77&3,90(each br,s,Pipe-CH₂) | 1730,1692, 1680(sh),1632, 1604 |
| 416 | 4-Py-CH₂NHCOO— | OAc | 95 | — | 1.54(s),2.46(s),4.98 (m),~4.6(br.,NCH₂) | 1720(sh),1704, 1680(sh),1638 |
| 417 | 4-Py-CH₂NHCOO— | OH | 96 | — | 1.51(s),2.41(s),4.92 (m),(DM) | 1720(sh),1698, 1680(sh),1636 |
| 418 | Me₂N(CH₂)₃COO— | OAc | 96 | 158–161 (dec) | 1.55(s),2.45(s),5.05 (m),2.80(s,NMe₂) | 1730,1710, 1690(sh) |
| 419 | Me₂N(CH₂)₃COO— | OH | 98 | 157–160 | 1.55(s),2.45(s),5.04 | 1730,1710, |

TABLE 9-continued

| | Hydrochloride of Lankacidin Derivative | | | | |
|---|---|---|---|---|---|
| Example No. | $R^3$ | $R^4$ | Yield (%) | m.p. (°C.) | NMR: 11-Me, COCOC$\underline{H}_3$, 8-H,(CDCl$_3$)others | IR (KBr) (carbonyl region) |
| 420 | Me$_2$N(CH$_2$)$_2$SCH$_2$COO— | OAc | 77 | — (dec) | (m),2.81(s,NMe$_2$) 1.54(s),2.45(s),5.06 (m),2.73(s,NMe$_2$) | 1690(sh) 1740,1705 |
| 421 | Me$_2$N(CH$_2$)$_2$SCH$_2$COO— | OH | 98 | — | 1.57(s),2.47(s),5.04 (m),2.83(br.s,NMe$_2$) | 1740,1705 |
| 422 | 4-Py-Pipe-COO— | OAc | 96 | 181–183 (dec) | 156(s),2.45(s),5.03 (m),3.74(br.s,Pipe-CH$_2$) | 17.20(sh),1700, 1690(sh),1640 |
| 423 | 4-Py-Pipe-COO— | OH | 91 | >300 | 1.55(s),2.44(s),5.00 (m),3.72(br,s,Pipe-CH$_2$) | 1700,1690(sh), 1640 |
| 424 | iPr$_2$NCH$_2$COO— | OAc | 95 | — | 1.60(s),2.47(s),5.09 (m),3.90(br,s,NCH$_2$CO) | 1725,1705, 1680 |
| 425 | iPr$_2$NCH$_2$COO— | OH | 98 | — | 1.58(s),2.47(s),5.08 (m),3.88(br,s,NCH$_2$CO) | 1725(sh), 1705,1680(sh) |

What is claimed is:

1. A compound of the formula

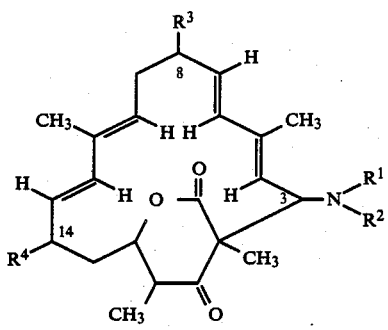

wherein
(i) one of $R^1$ and $R^2$ is hydrogen and the other is a group of the formula

wherein Z is oxygen or sulfur, and $R^5$ is
(a) hydrogen
(b) a group of the formula

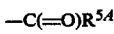

wherein $R^{5A}$ is C$_{1-3}$ alkyl
(c) a group of the formula

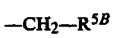

wherein $R^{5B}$ is C$_{1-8}$ alkyl which is unsubstituted or is substituted by (1) C$_{1-5}$ alkyl, (2) halogen substituted C$_{1-5}$ alkyl, (3) halogen, (4) phenyl or (5) a member of the group consisting of triazolylthio, tetrazolylthio, pyridylthio and thiazolylthio which groups are unsubstituted or are substituted by dimethylaminoethyl, methyl or amino,
(d) a group of the formula

wherein $Y^A$ is (1) hydroxy, (2) C$_{2-8}$ alkyanoyloxy, (3) C$_{1-3}$ alkoxycarbonyl, (4) halogen substituted C$_{1-3}$ alkoxycarbonyl, (5) halogen, (6) amino which is unsubstituted or is substituted with C$_{1-3}$ alkoxycarbonyl, C$_{2-5}$ alkanoyl or phenylsulfonyl, (7) hydroxycarbonyl, (8) alkylsulfonyloxy, (9) phenylsulfonyloxy, (10) tri-C$_{1-3}$ *alkylsiloxy*, (11) phenylthio, (12) C$_{1-3}$ alkylthio, (13) alkylsulfonyl, (14) azido or (15) benzothiazol-2-ylthio, and $R^{5C}$ is C$_{1-3}$ alkyl, (e) —$R^{5D}$
wherein $R^{5D}$ is phenyl, C$_{5-7}$ cycloalkyl or 2-aminothiazol-4-yl,
(f) a group of the formula

wherein $R^{5E}$ is hydroxy or C$_{1-3}$ alkoxy, and $R^{5F}$ is pyridin-2-ylthio or C$_{1-3}$ alkyl which is unsubstituted or is substituted by halogen, or
(g) a group of the formula

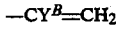

wherein $Y^B$ is hydrogen, C$_{2-5}$ alkanoyloxy, C$_{1-5}$ alkoxycarbonyloxy or tri-C$_{1-3}$ alkylsilyl, or
(ii) $R^1$ and $R^2$, taken together, represent a group of the formula

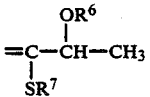

wherein $R^6$ is C$_{1-8}$ alkylcarbonyl, sulfonyl or C$_{1-3}$ alkoxycarbonyl, and $R^7$ is C$_{1-4}$ alkyl, one of $R^3$ and $R^4$ is hydroxyl or —OCOR$^{14}$ wherein $R^{14}$ is hydrogen or C$_{1-3}$ alkyl and the other is a member selected from the group consisting of —OCONR$^{15}$R$^{16}$ and —OCSNR$^{17}$R$^{18}$, wherein $R^{15}$ together with $R^{16}$ and $R^{17}$ together with $R^{18}$ with the nitrogen atom to which they are attached form piperazino, provided that, when $R^1$ is a hydrogen atom and $R^2$ represents

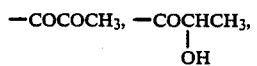

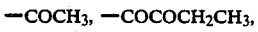

-continued

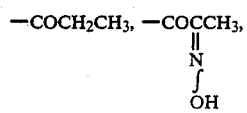

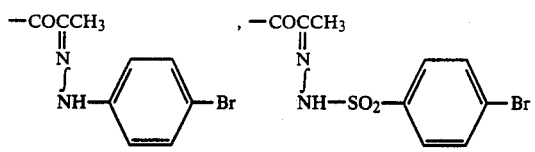

or a group of the formula;

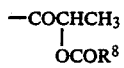

wherein $R^8$ is a straight-chain alkyl having 1–13 carbon atoms, $R^3$ is other than hydroxyl or a group of the formula $-OCOR^{14}$ wherein $R^{14}$ is $C_{1-3}$ alkyl and $R^4$ is other than hydroxyl or a group of the formula $-OCOR^{14}$ wherein $R^{14}$ is as defined above, or both $R^3$ and $R^4$ represent groups other than formyloxy, or a salt thereof.

2. A compound according to claim 1, wherein $R^1$ is

and $R^2$ is a hydrogen atom.

3. A compound according to claim 1, wherein $Y^B$ is acetyloxy or t-butoxycarbonyloxy.

4. A compound according to claim 2, wherein Z is sulfur and $R^5$ is acetyl.

5. A compound according to claim 2, wherein Z is oxygen and $R^5$ is acetyl.

6. The compound O(8)-(4-methylpiperazino)carbonyl-lankacidin A.

7. The compound O(8)-(4-methylpiperazino)carbonyl-lankacidin A hydrochloride.

8. The compound O(8)-(4-benzylpiperazino)carbonyl-lankacidin C.

9. The compound O(8)-(4-methylpiperazino)carbonyl-lankacidin C hydrochloride.

10. The compound O(8)-(4-methylpiperazino)carbonyl-lankacidin C.

11. The compound lankacidin A 8-[S-(2-dimethylaminoethyl)]thiocarbonate.

12. The compound lankacidin C 8-[S-(2-dimethylaminoethyl)]thiocarbonate.

13. The compound lankacidin A 8-diethylaminoacetate.

14. The compound lankacidin A 8-diethylaminoacetate hydrochloride.

15. The compound lankacidin C 8-diethylaminoacetate.

16. The compound lankacidin C 8-diethylaminoacetate hydrochloride.

17. The compound O(8)-(4-benzylpiperazino)carbonyl-lankacidin A.

18. The compound lankacidin A 8-diisopropylaminoacetate.

19. The compound lankacidin A 8-diisopropylaminoacetate hydrochloride.

20. The compound lankacidin C 8-diisopropylaminoacetate.

21. The compound lankacidin C 8-diisopropylaminoacetate hydrochloride.

* * * * *